US006936425B1

(12) United States Patent
Hensel et al.

(10) Patent No.: US 6,936,425 B1
(45) Date of Patent: Aug. 30, 2005

(54) ATTENUATED SALMONELLA SP12 MUTANTS AS ANTIGEN CARRIERS

(75) Inventors: Michael Hensel, Munich (DE); David William Holden, London (GB); Jacqueline Elizabeth Shea, High Wycombe (GB)

(73) Assignees: Microscience Limited, Wokingham Berkshire (GB); Imperial College Innovations Limited, London (GB)

( * ) Notice: Subject to any disclaimer, the term of this patent is extended or adjusted under 35 U.S.C. 154(b) by 0 days.

(21) Appl. No.: 09/763,620

(22) PCT Filed: Sep. 3, 1999

(86) PCT No.: PCT/EP99/06514

§ 371 (c)(1),
(2), (4) Date: Mar. 1, 2002

(87) PCT Pub. No.: WO00/14240

PCT Pub. Date: Mar. 16, 2000

(30) Foreign Application Priority Data

Sep. 4, 1998 (EP) .............................. 98116827

(51) Int. Cl.[7] .......................... G01N 33/53; C12N 1/12; A61K 39/00; C07H 21/02
(52) U.S. Cl. .................. 435/7.1; 435/252.1; 424/184.1; 536/23.1
(58) Field of Search .............................. 435/7.1, 252.1; 536/23.1; 424/184.1

(56) References Cited

U.S. PATENT DOCUMENTS

| | | |
|---|---|---|
| 5,397,697 A | 3/1995 | Lam et al. |
| 5,527,674 A | 6/1996 | Guerra et al. |
| 5,618,666 A | 4/1997 | Popoff et al. |
| 5,700,683 A | 12/1997 | Stover et al. |
| 5,700,928 A | 12/1997 | Hodgson et al. |
| 5,876,931 A | 3/1999 | Holden |
| 6,015,669 A | 1/2000 | Holden |
| 6,342,215 B1 | 1/2002 | Holden et al. |

FOREIGN PATENT DOCUMENTS

| | | | |
|---|---|---|---|
| WO | WO 92/01056 | 1/1992 | |
| WO | WO 93/04202 | 3/1993 | |
| WO | WO 94/26933 | 11/1994 | |
| WO | WO 96/17951 | 6/1996 | |
| WO | 96 17951 | 6/1996 | ............ C12Q/1/04 |

OTHER PUBLICATIONS

Hensel et al. " Functional analysis of ssAJ and ssa K/U operon, 13 genes encoding components of the type III secretion apparatus of Salmonella Pathogenicity Island 2" Molecular Microbiology vol. 24 (1), pp. 155–167, 1997.*
Hensel, et al., "Functional analysis of ssaJ and ssaK/U operon, 13 genes encoding components of the type III secretion apparatus of Salmonella pathogenicity island 2," Mol. Microbiol. 24(1): 155–167 (1997).

Medina, et al., "Pathogenicity island 2 mutants of S. typhimurium are efficient carriers for heterologous antigens and enable modulation of immune responses," Infect, Immun. 67(3): 1093–1099 (1999).
Ochman, et al., "Identification of a pathogenicity island required for Salmonella survival in host cells," Proc. Natl. Acad. Sci USA 93: 7800–7804 (1996).
"Salmonella typhimurium ssrA and ssrB genes," EMBL/Genbank Database Accession No. Z95891 (Jan. 8, 1998).
Valentine, "Identification of three highly attenuated Salmonells typhimurium mutants that are more immunogenic and protective in mice than a prototypical aroA mutant," Infect. Immun. 66(7): 3378–333 (1998).
Valdivia, et al., "Salmonella typhimirium pathogenicity island 2, partial sequence," EMBL/GenBank Database Accession No. AF0208080 (Aug. 7, 1998).
The type III secretion system of Salmonella Pathogenicity Island 2, D.W. Holden, FEBS Advanced Course—Protein Export and Assembly in Bacteria, Lunteren, The Netherlands; Apr. 25–May 1, 1998.
Hensel et al., "Functional analysis of ssaJ and ssaK/U operon, 13 genes . . . ", Molecular Microbiology, vol. 24, No. 1, Apr. 1997, pp. 155–167
Ochman et al., "Identification of a pathogenicity island required for Salmonella . . . ", The National Academy of Sciences of USA, vol. 93, Jul. 1996, pp. 7800–7804.
EMBL/GenBank databases Accession No. AF0208080; Aug. 7, 1998 Valdivia et al., Salmonella typhimurium pathogenicity island 2.
EMBL.GenBank databases Accession No. Z95891; Jan. 8, 1998 Salmonella typhimurium ssrA and ssrB genes.
Valentine, "Identificaton of three highly attenuated Salmonella typhimurium mutants that are more immunogenic . . .", Infection and Immunity, vol. 66, No. 7, Jul. 1998, pp. 3378–3383.
Medina et al., "Pathogenicity island 2 mutants of S. typhimurium are efficient carriers for heterologous . . . ", Infection and Immunity, vol. 67, No. 3, Mar. 1999, pp. 1093–1099.
Adachi, et al., "Isolation of Dictyostelium Discoideum Cytokinesis Mutants by Restriction Enzyme–Mediated Integration of the Blasticidin S Resistance Marker," Biochem. Biophys. Res. Comm. 205:1808–1814 (1994).

(Continued)

Primary Examiner—Rodney P. Swartz
Assistant Examiner—Khatol S Shahnan-Shah
(74) Attorney, Agent, or Firm—Holland & Knight LLP

(57) ABSTRACT

The present invention relates to vaccines, in particular, to an attenuated gram-negative cell comprising the SP12 gene locus, wherein at least one gene of the SP12 locus is inactivated, wherein the inactivation results in an attenuation/reduction of virulence compared to the wild type of said cell, and to a carrier for the presentation of an antigen to a host, which carrier is the attenuated gram-negative cell, wherein the cell comprises at least one heterologous nucleic acid molecule comprising a nucleic acid sequence coding for the antigen, wherein the cell is capable of expressing the nucleic acid molecule or capable of causing the expression of the nucleic acid molecule in a target cell.

20 Claims, 31 Drawing Sheets

OTHER PUBLICATIONS

Albus et al. "Virulence of Staphylococcus aureus mutants altered in type 5 capsule production," *Infect. Immun.* 59:1008–1014 (1991).

Aldhous, "Fast Tracks to Disease Genes," *Science* 265:2008–2010 (1994).

Anthony, et al., "Transformation and allelic replacement in Francisella spp.," *J. Gen. Microbiol.* 137:2697–2703 (1991).

Artiguenave, et al., "High–efficiency transposon mutagenesis by electroporation of a Pseudomonas fluorescens strain," *FEMS Microbiol. Lett.* 153:363–369 (1997).

Bainton, et al., "Immunity of children to diphtheria, tetanus, and poliomyelitis," *British Medical Journal* 1:854–57 (1979).

Black, et al., "Restriction enzyme–mediated integrated elevates transformation frequency and enables co–transfection of *Toxoplasma gondii*," *Mol. Biochem. Parasitol.* 74:55–63 (1995).

Blasco, et al., "Nitrate reductases of Escherichia coli: Sequence of the second nitrate reductase and comparison with that encoded by the narGHJI operon," *Mol. Gen. Genet.* 222:104–111 (1990).

Bolker, et al., "Tagging pathogenicity genes in *Ustilago maydis* by restriction enzyme–mediated integration (REMI)," *Mol. Gen. Genet.* 248:547–552 (1995).

Brown et al. (1997) 19th Fungal Genetics Conference, 18–23 Mar. 1997 (Asilomar Conference Centre, Pacific Grove, CA).

Brown, et al., "Molecular analysis of therib gene cluster of Salmonella serovar muenchen (strain M67): the genetic basis of the polymorphism between groups C2 and B," *Mol. Microbiol* 6: 1385–1394 (1992).

Camilli, et al., "Insertional Mutagenesis of *Listeria monocytogenes* wit ha Novel Tn917 Derivative That Allows direct Cloning of DNA Flanking Transposon Insertions," *J. Bacteriol.* 172:3738–3744 (1990).

Carter, et al., "The Route of Enteric Infection in Normal Mice," *J. Exp. Med.* 139:1189–1203 (1974).

Cheung et al. "Regulation of exoprotein expression in Staphylococcus aureus by a locus (sar) distinct from agr," *Proc. Natl. Acad. Sci.* USA 89:6462–6466 (1992).

Chiang & Mekalanos (1998) "Use of signature–tagged transposon mutagenesis to identify Vibrio cholerae genes critical for colonization," *Mol. Microbiol.* 27:797–805 (1998).

Chuang et al. "Global regulation of gene expression in Eschericia coli," *J. Bacteriol.* 175:2026–2036 (1993).

Cirillo, et al., "Macrophage–dependent induction of the Salmonella pathogenicity island 2 type III secretion system and its role in intracellular survival," Mol. Microbiol. 30: 175–188 (1998).

Coghlan, "Bar codes to tag bad genes,"0 *New Scientist* p. 18 (Jul. 29, 1995).

Correia et al. "Insertional inactivation of binding determinants of *Streptococcus crista* CC5A using Tn916," *Oral Microbiol. Immunol.* 10:220–226 (1995).

Dolganov & Grossman "Insertional inactivation of genes to isolate mutants of Synechococus sp. strain PCC 7942: isolation of filamentous strains," *J. Bacteriol.* 175:7644–7651 (1993).

Dunyaki, et al., "Identification of Salmonella pathogenecity island 2 (SPI2) genes in *Salmonell cholaraesuis* using signature–tagged mutagenesis," *Abstracts of the 97$^{th}$ General Meeting of the American Society for Microbiology* B–275, May 4–8, 1997.

Fields, et al., "A Salmonella Locus That Controls Resistance To Microbicidal Proteins From Phagocytic Cells," *Science* 243:1059–106 (1989).

Finlay, et al., "Identification And Characterization Of TnphoA Mutants Of Salmonalla That Are Unable To Pass Through A Polarized MDCK Epithelial Cell Monolayer," *Mol. Microbiol.* 2:757–766 (1988).

Fitts, "Development of a DNA–DNA Hybridization Test for the Presence of Salmonella in Foods," *Food Technology* pp. 95–102 (Mar. 1985).

Freestone, et al., "Stabilized 17D strain yellow fever vaccine:dose response studies, clinical reactions and effects on hepatic function," *Journal of Biological Standardization* 5:181–186 (1977).

Gaillard et al. (1986) "Transposon mutagenesia as a tool to study the role ofhemolysin in the virulence of Listeria monocytogenes," *Infect. Immun.* 52:50–55 (1986).

Galan, et al., "Molecular And Functional Characterization Of The Salmonella Invasion Gene invA: Homology Of InvA To Members Of A New Protein Family," (1992).

GenBank Accession No. A51688 "*Salmonella typhimurium*" (1997).

GenBank Accession No. A51689 "*Salmonella typhimurium*" (1997).

GenBank Accession No. AJ224892 "*Salmonella typhimurium* ssaE, sseA, sseB, sscA, sseC, sseD, sseE, sscB, sseF, sseG, ssaG, ssaH, ssal genes and partial ssaD, ssaJ genes," (1998).

GenBank Accession No. AJ224978 "Salmonella typhimurium," (1999).

GenBank Acession No. J05534 "*Escherichia coli* ATP–dependent cip protease proteolytic component (clpP) gene, complete cds," (1990).

GenBank Accession No. U51927 "*Salmonella typhimurium* SpiR and SpiB genes, partial cds, and SpiC and SpiA genes, complete cds," (1996).

GenBank Accession No. X56793 "*S. enterica* (group B) rib gene cluster," (1991).

GenBank Accession No. X61917 "*S. enterica* (group B) rib gene cluster," (1991).

GenBank Accession No. X99944 "*S. typhimurium* ssaA, ssaR, ssaT and ssaU genes," (1997).

GenBank Accession No. Y09357 "*S. typhimurium* ssaJ, ssaK, ssaL, ssaM, ssaV, ssaN, ssaO, ssaP, ssaQ genes," (1997).

GenBank Accession No. Z23278 "*E. coli* ClpX gene, complete cds," (1993).

Groisman & Ochman, "How To Become A Pathogen," *Trends Microbiol.* 2:289–293 (1994).

Groisman & Saie, "Salmonella Virulence: New Clues To Intramacrophage Survival," *Trends In Biochem. Sci.* 15:30–33 (1990).

Gentschev, et al., "The Escherichia coli hemolysin secretion apparatus—a versatile antigen delivery system in attenuated Salmonella," Behring Inst. Mitl. 98: 103–113 (1997), abstract only.

Gentschev, et al., "Development of antigen–delivery systems, based on the Escherichia coli hemolysin secretion pathway," Gene 179: 133–140 (1996), abstract only.

Gentschev, et al., "Synthesis and secretion of bacterial antigens by attenuated Salmonella via the Escherichia coli hemolysin secretion system," Behring Inst. Mitl. 95: 57–66 (1994), abstract only.

Groisman, et al., "Molecular, Functional And Evolutionary Analysis Of Sequences Specific To Salmonella," *Proc. Natl. Acad. Sci. USA* 90:1033–1037 (1993).

Groisman, et al., "Salmonella Typhimurium phoP Virulence Gene Is A Transcriptional Regulator," *Proc. Natl. Acad. Sci. USA* 86:7077–7081 (1989).

Guzman, et al., "Antibody Responses in the Lungs of Mice following Oral Immunization with Salmonella typhimurium aroA and Invasive *Escherichia coli* Strains Expressing the Filamentous Hemagglutinin of Bordetella pertussis," *Inf. Immun.* 59:4391–4397 (1991).

Guzman, et al., "Direct Expression of *Bordetella pertussis* Filamentous Hemagglutinin in *Escherichia coli* and *Salmonella typhimurium* arpA." *Inf.Immun.* 39:3787–3795 (1991).

Guzman, et al., "Expression of *Bordetella pertussis* filamentous hemagglutinin in *Escherichia coli* using a two cistron system," Microbiol. *Pathogenics* 12:383–389 (1992).

Guzman, et al., "Use of Salmonella spp carrier strains to delivery *Bordetella pertussis* antigens in mice using the oral route," in Biology of Salmonella (Cabello, et al., eds.) Plenum Press: New York, NY (1993).

Han et al. (1997) "Tn5 tagging of the phenol–degrading gene on the chromosome of *Pseudomonas putida*," *Mol. Cells* 7:40–44 (1997).

Hensel, "Salmonella Pathogenicity Island 2," *Mol. Microbiol.* 36:1015–1023 (2000).

Hensel, et al., "Functional analysis of ssaJ and the ssaK/U operon, 13 genes encoding components of the type III secretion apparatus of Salmonella Pathogenicity Island 2," *Mol. Microbiol.* 24: 155–167 (1997).

Hensel, et al., "Genes encoding putative effector proteins of the type III secretion system of Salmonella pathogenicity island 2 are required for bacterial virulencer and proliferation in macrophages," *Mol. Microbiol.* 30:163–174 (1998).

Hensel, et al., "Molecular and functional analysis indicates a mosaic structure of Salmonella pathogenicity island 2," *Mol. Microbiol.* 31:489–496 (1999).

Hensel, et al., "Simultaneous Identification Of Bacterial Virulence Genes By Negative Selection," *Science* 269:400–403 (1995).

Hensel, et al., "The genetic basis of tetrathionate respiration in *Salmonalla typhimurium*," *Mol. Microbiol.* 32:275–287 (1999).

Hensel, et al., "Analysis of the boundaries of Salmonella pathogenicity island 2 and the corresponding chromosomal region of *Escherichia coli* K–12," *Journal of Bacteriology* 179:1105–1111 (1997).

Holland, et al., "Tn916 Insertion Mutagenesis In Escherichia Coli And Haemophilus Influenzae Type b Following Conjugative Transfer," *J. Gen. Microbiol.* 138:509–515 (1992).

Jiang, et al., "Structure and sequence of th rfb (O antigen) gene cluster of *Salmonella serovar typhimurium* (strain LT2)," *Mol Microbiol* 5:695–713 (1991).

Juntenen–Backman, et al., "Safe immunization of allergic children against measles, mumps, and rubella," *AJDC* 141:1103–1105 (1987).

Kahrs et al. "Generalized transposon shuttle mutagenesis in Neisseria gonorrhoeae: a method for isolating epithelial cell invasion–defective mutants," *Mol. Microbiol.* 12:819–831 (1994).

Kim et al. "The hrpA and hrpC operons of Erwinia amylovora encode components of a type III pathway that secretes harpin," *J. Bacteriol.* 179(5):1690–1697 (1997).

Leahy et al. "Transposon mutagenesis in Acinetobacter calcoaceticus RAG–1," *J. Bacteriol.* 175:1838–1840 (1993).

Lee, "Type III secretion systems: machines to deliver bacterial proteins into eukaryotic cells!" Trends Microbiol. 5(4): 148–156 (1997).

Lee & Falkow, "Isolation of Hyperinvasive Mutants of Salmonella," *Methods Enzymol.* 265:531–545 (1994).

Levine, et al., "Salmonella vaccines" in *New Antibacterial Strategies* (Neu, HC, ed.), pp. 89–104, (Churchill Livingstone:London, 1990).

Levine, et al., eds., "Attenuated Salmonella as a live vector for expression of foreign antigens," in New Generation Vaccines, $2^{nd}$ ed., Marcell Dekker: New York, Chapter 27, pp. 331–361 (1997).

Lisitsyn, et al., "Cloning The Difference Between Two Complex Genomes," *Science* 259:946–951 (1993).

Lisitsyn, et al., "Direct Isolation Of Polymorphic Markers Linked To A Trait By Genetically Directed Representational Difference Analysis," *Nature Genetics* 6:57–63 (1994).

Lu, et al., "Tagged Mutations At The Tox1 Locus Of Cochliobolus Heterostrophus By Restriction Enzyme–Mediated Integration," *Proc. Natl. Acad. Sci. USA* 91:12649–12653 (1994).

Mahan, et al., "Selection Of Bacterial Virulence Genes That Are Specifically Induced in Host Tissues," *Science* 259:686–688 (1993).

Maurizi et al., "Sequence and Structure of Clp P, the Proteolytic Component of the ATP–Dependent Clp Protease of *Escherichia coli*," *J. Biol. Chem.* 265(21):12536–45 (1990).

Mecsas & Strauss, "Molecular mechanisms of bacterial virulence: type III secretion and pathogenicity islands," *Emerging Infectious Diseases* 2(4): 271–288 (1996).

Medina, et al., "Pathogenicity island 2 Mutants of *Salmonella typhimurium* Are Efficient Carriers for Heterologous Antigens and Enable Modulation of Immune Responses," *Infect. Immun.* 67:1093–1099 (1999).

Mei et al."Identification of Staphylococcus aureus virulence genes in a murine model of bacteraemia using signature–tagged mutagenesis," *Mol. Microbiol.* 26:399–407 (1997).

Mejia–Ruiz et al. "Isolation and characterization of an Azotobacter vinelandii algK mutant," *FEMS Microbiol. Lett.* 156:101–106 (1997).

Miller, et al., "A Two–Component Regulatory System (phoPphoQ) Controls Salmonella Typhimurium Virulence," *Proc. Natl. Acad. Sci. USA* 86:5054–5058 (1989).

Miller, et al., "Isolation Of Orally Attenuated Salmonella Typhimurium Following TriphoA Mutagenesis," *Infection Immun.* 57:2758–2763 (1989).

Morrison et al. "Isolation of transformation–deficient Streptococcus pneumoniae mutants defective in control of competence, using insertion–duplication mutagenesis with the erythromycin resistance determinant of pAM beta 1," *J. Bacteriol.* 159:870–876 (1984).

Myers & Myers "Isolation and characterization of a transposon mutant of Shewanella putrefaciens MR–1 deficient in fumarate reductase," *Lett. Appl. Microbiol.* 25:162–168 (1997).

Nelson, et al., "Genomic Mismatch Scanning: A New Approach To enetic Linkage Mapping," *Nature Genetics* 4:11–17 (1993).

Norgren et al. "A method for allelic replacement that uses the conjugative transposon Tn916: deletion of the emm6.1 allele in Streptococcus pyogenes JRS4," *Infect. Immun.* 57:3846–3850 (1989).

Ochman & Groisman, "Distribution of pathogenicity islands in *Salmonella* spp." *Infection and Immunity* 64:5410–12 (1996).

Ochman, et al., "Identification of a pathogenicity island for *Salmonella* survival in host cells," *Proc. Natl. Acad. Sci. USA* 93:7800–7804 (1996).

Pang et al. "Typhoid fever—important issues still remain," *Trends Microbiol.* 6:131–133 (1998).

Pascopella, et al., "Use Of In Vivo Complementation In Mycobacterium Tuberculosis To Identify A Genomic Fragment With Virulence," *Infection Immun.* 62:1313–1319 (1994).

Pellcic et al. "Genetic advances for studying Mycobacterium tuberculosis pathogenicity," *Molecular Microbiology* 28:413–420 (1998).

Piatti, et al., "Cloning and Characterization of S. typhi," Sociela Italiana di Microbiologia Medica Odontoiatrica e Clinica '93 (Translation), p. 82.

Plunkett, EMBL ID NO:EC29479, Accession No.: U29579 (Mar. 4, 2000).

Polissi et al. *Fourth European Meeting on the Molecular Biology of the Pneumococcus*, Abstrat A. 18 (1997).

Ramakrishnan et al. "Mycobacterium marinum causes both long–term subclinical infection and acute disease in the leopard frog (Rana pipiens)," *Infect. Immun.* 65:767–773 (1997).

Regue et al. "A generalized transducing bacteriophage for Serratia marcescens," *Res. Microbiol.* 142:23–27 (1991).

Rella et al. "Transposon insertion mutagenesis of Pseudomonas aeruginosa with a Tn5 derivative: application to physical mapping of the arc gene cluster," *Gene* 33:293–303 (1985).

Roberts et al. "Cloning of the egl gene of Pseudomonas solanacearum and analysis of its role in phytopathogenicity," *J. Bacteriol.* 170:1445–1451 (1988).

Roos et al. "Tagging genes and trapping promoters in Toxoplasma gondii by insertional mutagenesis," *Methods* 13:112–122 (1997).

Rott et al. "At least two separate gene clusters are involved in albicidin production by Xanthomonas aibilineans," *J. Bacteriol.* 178:4590–4596 (1996).

Roudier et al. "Characterization of translation termination mutations in the spv operon of the Salmonella virulence plasmid pSDL2," *J. Bacteriology* 174:6418–6423 (1992).

Russman, et al., "Delivery of epitopes by the Salmonella type III secretion system for vaccine development," *Science* 281:585–568 (1998).

Schiestl & Petes "Integration of DNA fragments by illegitimate recombination in Saccharomyces cerevisiae," *Proc. Natl. Acad. Sci. USA* 88:7585–7589 (1991).

Sharetzky et al. "A novel approach to insertional mutagenesis of Haemophilus influenzae," *J. Bacteriol.* 173:1561–1564 (1991).

Shea, et al., "Identification of a virulence locus encoding a second type III secretion system in *Salmonella typhimurium*," *Proc. Natl. Sci. USA* 93:2593–2597 (1996).

Shea, et al., "Influence of the *Salmonella typhimurium* pathogenicity island 2 type III secretion system on bacterial growth in the mouse," *Infection and Immunity* 67:213–219 (1999).

Slauch, et al., "In Vivo Expression Technology For Selection Of Bacterial Genes Specifically Induced In Host Tissues," *Methods Enzymnol*, 235:481–492 (1994).

Smith, et al., "Genetic Footprinting: A Genomic Strategy For Determining A Gene's Function Given its Sequence" *Proc. Natl. Acad. Sci. USA* 92:6479–6483 (1995).

Smith, et al., "Virulence Of Aspergillus Fumigatus Double Mutants Lacking Restriction And An Alkaline Protease in A Low–Dose Model Of Invasive Pulmonary Aspergilosis," *Infection Immun.* 62(4):1313–1319 (1994).

Staendner, et al., "Identification of *Salmonella typhi* promoters activated by invasion of eukaryotic cells," *Mol. Microbiol.* 18:891–902 (1995).

Stein, EMBL ID NO:St51867, Accession No.: U51867 (Mar. 4, 2000).

Stojiljkovik et al., "Ethanolamine utilization in Salmonella typhurium: nucleotide sequence, protein expression, and mutational analysis of the cchA cchB eutE eutJ eutG eutH gene cluster," *J. Bacteriol.* 177(5)1357–66 (1995).

Subramanian et al. "Rapid mappinf of Escherichia coli::Tn5 insertion mutations by REP–Tn5 PCR" *PCR Methods* 1:187–192 (1992).

Sutherland & Springett, "Effectiveness of BCG vaccination in England and Wales in 1983," *Tubercle* 68(2):81–92 (1987).

Tam & Lefebvre "Cloning of flagellar genes in Chlamydomonas reinhardtii by DNA insertional mutagenesis," *Genetics* 135:375–384 (1993).

Trieu–Cuot et al. "An integrative vector exploiting the transposition properties of Tn1545 for insertional mutagenesis and cloning of genes from gram–positive bacteria," *Gene* 106:21–27 (1991).

Tzschaschel, et al., "An Escherichia coli hemolysin transport system–based vector for the export of polypeptides: export of Shiga–like toxin IIeB subunit by Salmonella tyhphimurium aroA," *Nature Biotechnol.* 14: 765–769 (1996).

Valdivia & Falkow, "Fluorescence–based isolation of bacterial genes expressed within host cells," *Science* 277: 2007–2011 (1997).

Valentine, et al., "Identification of Three Highly Attenuated *Salmonella typhimurium* Mutants That are Moe Immunogenic and Protective in Mice than a Prototypical aroA Mutant," *infect. immun.* 66:3378–3383 (1998).

Walker, et al., "Specific Lung Mucosal and Systemic Immune Responses after Oral Immunization of Mice with *Salmonella typhimurium* aroA, *Salmonella typhi* Ty21a, and invasive *Escherichia coli* expressing Recombinant Pertussis Toxin S1 Subunit," *Inf. Immun.* 60:4260–4268 (1992).

Walsh & Cepko, "Widespread Dispersion Of Neuronal Clones Across Functional Regions of the Cerebral Cortex," *Science* 255:434–40 (1992).

Woolley et al. "Transfer of Tn1545 and Tn916 to Clostridium acetobutylicum," *Plasmid* 22:169–174 (1989).

\* cited by examiner

FIG. 2A

Alignment of SseB to EspA

```
SseB    1  M S Q N - I L W G S Q N P I V F K N - - - S F G V S N A D T G S Q D D L S Q Q N P F A E G Y Q V L     46
EspA    1  M D T S T T A S V A S A N A S T S T S M A Y D L G S M S K D D - V I D L F N K L G V F Q A A I L M F    49

SseB   47  L I L L M V I Q A T A N N K F I E V Q K N A E R A R N T Q E K S N E M D E V I A K A A K G - D A K T    95
EspA   50  A Y M Y Q A Q S D L S I A K F A D M N E A S K E S T T A Q K M A N L V D A K I A D V Q S S D K N A    98

SseB   96  K C E V F E D V I K Y M R D - - N G I L I D Q M T I D D Y M A K Y G D H G K L D K Q G L Q A I K A A   143
EspA  100  K A Q L P D E V K S Y I N D P R N D I T I S G - - I D N I N A Q L G - - - - - A Q D L Q T V K A A   141

SseB  144  L D N D A N R N T D L M S Q G Q T I Q K M S Q E L N A V L T Q L T Q L I S K W G E I S M I A Q K     193
EspA  142  I S A K A N N L T T T V N N S Q L I Q Q M S N T L N L L T S A R S D M Q S L Q Y R T I S L G         191

SseB  194  T Y S  196
EspA  192  K     192
```

FIG. 2B

Alignment of SseC to EspD, YopB and PepB

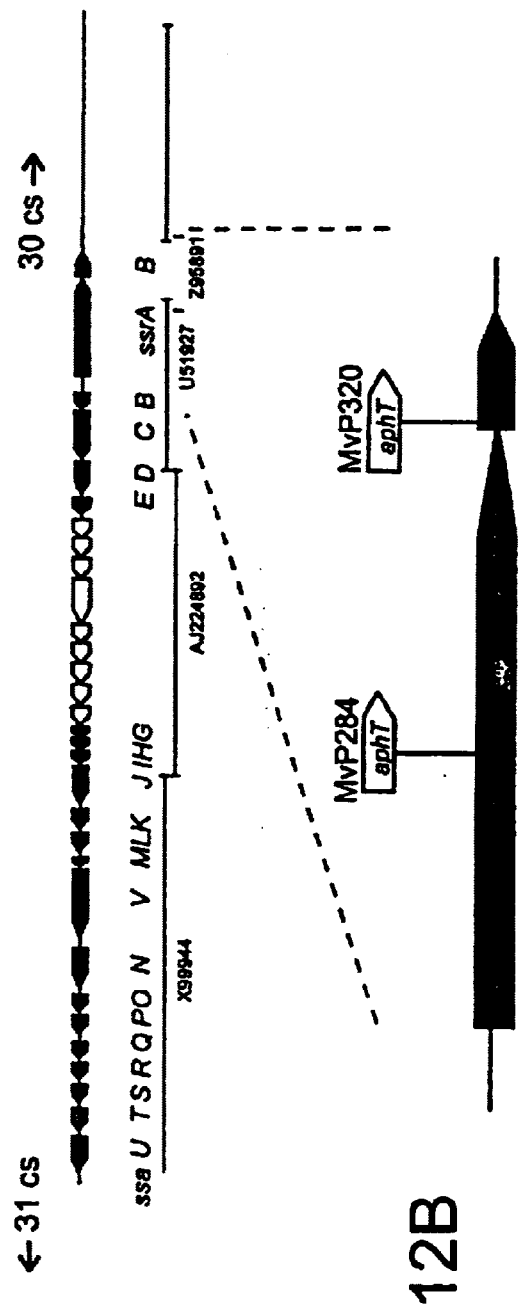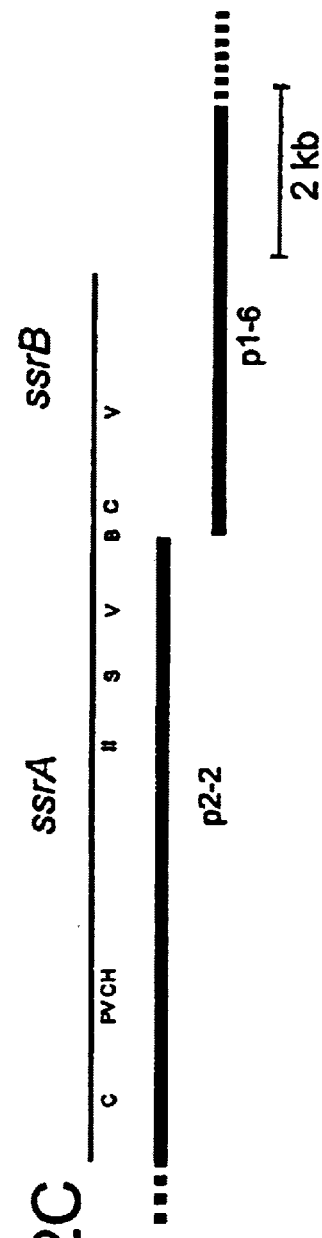
FIG. 12A  Position of mutations in MvP284 and MvP320
FIG. 12B
FIG. 12C Model for the transcriptional units for SPI2 virulence genes

Principle of Attenuation

Schematic Instruction for the Generation of Different Mutations with Increasing Grade of Attenuation

Principle of insertional mutation

FIG. 16
Selective Marker Cassette (SMC)
Permanent selective marker cassette
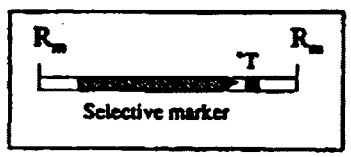
T = Optional transcriptional terminator if polar insertional mutation is required
Revertible selective marker cassette
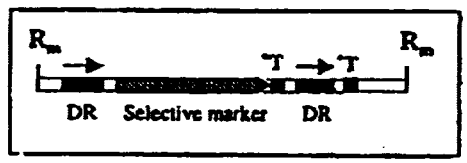
DR = direct repeat

FIG. 17

Gene Expression Cassette (GEC)

One Phase System

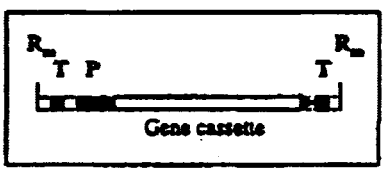

P = Promoter consisting of either a
- promoter acting constitutively in *Salmonella*
- a *Salmonella in vivo* inducible promoter or
- an other promoter T = Transcriptional terminator

Two Phase System

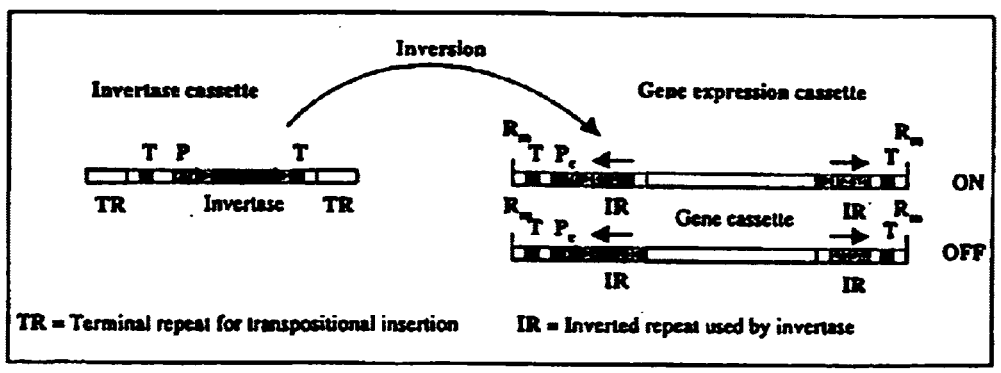

TR = Terminal repeat for transpositional insertion    IR = Inverted repeat used by invertase

Gene cassette:

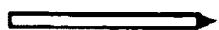   

Single gene expression unit    or    Concatemeric gene expression units

FIG. 18

Structural requirements of the gene expression unit for the delivery of heterologous antigens into the various *Salmonella* compartments Gene sequence → Cytosolic compartment Signal peptide — Gene sequence → Periplasmic compartment Signal peptide — Gene sequence — β-barrel → Outer membrane compartment
Spacer Gene sequence → Extracellular milieu
Type III secretory protein

FIG. 19
Transactivator Cassette (TC)
P = Promoter consisting of either a
- promoter acting constitutively in *Salmonella*
- a *Salmonella in vivo* inducible promoter or
- an other promoter
$P_c$ = Constitutive promoter
One Phase System
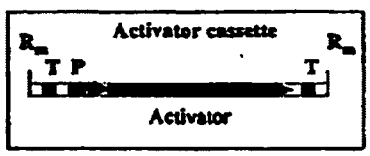
Two Phase System
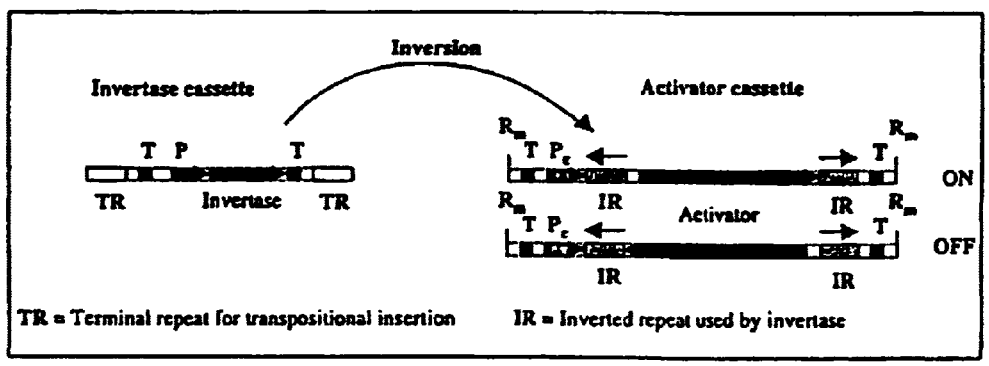
TR = Terminal repeat for transpositional insertion    IR = Inverted repeat used by invertase

FIG. 21A

```
CTGCAGTTGTCCGGTTATTGCTCGTCAAGCGAACAGATGCAAAAGGTGAGAGCGACTCTCGAATCATGGGGGGTCATGTA
TCGGGATGGTGTAATCTGTGATGACTTATTGGTACGAGAAGTGCAGGATGTTTTGATAAAAATGGGTTACCCGCATGCTG
AAGTATCCAGCGAAGGGCCGGGGAGCGTGTTAATTCATGATGATATACAAATGGATCAGCAATGGCGCAAGGTTCAACCA
TTACTTGCAGATATTCCCGGGTTATTGCACTGGCAGATTAGTCACTCTCATCAGTCTCAGGGGGATGATATTATTTCTGC
GATAATAGAGAACGGTTTAGTGGGGCTTGTCAATGTTAGCCCAATGCGGCGCTCTTTTGTTATCAGTGGTGTACTGGATG
AATCTCATCAACGCATTTTGCAAGAAACGTTAGCAGCATTAAAGAAAAAGGATCCCGCTCTTTCTTTAATTTATCAGGAT
ATTGCGCCTTCCCATGATGAAAGCAAGTATCTGCCTGCGCCAGTGGCTGGCTTTGTACAGAGTCGCCATGGTAATTACTT
ATTACTGACGAATAAAGAGCGTTTACGTGTAGGGGCATTGTTACCCAATGGGGGAGAAATTGTCCATCTGAGTGCCGATG
TGGTAACGATTAAACATTATGATACTTTGATTAACTATCCATTAGATTTTAAGTGAGTGGAAAATGACAACTTTGACCCG
GTTAGAAGATTTGCTGCTTCATTCGCGTGAAGAGGCCAAAGGCATAATTTTACAATTAAGGGCTGCCCGGAAACAGTTAG
AAGAGAACAACGGCAAGTTACAGGATCCGCAGCAATATCAGCAAAACACCTTATTGCTTGAAGCGATCGAGCAGGCCGAA
AATATCATCAACATTATTTATTATCGTTACCATAACAGCGCACTTGTAGTGAGTGAGCAAGAGTAAAGTAAAAATATCTT
AGAGCCTATCCCACCAGGCGTTAATTGGCGCAGCCAGTTTGGACACGGATAGCGCGCAAAAACCGCAGCGTACACGTAGT
ACGTGAGGTTTGACTCGCTACGCTCGCCCTTCGGGCCGCCGCTAGCGGCGTTCAAAACGCTAACGCGTTTTGGCGAGCAC
TGCCCAGGTTCAAAATGGCAAGTAAAATAGCCTAATGGATAGGCTCTTAGTTAGCACGTTAATTATCTATCGTGTATAT
GGAGGGGAATGATGATAAAGAAAAAGGCTGCGTTTAGTGAATATCGTGATTTAGAGCAAAGTTACATGCAGCTAAATCAC
TGTCTTAAAAAATTTCACCAAATCCGGGCTAAGGTGAGTCAACAGCTTGCTGAAAGGGCAGAGAGCCCCAAAAATAGCAG
AGAGACAGAGAGTATTCTTCATAACCTATTTCCACAAGGCGTTGCCGGGGTTAACCAGGAGGCCGAGAAGGATTTAAAGA
AAATAGTAAGTTTGTTTAAACAACTTGAAGTACGACTGAAACAACTTAATGCTCAAGCCCCGGTGGAGATACCGTCAGGA
AAAACAAAAAGGTAAAGCATAATGTCTTCAGGAAACATCTTATGGGGAAGTCAAAACCCTATTGTGTTTAAAAATAGCTT
CGGCGTCAGCAACGCTGATACCGGGAGCCAGGATGACTTATCCCAGCAAAATCCGTTTGCCGAAGGGTATGGTGTTTTGC
TTATTCTCCTTATGGTTATTCAGGCTATCGCAAATAATAAATTTATTGAAGTCCAGAAGAACGCTGAACGTGCCAGAAAT
ACCCAGGAAAAGTCAAATGAGATGGATGAGGTGATTGCTAAAGCAGCCAAAGGGGATGCTAAAACCAAAGAGGAGGTGCC
TGAGGATGTAATTAAATACATGCGTGATAATGGTATTCTCATCGATGGTATGACCATTGATGATTATATGGCTAAATATG
GCGATCATGGGAAGCTGGATAAAGGTGGCCTACAGGCGATCAAAGCGGCTTTGGATAATGACGCCAACCGGAATACCGAT
CTTATGAGTCAGGGGCAGATAACAATTCAAAAAATGTCTCAGGAGCTTAACGCTGTCCTTACCCAACTGACAGGGCTTAT
CAGTAAGTGGGGGGAAATTTCCAGTATGATAGCGCAGAAAACGTACTCATGAAAAAAGACCCGACCCTACAACAGGCACA
TGACACGATGCGGTTTTTCCGGCGTGGCGGCTCGCTGCGTATGTTGTTGGATGACGATGTTACACAGCCGCTTAATACTC
TGTATCGCTATGCCACGCAGCTTATGGAGGTAAAAGAATTCGCCGGCGCAGCGCGACTTTTTCAATTGCTGACGATATAT
GATGCCTGGTCATTTGACTACTGGTTTCGGTTAGGGGAATGCTGCCAGGCTCAAAAACATTGGGGGGAAGCGATATACGC
TTATGGACGCGCCGGCACAAATTAAGATTGATGCGCCGCAGGCGCCATGGCCGCAGCGGAATGCTATCTCGCGTGTGATA
ACGTCTGTTATGCAATCAAAGCGTTAAAGGCCGTGGTGCGTATTTGCGGCGAGGTCAGTGAACATCAAATTCTCCGACAG
CGTGCAGAAAAGATGTTACAGCAACTTTCTGACAGGAGCTAAAAATGAATCGAATTCACAGTAATAGCGACAGCGCGCA
GGAGTAACCGCCTTAACACATCATCACTTAAGCAATGTCAGTTGCGTTTCCTCGGGTTCGCTGGGAAAGCGCCAGCATCG
TGTGAATTCTACTTTTGGCGATGGCAACGCCGCGTGTCTGCTATCCGGGAAAATTAGTCTTCAGGAGGCAAGCAATGCGT
TGAAGCAACTGCTTGATGCCGTACCCGGAAATCATAAGCGTCCATCATTGCCTGACTTTTTGCAGACCAATCCCGCGGTT
TTATCAATGATGATGACGTCATTAATACTCAACGTCTTTGGTAATAACGCTCAATCGTTATGCCAACAGCTTGAGCGGGC
AACTGAGGTGCAAAATGCATTACGTAATAAGCAGGTAAAGGAGTATCAGGAGCAGATCCAGAAAGCGATAGAGCAGGAGG
ATAAAGCGCGTAAAGCGGGTATTTTTGGCGCTATTTTTGACTGGATTACCGGCATATTTGAAACCGTGATTGGCGCCTTA
AAAGTTGTGGAAGGTTTTCTGTCCGGAAATCCCGCAGAAATGGCTAGCGGCGTAGCTTATATGGCCGCAGGTTGTGCAGG
AATGGTTAAAGCCGGAGCCGAAACGGCAATGATGTGCGGTGCTGACCACGATACCTGTCAGGCAATTATTGACGTGACAA
GTAAGATTCAATTTGGTTGTGAAGCCGTCGCGCTGGCACTGGATGTTTTCCAGATTGGCCGTGCTTTTATGGCGACGAGA
GGTTTATCTGGCGCAGCTGCAAAAGTGCTTGACTCCGGTTTTGGCGAGGAAGTGGTTGAGCGTATGGTAGGTGCAGGGGA
AGCAGAAATAGAGGAGTTGGCTGAAAAGTTTGGCGAAGAAGTGAGCGAAAGTTTTTCCAAACAATTTGAGCCGCTTGAAC
GTGAAATGGCTATGGCGAATGAGATGGCAGAGGAGGCTGCCGAGTTTTCTCGTAACGTAGAAAATAATATGACGCGAAGC
GCGGGAAAAAGCTTTACGAAAGAGGGGGTGAAAGCCATGGCAAAAGAAGCGGCAAAAGAAGCCCTGGAAAAATGTGTGCA
AGAAGGTGGAAAGTTCCTGTTAAAAAAATTCCGTAATAAAGTTCTCTTCAATATGTTCAAAAAAATCCTGTATGCCTTAC
TGAGGGATTGTTCATTTAAAAGGCTTACAGGCTATCAGATGTGCAACCGAGGCGCCAGTCAGATGAATACTGGCATGGTT
AACACAGAAAAAGCGAAGATCGAAAAGAAAATAGAGCAATTAATAACTCAGCAACGGTTTCTGGATTTCATAATGCAACA
AACAGAAAACCAGAAAAGATAGAACAAAAACGCTTAGAGGAGCTTTATAAGGGACGGGTGCCGCGCTTAGAGATGTAT
TAGATACCATTGATCACTATAGTAGCGTTCAGGCGAGAATAGCTGGCTATCGCGCTTAATCTGAGGATAAAAATATGGAA
GCGAGTAACGTAGCACTGGTATTACCAGCGCCTTCCTTGTTAACACCTTCTTCCACTCCATCTCCCTCCGGGGAGGGAAT
GGGTACTGAATCAATGCTTCTGTTATTTGATGATATCTGGATGAAGCTAATGGAGCTTGCCAAAAAGCTGCGCGATATCA
TGCGCAGCTATAACGTAGAAAAACAACGGCTGGCCTGGGAACTGCAAGTCAATGTTTTACAGACGCAAATGAAAACAATT
GATGAAGCGTTTAGAGCATCAATGATTACTGCGGGTGGCGCAATGTTGTCGGGTGTACTGACGATAGGATTAGGGGCCGT
```

FIG. 21A-1

```
AGGCGGGGAAACCGGTCTTATAGCGGGTCAAGCCGTAGGCCACACAGCTGGGGGCGTCATGGGCCTGGGGGCTGGTGTAG
CGCAACGTCAAAGTGATCAAGATAAAGCGATTGCCGACCTGCAACAAAATGGGGCCCAATCTTATAATAAATCCCTGACG
GAAATTATGGAGAAAGCAACTGAAATTATGCAGCAAATCATCGGCGTGGGGTCGTCACTGGTCACGGTTCTTGCTGAAAT
ACTCCGGGCATTAACGAGGTAAACATGGTGCAAGAAATAGAGCAATGGTTACGTCGGCATCAGGTGTTTACTGAGCCTGC
ATATTTAGGGGAGACCGCCATATTACTTGGGCAGCAGTTTATATTATCGCCTTACCTGGTGATCTATCGTATTGAGGCAA
AAGAAATGATTATTTGTGAGTTCAGGCGCCTGACGCCCGGGCAACCTCGACCACAGCAATTGTTTCACTTACTGGGACTT
TTACGCGGGATATTTGTGCATCACCCGCAGTTAACATGTTTAAAGATGTTGATAATCACCGACGTTCTGGATGAAAAAAA
AGCCATGCTACGCAGGAAATTATTGCGCATCCTGACAGTAATGGGAGCGACCTTTACACAGCTTGATGGCGATAACTGGA
CAGTTTTATCCGCCGAGCATCTTATCCAGCGACGTTTTTAAATGACCTTCCTGACGTAAATCATTATCACGTGAAAATAA
CAATCAATAGGTATGATGATGAAAGAAGATCAGAAAAATAAAATACCCGAAGACATTCTGAAACAGCTATTATCCGTTGA
TCCGGAAACCGTTTATGCCAGTGGTTACGCCTCATGGCAGGAGGGGGATTATTCGCGCGCCGTAATCGATTTTAGTTGGC
TGGTGATGGCCCAGCCATGGAGTTGGCGTGCCCATATTGCATTGGCTGGCACCTGGATGATGCTTAAAGAATACACGACG
GCCATTAATTTCTATGGACATGCCTTGATGCTGGATGCCAGCCATCCAGAACCGGTTTACCAAACGGGCGTCTGTCTCAA
AATGATGGGGAACCCGGGTTGGCGAGAGAGGCTTTTCAAACCGCAATCAAGATGAGTTATGCGGATGCCTCATGGAGTG
AGATTCGCCAGAATGCGCAAATAATGGTTGATACTCTTATTGCTTAAATAACAGAACGAAATATGAAAATTCATATTCCG
TCAGCGGCAAGTAATATAGTCGATGGTAATAGTCCTCCTTCCGATATACAAGCGAAGGAGGTATCGTTTCCTCCCCCTGA
AATTCCAGCGCCTGGCACCCCCGCAGCCCCTGTGCTGCTTACGCCTGAACAAATAAGGCAGCAGAGGGATTATGCGATAC
ATTTTATGCAATACACTATTCGTGCGCTGGGTGCGACAGTCGTGTTTGGGTTATCGGTTGCTGCAGCGGTAATTTCTGGC
GGGGCAGGATTACCCATTGCTATTCTTGCGGGGGCGGCGCTCGTGATTGCTATTGGGGATGCTTGCTGTCGTATCATAA
TTATCAATCGATATGTCAGCAAAAGGAGCCATTACAAACCGCCAGTGATAGCGTTGCTCTTGTGGTCAGTGCGCTGGCCT
TAAAATGTGGGGCAAGTCTTAACTGCGCTAACACCCTTGCTAATTGTCTTTCTTTATTAATACGTTCAGGAATCGCTATT
TCTATGTTGGTTTTACCCCTACAGTTTCCACTGCCCGCGGCTGAAAATATTGCGGCCTCTTTGGACATGGGGAGTGTAAT
TACCTCCGTTAGCCTGACGGCGATAGGTGCGGTACTGGATTATTGCCTTGCCCGCCCCTCTGGCGACGATCAGGAAATT
CTGTTGATGAACTTCATGCCGATCCCAGTGTGTTATTGGCGGAACAAATGGCAGCGCTCTGTCAATCTGCTACTACACCT
GCACCTGCATTAATGGACAGTTCTGATCATACATCTCGGGGAGAACCATGAAACCTGTTAGCCCAAATGCTCAGGTAGGA
GGGCAACGTCCTGTTAACGCGCCTGAGGAATCACCTCCATGTCCTTCATTGCCACATCCGGAAACCAATATGGAGAGTGG
TAGAATAGGACCTCAACAAGGAAAAGAGCGGGTATTGGCCGGACTTGCGAAACGAGTGATAGAGTGTTTTCCAAAAGAAA
TTTTTAGTTGGCAAACGGTTATTTTGGGCGGACAGATTTTATGCTGTTCCGCTGGAATAGCATTAACAGTGCTAAGTGGT
GGAGGCGCGCCGCTCGTAGCCCTGGCAGGGATTGGCCTTGCTATTGCCATCGCGGATGTCGCCTGTCTTATCTACCATCA
TAAACATCATTTGCCTATGGCTCACGACAGTATAGGCAATGCCGTTTTTATATTGCTAATTGTTTCGCCAATCAACGCA
AAAGTATGGCGATTGCTAAAGCCGTCTCCCTGGGCGGTAGATTAGCCCTTAACCGCGACGGTAATGACTCATTCATACTGG
AGTGGTAGTTTGGGACTACAGCCTCATTTATTAGAGCGTCTTAATGATATTACCTATGGACTAATGAGTTTTACTCGCTT
CGGTATGGATGGGATGGCAATGACCGGTATGCAGGTCAGCAGCCCATTATATCGTTTGCTGGCTCAGGTAACGCCAGAAC
AACGTGCGCCGGAGTAATCGTTTTCAGGTATATACCGGATGTTCATTGCTTTCTAAATTTTGCTATGTTGCCAGTATCCT
TACGATGTATTTATTTTAAGGAAAAGCATTATGGATATTGCACAATTAGTGGATATGCTCTCCCACATGGCGCACCAGGC
AGGCCAGGCCATTAATGACAAAATGAATGGTAATGATTTGCTCAACCCAGAATCGATGATTAAAGCGCAATTTGCCTTAC
AGCAGTATTCTACATTTATTAATTACGAAAGTTCACTGATCAAAATGATCAAGGATATGCTTAGTGGAATCATTGCTAAA
ATCTGAAGTTATTAGCGACGATGTTCGACGGTTGCTGCTGGAAATCATGTTTGCGGGCGTTAACCATAGCCTGATTTCCC
AGGTACATGCGATGTTACCAGCGCTAACGGTTATTGTTCCGGATAAAAAATTACAGTTGGTATGTCTGGCATTATTGTTG
GCGGGTTTAAATGAGCCGCTAAAAGCCGCGAAAATTTTATCGGATATAGATTTGCCAGAGGCTATGGCGCTGCGTCTGTT
ATTTCCTGCACCAAATGAGGGGTTTGAAAATTGAATATTTCTGATATGAGCGTAGTGCCTGTAAGCACTCAATCTTATGT
AAAGTCCTCTGCAGAACCGAGCCAGGAGCAAATTAATTTTTTTGAACAATTGCTGAAAGATGAAGCATCCACCAGTAACG
CCAGTGCTTTATTACCGCAGGTTATGTTGACCAGACAAATGGATTATATGCAGTTAACGGTAGGCGTCGATTATCTTGCC
AGAATATCAGGCGCAGCATCGCAAGCGCTTAATAAGCTGGATAACATGGCATGAAGGTTCATCGTATAGTATTTCTTACT
GTCCTTACGTTCTTTCTTACGGCATGTGATGTGGATCTTTATCGCTCATTGCCAGAAGATGAAGCGAATCAAATGCTGGC
ATTACTTATGCAGCATCATATTGATGCGGAAAAAAAACAGGAAGAGGATGGTGTAACCTTACGTGTCGAGCAGTCGCAGT
TTATTAATGCGGTTGAGCTACTTAGACTTAACGGTTATCCGCATAGGCAGTTTACAACGCGGATAAGATGTTTCCGGCT
AATCAGTTAGTGGTATCACCCCAGGAAGAACAGCAGAAGATTAATTTTTTAAAAGAACAAAGAATTGAAGGAATGCTGAG
TCAGATGGAGGGCGTGATTAATGCAAAAGTGACCATTGCGCTACCGACTTATGATGAGGGAAGTAACGCTTCTCCGAGCT
CAGTTGCCGTATTTATAAAATATTCACCTCAGGTCAATATGGAGGCCTTTCGGGTAAAAATTAAAGATTTAATAGAGATG
TCAATCCCTGGGTTGCAATACAGTAAGATTAGTATCTTGATGCAGCCTGCTGAATTC
```

FIG. 21B

```
AGCATTGACATAAAAACTTACAATTTGAAAAATTATTTATTAAATAAACTGTTACGATGTTTTTACATCGCCATCTTATT
AAAAAGTAATTGTAGTCATCGACTGGGTTATATATGAAGAAATTTATCTTCCTAATGATAACACCATCGATTAATCTTCT
GATGAAACTATATGTACTGCGATAGTGATCAAGTGCCAAAGATTTTGCAACAGGCAACTGGAGGGAAGCATTATGAATTT
GCTCAATCTCAAGAATACGCTGCAAACATCTTTAGTAATCAGGCTAACTTTTTTATTTTTATTAACAACAATAATTATTT
GGCTGCTATCTGTGCTTACCGCAGCTTATATATCAATGGTTCAGAAACGGCAGCATATAATAGAGGATTTATCCGTTCTA
TCCGAGATGAATATTGTACTAAGCAATCAACGGTTTGAAGAAGCTGAACGTGACGCTAAAAATTTAATGTATCAATGCTC
ATTAGCGACTGAGATTCATCATAACGATATTTTCCCTGAGGTGAGCCGGCATCTATCTGTCGGTCCTTCAAATTGCACGC
CGACGCTAAACGGAGAGAAGCACCGTCTCTTTCTGCAGTCCTCTGATATCGATGAAAATAGCTTTCGTCGCGATAGTTTT
ATTCTTAATCATAAAAATGAGATTTCGTTATTATCTACTGATAACCCTTCAGATTATTCAACTCTACAGCCTTTAACGCG
AAAAAGCTTTCCTTTATACCCAACCCATGCCGGGTTTTACTGGAGTGAACCAGAATACATAAACGGCAAAGGATGGCACG
CTTCCGTTGCGGTTGCCGATCAGCAAGGCGTATTTTTTGAGGTGACGGTTAAACTTCCCGATCTCATTACTAAGAGCCAC
CTGCCATTAGATGATAGTATTCGAGTATGGCTGGATCAAAACAACCACTTATTGCCGTTTTCATACATCCCGCAAAAAAT
ACGTACACAGTTAGAAAATGTAACGCTGCATGATGGATGGCAGCAAATTCCCGGATTTCTGATATTACGCACAACCTTGC
ATGGCCCCGGATGGAGTCTGGTTACGCTGTACCCATACGGTAATCTACATAATCGCATCTTAAAAATTATCCTTCAACAA
ATCCCCTTTACATTAACAGCATTGGTGTTGATGACGTCGGCTTTTTGCTGGTTACTACATCGCTCACTGGCCAAACCGTT
ATGGCGTTTTGTCGATGTCATTAATAAAACCGCAACTGCACCGCTGAGCACACGTTTACCAGCACAACGACTGGATGAAT
TAGATAGTATTGCCGGTGCTTTTAACCAACTGCTTGATACTCTACAAGTCCAATACGACAATCTGGAAAACAAAGTCGCA
GAGCGCACCCAGGCGCTAAATGAAGCAAAAAAACGCGCTGAGCGAGCTAACAAACGTAAAAGCATTCATCTTACGGTAAT
AAGTCATGAGTTACGTACTCCGATGAATGGCGTACTCGGTGCAATTGAATTATTACAAACCACCCCTTTAAACATAGAGC
AACAAGGATTAGCTGATACCGCCAGAAATTGTACACTGTCTTTGTTAGCTATTATTAATAATCTGCTGGATTTTTCACGC
ATCGAGTCTGGTCATTTCACATTACATATGGAAGAAACAGCGTTACTGCCGTTACTGGACCAGGCAATGCAAACCATCCA
GGGGCCAGCGCAAAGCAAAAAACTGTCATTACGTACTTTTGTCGGTCAACATGTCCCTCTCTATTTTCATACCGACAGTA
TCCGTTTACGGCAAATTTTGGTTAATTTACTCGGGAACGCGGTAAAATTTACCGAAACCGGAGGGATACGTCTGACGGTC
AAGCGTCATGAGGAACAATTAATATTTCTGGTTAGCGATAGCGGTAAAGGGATTGAAATACAGCAGCAGTCTCAAATCTT
TACTGCTTTTTATCAAGCAGACACAAATTCGCAAGGTACAGGAATTGGACTGACTATTGCGTCAAGCCTGGCTAAAATGA
TGGGCGGTAATCTGACACTAAAAAGTGTCCCCGGGGTTGGAACCTGTGTCTCGCTAGTATTACCCTTACAAGAATACCAG
CCGCCTCAACCAATTAAAGGGACGCTGTCAGCGCCGTTCTGCCTGCATCGGCAACTGGCTTGCTGGGGAATACGCGGTGA
ACCACCCCACCAGCAAAATGCGCTTCTCAACGCAGAGCTTTTGTATTTCTCCGGAAAACTCTACGACCTGGCGCAACAGT
TAATATTGTGTACACCAAATATGCCAGTAATAAATAATTTGTTACCACCCTGGCAGTTGCAGATTCTTTTGGTTGATGAT
GCCGATATTAATCGGGATATCATCGGCAAAATGCTTGTCAGCCTGGGCCAACACGTCACTATTGCCGCCAGTAGTAACGA
GGCTCTGACTTTATCACAACAGCAGCGATTCGATTTAGTACTGATTGACATTAGAATGCCAGAAATAGATGGTATTGAAT
GTGTACGATTATGGCATGATGAGCCGAATAATTTAGATCCTGACTGCATGTTTGTGGCACTATCCGCTAGCGTAGCGACA
GAAGATATTCATCGTTGTAAAAAAAATGGGATTCATCATTACATTACAAAACCAGTGACATTGGCTACCTTAGCTCGCTA
CATCAGTATTGCCGCAGAATACCAACTTTTACGAAATATAGAGCTACAGGAGCAGGATCCGAGTCGCTGCTCAGCGCTAC
TGGCGACAGATGATATGGTCATTAATAGCAAGATTTTCCAATCACTGGACCTCTTGCTGGCTGATATTGAAAATGCCGTA
TCGGCTGGAGAAAAAATCGATCAGTTAATTCACACATTAAAAGGCTGTTTAGGTCAAATAGGGCAGACTGAATTGGTATG
CTATGTCATAGACATTGAGAATCGCGTAAAAATGGGGAAAATCATCGCGCTGGAGGAACTAACCGACTTACGCCAGAAAA
TACGTATGATCTTCAAAAACTACACCATTACTTAATATTATCTTAATTTTCGCGAGGGCAGCAAAATGAAAGAATATAAG
ATCTTATTAGTAGACGATCATGAAATCATCATTAACGGCATTATGAATGCCTTATTACCCTGGCCTCATTTTAAAATTGT
AGAGCATGTTAAAAATGGTCTTGAGGTTTATAATGCCTGTTGTGCATACGAGCCTGACATACTTATCCTTGATCTTAGTC
TACCTGGCATCAATGGCCTGGATATCATTCCTCAATTACATCAGCGTTGGCCAGCAATGAATATTCTGGTTTACACAGCA
TACCAACAAGAGTATATGACCATTAAAACTTTAGCCGCAGGTGCTAATGGCTATGTTTTAAAAAGCAGTAGTCAGCAAGT
TCTGTTAGCGGCATTGCAAACAGTAGCAGTAAACAAGCGTTACATTGACCCAACGTTGAATCGGGAAGCTATCCTGGCTG
AATTAAACGCTGACACGACCAATCATCAACTGCTTACTTTGCGCGAGCGTCAGGTTCTTAAACTTATTGACGAGGGGTAT
ACCAATCATGGGATCAGCGAAAAGCTACATATCAGTATAAAAACCGTCGAAACACACCGGATGAATATGATGAGAAAGCT
ACAGGTTCATAAAGTGACAGAGTTACTTAACTGTGCCCGAAGAATGAGGTTAATAGAGTATTAACCAGGGGCGTCCGATG
GTATTAAGCATTGGTCATATTTTGATGAGCCTTACGCCACGCAGTATTGCTCATCATCGACAAAATCCATACGGATGCCC
TGGTATGCCGCACCATTTATCACTACCTTAGTCTTCATTTGATCATGATATAGTAGAATCCCCTTATTTAACGGGCTTTA
CCATGTCGTATTCTATCGGCGAATTTGCCAGACTATGCGGTATCAATGCCGCCACGCTAAGGGCATGGCAGCGACGCTAT
G
```

FIG. 22A sseA
ATGATGATAAAGAAAAAGGCTGCGTTTAGTGAATATCGTGATTTAGAGCAAAGTTACATGCAGCTAAATCACTGTCTTAA
AAAATTTCACCAAATCCGGGCTAAGGTGAGTCAACAGCTTGCTGAAAGGGCAGAGAGCCCCAAAAATAGCAGAGAGACAG
AGAGTATTCTTCATAACCTATTTCCACAAGGCGTTGCCGGGGTTAACCAGGAGGCCGAGAAGGATTTAAAGAAAATAGTA
AGTTTGTTTAAACAACTTGAAGTACGACTGAAACAACTTAATGCTCAAGCCCCGGTGGAGATACCGTCAGGAAAAACAAA
AAGGTAA

FIG. 22B sseB
ATGTCTTCAGGAAACATCTTATGGGAAGTCAAAACCCTATTGTGTTTAAAAATAGCTTCGGCGTCAGCAACGCTGATAC
CGGGAGCCAGGATGACTTATCCCAGCAAAATCCGTTTGCCGAAGGGTATGGTGTTTTTGCTTATTCTCCTTATGGTTATTC
AGGCTATCGCAAATAATAAATTTATTGAAGTCCAGAAGAACGCTGAACGTGCCAGAAATACCCAGGAAAAGTCAAATGAG
ATGGATGAGGTGATTGCTAAAGCAGCCAAAGGGGATGCTAAAACCAAAGAGGAGGTGCCTGAGGATGTAATTAAATACAT
GCGTGATAATGGTATTCTCATCGATGGTATGACCATTGATGATTATATGGCTAAATATGGCGATCATGGGAAGCTGGATA
AAGGTGGCCTACAGGCGATCAAAGCGGCTTTGGATAATGACGCCAACCGGAATACCGATCTTATGAGTCAGGGGCAGATA
ACAATTCAAAAAATGTCTCAGGAGCTTAACGCTGTCCTTACCCAACTGACAGGGCTTATCAGTAAGTGGGGGGAAATTTC
CAGTATGATAGCGCAGAAAACGTACTCATGA

FIG. 22C sseC
ATGAATCGAATTCACAGTAATAGCGACAGCGCCGCAGGAGTAACCGCCTTAACACATCATCACTTAAGCAATGTCAGTTG
CGTTTCCTCGGGTTCGCTGGGAAAGCGCCAGCATCGTGTGAATTCTACTTTTGGCGATGGCAACGCCGCGTGTCTGCTAT
CCGGGAAAATTAGTCTTCAGGAGGCAAGCAATGCGTTGAAGCAACTGCTTGATGCCGTACCCGAAATCATAAGCGTCCA
TCATTGCCTGACTTTTTGCAGACCAATCCCGCGGTTTTATCAATGATGATGACGTCATTAATACTCAACGTCTTTGGTAA
TAACGCTCAATCGTTATGCCAACAGCTTGAGCGGGCAACTGAGGTGCAAAATGCATTACGTAATAAGCAGGTAAAGGAGT
ATCAGGAGCAGATCCAGAAAGCGATAGAGCAGGAGGATAAAGCCGTAAAGCGGGTATTTTTGGCGCTATTTTTGACTGG
ATTACCGGCATATTTGAAACCGTGATTGGCGCCTTAAAAGTTGTGGAAGGTTTTCTGTCCGGAAATCCCGCAGAAATGGC
TAGCGGCGTAGCTTATATGGCCGCAGGTTGTGCAGGAATGGTTAAAGCCGGAGCCGAAACGGCAATGATGTGCGGTGCTG
ACCACGATACCTGTCAGGCAATTATTGACGTGACAAGTAAGATTCAATTTGGTTGTGAAGCCGTCGCGCTGGCACTGGAT
GTTTTCCAGATTGGCCGTGCTTTTATGGCGACGAGAGGTTTATCTGGCGCAGCTGCAAAAGTGCTTGACTCCGGTTTTGG
CGAGGAAGTGGTTGAGCGTATGGTAGGTGCAGGGGAAGCAGAAATAGAGGAGTTGGCTGAAAAGTTTGGCGAAGAAGTGA
GCGAAAGTTTTTCCAAACAATTTGAGCCGCTTGAACGTGAAATGGCTATGGCGAATGAGATGGCAGAGGAGGCTGCCGAG
TTTTCTCGTAACGTAGAAAATAATATGACGCGAAGCGCGGGAAAAAGCTTTACGAAGAGGGGGTGAAAGCCATGGCAAA
AGAAGCGGCAAAAGAAGCCCTGGAAAAATGTGTGCAAGAAGGTGGAAAGTTCCTGTTAAAAAAATTCCGTAATAAAGTTC
TCTTCAATATGTTCAAAAAAATCCTGTATGCCTTACTGAGGGATTGTTCATTTAAAGGCTTACAGGCTATCAGATGTGCA
ACCGAGGGCGCCAGTCAGATGAATACTGGCATGGTTAACACAGAAAAAGCGAAGATCGAAAAGAAAATAGAGCAATTAAT
AACTCAGCAACGTTTCTGGATTTCATAATGCAACAAACAGAAAACCAGAAAAAGATAGAACAAAAACGCTTAGAGGAGC
TTTATAAGGGGACGGGTGCCGCGCTTAGAGATGTATTAGATACCATTGATCACTATAGTAGCGTTCAGGCGAGAATAGCT
GGCTATCGCGCTTAA

FIG. 22D sseD
ATGGGTACTGAATCAATGCTTCTGTTATTTGATGATATCTGGATGAAGCTAATGGAGCTTGCCAAAAAGCTGCGCGATAT
CATGCGCAGCTATAACGTAGAAAAACAACGGCTGGCCTGGGAACTGCAAGTCAATGTTTTACAGACGCAAATGAAAACAA
TTGATGAAGCGTTTAGAGCATCAATGATTACTGCGGGTGGCGCAATGTTGTCGGGTGTACTGACGATAGGATTAGGCGCC
GTAGGCGGGAAACCGGTCTTATAGCGGGTCAAGCCGTAGGCCACACAGCTGGGGCGTCATGGGCCTGGGGCTGGTGT
AGCGCAACGTCAAAGTGATCAAGATAAAGCGATTGCCGACCTGCAACAAAATGGGGCCCAATCTTATAATAAATCCCTGA
CGGAAATTATGGAGAAAGCAACTGAAATTATGCAGCAAATCATCGGCGTGGGGTCGTCACTGGTCACGGTTCTTGCTGAA
ATACTCCGGGCATTAACGAGGTAA

FIG. 22E sseE

ATGGTGCAAGAAATAGAGCAATGGTTACGTCGGCATCAGGTGTTTACTGAGCCTGCATATTTAGGGGAGACCGCCATATT
ACTTGGGCAGCAGTTTATATTATCGCCTTACCTGGTGATCTATCGTATTGAGGCAAAAGAAATGATTATTTGTGAGTTCA
GGCGCCTGACGCCCGGGCAACCTCGACCACAGCAATTGTTTCACTTACTGGGACTTTTACGCGGGATATTTGTGCATCAC
CCGCAGTTAACATGTTTAAAGATGTTGATAATCACCGACGTTCTGGATGAAAAAAAAGCCATGCTACGCAGGAAATTATT
GCGCATCCTGACAGTAATGGGAGCGACCTTTACACAGCTTGATGGCGATAACTGGACAGTTTTATCCGCCGAGCATCTTA
TCCAGCGACGTTTTTAA

FIG. 22F sseF

ATGAAAATTCATATTCCGTCAGCGGCAAGTAATATAGTCGATGGTAATAGTCCTCCTTCCGATATACAAGCGAAGGAGGT
ATCGTTTCCTCCCCCTGAAATTCCAGCGCCTGGCACCCCCGCAGCCCCTGTGCTGCTTACGCCTGAACAAATAAGGCAGC
AGAGGGATTATGCGATACATTTTATGCAATACACTATTCGTGCGCTGGGTGCGACAGTCGTGTTTGGGTTATCGGTTGCT
GCAGCGGTAATTTCTGGCGGGGCAGGATTACCCATTGCTATTCTTGCGGGGCGGCGCTCGTGATTGCTATTGGGGATGC
TTGCTGTGCGTATCATAATTATCAATCGATATGTCAGCAAAAGGAGCCATTACAAACCGCCAGTGATAGCGTTGCTCTTG
TGGTCAGTGCGCTGGCCTTAAAATGTGGGCAAGTCTTAACTGCGCTAACACCCTTGCTAATTGTCTTTCTTTATTAATA
CGTTCAGGAATCGCTATTTCTATGTTGGTTTTACCCCTACAGTTTCCACTGCCCGCGGCTGAAAATATTGCGGCCTCTTT
GGACATGGGGAGTGTAATTACCTCCGTTAGCCTGACGGCGATAGGTGCGGTACTGGATTATTGCCTTGCCCGCCCCTCTG
GCGACGATCAGGAAAATTCTGTTGATGAACTTCATGCCGATCCCAGTGTGTTATTGGCGGAACAAATGGCAGCGCTCTGT
CAATCTGCTACTACACCTGCACCTGCATTAATGGACAGTTCTGATCATACATCTCGGGGAGAACCATGA

FIG. 22G sseG

ATGAAACCTGTTAGCCCAAATGCTCAGGTAGGAGGGCAACGTCCTGTTAACGCGCCTGAGGAATCACCTCCATGTCCTTC
ATTGCCACATCCGGAAACCAATATGGAGAGTGGTAGAATAGGACCTCAACAAGGAAAAGAGCGGGTATTGGCCGGACTTG
CGAAACGAGTGATAGAGTGTTTTCAAAAGAAATTTTTAGTTGGCAAACGGTTATTTTGGGCGGACAGATTTTATGCTGT
TCCGCTGGAATAGCATTAACAGTGCTAAGTGGTGGAGGCGCGCCGCTCGTAGCCCTGGCAGGGATTGGCCTTGCTATTGC
CATCGCGGATGTCGCCTGTCTTATCTACCATCATAAACATCATTTGCCTATGGCTCACGACAGTATAGGCAATGCCGTTT
TTTATATTGCTAATTGTTTCGCCAATCAACGCAAAAGTATGGCGATTGCTAAAGCCGTCTCCCTGGGCGGTAGATTAGCC
TTAACCGCGACGGTAATGACTCATTCATACTGGAGTGGTAGTTTGGGACTACAGCCTCATTTATTAGAGCGTCTTAATGA
TATTACCTATGGACTAATGAGTTTTACTCGCTTCGGTATGGATGGGATGGCAATGACCGGTATGCAGGTCAGCAGCCCAT
TATATCGTTTGCTGGCTCAGGTAACGCCAGAACAACGTGCGCCGGAGTAA

FIG. 22H ssaA

ATGAAAAAAGACCCGACCCTACAACAGGCACATGACACGATGCGGTTTTTCCGGCGTGGCGGCTCGCTGCGTATGTTGTT
GGATGACGATGTTACACAGCCGCTTAATACTCTGTATCGCTATGCCACGCAGCTTATGGAGGTAAAAGAATTCGCCGGCG
CAGCGCGACTTTTTCAATTGCTGACGATATATGATGCCTGGTCATTTGACTACTGGTTTCGGTTAGGGGAATGCTGCCAG
GCTCAAAAACATTGGGGGGAAGCGATATACGCTTATGGACGCGCGGCACAAATTAAGATTGATGCGCCGCAGGCGCCATG
GGCCGCAGCGGAATGCTATCTCGCGTGTGATAACGTCTGTTATGCAATCAAAGCGTTAAAGGCCGTGGTGCGTATTTGCG
GCGAGGTCAGTGAACATCAAATTCTCCGACAGCGTGCAGAAAAGATGTTACAGCAACTTTCTGACAGGAGCTAA

FIG. 22I ssaB

ATGATGATGAAAGAAGATCAGAAAAATAAATACCCGAAGACATTCTGAAACAGCTATTATCCGTTGATCCGGAAACCGT
TTATGCCAGTGGTTACGCCTCATGGCAGGAGGGGATTATTCGCGCGCCGTAATCGATTTTAGTTGGCTGGTGATGGCCC
AGCCATGGAGTTGGCGTGCCCATATTGCATTGGCTGGCACCTGGATGATGCTTAAAGAATACACGACGGCCATTAATTTC
TATGGACATGCCTTGATGCTGGATGCCAGCCATCCAGAACCGGTTTACCAAACGGGCGTCTGTCTCAAAATGATGGGGGA
ACCCGGGTTGGCGAGAGAGGCTTTTCAAACCGCAATCAAGATGAGTTATGCGGATGCCTCATGGAGTGAGATTCGCCAGA
ATGCGCAAATAATGGTTGATACTCTTATTGCTTAA

FIG. 22J ssaD
ATGGCATATCTCATGGTTAATCCAAAGAGTTCCTGGAAAATACGTTTTTTAGGTCACGTTTTACAAGGCCGGGAAGTATG
GCTGAATGAAGGTAACCTGTCACTGGGGGAGAAGGGATGCGATATTTGTATTCCGCTGGCTATAAATGAAAAAATTATTC
TGAGAGAACAGGCAGATAGTTTATTTGTTGATGCCGGGAAAGCCAGAGTTAGAGTTAATGGCCGCAGATTTAATCCAAAT
AAGCCGCTACCATCCAGTGGGGTTTTGCAGGTTGCGGGAGTGGCTATCGCGTTTGGTAAACAGGATTGTGAACTTGCTGA
TTATCAAATACCCGTTTCCAGATCAGGGTACTGGTGGTTGGCTGGCGTATTCTTGATTTTCATCGGTGGAATGGGTGTCC
TGTTAAGTATTAGTGGTCAGCCTGAAACGGTAAATGACTTACCTTTGCGGGTTAAGTTTTTATTAGACAAAAGCAATATT
CATTATGTGCGGGCGCAATGGAAAGAAGATGGCAGCCTGCAGTTGTCCGGTTATTGCTCGTCAAGCGAACAGATGCAAAA
GGTGAGAGCGACTCTCGAATCATGGGGGGTCATGTATCGGGATGGTGTAATCTGTGATGACTTATTGGTACGAGAAGTGC
AGGATGTTTTGATAAAAATGGTTACCCGCATGCTGAAGTATCCAGCGAAGGGCCGGGGAGCGTGTTAATTCATGATGAT
ATACAAATGGATCAGCAATGGCGCAAGGTTCAACCATTACTTGCAGATATTCCCGGGTTATTGCACTGGCAGATTAGTCA
CTCTCATCAGTCTCAGGGGATGATATTATTTCTGCGATAATAGAGAACGGTTTAGTGGGGCTTGTCAATGTTAGCCCAA
TGCGGCGCTCTTTTGTTATCAGTGGTGTACTGGATGAATCTCATCAACGCATTTTGCAAGAAACGTTAGCAGCATTAAAG
AAAAAGGATCCCGCTCTTTCTTTAATTTATCAGGATATTGCGCCTTCCCATGATGAAAGCAAGTATCTGCCTGCGCCAGT
GGCTGGCTTTGTACAGAGTCGCCATGGTAATTACTTATTACTGACGAATAAAGAGCGTTTACGTGTAGGGGCATTGTTAC
CCAATGGGGGAGAAATTGTCCATCTGAGTGCCGATGTGGTAACGATTAAACATTATGATACTTTGATTAACTATCCATTA
GATTTTAAGTGA

FIG. 22K ssaE
ATGACAACTTTGACCCGGTTAGAAGATTTGCTGCTTCATTCGCGTGAAGAGGCCAAAGGCATAATTTTACAATTAAGGGC
TGCCCGGAAACAGTTAGAAGAGAACAACGGCAAGTTACAGGATCCGCAGCAATATCAGCAAAACACCTTATTGCTTGAAG
CGATCGAGCAGGCCGAAAATATCATCAACATTATTTATTATCGTTACCATAACAGCGCACTTGTAGTGAGTGAGCAAGAG
TAA

FIG. 22L ssaG
ATGGATATTGCACAATTAGTGGATATGCTCTCTCCCACATGGCGCACCACGCAGGCCAGGCCATTAATGACAAAATGAATGG
TAATGATTTGCTCAACCCAGAATCGATGATTAAAGCGCAATTTGCCTTACAGCAGTATTCTACATTTATTAATTACGAAA
GTTCACTGATCAAAATGATCAAGGATATGCTTAGTGGAATCATTGCTAAAATCTGA

FIG. 22M ssaH
ATGTTTGCGGGCGTTAACCATAGCCTGATTTCCCAGGTACATGCGATGTTACCAGCGCTAACGGTTATTGTTCCGGATAA
AAAATTACAGTTGGTATGTCTGGCATTATTGTTGGCGGGTTTAAATGAGCCGCTAAAAGCCGCGAAAATTTTATCGGATA
TAGATTTGCCAGAGGCTATGGCGCTGCGTCTGTTATTTCCTGCACCAAATGAGGGGTTTGAAAATTGA

FIG. 22N ssaI
ATGAGCGTAGTGCCTGTAAGCACTCAATCTTATGTAAAGTCCTCTGCAGAACCGAGCCAGGAGCAAATTAATTTTTTTGA
ACAATTGCTGAAAGATGAAGCATCCACCAGTAACGCCAGTGCTTTATTACCGCAGGTTATGTTGACCAGACAAATGGATT
ATATGCAGTTAACGGTAGGCGTCGATTATCTTGCCAGAATATCAGGCGCAGCATCGCAAGCGCTTAATAAGCTGGATAAC
ATGGCATGA

FIG. 22O ssaJ
ATGAAGGTTCATCGTATAGTATTTCTTACTGTCCTTACGTTCTTTCTTACGGCATGTGATGTGGATCTTTATCGCTCATT
GCCAGAAGATGAAGCGAATCAAATGCTGGCATTACTTATGCAGCATCATATTGATGCGGAAAAAAAACAGGAAGAGGATG
GTGTAACCTTACGTGTCGAGCAGTCGCAGTTTATTAATGCGGTTGAGCTACTTAGACTTAACGGTTATCCGCATAGGCAG
TTTACAACGGCGGATAAGATGTTTCCGGCTAATCAGTTAGTGGTATCACCCCAGGAAGAACAGCAGAAGATTAATTTTTT
AAAAGAACAAAGAATTGAAGGAATGCTGAGTCAGATGGAGGCGTGATTAATGCAAAAGTGACCATTGCGCTACCGACTT
ATGATGAGGGAAGTAACGCTTCTCCGAGCTCAGTTGCCGTATTTATAAAATATTCACCTCAGGTCAATATGGAGGCCTTT
CGGGTAAAAATTAAAGATTTAATAGAGATGTCAATCCCTGGGTTGCAATACAGTAAGATTAGTATCTTGATGCAGCCTGC
TGAATTCAGAATGGTAGCTGACGTACCCGCGAGACAAACATTCTGGATTATGGACGTTATCAACGCCAATAAAGGGAAGG
TGGTGAAGTGGTTGATGAAATACCCTTATCCGTTGATGTTATCGTTGACAGGACTGTTATTAGGAGTGGGCATCCTGATC
GGCTATTTTTGCCTGAGACGCCGTTTTTGA

FIG. 22P ssrA
ATGAATTTGCTCAATCTCAAGAATACGCTGCAAACATCTTTAGTAATCAGGCTAACTTTTTTATTTTTATTAACAACAAT
AATTATTTGGCTGCTATCTGTGCTTACCGCAGCTTATATATCAATGGTTCAGAAACGGCAGCATATAATAGAGGATTTAT
CCGTTCTATCCGAGATGAATATTGTACTAAGCAATCAACGGTTTGAAGAAGCTGAACGTGACGCTAAAAATTTAATGTAT
CAATGCTCATTAGCGACTGAGATTCATCATAACGATATTTTCCCTGAGGTGAGCCGGCATCTATCTGTCGGTCCTTCAAA
TTGCACGCCGACGCTAAACGGAGAGAAGCACCGTCTCTTTCTGCAGTCCTCTGATATCGATGAAAATAGCTTTCGTCGCG
ATAGTTTTATTCTTAATCATAAAAATGAGATTTCGTTATTATCTACTGATAACCCTTCAGATTATTCAACTCTACAGCCT
TTAACGCGAAAAAGCTTTCCTTTATACCCAACCCATGCCGGGTTTTACTGGAGTGAACCAGAATACATAAACGGCAAAGG
ATGGCACGCTTCCGTTGCGGTTGCCGATCAGCAAGGCGTATTTTTTGAGGTGACGGTTAAACTTCCCGATCTCATTACTA
AGAGCCACCTGCCATTAGATGATAGTATTCGAGTATGGCTGGATCAAAACAACCACTTATTGCCGTTTTCATACATCCCG
CAAAAAATACGTACACAGTTAGAAAATGTAACGCTGCATGATGGATGGCAGCAAATTCCCGGATTTCTGATATTACGCAC
AACCTTGCATGGCCCCGGATGGAGTCTGGTTACGCTGTACCCATACGGTAATCTACATAATCGCATCTTAAAAATTATCC
TTCAACAAATCCCCTTTACATTAACAGCATTGGTGTTGATGACGTCGGCTTTTTGCTGGTTACTACATCGCTCACTGGCC
AAACCGTTATGGCGTTTTGTCGATGTCATTAATAAAACCGCAACTGCACCGCTGAGCACACGTTTACCAGCACAACGACT
GGATGAATTAGATAGTATTGCCGGTGCTTTTAACCAACTGCTTGATACTCTACAAGTCCAATACGACAATCTGGAAAACA
AAGTCGCAGAGCGCACCCAGGCGCTAAATGAAGCAAAAAAACGCGCTGAGCGAGCTAACAAACGTAAAAGCATTCATCTT
ACGGTAATAAGTCATGAGTTACGTACTCCGATGAATGGCGTACTCGGTGCAATTGAATTATTACAAACCACCCCTTTAAA
CATAGAGCAACAAGGATTAGCTGATACCGCCAGAAATTGTACACTGTCTTTGTTAGCTATTATTAATAATCTGCTGGATT
TTTCACGCATCGAGTCTGGTCATTTCACATTACATATGGAAGAAACAGCGTTACTGCCGTTACTGGACCAGGCAATGCAA
ACCATCCAGGGGCCAGCGCAAAGCAAAAAACTGTCATTACGTACTTTTGTCGGTCAACATGTCCCTCTCTATTTTCATAC
CGACAGTATCCGTTTACGGCAAATTTTGGTTAATTTACTCGGGAACGCGGTAAAATTTACCGAAACCGGAGGGATACGTC
TGACGGTCAAGCGTCATGAGGAACAATTAATATTTCTGGTTAGCGATAGCGGTAAAGGGATTGAAATACAGCAGCAGTCT
CAAATCTTTACTGCTTTTTATCAAGCAGACACAAATTCGCAAGGTACAGGAATTGGACTGACTATTGCGTCAAGCCTGC
TAAAATGATGGGCGGTAATCTGACACTAAAAAGTGTCCCCGGGGTTGGAACCTGTGTCTCGCTAGTATTACCCTTACAAG
AATACCAGCCGCCTCAACCAATTAAAGGGACGCTGTCAGCGCCGTTCTGCCTGCATCGGCAACTGGCTTGCTGGGGAATA
CGCGGTGAACCACCCCACCAGCAAAATGCGCTTCTCAACGCAGAGCTTTTGTATTTCTCCGGAAAACTCTACGACCTGGC
GCAACAGTTAATATTGTGTACACCCAAATATGCCAGTAATAAATAATTTGTTACCACCCTGGCAGTTGCAGATTCTTTTGG
TTGATGATGCCGATATTAATCGGGATATCATCGGCAAAATGCTTGTCAGCCTGGGCCAACACGTCACTATTGCCGCCAGT
AGTAACGAGGCTCTGACTTTATCACAACAGCAGCGATTCGATTTAGTACTGATTGACATTAGAATGCCAGAAATAGATGG
TATTGAATGTGTACGATTATGGCATGATGAGCCGAATAATTTAGATCCTGACTGCATGTTTGTGGCACTATCCGCTAGCG
TAGCGACAGAAGATATTCATCGTTGTAAAAAAAATGGGATTCATCATTACATTACAAAACCAGTGACATTGGCTACCTTA
GCTCGCTACATCAGTATTGCCGCAGAATACCAACTTTTTACGAAATATAGAGCTACAGGAGCAGGATCCGAGTCGCTGCTC
AGCGCTACTGGCGACAGATGATATGGTCATTAATAGCAAGATTTTCCAATCACTGGACCTCTTGCTGGCTGATATTGAAA
ATGCCGTATCGGCTGGAGAAAAAATCGATCAGTTAATTCACACATTAAAAGGCTGTTTAGGTCAAATAGGGCAGACTGAA
TTGGTATGCTATGTCATAGACATTGAGAATCGCGTAAAAATGGGGAAAATCATCGCGCTGGAGGAACTAACCGACTTACG
CCAGAAAATACGTATGATCTTCAAAAACTACACCATTACTTAA

FIG. 22Q ssrB
ATGAAAGAATATAAGATCTTATTAGTAGACGATCATGAAATCATCATTAACGGCATTATGAATGCCTTATTACCCTGGCC
TCATTTTAAAATTGTAGAGCATGTTAAAAATGGTCTTGAGGTTTATAATGCCTGTTGTGCATACGAGCCTGACATACTTA
TCCTTGATCTTAGTCTACCTGGCATCAATGGCCTGGATATCATTCCTCAATTACATCAGCGTTGGCCAGCAATGAATATT
CTGGTTTACACAGCATACCAACAAGAGTATATGACCATTAAAACTTTAGCCGCAGGTGCTAATGGCTATGTTTTAAAAG
CAGTAGTCAGCAAGTTCTGTTAGCGGCATTGCAAACAGTAGCAGTAAACAAGCGTTACATTGACCCAACGTTGAATCGG
AAGCTATCCTGGCTGAATTAAACGCTGACACGACCAATCATCAACTGCTTACTTTGCGCGAGCGTCAGGTTCTTAAACTT
ATTGACGAGGGTATACCAATCATGGGATCAGCGAAAAGCTACATATCAGTATAAAAACCGTCGAAACACACCGGATGAA
TATGATGAGAAAGCTACAGGTTCATAAAGTGACAGAGTTACTTAACTGTGCCCGAAGAATGAGGTTAATAGAGTATTAA

FIG. 23A

SseA
MMIKKKAAFSEYRDLEQSYMQLNHCLKKPHQIRAKVSQQLAERAESPKNSRETESILHNLPPQVAGVNQEABKDLKKIV
SLFKQLEVRLKQLNAQAPVEIPSGKTKR

FIG. 23B

SseB
MSSGNILWGSQNPIVFKNSFGVSNADTGSQDDLSQQNPFAEGYGVLLILLMVIQAIANNKFIEVQKNAERARNTQEKSNE
MDEVIAKAAKGDAKTKEEVPEDVIKYMRDNGILIDGMTIDDYMAKYGDHGKLDKGGLQAIKAALDNDANRNTDLMSQGQI
TIQKMSQELNAVLTQLTGLISKNGEISSMIAQKTYS

FIG. 23C

SseC
MNRIHSNSDSAAGVTALTHHHLSNVSCVSSGSLGKRQHRVNSTFGDGNAACLLSGKISLQEASNALKQLLDAVPGNHKRP
SLPDFLQTNPAVLSMMMTSLILNVFGNNAQSLCQQLERATEVQNALRNKQVKEYQEQIQKAIEQEDKARKAGIFGAIFDW
ITGIFETVIGALKVVEGFLSGNPAEMASGVAYMAAGCAGMVKAGAETAMMCGADHDTCQAIIDVTSKIQFGCEAVALALD
VFQIGRAFMATRGLSGAAAKVLDSGFGEEVVERMVGAGEABIEELAEKFGEEVSESFSKQFEPLEREMAMANEMAKEAAE
FSRNVENMMTRSAGKSFTKEGVKAMAKEAAKEALEKCVQEGGKFLLKKFRNKVLPNMPKKILYALLRDCSPKGLQAIRCA
TEGASQMNTGMVNTEKAKIEKKIEQLITQQRFLDFIMQQTENQKKIEQKRLEELYKGTGAALRDVLDTIDHYSSVQARIA
GYRA

FIG. 23D

SseD
MEASNVALVLPAPSLLTPSSTPSPSGEGMGTESMLLLFDDIWMKLMELAKKLRDIMRSYNVEKQRLAWELQVNVLQTQMK
TIDEAFRASMITAGGAMLSGVLTIGLGAVGGETGLIAGQAVGHTAGGVMGLGAGVAQRQSDQDKAIADLQQNGAQSYNKS
LTEIMEKATEINQQIIGVGSSLVTVLAEILRALTR

FIG. 23E

SseE
MVQEIEQWLRRHQVFTEPAYLGETAILLGQQFILSPYLVIYRIEAKEMIICEFRRLTPGQPRPQQLFHLLGLLRGIFVHH
PQLTCLKMLIITDVLDEKKAMLRRKLLRILTVMGATFTQLDGDNWTVLSAEHLIQRRF

FIG. 23F

SseF
MKIHIPSAASNIVDGNSPPSDIQAKEVSFPPPPEIPAPGTPAAPVLLTPEQIRQQRDYAIHFMQYTIRALGATVVFGLSVA
AAVISGGAGLPIAILAGAALVIAIGDACCAYHNYQSICQQKEPLQTASDSVALVVSALALKCGASLNCANTLANCLSLLI
RSGIAISMLVLPLQFPLPAAENIAASLDMGSVITSVSLTAIGAVLDYCLARPSGDDQENSVDELHADPSVLLAEQMAALC
QSATTPAPALMDSSDHTSRGEP

FIG. 23G

SseG
MKPVSPNAQVGGQRPVNAPEESPPCPSLPHPETNMESGRIGPQQGKERVLAGLAKRVIECFPKEIFSWQTVILGGQILCC
SAGIALTVLSGGGAPLVALAGIGLAIAIADVACLIYHHHHLPMAHDSIGNAVPYIANCFANQRKSMAIAKAVSLGGRLA
LTATVMTHSYWSGSLGLQPHLLERLMDITYGLMSFTRFGMDGMAMTGMQVSSPLYRLLAQVTPEQRAPE

FIG. 23H

SscA
MKKDPTLQQAHDTMRFFRRGGSLRMLLDDDVTQPLNTLYRYATQLMEVKEFAGAARLFQLLTIYDANSFDYWFRLGECCQ
AQKHWGEAIYAYGRAAQIKIDAPQAPWAAAECYLACDNVCYAIKALKAVVRICGEVSEHQILRQRAEKMLQQLSDRS

FIG. 23I

SscB
MMMKEDQKNKIPEDILKQLLSVDPETVYASGYASWQEGDYSRAVIDFSWLVMAQPWSWRAHIALAGTWMMLKEYTTAINF
YGHALMLDASHPEPVYQTGVCLKMMGEPGLAREAFQTAIKMSYADASWSEIRQNAQIMVDTLIA

FIG. 23J

SsaD
MAYLMVNPKSSWKIRFLGHVLQGREVWLNEGNLSLGEKGCDICIPLAINEKIILREQADSLFVDAGKARVRVNGRRFNPN
KPLPSSGVLQVAGVAIAFGKQDCELADYQIPVSRSGYWWLAGVFLIFIGGMGVLLSISGQPETVNDLPLRVKFLLDKSNI
HYVRAQWKEDGSLQLSGYCSSSEQMQKVRATLESWGVMYRDGVICDDLLVREVQDVLIKMGYPHAEVSSEGPGSVLIHDD
IQMDQQWRKVQPLLADIPGLLHWQISHSHQSQGDDIISAIIENGLVGLVNVSPMRRSFVISGVLDESHQRILQETLAALK
KKDPALSLIYQDIAPSHDESKYLPAPVAGFVQSRHGNYLLLTNKERLRVGALLPNGGEIVHLSADVVTIKHYDTLIHYPL
DPK

FIG. 23K

SsaE
MTTLTRLEDLLLHSREEAKGIILQLRAARKQLEENNGKLQDPQQYQQNTLLLEAIEQAENIINIIYYRYHNSALVVSEQE

FIG. 23L

SsaG
MDIAQLVDMLSHMAHQAGQAINDKMNGNDLLNPESMIKAQFALQQYSTFINYESSLIKMIKDMLSGIIAKI

FIG. 23M

SsaH
MPAGVNHSLISQVHAMLPALTVIVPDKKLQLVCLALLLAGLNEPLKAAKILSDIDLPEAMALRLLFPAPNEGFEN

FIG. 23N

SsaI
MSVVPVSTQSYVKSSAEPSQEQIDFFEQLLKDEASTSNASALLPQVMLTRQMDYMQLTVGVDYLARISGAASQALNKLDN
MA

FIG. 23O

SsaJ
MKVHRIVPLTVLTFFLTACDVDLYRSLPEDEANQMLALLMQHHIDAEKKQEEDGVTLRVEQSQFINAVELLRLNGYPHRQ
FTTADKMFPANQLVVSPQEEQQKINFLKEQRIEGMLSQMEGVINAKVTIALPTYDEGSNASPSSVAVFIKYSPQVNMEAF
RVKIKDLIEMSIPGLQYSKISILMQPAEFRMVADVPARQTFWIMDVINAMKGKVVKWLMKYPYPLMLSLTGLLLGVGILI
GYFCLRRRF

FIG. 23P

SsrA
MNLLNLKMTLQTSLVIRLTFLFLLTTIIWLLSVLTAAYISMVQKRQHIIEDLSVLSEMNIVLSNQRFEEAERDAKMLMY
QCSLATEIHHNDIFPEVSRHLSVGPSNCTPTLNGEKHRLFLQSSDIDENSFRRDSFILNHKONEISLLSTDNPSDYSTLQP
LTRKSFPLYPTHAGFYWSEPEYINGKGWHASVAVADQQGVFFEVTVKLPDLITKSHLPLDDSIRVWLDQNNHLLPFSYIP
QKIRTQLENVTLHDGWQQIPGFLILRTTLHGPGWSLVTLYPYGNLHNRILKIILQQIPFTLTALVLMTSAPCWLLHRSLA
KPLWRFVDVINKTATAPLSTRLPAQRLDELDSIAGAFNQLLDTLQVQYDNLENKVAERTQALNEAKKRAERANKRKSIHL
TVISHELRTPMNGVLGAIELLQTTPLNIEQQGLADTARNCTLSLLAIINNLLDFSRIESGHFTLHMEETALLPLLDQAMQ
TIQGPAQSKKLSLRTFVGQHVPLYPHTDSIRLRQILVNLLGNAVKFTETGGIRLTVKRHEEQLIFLVSDSGKGIEIQQQS
QIFTAFYQADTNSQGTGIGLTIASSLAKMKGGNLTLKSVPGVGTCVSLVLPLQEYQPPQPIKGTLSAPFCLHRQLACNGI
RGEPPHQQNALLNAELLYFSGKLYDLAQQLILCTPNMPVINNLLPPWQLQILLVDDADINRDIIGKNLVSLGQHVTIAAS
SNEALTLSQQQRFDLVLIDIRMPEIDGIECVRLWHDEPNNLDPDCMFVALSASVATEDIHRCKKNGIHHYITKPVTLATL
ARYISIAAEYQLLRNIELQEQDPSRCSALLATDDMVINSKIFQSLDLLLADIENAVSAGEKIDQLIHTLKGCLGQIGQTE
LVCYVIDIENRVKMGKIIALEELTDLRQKIRMIFKNYTIT

FIG. 23Q

SarB
MKEYKILLVDDHEIIINGIMNALLPWPHFKIVEHVKNGLEVYNACCAYEPDILILDLSLPGINGLDIIPQLHQRWPAMNI
LVYTAYQQEYMTIKTLAAGANGYVLKSSSQQVLLAALQTVAVNKRYIDPTLNREAILAELNADTTNHQLLTLREROVLKL
IDEGYTNHGISEKLHISIKTVETHRMNMMRKLQVHKVTELLNCARRMRLIEY

FIG. 24A

Promoter A2
GCTTCCCTCCAGTTGCCTGTTGCAAAATCTTTGGCACTTGATCACTATCGCAGTACATATAGTTTCATCAGAAGATTAAT
CGATGGTGTTATCATTAGGAAGATAAATTTCTTCATATATAACCCAGTCGATGACTACAATTACTTTTTAATAAGATGGC
GATGTAAAAACATCGTAACAGTTTATTTAATAAATAATTTTTCAAATTGTAAGTTTTTATGTCAATGCTGAAAATGTAAT
TGTGAATTTATCGGAAAATCCGAATGATAGAATCGCCTGTGACAAGGTATATGTAGACAGCATCCTGATATTGTACAAGA
AGAGATAGTCGAAATAAATGTGAATCAGGCTTTTTACGGATGTGGTTGTGAGCGAATTTGATAGAAAC

FIG. 24B

Promoter B
TAAAAATATCTTAGAGCCTATCCCACCAGGCGTTAATTGGCGCAGCCAGTTTGGACACGGATAGCGCGCAAAAACCGCAG
CGTACACGTAGTACGTGAGGTTTGACTCGCTACGCTCGCCCTTCGGGCCGCCGCTAGCGGCGTTCAAAACGCTAACGCGT
TTTGGCGAGCACTGCCCAGGTTCAAAATGGCAAGTAAAATAGCCTAATGGGATAGGCTCTTAGTTAGCACGTTAATTATC
TATCGTGTATATGGAGGGGAAT

ATTENUATED SALMONELLA SPI2 MUTANTS AS ANTIGEN CARRIERS

This is a 371 of Application No. PCT/EP99/06514, filed Sep. 3, 1999 and claims priority to European application No. 98116827.1, filed Sep. 4, 1998.

BACKGROUND OF THE INVENTION

In 1996, over 17 million people world-wide, mainly in developing countries, were killed by various infections. The appearance and spread of antibiotic resistances coupled with the increase in world-wide travel has led to an increasing risk for the outbreak of pandemic infections. This possibility must be taken very seriously since, for some pathogenic bacteria, the therapeutic alternatives available have been reduced to a single option. Intriguingly, pathogenic bacteria have also been discovered to be a relevant factor in many chronic diseases. Stomach cancer, for example, is the second most common cancer world-wide and is directly linked with chronic *Helicobacter pylori* infections. *Chlamydia pneumoniae* has been detected in arteriosclerotic plaques and recently this bacterium has been found in the diseased regions of the brain of people suffering from Alzheimer's disease. Many autoimmune diseases, such as rheumatoid arthritis, seem to have bacterial origin. *Borrelia burgdorferi* is, in addition to many other bacteria, a prominent example of an organism causing disease affecting increasing numbers of people. Finally, Nanobacteria have been identified in the chronically diseased kidneys of patients with crystalline deposits. Other serious chronic diseases are caused by viral pathogens, the most clinically relevant are Hepatitis B and C viruses (liver cancer) and the human papilloma virus (cervical cancer).

The increasing clinical importance of bacterial pathogens has provoked increased discussion regarding the paradigm of medicinal treatment or prevention as the means to handle chronic diseases. Consistently, some chronic diseases have been successfully cured by antibiotic treatment. However, as indicated above, all micro-organisms are genetically capable of rapidly generating progenies with adequate antibiotic resistances, thus impeding efficient routine treatment. Conclusively, vaccines represent an excellent alternative to pharmacological drugs, and, considering the financial aspect that disease prevention is less cost-intensive than therapy, the option of vaccination is even more attractive. Therefore, the therapeutic vaccination approach has become particularly relevant, especially with respect to the treatment of cancer and chronic bacterial or viral diseases.

The most frequently practised approach uses oral delivery of either inactivated pathogens (dead vaccine) or parenteral injections of a defined mixture of purified components (subunit vaccines). Most of the dead vaccines are efficacious, however, the risk that the inactivation procedure was incomplete and that the vaccinee may become infected remains a problem. Furthermore, dead vaccines very often do not cover all genetic variants that appear in nature. The subunit vaccines abolish most of the disadvantages of the traditional dead vaccines. However, they require technologically advanced antigen and adjuvant preparations, which makes such vaccines relatively expensive. Furthermore, the subunit vaccines are preferentially inoculated by the parenteral route, which is not the optimal route for eliciting a broad immune response. In particular, the mucosal branch of the immune system, which is the primary line of protection against many pathogens, is strongly neglected by parenteral immunisations.

Another generation of vaccines is represented by live attenuated vaccines, which are based on pathogenic bacteria or viruses that have been mutated to apathogenic variants. These variants multiply in vivo for a limited period of time before they are completely cleared by the host. Their limited prevalence in the host tissue is sufficient to adequately provoke the host immune system, which is then able to establish a protective immune response. From the safety aspect, live attenuated bacterial vaccines are more favoured than live attenuated viral vaccines. Should a live bacterial vaccine becomes threating for a vaccinee, the attenuated bacteria can generally be controlled by antibiotic treatment. In contrast, live viral vaccines, which use the replication apparatus of the host cell, are almost impossible to control. Live bacterial vaccines are typically administered orally and serve as excellent stimulators of the mucosal immune system. Moreover, live bacterial vaccines are also good stimulators of the systemically active immune system, namely the humoral and cellular branches. Due to these excellent immuno-stimulatory characteristics, live bacterial vaccine strains, such as Salmonella, are ideal carriers for expressing antigens from a heterologous pathogen. Such bivalent (or multivalent) vaccines mediate protection against two pathogens: the pathogen homologous to the carrier as well as the pathogen whose protective antigen(s) are expressed by the carrier. Although no bivalent bacterial vaccine expressing heterologous antigens is currently in use, potential carriers currently under investigation include Bacille Calmette-Guerin (BCG), Salmonella species, *Vibrio cholerae* and *Escherichia coli.*

In the attenuation process, mutations are preferentially targeted to genes that support the survival of the pathogen in the host. Initially, chemical mutation regimes were applied to the *Salmonella typhi* strain Ty2, resulting in what were thought to be perfectly attenuated pathogens capable of mediating protective immunity, in contrast to the dead homologue. However, subsequent large-scale clinical trails revealed that such strains were still not sufficiently efficacious in the prevention of typhoid fever. It appears that such strains were mutated in several genes, resulting in an over-attenuation, which adversely affects the immunogenic potential of the strain. Novel typhoid vaccine strains have been developed by the introduction of genetically defined mutations. Most of these mutations have been established in *S. typhimurium*. Infection with *S. typhimurium* causes typhoid fever-like symptoms in mice and murine salmonellosis is a well accepted model for human typhoid. Such vaccine strains contain mutations in proteins causing deficiencies in the biosynthesis of aromatic amino acids (e.g. aroA, aroC and aroD) or purines (e.g. purA and purE), in the adenylate cyclase gene (cya) or the cAMP receptor protein (crop), or possess mutations affecting the regulation of several virulence factors (phoP and phoQ). However, although a number of attenuated mutants have been generated and characterised in the mouse model with regard to their role in virulence, relatively few of them have been evaluated as vaccine carriers in humans. The reason for this is that the mutants used are either still too virulent, causing severe side effects in the host, or are not sufficiently immunogenic, due to inadequate presentation to the immune system, which requires a critical level of persistence of the vaccine strain in the host for activation.

A recent study revealed that the inactivation of individual Salmonella genes causing attenuation of virulence directly influences the quality of an immune response against the vaccine carrier strain. From this finding, one can conclude that it might be possible to generate a variety of differently attenuated Salmonella vaccine strains, each with a unique profile and individual capabilities for eliciting an immune response. With this repertoire, it might be possible to tailor a vaccine strain according to specific immunological demands. As a logical consequence, one should also be able to develop attenuated Salmonella vaccine strains for either prophylactic or therapeutic purposes. However, the means by which such a representative repertoire of Salmonella vaccine strains is obtained and further developed into an efficacious vaccine must be determined.

In cases in which a Salmonella vaccine strain is used as a carrier for heterologous antigens, additional parameters must be considered. Traditionally, heterologous antigens have been expressed in the Salmonella cytosol. In the mouse typhoid model, it was demonstrated that, when heterologous antigens are expressed at high levels in the Salmonella cytosol, inclusion bodies are often formed, which negatively influence the immunogenicity of the recombinant live vaccine strain in the vaccinated host. It was concluded that the formation of inclusion bodies might be fatal for the bacterium, further decreasing vitality and increasing attenuation, and thus lowering the immunogenicity. Indeed, specific expression systems that circumvent this secondary attenuation principle, e.g. the 2-phase regulated expression system, can improve the efficacy of the presentation of heterologous antigens to the host immune system.

It has been demonstrated that secretion of antigens by live attenuated Salmonella can be superior to intracellular expression of the same antigens both in eliciting protective T-cell responses (Hess et al., 1996;, Hess et al., 1997b) and in eliciting elevated levels of antigen-specific antibody (Gentschev et al., 1998). Efficiencies of HlyA-directed secretion systems, however, are usually low (30% or less of total synthesized antigen) (Hess et al., 1997a; Hess et al., 1996), and the system seems to be problematical in S. typhi for export of heterologous antigens (Orr et al., 1999).

A similar immunological profile is induced by the two type III secretion systems, which are encoded by the Salmonella Pathogenicity Islands 1 and 2. These complex secretion machineries naturally deliver "effector proteins" into the cytosol of the infected host cell, supporting the survival of the pathogen within the host cell. By means of gene technology, the "effector proteins" can be converted into carrier vehicles for epitopes from heterologous antigens. Such chimeric "effector proteins" lose their virulent character but retain their secretory character. Consequently, the chimeric "effector protein" is delivered into the lumen of the host cell, where it is appropriately processed and subsequently stimulates the cytotoxic branch of the host immune system.

The most abundant protein secreted by Salmonella is flagellin (see, for example (Hueck et al., 1995)). In S. typhimurium, flagellin occurs in two allelic variants, FliC or FljB, while S. typhi carries only the FliC gene. Flagellin is secreted via the flagellum-specific export (FEX) pathway (Macnab, 1996; Minamino and Macnab, 1999), which is homologous to the type III secretion pathway (Hueck, 1998). It also has been shown recently that the FEX pathway functions in secretion of non-flagella proteins in Yersinia enterocolitica (Young et al., 1999). Like in type III secretion, the amino terminus of FliC directs secretion. Thus, a truncated version of 183 amino terminal amino acids of FliC (full length is 495 aa) is constitutively secreted in large amounts (Kuwajima et al., 1989). In analogy to type III secretion, the effective secretion signal in FliC may be as short as 10 to 20 amino acids. The FliC or FljB secretion signals can potentially be used to secrete large quantities of a heterologous protein which can serve as an antigen in heterologous vaccination. It is likely that the amount of secreted antigen can be even further increased in regulatory mutants affecting the expression of flagella biosynthesis genes (Macnab, 1996; Schmitt et al., 1996) or by using recombinant promoters to drive expression of the flagellin gene.

Secretion via the FEX pathway can allow the delivery of large amounts of antigen into the Salmonella-containing phagosome for early and efficient antigen processing and antigen presentation to the host immune system. Especially the MHC class 11 dependent branch of the host immune system is strongly supported by the FEX pathway mediated antigen delivery.

The other known, export machineries and surface display systems of Gram-negative bacteria can be also applied to bacterial vaccine carriers such as Salmonella. In general, a good immune response is achieved when the antigen is presented on the Salmonella surface. However, as little is known about the immunological consequence of such antigen presentation systems, further experimental work is needed.

Additional immuno-modulatory effects can be achieved when environmentally regulated Salmonella promoters are used for the expression of heterologous antigens. For instance, the expression of a heterologous gene in a Salmonella carrier strain under control of the in vivo regulated stress response htrA gene promoter resulted in a stronger immune response than was obtained when under control of the anaerobically inducible promoter of the nirB gene.

According to a first aspect, the present invention relates to an isolated nucleic acid molecule comprising a nucleic acid sequence comprising at least 50 nucleotides a) of the nucleic acid sequence of one of FIGS. 21A, B, b) of an allele of the nucleic acid sequence of one of FIGS. 21A, B or c) of a nucleic acid sequence which under stringent conditions hybridizes with the nucleic acid sequence of one of FIGS. 21A, B.

Stringent hybridization conditions in the sense of the present invention are defined as those described by Sambrook et al., Molecular Cloning, A Laboratory Manual, Cold Spring Harbor Laboratory Press (1989), 1.101–1.104. According to this, hybridization under stringent conditions means that a positive hybridization signal is still observed after washing for 1 hour with 1×SSC buffer and 0.1% SDS at 55° C., preferably at 62° C. and most preferably at 68° C., in particular, for 1 hour in 0.2×SSC buffer and 0.1% SDS at 55° C., preferably at 62° C. and most preferably at 68° C.

In particular, the present invention relates to such a nucleic acid molecule which comprises the complete coding regions or parts thereof of the genes ssaD, ssaE, sseA, sseB, sscA, sseC, sseD, sseE, sscB, sseF, sseG, ssaG, ssaH, ssaE, ssaJ, ssrA and ssrB. The invention pertains also to such nucleic acids, wherein at least one coding region of said genes is functionally deleted.

In one embodiment, the nucleic acid molecule comprises an insertion cassette to facilitate the insertion of a heterologous nucleic acid molecule by transposon or phage mediated mechanism.

Furthermore, said nucleic acid molecules can comprise at least one heterologous nucleic acid molecule. In this case the heterologous nucleic acid molecule may be fused 5' or 3', inserted or deletion-inserted to the inventive nucleic acid molecule. By the term "deletion-inserted" it is understood that the insertion of the heterologous nucleic acid molecule is associated with a concurrent deletion of parts of the inventive nucleic acid molecule. Preferably, the nucleic acid molecule is inserted or deletion-inserted and in one preferred embodiment the heterologous nucleic acid molecule is flanked 5' and 3' by sequences of the nucleic acid molecule according to the invention, wherein each of said sequences has a length of at least 50 nucleotides, preferably 200–250 nucleotides.

Preferred, the heterologous nucleic acid molecule codes for a polypeptide or peptide, more preferred it codes for a bacterial or viral antigen or a homologue thereof or for a tumor antigen.

It is preferred that the nucleic acid molecule also comprises at least one gene expression cassette to allow for efficient expression of the heterologous nucleic acid molecule. Such gene expression cassette usually comprises elements such as promoters and/or enhancers which improve the expression of the heterologous nucleic molecule acids. Usually, such gene expression cassette comprises elements for the termination of transcription. The presence of transcription terminators, however, may be not preferred in cases where the heterologous nucleic acid molecule is to be transcribed together with other genes into a cistronic mRNA.

The nucleic acid molecule, one or more selective marker cassettes and one or more transactivator cassettes and optionally invertase cassettes for allowing the expression of the heterologous nucleic acid molecules in a one-phase system or a two-phase system. Furthermore, sequences may be present which code for a polypeptide or peptide-targeting domain and, thus, allow for the targeting of the expression product of the heterologous nucleic acid molecule to a predetermined cell compartment such as cytosol, periplasma or outer membrane, or the secretion of said expression product, or which code for an immunostimulatory domain.

According to another aspect, the invention relates to a recombinant vector which comprises the nucleic acid molecule described above. Another aspect of the invention pertains to a cell comprising a modified inventive nucleic acid molecule as described above by insertion of a heterologous sequence or the recombinant vector. The cell may be a prokaryotic cell such as a gram-negative cell, e.g. a Salmonella cell, or it can be a eukaryotic cell such as a mammalian cell, e.g. a human cell, and, in particular, a macrophage.

According to a still further aspect, the present invention relates to a peptide or polypeptide comprising a peptide sequence comprising at least 20 amino acids a) of the sequence of one of FIGS. 23A–Q, or b) of a sequence which is 60%, preferred 65% and more preferred 70%. homologous to the sequence of one of FIGS. 23A–Q. In particular, the invention relates to a polypeptide comprising the sequence a) of one of FIGS. 23A–Q, or b) which is 60%, preferred 65% and more preferred 70% homologous to the sequence of one of FIGS. 23A–Q.

Percent (%) homology are determined according to the following equation:

$$H = \frac{n}{L} \times 100$$

wherein H are % homology, L is the length of the basic sequence and n is the number of nucleotide or amino acid differences of a sequence to the given basic sequence.

Another aspect of the present invention relates to an antibody which is directed against an epitope which is comprised of the aforementioned peptide or polypeptide. The antibody may be polyclonal or monoclonal.

Methods for producing such an antibody are known to the person skilled in the art.

A further aspect of the present invention relates to a fusion protein comprising the polypeptide according to any one of the claims 17 and 18 having inserted or deletion-inserted or being fused C- or $NH_2$-terminally with at least one heterologous polypeptide. The heterologous polypeptide preferred is an antigen, more preferred a bacterial or viral antigen or a tumor antigen.

The present invention furthermore provides instructions for the development of a variety of potential live Salmonella vaccine strains with different attenuation levels, which subsequently serve as platforms for the development of recombinant live Salmonella vaccine carrier strains that express antigens from heterologous pathogens, thus serving as multivalent vaccines. Such recombinant live Salmonella vaccine carriers are equipped with modules comprising variable gene cassettes that regulate the expression of heterologous antigens in Salmonella and determine presentation of the heterologous antigens to the host immune system. By combinations of both systems, differently attenuated live Salmonella vaccine strains and variable gene cassettes, a variety of recombinant live vaccine carrier strains can be generated that have; due to their variable immunogenic characteristics, a broad application spectrum for both prophylactic and therapeutic use. The basic attenuation principle originates from novel mutations in the Salmonella Pathogenicity Island 2 (SPI2) gene locus. Additional mutations, which can be used either alone or in combination with mutations in sse or SPI-2 genes or in combination with the aroA mutation for optimal attenuation of live vaccine carrier strains, have been reported recently (Heithoff et al., 1999; Valentine et al., 1998). By combination of the individual mutations in the SPI-2 gene locus with each other and with other known attenuating gene mutations, such as aroA, etc., a broad repertoire of attenuation and immunogenicity can be achieved. Different expression cassettes can be introduced on these platforms, allowing further modulation of the immune response directed against the heterologous antigens. Finally, a library of individual recombinant live Salmonella vaccine carrier strains is generated, covering a broad spectrum of immuno-stimulatory potential, from which a genuine live vaccine strain can be tailored for the optimal protection or treatment of humans and/or animals against specific pathogens or disease.

Thus, in a further aspect, the present invention is an attenuated gram-negative cell comprising the SPI2 gene locus, wherein at least one gene of the SPI2 locus is inactivated, wherein said inactivation results in an attenuation/reduction of virulence compared to the wild type of said cell.

Genes present in the Salmonella pathogenicity island 2 that encode for a variety of proteins involved in type III secretion and those that are required for systemic spread and survival within phagocytic cells are ideal candidates for attenuation of pathogenic Salmonella ssp.

Several gram-negative bacterial pathogens secrete certain virulence proteins via specialised type III secretion systems. Virulence factors enable pathogenic bacteria to colonise a niche in the host despite specific attacks of the immune system. The type III secretion systems comprise a large number of proteins required to transfer specific effector proteins into eukaryotic host cells in a contact-dependent manner, thus they have also been called contact-dependent secretory systems. Although several components of the secretion system apparatus show evolutionary and functional conservation across bacterial species, the effector proteins are less well conserved and have different functions. The Yersinia effectors YpkA and YopH have threonine/serine kinase and tyrosine phosphatase activities, respectively. The actions of these and other Yops inhibit bacterial phagocytosis by host cells, which is thought to enable extracellular bacterial proliferation. The Shigella Ipa proteins, secreted by the mxi/spa type III secretion system, promote entry of this bacterium into epithelial cells. EspA, EspB and EspD, encoded by the locus of enterocyte effacement (LEE) of enteropathogenic *Escherichia coli* (EPEC) are required for translocation of proteins that cause cytoskeletal rearrangements and the formation of pedestal-like structures on the host cell surface.

For the purposes of the present invention an "gram-negative cell comprising the SPI2 gene locus" is a cell having a gene locus that harbors genes required for the systemic spread and survival within phagocytic cells and, thus, is a homologue or functional equivalent of the SPI2 locus from Salmonella. Preferred, the inventive attenuated gram-negative cell is an Enterobactericae cell, more preferred, a Salmonella cell, a Shigella cell or a Vibrio cell. In general, cells having a broad host range are preferred. Typical hosts are mammals, e.g. man, and birds, e.g. chicken. Salmonella cells are more preferred, and particularly preferred is Salmonella serotype *typhimurium* Definitive Type 104 (DT 104).

*Salmonella typhimurium* is unusual in that it contains two type III secretion systems for virulence determinants. The first controls bacterial invasion of epithelial cells, and is encoded by genes within a 40 kb pathogenicity island (SPI1). The other is encoded by genes within a second 40 kb pathogenicity island (SPI2) and is required for systemic growth of this pathogen within its host. The genes located on pathogenicity island SPI1 are mainly responsible for early steps of the infection process, the invasion of non-phagocytic host cells by the bacterium. For most of the SPI1 genes, mutations result in a reduced invasiveness in vitro. However, mutants that are defective in invasion are not necessarily avirulent; studies in mice demonstrated that, while these mutations in SPI1 genes significantly reduced virulence upon delivery by the oral route, they had no influence on virulence following an intraperitoneal route of infection. Taken together, these results indicate that mutations in genes within the pathogenicity island SPI1 do not abolish systemic infection and are therefore not very useful for the development of a safe, attenuated Salmonella carrier strain. In comparison, virulence studies of SPI2 mutants have shown them to be attenuated by at least five orders of magnitude compared with the wild-type strain after both oral and intraperitoneal inoculation of mice.

Many of the genes encoding components of the SPI2 secretion system are located in a 25 kb segment of SPI2. SPI2 contains genes for a type III secretion apparatus (ssa) and a two component regulatory system (ssr), as well as candidate genes for a set of secreted effectors (sse) and their specific chaperones (ssc). On the basis of similarities with genes present in other bacterial pathogens, the first 13 genes within the ssaK/U operon and ssaJ encode components of the secretion system apparatus. A number of additional genes, including ssaC (orf 11 in Shea et al., 1996; spiA in Ochman et al., 1996) and ssrA (orf 12 in Shea et al., 1996; spiR in Ochman et al., 1996), which encode a secretion system apparatus protein and a two component regulatory protein, respectively, are found in a region approximately 8 kb from ssaJ.

Preferably, the inventive attenuated gram-negative cell has inactivated at least one gene selected from effector (sse) gene secretion apparatus (ssa) genes, chaperon (ssc) genes and regulation (ssr) genes. More preferably, the at least one inactivated gene is an sse, ssc and/or ssr gene, even more preferred is an sse and/or ssc gene.

As far as the sse genes are affected by the inactivation, the inactivated gene is preferably sseC, sseD, sseE or a combination thereof. As far as the ssr genes are affected by the inactivation, preferably at least ssrB is inactivated. As far as the ssc genes are affected by the inactivation, preferably at least sscB is inactivated.

The inactivation of said gene of the SPI2 locus (or functional homologue thereof in cells other than Salmonella) is effected by a mutation which may comprise deletion. Preferred are deletions of at least six nucleotides, and more preferred is a deletion of the partial and, in particular, the complete coding sequence for said gene. The mutation may also comprise the insertion of a heterologous nucleic acid molecule into said gene to be inactivated or a combination of deletion and insertion.

Pathogenic Salmonella ssp. serve a basis for the construction of a panel of different live Salmonella vaccine prototypes generated by gradual attenuations accomplished through the introduction of defined SPI2 gene locus mutations. Each resulting individual live Salmonella vaccine prototype is further transformed into a multivalent recombinant vaccine by the introduction of exchangeable DNA modules carrying (1) genetically engineered genes from heterologous pathogens and (2) adequate expression systems executing efficacious antigen presentation to the host immune system. In concert, these features elicit a specific immune response that either protects vaccinated hosts against subsequently invading Salmonella and/or other pathogens (prophylactic vaccination) or eliminates persistant pathogens, such as *Helicobacter pylori* (therapeutic vaccination).

Pathogenic Salmonella ssp. are gradually attenuated by mutations in individual virulence genes that are part of the SPI2 gene locus, e.g. an sse gene coding for an effector protein, such as sseC, sseD or sseE, or an ssc gene, such as sscB, coding for a chaperone, or an ssr gene, such as ssrB, coding for a regulator. Individual mutation of each of these genes leads to a unique individual grade of attenuation, which, in turn, effects a characteristic immune response at the mucosal, humoral and cellular levels. The individual grade of attenuation can be moderately increased by combinations of at least two gene mutations within the SPI2 gene locus or by combination with a mutation in another Salmonella gene known to attenuate virulence, e.g. an aro gene, such as aroA. A stronger grade of attenuation is achieved by mutation of a virulence gene that is part of a polycistronic gene cluster encoding several virulence factors, such as the transcriptional unit comprising the sseC, sseD, sseE and sscB genes, such that the mutation exerts a polar effect, disrupting expression of the following genes. The grade of attenuation may directly depend on the number of virulence genes that are affected by the polar mutation as well as their individual characteristics. Finally, the strongest attenuation is achieved when regulatory genes, such as ssrB, are mutated. Again, each mode of attenuation of a Salmonella ssp. leads to the generation of a live Salmonella vaccine strain that evokes an immune response at the mucosal, humoral and cellular levels that is characteristic for the type and/or combination of attenuating mutations present in that strain. The panel of differently attenuated live Salmonella vaccine strains that is generated represents a pool of potential carrier strains from which that carrier can be selected that provokes the most efficacious immune response for either the prevention or eradiction of disease in conjunction with the heterologous antigens that are expressed.

Mutations leading to attenuation of the indicated Salmonella virulence genes are preferentially introduced by recombinant DNA technology as defined deletions that either completely delete the selected virulence gene or result in a truncated gene encoding an inactive virulence factor. In both cases, the mutation involves a single gene and does not affect expression of neighbouring genes (non-polar mutation). An insertional mutation in one of the indicated virulence genes is preferred when the selected gene is part of a polycistronic virulence gene cluster and all of the following virulence genes are included in the attenuation process (polar mutation). Insertional mutations with non-polar effects are in general restricted to genes that are either singly transcribed or are localised at the end of a polycistronic cluster, such as ssrB. However, other attenuating mutations can arise spontaneously, by chemical, energy or other forms of physical mutagenesis or as a result of mating or other forms of genetic exchange.

Thus, the mutation which results in the preparation of the inventive attenuated gram-negative cell may be a polar or non-polar mutation. Furthermore, the grade of attenuation may be modified by inactivating an additional gene outside of the SPI2 locus, for example, another virulence gene or a gene that is involved in the biosynthesis of a metabolite or a precursor thereof such as the aro genes, in particular, aroA, or any other suitable gene such as superoxide dismutase (SOD).

The attenuated cell according to the invention may furthermore comprise elements which facilitate the detection of said cell and/or the expression of an inserted heterologous nucleic acid molecule. An example of an element which facilitates the detection of the attenuated cell is a selective marker cassette, in particular, a selective marker cassette which is capable of conferring antibiotic resistance to the cell. In one embodiment, the selective marker cassette confers an antibotic resistance for an antibiotic which is not used for therapy in a mammal. Examples of elements which facilitate the expression of a heterologous nucleic acid molecule are a gene expression cassette which may comprise one or more promoter, enhancer, optionally transcription terminator or a combination thereof, a transactivator cassette, an invertase cassette for 1-phase or 2-phase expression of a heterologous nucleic acid. An example of an element which facilitates the insertion of a heterologous-nucleic acid molecule is an insertion cassette.

In another aspect, the invention provides a carrier for the presentation of an antigen to a host, which carrier is an attenuated gram-negative cell according to any one of the claims 22 to 49, wherein said cell comprises at least one heterologous nucleic acid molecule comprising a nucleic acid sequence coding for said antigen, wherein said cell is capable of expressing said nucleid acid molecule or capable of causing the expression of said nucleic acid molecule in a target cell.

Preferably, said nucleic acid molecules comprises a nucleic acid sequence coding for a bacterial or viral antigen or for a tumor antigen. Examples of bacterial antigens are antigens from *Helicobacter pylori, Chlamydia pneumoniae, Borrelia burgdorferi* and Nanobacteria. Examples of viral antigens are antigens from Hepatitis virus, e.g. Hepatitis B and C, human papilloma virus and Herpes virus. The heterologous nucleic acid molecule may comprise a nucleic acid sequence which codes for at least one polypeptide or peptide-targeting domain and/or immunostimulatory domain. Thus, the expression product of said heterologous nucleic acid molecule may be targeted specifically to predetermined compartments such as periplasma, outer membrane, etc. The heterologous nucleic acid molecule may code for a fusion protein.

According to one embodiment the heterologous nucleic acid molecule is inserted into the SPI2 locus, preferred, into an sse gene and, more preferred, into sseC, sseD and/or sseE, in particular, sseC.

The insertion may be a polar insertion or an unpolar insertion. Generally, the introduction of an unpolar insertion is preferred, since it allows for the expression of the remaining genes of a polycistronic gene cluster, which can be used for the generation of carriers having different grades of attenuation.

Attenuated live Salmonella vaccines are used as carriers for specific antigens from heterologous pathogens, e.g. Helicobacter, etc., thus acting as a multivalent vaccine. The heterologous antigens are provided by a gene expression cassette (GEC) that is inserted by genetic engineering into the genome of an attenuated Salmonella strain. Preferentially, insertion of the gene expression cassette is targeted to one of the indicated virulence genes, thereby causing an insertional mutation as described in previous paragraph. In another application form, expression of the heterologous genes in the gene expression cassette is regulated by trans-acting factors encoded by a trans-activator cassette (TC) or an invertase cassette performing a 2-phase variable expression mode. Preferentially, the insertion of the trans-activator cassette is targeted to a second chosen virulence gene, which is then inactivated. Alternatively, the gene expression cassette or the trans-activator cassette or the invertase cassette can be introduced into the Salmonella genome by transposon-mediated insertion, which has no attenuation effect.

The principles of genetic engineering are required to generate either deletion or insertional mutations in Salmonella virulence genes. Generally, a suicide plasmid carrying a mutated virulence gene cassette containing a selective marker cassette (SMC) either alone or in combination with a gene expression cassette or a trans-activator cassette or the invertase cassette is introduced into the receptor Salmonella strain by conjugation. The original virulence gene is replaced with the mutated virulence gene cassette via homologous recombination, and the suicide plasmid, unable to replicate in the Salmonella receptor strain, becomes rapidly depleted. Successfully recombined Salmonella can be selected based on properties (such as, but not limited to, antibiotic resistance) conferred by the product of the gene(s) within the selective marker cassette. The mutated virulence gene cassette comprises DNA sequences that are homologous to the genome of the receptor Salmonella strain where the original virulence gene is localised. In the case where the original virulence gene is to be completely deleted, only those genomic DNA sequences that border the original virulence gene (indicated as flanking regions) are included in the mutated virulence gene cassette. The general architecture of a mutated virulence gene cassette includes at each end a DNA sequence of at least 50 nucleotides, ideally 200–250 nucleotides, that is homologous to the genome segment where the original virulence gene is localised. These DNA sequences flank a selective marker cassette and the other cassettes, such as the gene expression cassette (GEC) or the trans-activator cassette (TC) or the invertase cassette. As indicated above, these cassettes are used to generate insertional mutations which disrupt original gene expression. For in-frame deletions, a selective marker cassette is preferentially used.

The selective marker cassette (SMC) principally consists of a gene mediating resistance to an antibioticum which is able to inactivate the receptor Salmonella strain but which is actually not used in the treatment of Salmonellosis. Alternatively, another selectable marker can be used. The selective marker cassette is inserted in-frame in the targeted virulence gene and, consequently, the expression of the marker gene is under the control of the virulence gene promoter. Alternatively, the cassette is inserted within a polycistronic transcriptional unit, in which case the marker gene is under control of the promoter for this unit. In another application, the selective marker gene is under control of its own promoter; in this case a transcriptional terminator is included downstream of the gene. The selective marker is needed to indicate the successful insertion of the mutated virulence gene cassette into the genome of the receptor Salmonella strain. Furthermore, the antibiotic resistance marker is needed to facilitate the pre-clinical immunological assessment of the various attenuated Salmonella strains. In another application form, the selective marker is flanked by direct repeats, which, in the absence of selective pressure, lead to the recombinatorial excision of the selective marker cassette from the genome, leaving the short sequence of the direct repeat. Alternatively, the selective marker cassette can be completely removed by recombinant DNA technology. Firstly, the selective marker cassette is removed by adequate restriction endonuclease from the original mutated virulence gene cassette on the suicide plasmid leaving the flanking region sequences which are homologous to the Salmonella genome. The suicide plasmid is then transferred into the attenuated receptor Salmonella strain by conjugation where the SMC-depleted mutated virulence gene cassette replaces the SMC-carrying mutated virulence gene cassette by recombination. After removal of the selective marker, the attenuated Salmonella strain is free for the application in humans. Transcriptional terminator sequences are generally included in the cassettes when polar mutations are established.

The gene expression cassette (GEC) comprises elements that allow, facilitate or improve the expression of a gene. In a functional mode the gene expression cassette additionally comprises one or more gene expression units derived from either complete genes from a heterologous source or fragments thereof, with a minimal size of an epitope. Multiple gene expression units are preferentially organised as a concatemeric structure. The genes or gene fragments are further genetically engineered, such that the resulting proteins or fusion proteins are expressed in the cytosol, in the periplasm, surface displayed or secreted. Furthermore the genes or gene fragments can be fused with DNA sequences encoding immunologically reactive protein portions, e.g. cytokines or attenuated bacterial toxins. The genes or gene fragments are either controlled in a one-phase mode from a promoter within the gene expression cassette or in a 2-phase mode or indirectly by a trans-activator cassette (TC). In the one-phase mode the promoter is preferentially a Salmonella promoter that is activated, i.e. induced, by environmental signals but also constitutive promoters of different strength can be used. In the 2-phase mode, the expression of the gene cassette is controlled by an invertase that derived from an invertase cassette. The invertase catalyses the inversion of a DNA segment comprising the gene cassette. The DNA segment is flanked on each end by an inverted repeat which is the specific substrate for the invertase finally causing two orientation of the gene cassette with respect to the gene expression cassette promoter. In the ON-orientation the gene cassette is correctly placed allowing transcription of the gene cassette. In OFF, the orientation of the gene cassette is incorrect and no transcription occurs. The invertase cassette comprises of an invertase that is controlled by a constitutive promoter or a Salmonella promoter induced or derepressed by environmental signals.

Heterologous antigens encoded within the gene expression cassette can be expressed under the control of a promoter, e.g. a tissue-specific promoter, which may be constitutive or inducible. The expression can be activated in a target cell, whereby a signal is transmitted from the target cell to the interior of the Salmonella cell, which signal induces the expression. The target cell, for example, can be a macrophage. The expression product may comprise a targeting domain or immunostimulatory domain, e.g. in the form of a fusion protein. The heterologous protein itself also may be a fusion protein. The heterologous antigens can be optionally expressed as cytosolic, periplasmic, surface displayed or secretory proteins or fusion proteins in order to achieve an efficacious immune response. The antigen encoding sequences may be fused to accessory sequences that direct the proteins to the periplasm or outer membrane of the Salmonella cell or into the extracellular milieu. If the heterologous polypeptides are secreted, secretion can occur using a type III secretion system. Secretion by the SPI2 type III secretion system is suitable. Proteins that are destined for the cytosolic compartment of the Salmonella do not need accessory sequences, in this case, naturally occurring accessory sequences must be removed from the genes encoding such antigens.

The accessory sequences for the periplasmatic compartment of Salmonella comprise a DNA sequence deduced from the amino-terminally localised signal peptide of a heterologous protein naturally translocated via the general secretion pathway, e.g. CtxA, etc.

The accessory sequences for the outer membrane compartment of Salmonella preferentially comprise DNA sequences deduced from the functionally relevant portions of a type IV secretory (autotransporter) protein, e.g. AIDA or IgA protease. The appropriate fusion protein contains an amino-terminally localised signal peptide and, at the carboxy-terminus, a β-barrel shaped trans-membrane domain to which the foreign, passenger protein is coupled via a spacer that anchors the passenger protein to the bacterial surface.

The accessory sequences for secretion into the extracellular milieu comprise DNA sequences deduced from proteins naturally secreted by the type III secretion system. In a generally functional fusion protein, the heterologous antigen is fused in the centre of a protein naturally secreted by the type III pathway or at the carboxy-terminal end of the respective protein.

The transactivator cassettes (TC) provide activators which generally improve expression of the heterologous antigens encoded by the various gene expression cassettes. Such activators either directly (RNA polymerase) or indirectly (transcriptional activator) act on the transcription level in a highly specific order. Preferentially, the expression of such activators are controlled by Salmonella promoters which are induced in vivo by environmental signals. In another application form the synthesis of the activator within the transactivator cassette is regulated in a 2-phase mode. The invertase expressed by the invertase cassette places the activator encoding DNA fragment in two orientations with respect to the transcriptional promoter. In the ON-orientation the activator gene is in the correct transcriptional order. In the OFF-modus the activator is incorrectly orientated and no expression occurs.

In the simple system, the gene product of the transactivator cassette exerts its effect directly on the promoter present in the gene expression cassette, directly activating or de-repressing expression of the heterologous gene. In the complex system, activation of the promoter in the heterologous gene expression cassette is dependent upon two or more interacting factors, at least one of which (encoded in the transactivator cassette) may be regulated by external signals. Further complexity is found in cascade systems, in which the external signal does not directly exert its effect on the transactivator cassette, but rather through a multi-step process, or in which the gene product of the transactivator cassette does not directly exert its effect on the heterologous gene expression cassette, but rather through a multi-step process.

According to still another aspect, the present invention is an attenuated gram-negative cell comprising the SPI2 gene locus, characterized by a lack of at least one SPI2 polypeptide, wherein said lack results in an attenuation/reduction of virulence compared to the wild type of said cell. Preferably, said missing SPI2 polypeptide is one or more effector polypeptide, secretion apparatus polypeptide, chaperon polypeptide or regulatory polypeptide. Furthermore, said attenuated cell may be a carrier which then is characterized by the presence of at least one heterologous peptide or polypeptide having immunogenic properties.

A further aspect of the present invention is a pharmaceutical composition which comprises as an active agent an immunologically protective living vaccine which is an attenuated gram-negative cell or carrier according to the invention. The pharmaceutical composition will comprise additives such as pharmaceutically acceptable diluents, carriers and/or adjuvants. These additives are known to the person skilled in the art. Usually, the composition will administered to a patient via a mucosa surface or via or via the parenteral route.

Further aspects of the present invention include a method for the preparation of a living vaccine, which comprises providing a living gram-negative cell comprising the SPI2 locus and inactivating at least one gene of the SPI2 locus to obtain an attenuated gram-negative cell of the invention, and optionally inserting at least one heterologous nucleic acid molecule coding for an antigen to obtain a carrier according to the invention. A further aspect pertains to a method for the preparation of a living vaccine composition comprising formulating an attenuated cell or a carrier according to the invention in a pharmaceutically effective amount together with pharmaceutically acceptable diluents, carriers and/or adjuvants. A further aspect of the invention relates to a method for the detection of an attenuated cell or a carrier according to the invention, comprising providing a sample containing said cell and detecting a specific property not present in a wild type cell. Methods for detecting a specific property of the attenuated cell or carrier, which is not present in wild type, are known to the person skilled in the art. For example, if this specific property of the attenuated cell comprises a deletion of one or more parts of the SPI2 locus, then the presence of said cell can be detected by providing a pair of specific primers which are complementary to sequences flanking this deletion and amplifying a fragment of specific length using amplification methods such as PCR. Methods for detecting the presence of an inventive carrier comprise PCR amplification of an inserted fragment or a fragment spanning the insertion boundary, hybridization methods or the detection of the heterologous expression product or of a selective marker.

A further aspect of the invention is a method for establishing a library of attenuated gram-negative cells or carriers, respectively, according to the invention. The method comprises the preparation of attenuated recombinant vaccine strains, each having a different mutation in the SPI2 locus which results in a different degree of attenuation. The pathogenicity or virulence potential of said strains can then be determined using known methods such as determination of the LD50, and the strains are rated according to the different pathogenicities, i.e. a different grade of attenuation. Preferably, the method comprises also the determination of other parameters of interest such as the immunogenicity or the immuno-stimulatory response raised in a host. Methods for determining the immuno-stimulatory potential are known to the person skilled in the art and some of them are described in Example 6. Preferably, the immuno-stimulatory potential of the inventive attenuated cells or carriers is determined at humoral, cellular and/or mucosal level. In this way it is possible to establish a library of attenuated cells or carriers having a predetermined attenuation degree and predetermined immuno-stimulatory properties. Thus, for each application, the strain having the desired properties can be selected specifically. For example, it will be usually preferred to select a strong attenuated strain for administration to patients which receive immunosuppressive drugs.

In a similar way, the invention allows for the establishment of libraries of attenuated carriers having defined pathogenicities and optionally immunogenicities. The establishment of a carrier library additionally will comprise the determination of the antigen presentation of said carrier strains to a host, whereby a panel of different carriers strains will be obtained having defined properties with respect to pathogenicity, immuno-stimulatory potential of carrier antigens and immuno-stimulatory potential of the heterologous antigen.

Another aspect of the invention is the use of the attenuated cell or carrier according to the invention for the preparation of a drug for the preventive or therapeutic treatment of an acute or chronic disease caused essentially by a bacterium or virus. For example, for the prevention or treatment of a Salmonella infection one will administer an attenuated Salmonella cell to raise the immune response of an affected patient. Similarly, a carrier according to the invention may be used for the preparation of a drug for the preventive or therapeutic treatment of a tumor.

The individual immuno-protective potential of each of the established recombinant Salmonella vaccine strains is determined in a mouse model using a pathogenic *Salmonella typhimurium* as the challenge strain.

Determination of the virulence potential of the recombinant Salmonella vaccine strain: (1) Competitive index or LD50; (2) Systemic prevalence in blood, liver and spleen strictly excluded.

Determination of the immuno-stimulatory potential of the carrier strain with a cytosolically expressed heterologous test antigen: (1) Single oral immunisation and subsequent evaluation of the short- and long-term immune response: (a) analysis of the humoral immune response profile, (b) analysis of the mucosal immune response profile, (c) analysis of the cellular immune response profile; (2) Multiple oral immunisations and subsequent evaluation of the short- and long-term immune response: (a) analysis of the humoral immune response profile, (b) analysis of the mucosal immune response profile, (c) analysis of the cellular immune response profile.

Determination of the immuno-stimulatory potential of the carrier strain for the delivery of heterologous DNA (DNA vaccination).

Preferentially, the Salmonella acceptor strain has a broad host range, exhibiting significant pathogenicity in both animals and humans. Ideally, this is a Salmonella strain that is strongly pathogenic for mice, such as S. typhimurium. After successful development of the recombinant Salmonella vaccine strain, the strain is directly applicable for use in both animals and humans. If such an ideal Salmonella acceptor strain is not satisfactory for the respective host, other host-specific Salmonella must be selected, such as S. typhi for humans.

Other aspects of the invention relate to the use of a nucleic acid molecule as shown in FIG. 21A or B or one of the FIGS. 22A–Q, optionally modified as described hereinabove or of a vector as described hereinabove for the preparation of an attenuated cell, a living vaccine or a carrier for the presentation of an antigen to a host and to the use of the Salmonella SPI2 locus for the preparation of an attenuated cell, a living vaccine or preferably a carrier for the presentation of an antigen to a host. In this context the term "Salmonella SPI2 locus" refers to any nucleic acid sequence, coding or not coding, and to the expression product of coding sequences.

A still further aspect of the present invention is the use of a virulence gene locus of a gram-negative cell for the preparation of a carrier for the presentation of an antigen to a host.

Another aspect of the invention relates to a method of therapeutically or prophylactically vaccinating an animal, e.g. a mammal, e.g. a human, against a chronic disease caused primarily by a infectious organism including preparation and administering a vaccine of the invention.

Still another aspect of the present invention is an isolated nucleic acid molecule comprising a nucleic acid of at least 100 nucleotides a) of the nucleic acid sequence of one of FIGS. 24A, B, b) of a nucleic acid sequence which under stringent conditions hybridizes with the nucleic acid sequence of one of FIGS. 24A, B.

In particular, said aspect relates to said nucleic acid molecule which is capable of inducing the expression of a nucleic acid sequence conding for a peptide or polypeptide operatively linked to said nucleic acid molecule.

The in vivo inducible promoter Pivi comprises a DNA fragment which carries sequences for an operator and a transcriptional promoter. Such in vivo inducible promoter can be identified by applying an adequate reporter gene approach. Two of such in vivo inducible promoters have been identified within the SPI2 locus which initiate expression of the ssaBCDE operon (promoter A2) and the sseAB-sscAsseCDEsscBsseFG operon (promoter B), respectively. These promoters are induced by a regulative system comprising the ssrA and ssrB gene products. This regulative system is part of the SPI2 locus responsible for the activation of additional SPI2 locus genes. The regulative system is activated in macrophages by environmental signal(s) via sensor protein SsrA. The SsrB protein finally binds at a defined DNA sequence which initiates transcription through the RNA polymerase.

In an application form the DNA fragment comprising operator/promoter sequences is inserted in front of an invertase gene or an activator gene or a gene expression cassette, thereby executing an in vivo inducible expression in bacteria carrying at least the ssrA and ssrB genes or the complete SPI2 locus.

Thus, in a further aspect, the invention relates to an expression system for the in vivo inducible expression of a heterologous nucleic acid in a target cell, comprising a carrier cell for said heterologous nucleic acid, wherein said carrier cell comprises (a) a polypeptide having the amino acid sequence shown in FIG. 23P (ssrA) or a functional homologue thereof, (b) a polypeptide having the amino acid sequence shown in FIG. 23Q (ssrB) or a functional homologue thereof, and (c) the nucleic acid molecule of one of FIGS. 24A, B or a functional homologue thereof, as described above.

The target cell may be any suitable cell but preferably it is a macrophage. The carrier cell preferably is a Salmonella cell. The target cell may also comprise one or more of the elements described above such as selective marker cassettes, gene expression cassettes, transactivator cassettes, invertase cassettes and/or insertion cassettes. Furthermore, it may comprise a heterologous nucleic acid, in particular, the heterologous nucleic acids may be inserted into a gene expression cassette, thus rendering the GEC functional.

A still further aspect of the invention relates to the use of a nucleic acid molecule comprising at least 100 nucleotides of the nucleic acid sequence shown in one of FIGS. 24A, B or hybridizing therewith and having promoter activity, for the in vivo inducible expression of a heterologous nucleic acid molecule.

A further aspect of the present invention is the use of said nucleic acid molecule for the detection of in vivo inducible promoters.

EXPERIMENTAL PROCEDURES

The strains, material, and methods used in the type III secretion system of the Salmonella Pathogenicity Island 2 (SPI2) work described above are as follows:

Mice

Female BALB/c (H-$2^d$) of 6–12 weeks of age were maintained under standard conditions according to institutional guidelines. This study was approved by an ethic committee for animal use in experimental research.

Bacterial Strains, Phages and Plasmids

The bacterial strains, phages and plasmids used in this study are listed in Table 1. Unless otherwise indicated, bacteria were grown at 37° C. in Luria Bertani (LB) broth or agar, supplemented with ampicillin (50 μg/ml), kanamycin (50 μg/ml), or chloramphenicol (50 μg/ml) where appropriate. Eukaryotic cells were grown in RPMI 1640 supplemented with 10% of foetal calf serum (FCS), 100 U/ml penicillin, 50 μg/ml streptomycin, $5 \times 10^{-5}$ M 2-mercaptoethanol and 1 mM L-glutamine (GIBCO BRL; Prisley, Scotland). To achieve constitutive expression of β-gal, the plasmid pAH97 (Holtel et al., 1992) was electroporated into the carrier strains as described elsewhere (O'Callaghan and Charbit, 1990).

TABLE 1

Phages, plasmids and bacterial strains used in this work.

| Phage, plasmid or strain | Description | Reference |
| --- | --- | --- |
| Phages | | |
| λ1 | clone from a library of S. typhimurium genomic DNA in λ1059 | Shea et al., 1996 |
| λ2 | clone from a library of S. typhimurium genomic DNA in λ1059 | Shea et al., 1996 |
| λ5 | clone from a library of S. typhimurium genomic DNA in λ1059 | Shea et al., 1996 |

TABLE 1-continued

Phages, plasmids and bacterial strains used in this work.

| Phage, plasmid or strain | Description | Reference |
|---|---|---|
| Plasmids | | |
| pBluescriptKS+, pBluescriptSK+ | Amp$^r$; high copy number cloning vectors | Stratagene, Heidelberg |
| pUC18 | Amp$^r$; high copy number cloning vector | Gibco-BRL, Eggenstein |
| pT7-Blue | Amp$^r$; high copy number cloning vector | Novagen, Heidelberg |
| pCVD442 | suicide vector | Donnenberg et al., 1991 |
| pACYC184 | Cm$^r$,Tet$^r$; low copy number cloning vector | Chang and Cohen, 1978 |
| pGPL01 | R6K ori, Amp$^r$; λpir-dependent suicide vector for luc fusions | Gunn and Miller, 1996 |
| pLB02 | R6K ori, Amp$^r$; λpir-dependent suicide vector for luc fusions | Gunn and Miller, 1996 |
| pGP704 | R6K ori, Amp$^r$; λpir-dependent suicide vector | Miller and Mekalanos, 1988 |
| pKAS32 | Amp$^r$; λpir-dependent suicide vector; rpsl$^s$ | Skorupski and Taylor, 1996 |
| pNQ705 | R6K ori, Cm$^r$; λpir-dependent suicide vector | Forsberg et al., 1994 |
| pSB315 | Kan$^r$, Amp$^r$ | Galán et al., 1992 |
| p1-6 | Amp$^r$, 4.8 kb PstI/BamHI fragment of λ1 in pT7-Blue | this work |
| p1-20 | 1.7 kb BamHI/HincII fragment of p1-6 in pKS+ | this work |
| p1-21 | aphT cassette in EcoRV site of p1-20 | this work |
| p1-22 | XbaI/KpnI insert of p1-21 in pKAS32 | this work |
| p2-2 | Amp$^r$, 5,7 kb BamHI fragment of λ2 in pUC18 | this work |
| p2-20 | 1.6 kb HindIII/HincII fragment of p2-2 in HindIII/SmaI-digested pKS+ | this work |
| p2-21 | aphT cassette in HincII site of p2-20 | this work |
| p2-22 | insert of p2-21 in pKAS32 | this work |
| p2-50 | 3.7 kb BamHI/KpnI fragment of p2-2 in pKS+ | this work |
| p5-2 | Amp$^r$; 5.7 kb EcoRI fragment of λ5 in pKS+ | this work |
| p5-30 | 3.0 kb PstI/EcoRI fragment of p5-2 in pUC18 | this work |
| p5-31 | aphT cassette in EcoRV site of p5-30 | this work |
| p5-33 | SphI/EcoRI insert of p5-31 in pGP704 | this work |
| p5-4 | Amp$^r$; 5.8 kb HindIII fragment of λ5 in pSK+ | this work |
| p5-40 | 4.5 kb SstI/HindIII fragment of p5-2 in pKS+ | this work |
| p5-41 | aphT cassette in SmaI site of p5-40 | this work |
| p5-43 | KpnI/SstI insert of p5-41 in pNQ705 | this work |
| p5-5 | Amp$^r$; PstI digestion of p5-4 and religation of the larger fragment | this work |
| p5-50 | 2.6 kb BamHI/ClaI fragment of p5-2 in pKS+ | this work |
| p5-51 | aphT cassette in HindIII site of p5-50 after Klenow fill-in | this work |
| p5-53 | XbaI/SalI insert of p5-51 in pGP704 | this work |
| p5-60 | ClaI-digestion of p5-2 and religation of larger fragment | this work |
| p5-8 | Amp$^r$, 2.2 kb PstI/HindIII fragment of p5-2 in pSK+ | this work |
| psseA | Cm$^r$; sseA in pACYC184 | this study |
| psseB | Cm$^r$; sseB in pACYC184 | this study |
| psseC | Cm$^r$; sseC in pACYC184 | this work |
| E. Coli strains | | |
| DH5α | see reference | Gibco-BRL |
| S17-1 λpir | λpir phage lysogen (see reference) | Miller and Mekalanos, 1988 |
| CC118 λpir | λpir phage lysogen (see reference) | Herrero et al., 1990 |
| XL1-Blue | see reference | Stratagene |
| S. typhimurium strains | | |
| NCTC12023 | wild-type | Colindale, UK |
| CS015 | phoP-102::Tn10d-Cm | Miller et al., 1989 |
| CS022 | phoP$^c$ | Miller et al., 1989 |
| P2D6 | ssaV::mTn5 | Shea et al., 1996 |
| P3F4 | ssrA::mTn5 | Shea et al., 1996 |
| P4H2 | hilA::mTn5 | Monack et al., 1996 |
| P6E11 | spaRS::mTn5 | Shea et al., 1996 |
| P8G12 | ssrB::mTn5 | Shea et al., 1996 |
| P9B6 | ssaV::mTn5 | Shea et al., 1996 |
| P9B7 | ssaT::mTn5 | Shea et al., 1996 |
| P11D10 | ssaJ::mTn5 | Shea et al., 1996 |
| NPssaV | ssaV::aphT, Km$^r$; non-polar mutation | Deiwick et al., 1998 |
| HH100 | sseAΔ:::aphT, Km$^r$; non-polar mutation | this study |
| HH101 | HH100 containing psseA | this study |
| HH102 | sseBΔ:::aphT, Km$^r$; non-polar mutation | this study |
| HH103 | HH102 containing psseB | this study |
| HH107 | sseFΔ:::aphT, Km$^r$; non-polar mutation | this study |
| HH108 | sseG::aphT, Km$^r$; non-polar mutation | this study |
| MvP102 | ΔsseEsscB,_Km$^r$; non-polar mutation | this work |
| MvP103 | sseC::aphT, Km$^r$; non-polar mutation | this work |
| MvP103[psseC] | MvP103 containing psseC | this work |
| MvP131 | ssaB::luc in S. typhimurium NCTC12023 | this work |
| MvP127 | sseA::luc in S. typhimurium NCTC12023 | this work |
| MvP239 | sipC::lacZY, EE638 in S. typhimurium NCTC12023 | Hueck et al., 1995; this work |
| MvP244 | ssaB::luc in S. typhimurium P8G12 | this work |
| MvP266 | ssaH::luc in S. typhimurium NCTC 12023 | this work |
| MvP284 | ssrA::aphT, Km$^r$; non-polar mutation | this work |
| MvP320 | ssrB::aphT, Km$^r$; non-polar mutation | this work |
| MvP337 | in-frame deletion in sseC | this work |
| MvP338 | in-frame deletion in sseD | this work |
| MvP339 | in-frame deletion in sscB | this work |
| MvP340 | in-frame deletion in ssrA | this work |
| SL7207 | S. typhimurium 2337-65 hisG46, DEL407 aroA::Tn1(Tc-s) | gift from B.A.D. Stocker |
| III-57 sseC | ΔsseC | this work |

EXAMPLE 1

Distribution of the Pathogenicity Island SPI-2 Within Different Salmonella Strains The presence of open reading frames of the SPI-2 region in various Salmonella isolates and *E. coli* K-12 was analyzed by Southern hybridization as shown in Table 2.

TABLE 2

Prevalence of SPI-2 genes in various Salmonella ssp. deduced from representative gene probes

| Species | subspec. | serovar/serotype | ssrAB | ORF |
|---|---|---|---|---|
| S. enterica | I | typhimurium | + | + |
| S. enterica | I | typhi | + | + |
| S. enterica | II | | + | + |
| S. enterica | IIIa | | + | + |
| S. enterica | IIIb | | + | + |
| S. enterica | IV | | + | + |
| S. enterica | VI | | + | + |
| S. enterica | VII | | + | + |
| S. bongori | | 66:z41:-- | − | + |
| S. bongori | | 44:z48:-- | − | + |
| E. coli K-12 | | | − | − |

Presence or absence of hybridizing bands is indicated by + or −, respectively.

Hybridization

Genomic DNA of various Salmonella strains and E. coli K-12 was prepared as previously (Hensel et al., 1997a). For Southern hybridization analysis, genomic DNA was digested with EcoRI or EcoRV, fractionated on 0.6% agarose gels and transferred to Hybond N+ membranes (Amersham, Braunschweig). Various probes corresponding to the SPI-2 region were obtained as restriction fragments of the subcloned insert of λ1. Probes corresponding to ORF 242 and ORF 319 were generated by PCR using primer sets D89 (5'-TTTTTACGTGAAGCGGGGTG-3') (SEQ ID NO:44) and D90 (5'-GGCATTAGCGGATGTCTGACTG-3'), (SEQ ID NO:45) and D91 (5'-CACCAGGAACCATTTTCTCTGG-3') (SEQ ID NO:46) and D92 (5'-CAGCGATGACGATATTCGACAAG-3') (SEQ ID NO:47), respectively. PCR was performed according to the specifications of the manufacturer (Perkin-Elmer, Weiterstadt). PCR products were submitted to agarose gel electrophoresis and fragments of the expected size were recovered and purified. Hybridization probes were labeled using the DIG labeling system as described by the manufacturer (Boehringer, Mannheim).

EXAMPLE 2

Characterization of sse Genes and Construction of sseC::aphT, sseD::aphT and sseEΔ Mutant S. typhimurium Strains MvP103, MvP101 and MvP102

Organization of sse and ssc Genes

In order to characterize SPI2 genetically and functionally, a central region of the pathogenicity island (FIG. 1A) has been cloned and sequenced. DNA fragments covering the region between ssaC and ssaJ were subcloned in plasmids p5-2 and p5-4 as indicated in FIG. 1C. The arrangement and designation of genes in the 8 kb region between ssaC and ssaK is shown in FIG. 1B. This sequence will be available from the EMBL database under accession number AJ224892 in the near future. The sequenced region extends the open reading frame (ORF) of a gene encoding a putative subunit of the type III secretion apparatus referred to as spiB (Ochman et al., 1996). For consistency with the universal nomenclature for type III secretion system subunits (Bogdanove et al., 1996) and the nomenclature of other SPI2 genes (Hensel et al., 1997b), this gene has been designated ssaD. The deduced amino acid sequence of ssaD is 24% identical to YscD of Y. enterocolitica. This is followed by an ORF with coding capacity for a 9.3 kDa protein, 34% identical to YscE of Y. enterocolitica. Therefore, this gene is designated ssaE. A sequence of 263 bp separates ssaE and a set of nine genes, several of which encode proteins with sequence similarity to secreted effector proteins or their chaperones from other pathogens. These genes are separated by short intergenic regions or have overlapping reading frames and it is likely that some are co-transcribed and translationally coupled. Therefore, the genes with similarity to those encoding chaperones were designated sscA and sscB, and the others sseA–E. The amino acid sequence deduced from sscA shows 26% identity/49% similarity over 158 amino acid residues to SycD, the product of IcrH of Y. pseudotuberculosis which acts as a secretion-specific chaperone for YopB and YopD (Wattiau et al., 1994). The amino acid sequence deduced from sscB shows 23% identity/36% similarity over 98 amino acid residues to IppI of Shigella flexneri. IppI is a chaperone for S. flexneri invasion proteins (Ipas) (Baundry et al., 1988). As is the case for the secretion chaperones SycD, IppI and SicA (Kaniga et al., 1995), SscB has an acidic pI (Table 3), whereas SscA has an unusually high pI of 8.8. SseB is 25% identical/47% similar to EspA of EPEC over the entire length of the 192 amino acid residue protein (FIG. 2b). SseD is 27% identical/51% similar to EspB of EPEC over 166 amino acid residues. SseC has sequence similarity to a class of effector proteins involved in the translocation of other effectors into the target host cell. These include YopB of Y. enterocolitica, EspD of EPEC and PepB of Pseudomonas aerugunosa. SseC is approximately 24% identical/48% similar to both EspD of EPEC and YopB of Y. enterocolitica (FIG. 2a). EspD and YopB have two hydrophobic domains that are predicted to insert into target cell membranes (Pallen et al., 1997). SseC contains three hydrophobic regions that could represent membrane-spanning domains. Other features of these predicted effector proteins are shown in Table 1. Using the TMpredict program (Hofmann and Stoffel, 1993), transmembrane helices are predicted for all the effector proteins apart from SseA which is very hydrophilic. Alignments of SseC to homologs in other pathogens are shown in FIG. 2b. Conserved amino acids are mainly clustered in the central, more hydrophobic portion of the protein, but unlike YopB, there is no significant similarity to the RTX family of toxins. The conserved residues in SseD are present mainly in the N-terminal half of the protein. Comparison of the deduced amino acid sequences of sseABCDEF with entries in the PROSITE database did not reveal the presence of any characteristic protein motifs. We subjected the predicted amino acid sequences of the sse genes to searches using the programs COIL and MULTICOIL as described by Pallen et al. (1997). SseA and SseD are predicted to have one trimeric coil each, and SseC is predicted to have two trimeric coils (Table 3). Since EspB and EspD are predicted to have one and two trimeric coils, respectively (Pallen et al., 1997), this provides further evidence that these proteins are functionally related.

TABLE 3

Features of predicted proteins.

| Protein | M, (kDa) | pI | Tm predictions | Predicted coils |
|---|---|---|---|---|
| SseA | 12.5 | 9.3 | hydrophilic | at least one (trimer) |
| SseB | 21.5 | 4.7 | one transmembrane helix | none |
| SseC | 52.8 | 6.3 | three transmembrane helices | at least two (trimers) |
| SseD | 20.6 | 4.8 | three transmembrane helices | at least one (trimer) |
| SseE | 16.3 | 9.7 | one transmembrane helix | none |
| SscA | 18.1 | 8.8 | hydrophilic | none |
| SscB | 16.4 | 4.7 | hydrophilic | none |

Expression of SPI2 Genes

Generation of Antibodies Against Recombinant SPI2 Proteins

In order to monitor the expression of the SPI2 genes sseB, sscA and ssaP, a Western blot analysis of total bacterial cells with polyclonal antibodies raised against recombinant SPI2 proteins SseB, SscA, and SsaP was performed.

Protein gel electrophoresis and Western blotting were performed as described elsewhere (Laemmli, 1970 and Sambrook et al., 1989). Plasmids for the expression of recombinant SPI2 protein were constructed by cloning the individual SPI2 genes in plasmids pQE30, pQE31 or pQE32 (Qiagen, Hilden) in order to generate in-frame fusion to the N-terminal 6His tag. Recombinant SPI2 genes were expressed in *E. coli* M 15 [pREP] (Qiagen) and purified by metal chelating chromatography according to recommendations of the manufacturer (Qiagen). For immunisation, about 1 mg of recombinant SPI2 proteins were emulsified with complete and incomplete Freund's adjuvant for primary and booster immunizations, respectively. Rabbits were immunized subcutaneously according to standard protocols (Harlow and Lane, 1988). SPI2 proteins were detected with antisera raised against recombinant SPI2 proteins after electrophoretical separation of proteins from total cells and transfered onto a nitrocellulose membrane (Schleicher and Schuell) using a 'Semi-Dry' blotting device (Bio-Rad) according to the manufacturers manual. Bound antibody was visualized using a secondary antibody-alkaline phosphatase conjugate according to standard protocols (Harlow and Lane).

Generation of Reporter Gene Fusions:

Fusions of the reporter gene firefly luciferase (luc) to various genes in SPI2 were obtained using the suicide vectors pLBO2 and pGPLO1 (Gunn and Miller, 1996), which were kindly provided by Drs. Gunn and Miller (Seattle).

For the generation of a fusion to ssaB, a 831 bp EcoRV fragment of p2-2 was subcloned in EcoRV digested pSK+. For the generation of a transcriptional fusion to sseA, a 1060 bp SmaI/HincII fragment of p5-4 was subcloned in pSK+. The inserts of the resulting constructs were recovered as a EcoRI/KpnI fragment and ligated with EcoRI/KpnI digested reporter vectors pGPLO1 and pLBO2. For the generation of a transcriptional fusion to ssaJ, a 3 kb SmaI/KpnI fragment of p5-2 was directly subcloned in pGPLO1 and pLBO2.

Constructs with transcriptional fusions of SPI2 genes to luc were than integrated into the chromosome of *S. typhimurium* by mating between *E. coli* S17-1 λpir harbouring the respective construct and a spontaneous mutant of *S. typhimurium* resistant to 100 $\mu g \times ml^{-1}$ nalidixic acid and selection for exconjugants resistant to carbenicillin and nalidixic acid. The targeted integration in SPI2 (for constructs using pGLPO1) or the zch region (for constructs using pLBO2) was confirmed by Southernanalysis. Fusions were then moved into a mouse-passaged strain of *S. typhimurium* NCTC12023 by P22 transduction according to standard procedures (Maloy et al., 1996).

Assay of Reporter Genes

β-galactosidase activities of reporter gene fusions were determined according to standard procedures (Miller, 1992).

Bacterial strains harbouring firefly luciferase, fusions to SPI2 genes (strain MvP127, sseA::luc, strain MvP131, ssaB::luc, strain MvP266, ssaH::luc) were grown in medium with various $Mg^{2+}$ concentrations. The luciferase activity of aliquots of the cultures was determined using the Promega (Heidelberg) luciferase assay kit or custom made reagents accordingly.

Briefly, bacteria were pelleted by centrifugation for 5 min. at 20000×g at 4° C. and resuspended in lysis buffer (100 mM $KHPO_4$, pH 7.8, 2 mM EDTA, 1% Triton X-100, 5 mg×ml$^{-1}$ bovine serum albumin, 1 mM DTT, 5 mg×ml$^{-1}$ lysozyme). Lysates were incubated for 15 min at room temperature with repeated agitation and subjected to a freeze/thaw cycle. Aliquots of the lysates (25 µl) were transferred to microtiter plates (MicroFLUOR, Dynatech) and immediately assayed after addition of 50 µl luciferase reagent (20 mM Tricine-HCl, pH 7.8, 1.07 mM $(MgCO_3)_4Mg(OH)_2$, 100 µM EDTA, 33.3 mM DTT, 270 µM $Li_3$-coenzyme A, 470 µM D(-)-luciferin, 530 µM Mg-ATP) for photon emission using the TriLux MicroBeta luminometer (Wallac, Turku). All assays were done in triplicates and repeated on independent occasions.

Expression of SPI2 Genes Such as ssaB and ssaH is Induced by Low $Mg^{2+}$ Concentrations of the Growth Medium

*S. typhimurium* wild-type strain and strains harbouring luc reporter-gene fusions to ssaB (strain MvP131) and to ssaH (strain MvP266) were grown to mid-log phase (OD at 600 nm of about 0.5) in minimal media containing high amounts of $Mg^{2+}$ (10 mM $MgCl_2$). This medium is referred to as medium G. Bacteria were recovered by centrifugation, washed three times in minimal medium containing 8 µM $Mg^{2+}$. This medium is referred to as medium F. Bacteria were resuspended in medium F or medium G and growth at 37° C. was continued. Aliquots of the cultures of strains MvP131 and MvP266 were withdrawn at the several different time points indicated and subjected to analysis of luciferase activity. Aliquots of the wild-type strain were withdrawn at the same time points. Protein from total bacterial cells was separated by SDS-PAGE and transferred to nicrocellulose membranes. These blots were incubated with antibodies raised against recombinant SsaP and SscA protein in order to detect proteins synthesized after the magnesium concentration shift in the magnesium concentration. After shifting bacteria from a growth medium with high amounts of $Mg^{2+}$ to a medium with limiting amounts of $Mg^{2+}$, the expression of SPI2 genes was highly induced. This induction can be monitored by using the reporter gene luc fused into different positions of SPI2. Furthermore, proteins synthesized after induction of SPI2 were detected by Western Blots. However, even in the presence of high amounts of $Mg^{2+}$, a low level of expression of SPI2 genes was observed.

Expression of SPI2 Genes Such as sseA and ssaB is Modulated by PhoP/PhoQ Regulation No expression of sseB or sscA was observed during growth in various rich media, or cell culture media with or without serum. However, low amount of SsaP were detected after growth in LB or other rich media such as brain hart infusion (BHI). Growth in minimal medium containing less than 30 µM $Mg^{2+}$ induces the expression of SPI2 genes. Such effect of the $Mg^{2+}$ concentration has so far only been observed for PhoP/PhoQ-regulated genes. This observation is in contrast to a previous report by Valdivia and Falkow (1997) who postulated that SPI2 gene expression is independent of PhoP/PhoQ. However, in a PhoP$^c$ (constitutive) strain background (CSO22, Miller et al., 1989) expression of SPI2 genes was not constitutive but still dependent on the $Mg^{2+}$ concentration of the medium. This indicates that SPI2 gene expression is modulated by PhoP/PhoQ, but that further regulatory elements such as SsrA/B are needed.

DNA Cloning and Sequencing

DNA preparations and genetic manipulations were carried out according to standard protocols (Sambrook et al, 1989). Plasmid DNA transformation of bacterial cells was performed by electroporation (O'Callaghan and Charbit, 1990).

Clones harbouring fragments of SPI2 were identified from a library of genomic DNA of S. typhimurium in λ 1059 which has been described previously (Shea et al., 1996). The sse and ssc genes were subcloned from clone λ5 on a 5.7 kb EcoRI fragment (p5-2) and a 5.8 kb HindIII fragment (p5-4) in pBluescriptKS+ as indicated in FIG. 1 and Table 1.

DNA sequencing was performed using a primer-walking strategy. The dideoxy method (Sanger et al., 1977) was applied using the Pharmacia T7 sequencing system for manual sequencing and the dye terminator chemistry for automatic analysis on a ABI377 sequencing instrument. Assembly of contigs from DNA sequences was performed by means of AssemblyLign and MacVector software (Oxford Molecular, Oxford). For further sequence analyses, programs of the GCG package version 8 (Devereux et al., 1984) were used on the HGMP network.

Construction of Non-polar Mutations

The construction of non-polar mutations in sseC (MvP103), sseD (MvP101) and sseE (MvP102) are described below. All chromosomal modifications were confirmed by PCR and Southern hybridization analysis (Southern, 1975. J. Mol. Biol. 98: 503–517).

Mutant MvP103, sseC. A 2.6 kb fragment was recovered after BamHI and ClaI digestion of p5-2 and subcloned in BamHI/ClaI-digested pBluescript II KS+. The resulting construct termed p5-50 was digested by HindIII, blunt ended using the Klenow fragment of DNA polymerase and ligated to the aphT cassette. A 900 bp HincII fragment of pSB315 containing an aminoglycoside 3'-phosphotransferase gene (aphT) from which the transcriptional terminator had been removed (Galán et al., 1992) was ligated in the same orientation into the blunted-ended HindIII site of plasmid p550. After transformation of E. coli XL-1 Blue and selection for resistance against kanamycin and carbenicillin (50 μg/ml each) one clone has been chosen and the harbouring plasmid isolated. This plasmid was termed p5-51 and its identity confirmed by restriction analysis. It was further digested with SalI and XbaI and the insert of 3.5 kb was ligated to SalI/XbaI-digested pGP704. This plasmid was electroporated into E. coli CC118 λpir and the transformants selected for resistance to kanamycin and carbenicillin (50 ìg/ml each). As done before, one clone was chosen, its plasmid with the according DNA fragment in pGP704, termed p5-53, isolated and confirmed by restriction analysis. Plasmid p5-53 was electroporated into E. coli S17-1 λpir and transferred into S. typhimurium NCTC12023 (resistant to nalidixic acid, 100 μg/ml) by conjugation as has been described previously (de Lorenzo and Timmis, 1994). Exconjugants in which the sseC gene had been replaced by the cloned gene disrupted by insertion of the aphT cassette were selected by resistance to kanamycin and nalidixic acid (100 μg/ml). The resulting exconjugants were finally tested for a lactose-negative phenotype and their sensitivity to carbenicillin. Selected clones were further examined by Southernblot analysis. In order to exclude possible mutations which have been acquired during the cloning procedure the mutated sseC allele was transferred into a fresh Salmonella background by P22 transduction (described by Maloy et al., 1996). The resulting Salmonella strain MvP103 was examined for the presence of the resistance cassette within the sseC gene by the use of PCR. Amplification was performed by using the primers E25 (5'-GAAATCCCGCAGAAATG-3') (SEQ ID NO:48) and E28 (5'-AAGGCGATAATATAAAC-3') (SEQ ID NO:49). The resulting fragment had a size of 1.6 kb for S. typhimurium wild-type and 2.5 kb for strain MvP103.

For complementation of non-polar mutations in sseC, the corresponding genes were amplified by PCR from genomic DNA using a series of primers corresponding to the region 5' of the putative start codons and to the 3' ends of the genes. These primers introduced BamHI restriction sites at the termini of the amplified genes. After digestion with BamHI, the genes were ligated to BamHI-digested pACYC184 (Chang and Cohen, 1978) and transferred into E. coli DH5α. The orientation of the insert was determined by PCR, and in addition, DNA sequencing was performed to confirm the orientation and the correct DNA sequence of the inserts. Plasmids with inserts in the same transcriptional orientation as the Tet$^r$ gene of pACYC184 were selected for complementation studies and electroporated into the S. typhimurium strains harbouring corresponding non-polar mutations.

Mutant MvP101, sseD. A 3.0 kb fragment was recovered after PstI and EcoRI digestion of p5-2 and subcloned in PstI/EcoRI-digested pUC18. The resulting construct termed p5-30 was digested by EcoRV and treated with alkaline phosphatase. The aphT cassette was isolated as described above and ligated to the linearized plasmid p5-30 in the same orientation in the unique EcoRV site. After transformation of E. coli XL-1 Blue and selection against kanamycin and carbenicillin (50 μg/ml each) one clone has been chosen and the harbouring plasmid isolated. This plasmid was termed p5-31 and its identity confirmed by restriction analysis. p5-31 was further digested with SphI and EcoRI, a 4.0 kb fragment isolated and ligated to SphI/EcoRI-digested pGP704. This plasmid was electroporated into E. coli CC118 λpir and transformants selected to kanamycin and carbenicillin (50 μg/ml each). As done before, one clone was chosen, its plasmid with the according DNA fragment in pGP704, termed p5-33, isolated and confirmed by restriction analysis. Plasmid p5-33 was electroporated into E. coli S17-1 λpir and transferred into S. typhimurium NCTC12023 (resistant to nalidixic acid) by conjugation as has been described previously (de Lorenzo and Timmis, 1994). Exconjugants in which the sseD gene had been replaced by the cloned gene disrupted by insertion of the aphT cassette were selected by resistance to kanamycin and nalidixic acid (100 μg/ml). The resulting exconjugants were finally tested for a lactose-negative phenotype and their sensitivity to carbenicillin. Selected clones were further examined by Southernblot analysis. In order to exclude possible mutations which might have been accumulated during the cloning procedure the mutated sseD allele was transferred into a fresh Salmonella background by P22 transduction (described by Maloy et al., 1996). The resulting Salmonella strain MvP101 was examined for the presence of the resistance cassette within the sseD gene by the use of PCR. Amplification was performed by using the primers E6 (5'-AGAGATGTATTAGATAC-3') (SEQ ID NO:50) and E28 (5'-AAGGCGATAATATAAAC-3')(SEQ ID NO:49). The resulting fragment had a size of 0.8 kb for S. typhimurium wild-type_was used and 1.7 kb in the case of strain MvP101.

Mutant MvP102, deletion of parts of sseE and sscB. A 4.5 kb fragment was recovered after SstI and HindIII digestion of p5-2 and subcloned in SstI/HindIII-digested pKS+. The resulting construct termed p5-40 was digested by SmaI, digested with alkaline phospatase and ligated to the aphT cassette in the same orientation into the unique SmaI site created in the sseE/sseB deletion plasmid p5-40 as described above. After transformation of E. coli XL-1 Blue and selection against kanamycin and carbenicillin (50 μg/ml each) one clone was chosen and the harbouring plasmid isolated. This plasmid was termed p5-41 and its identity confirmed via restriction analysis. It was further digested with KpnI and SstI and the insert was ligated to KpnI/SstI-digested pNQ705. This plasmid was electroporated into *E. coli* CC118 λpir and transformed bacteria selected to kanamycin and chloramphenicol (50 μg/ml each). As done before, one clone was chosen, its plasmid with the according DNA fragment in pNQ705, termed p5-43, isolated and confirmed by restriction analysis. The resulting plasmid was used to transfer the mutated gene onto the Salmonella chromosome as described above. Resulting clones have been further examined by Southernblot analysis. To exclude possible mutations which might have been acquired during the cloning procedure the mutated sseE/sscB allele was transferred into a fresh Salmonella background by P22 transduction (described by Maloy et al., 1996). The resulting Salmonella strain MvP102 was examined for the presence of the resistance cassette within the sseE/sseB gene by the use of PCR. Amplification was performed by using the primers E6 (5'-AGAGATGTATTAGATAC-3' (SEQ ID NO:50) and E4 (5'-GCAATAAGAGTATCAAC-3') (SEQ ID NO:51). The resulting fragment had a size of 1.6 kb for *S. typhimurium* wild-type and a size of 1.9 kb for strain MvP102.

Construction of Mutant Strains Carrying In-frame Deletions in sseC, sseD and sscB:

Based on the observation that a non-polar in sseE did not result in a significant attenuation of virulence in the mouse model (Hensel et al., 1998), the generation of a deletion mutant for the sseE gene is not of interest for the generation of carrier strains.

Construction of an In-frame Deletion in sseC, Mutant MvP337

A deletion of 158 bp between codon 264 and 422 of sseC was generated. Plasmid p5-2 was digested by ClaI and the larger fragment containing the vector portion was recovered and self-ligated to generate p5-60. Plasmid p5-60 was linearized by digestion with HindIII, which cuts once within the sseC gene. Primers sseC-del-1 (5'-GCT AAG CTT CGG CTC AAA TTG TTT GGA AAA C-3') (SEQ ID NO:52) and sseE-del-2 (5'- GCT AAG CTT AGA GAT GTA TFA GAT ACC-3') (SEQ ID NO:53) were designed to introduce HindIII sites. PCR was performed using linearized p5-60 as template DNA. The TaqPlus polymerase (Stratagene) was used according to the instructions of the manufacturer. Reactions of 100 μl volume were set up using 10 μl of 10×TaqPlus Precision buffer containing magnesium chloride, 0.8 μl of 100 mM dNTPs, 250 ng DNA template (linearized p5-8), 250 ng of each primer and 5 U of TaqPlus DNA polymerase. PCR was carried out for 35 cycles of: 95EC for 1 minute, 60EC for 1 minute, 72EC for 6 minutes. Then a final step of 72EC for 10 minutes was added. 10 μl of the PCR reaction were analyzed. A product of the expected size was recovered, digested by HindIII, self-ligated, and the ligation mixture was used to transform *E. coli* DH5α to resistance to carbenicillin. Plasmids were isolated from transformants and the integrity of the insert and the deletion was analyzed by restriction digestion and DNA sequencing. The insert of a confirmed construct was isolated after digestion with XbaI and KpnI and ligated to XbaI/KpnI-digested vector pKAS32. The resulting construct was used to transform *E. coli* S17-1 λpir to resistance to carbenicillin, and conjugational transfer of the plasmid to *S. typhimurium* (Nal$^R$, Strep$^R$) was performed according to standard procedures (de Lorenzo and Timmis, 1994). Exconjugants that had integrated the suicide plasmid by homologous recombination were selected by resistance to nalidixic acid and carbenicillin, and screened for sensitivity to streptomycin. Such clones were grown in LB to OD600 of about 0.5 and aliquots were plated on LB containing 250 μg/ml streptomycin to select for colonies which had lost the integrated plasmid and undergone allelic exchange. Clones resistant to streptomycin but sensitive to carbenicillin were used for further analysis. Screening of mutants with a deletion within the sseC locus was performed by PCR using primers sseC-For (5'-ATT GGA TCC GCA AGC GTC CAG AA-3') (SEQ ID NO 54) and sseC-Rev (5-TAT GGA TCC TCA GAT TAA GCG CG-3') (SEQ ID NO:55). Amplification of DNA from clones containing the wild-type sseC allele resulted in a PCR product of 1520 bp, use of DNA from clones harbouring a sseC allele with an internal deletion resulted in a PCR product of 1050 bp. The integrity of clones harbouring the sseC deletion was further confirmed by Southern analysis of the sseC locus. Finally, the sseC locus containing the internal in-frame deletion was moved into a fresh strain background of *S. typhimurium* by P22 transduction (Maloy et al., 1996) and the resulting strain was designated MvP337.

Construction of an In-frame Deletion in sseD, Mutant Strain MvP338

A deletion of 116 bp between codon 26 and 142 of sseD was generated. Plasmid p5-2 was digested by HindIII/PstI and a fragment of 2.1 kb was isolated and subcloned in HindIII/PstI-digested vector pBluescript SK+. The resulting construct was designated p5-8. p5-8 was linearized by digestion with EcoRV, which cuts twice within the sseD gene. Primers sseD-del-1 (5'-ATA GAA TTC GGA GGG AGA TGG AGT GGA AG-3') (SEQ ID NO:56) and sseD-del-2 (5'-ATA GAA TTC GAA GAT AAA GCG ATT GCC GAC-3') (SEQ ID NO:57) were designed to introduce EcoRI sites. PCR was performed using linearized p5-8 as template DNA. The TaqPlus polymerase (Stratagene) was used according to the instructions of the manufacturer. Reactions of 100 μl volume were set up using 10 μl of 10×TaqPlus Precision buffer containing magnesium chloride, 0.8 μl of 100 mM dNTPs, 250 ng DNA template (linearized p5-8), 250 ng of each primer and 5 U of TaqPlus DNA polymerase. PCR was carried out for 35 cycles of: 95EC for 1 minute, 60EC for 1 minute, 72EC for 5 minutes. Then a final step of 72EC for 10 minutes was added. 10 μl of the PCR reaction were analyzed. A product of the expected size was recovered, digested by EcoRI, self-ligated, and the ligation mixture was used to transform *E. coli* DH5α to resistance to carbenicillin. Plasmids were isolated from transformants and the integrity of the insert and the deletion was analyzed by restriction mapping and DNA sequencing. The insert of a confirmed construct was isolated after digestion with XbaI and KpnI and ligated to XbaI/KpnI-digested vector pKAS32. The resulting construct was used to transform *E. coli* S17-1 λpir to resistance to carbenicillin, and conjugational transfer of the plasmid to *S. typhimurium* (Na$^R$, Strep$^R$) was performed according to standard procedures (de Lorenzo and Timmis, 1994). Exconjugants that had integrated the suicide plasmid by homologous recombination were selected by resistance to nalidixic acid and carbenicillin, and screened for sensitivity to streptomycin. Such clones were grown in LB to OD600 of about 0.5 and aliquots were plated on LB containing 250 μg/ml streptomycin to select for colonies which had lost the integrated plasmid and undergone allelic exchange. Clones resistant to streptomycin but sensitive to carbenicillin were used for further analysis. Screening of mutants with a deletion within the sseD locus was performed by PCR using primers sseD-For (5'-GAA GGA TCC ACT CCA TCT CCC TC-3') (SEQ ID NO:58) and sseD-Rev (5-GAA GGA TCC ATT TGC TCT ATT TCT TGC-3') (SEQ ID NO:59). Amplification of DNA from clones containing the wild-type sseD allele resulted in a PCR product of 560 bp, use of DNA from clones harbouring a sseD allele with an internal deletion resulted in a PCR product of 220 bp. The integrity of clones harbouring the sseD deletion was further confirmed by Southernanalysis of the sseD locus. Finally, the sseD locus containing the internal in-frame deletion was moved into a fresh strain background of S. typhimurium by P22 transduction (Maloy et al., 1996) and the resulting strain was designated MvP338.

Construction of an In-frame Deletion in sscB, Mutant Strain MvP339

A deletion of 128 bp between codon 32 and 160 of sscB was generated. A 3 kb BglII fragment of plasmid p5-2 was ligated into the BamHI site of pBluescript KS+ to generate plasmid p5-70. Plasmid p5-70 was linearized by digestion with NcoI, which cuts once within the sscB gene. Primers sscB-del-1 (5'-ATG GGA TCC GAG ATT CGC CAG AAT GCG CAA-3') (SEQ ID NO:60) and sscB-del-2 (5'-ATG GGA TCC ACT GGC ATA AAC GGT TTC CGG-3') (SEQ ID NO:61) were designed to introduce BamHI sites. PCR was performed using linearized p5-70 as template DNA. The TaqPlus polymerase (Stratagene) was used according to the instructions of the manufacturer. Reactions of 100 µl volume were set up using 10 µl of 10×TaqPlus Precision buffer containing magnesium chloride, 0.8 µl of 100 mM dNTPs, 250 ng DNA template (linearized p5-70), 250 ng of each primer and 5 U of TaqPlus DNA polymerase. PCR was carried out for 35 cycles of: 95EC for 1 minute, 60EC for 1 minute, 72EC for 6 minutes. Then a final step of 72EC for 10 minutes was added. 10 µl of the PCR reaction were analyzed. A product of the expected size was recovered, digested by BamHI, self-ligated, and the ligation mixture was used to transform E. coli DH5α to resistance to carbenicillin. Plasmids were isolated from transformants and the integrity of the insert and the deletion was analyzed by restriction analysis and DNA sequencing. The insert of a confirmed construct was isolated after digestion with XbaI and KpnI and ligated to XbaI/KpnI-digested vector pKAS32. The resulting construct was used to transform E. coli S17-1 λpir to resistance to carbenicillin, and conjugational transfer of the plasmid to S. typhimurium (Nal$^R$, Strep$^R$) was performed according to standard procedures (de Lorenzo and Timmis, 1994). Exconjugants that had integrated the suicide plasmid by homologous recombination were selected by resistance to nalidixic acid and carbenicillin, and screened for sensitivity to streptomycin. Such clones were grown in LB to OD600 of about 0.5 and aliquots were plated on LB containing 250 ìg/ml streptomycin to select for colonies which had lost the integrated plasmid and undergone allelic exchange. Clones resistant to streptomycin but sensitive to carbenicillin were used for further analysis. Screening of mutants with a deletion within the sseC locus was performed by PCR using primers sscB-For (5'-ATT GGA TCC TGA CGT AAA TCA TTA TCA-3') (SEQ ID NO:62) and sscB-Rev (5-ATT GGA TCC TTA AGC AAT AAG TGA ATC-3') (SEQ ID NO:63). Amplification of DNA from clones containing the wild-type sscB allele resulted in a PCR product of 480 bp, use of DNA from clones harbouring a sscB allele with an internal deletion resulted in a PCR product of 100 bp. The integrity of clones harbouring the sseC deletion was further confirmed by Southernanalysis of the sscB locus. Finally, the sscB locus containing the internal in-frame deletion was moved into a fresh strain background of S. typhimurium by P22 transduction (Maloy et al., 1996) and the resulting strain was designated MvP339.

Construction of a Deletion Mutation in the sseC Gene

In a further approach the complete sequence of the chromosomal sseC gene was deleted by allelic replacement with a deleted copy of the gene. The deletion was constructed in a suicide plasmid (pCVD442 (Donnenberg et al., 1991). First, two DNA fragments flanking the sseC gene (fragment A, carrying artificial SalI and XbaI sites at its 5' and 3' ends, respectively; and fragment B, carrying artificial XbaI and SacI sites at its 5' and 3' ends, respectively) were amplified by PCR. The oligonucleotides used for PCR were: 1.) sseDelfor1 GCTGTCGACTTGTAGTGAGTGAG-CAAG (3' nucleotide corresponds to bp 941 in included sequence: FIG. 21A) (SEQ ID NO:70); 2.) sseCDelrev2 GGATCTAGATTTTAGCTCCTGTCAGAAAG (3' nucleotide corresponds to bp 2585 in included sequence, oligo binds to reverse strand) (SEQ ID NO:71); 3.) sseCDelfor2 GGATCTAGATCTGAGGATAAAAATATGG (3' nucleotide corresponds to bp 4078 in included sequence) (SEQ ID NO:72); 4.) sseDelrev1 GCTGAGCTCTGCCGCTGACG-GAATATG (3' nucleotide corresponds to bp 5592 in included sequence, oligo binds to reverse strand) (SEQ ID NO:73). The resulting PCR fragments were fused together via the XbaI site. The resulting fragment was cut with SalI and SacI and cloned into pCVD442 cut with SalI and SacI. The resulting plasmid was introduced into S. typhimurium NCTC12023 by conjugation and chromosomal integrants of the plasmid into the sseC locus were selected for by the plasmid-encoded ampicillin resistance marker. In a second step, clones which had lost the plasmid were screened for by loss of ampicillin resistance. The resulting clones were tested for chromosomal deletion of the sseC gene by PCR, and deletion of a 1455 bp fragment, comprising the entire sseC open reading frame, was confirmed. This ΔsseC mutant strain was named III-57ΔsseC.

Construction of a sseC-aroA Double Mutant

In order to construct a double mutant which can serve as a prototype for a live attenuated vaccine, the sseC:aphT (Km') marker from MvP103 was transferred by P22 phage transduction into S. typhimurium SL7207 (hisG46 DEL407 [aroA544:Tn10], Tc$^R$) a strain carrying a stable deletion in the aroA gene.

EXAMPLE 3

Invasion and Intracellular Growth in Tissue Culture Intramacrophage Replication of Mutant Strains Several strains which are defective in their ability to replicate inside macrophages and macrophage-like cell lines have been tested, as macrophage survival and replication are thought to represent an important aspect of Salmonella pathogenesis in vivo (Fields et al., 1986). It has been reported previously that a number of SPI2 mutant strains were not defective for survival or replication within RAW macrophages (Hensel et al., 1997b) but subsequent experiments have revealed that some SPI2 mutants can be shown to have a replication defect if aerated stationary phase bacterial cultures opsonized with normal mouse serum are used (see also accompanying paper: Cirillo et al., 1998). The increase in cfu for different strains in RAW macrophages over a 16 h period is shown in FIG. 3. Replication defects were observed for strains carrying mutations in ssaV (encoding a component of the secretion apparatus), sseB and sseC and to a lesser extent for strains carrying mutations in sseE. Partial complementation of this defect was achieved with strains harbouring plasmids carrying functional copies of sseB and sseC, HH103 and MvP103[psseC], respectively. The ability of SPI2 mutant strains to replicate inside the J774.1 macrophage cell line (FIG. 4A) and in periodate-elicited peritoneal macrophages from C3H/HeN mice (FIG. 4B) has also been tested. Similar replication defects of S. typhimurium carrying transposon or non-polar mutations in SPI2 genes were observed, regardless of the phagocyte cell-type examined, although the peritoneal elicited cells had superior antimicrobial activity compared to either cell line.

Macrophage Survival Assays

RAW 264.7 cells (ECACC 91062702), a murine macrophage-like cell line, were grown in Dulbecco's modified Eagle's medium (DMEM) containing 10%$_{foetal}$ calf serum (FCS) and 2 mM glutamine at 37° C. in 5% $CO_2$. S. typhimurium strains were grown in LB to stationary phase and diluted to an $OD_{600}$ of 0.1 and opsonized for 20 min in DMEM containing 10% normal mouse serum. Bacteria were then centrifuged onto macrophages seeded in 24 well tissue culture plates at a multiplicity of infection of approximately 1:10 and incubated for 30 min. Following infection, the macrophages were washed twice with PBS to remove extracellular bacteria and incubated for 90 min (2 h post-infection) or 16 h in medium containing gentamicin (12 μg/ml). Infected macrophages were washed twice with PBS and lysed with 1% Triton X-100 for 10 min and appropriate aliquots and dilutions were plated onto LB agar to enumerate cfu.

Survival of opsonized S. typhimurium strains in J774.1 cells (Ralph et al., 1975) or C3H/HeN murine peritoneal exudate cells (from Charles River Laboratories, Wilmington, Mass.) was determined essentially as described by DeGroote et al. (1997), but without the addition of interferon-γ. Briefly, peritoneal cells harvested in PBS with heat-inactivated 10%$_{foetal}$ calf serum 4 days after intraperitoneal injection of 5 mM sodium periodate (Sigma, St. Louis, Mo.) were plated in 96-well flat-bottomed microtiter plates (Becton-Dickinson, Franklin Lakes, N.J.) and allowed to adhere for 2 h. Non-adherent cells were flushed out with prewarmed medium containing 10% heat-inactivated$_{foetal}$ calf serum. In previous studies, we have established that >95% of the cells remaining after this procedure are macrophages. S. typhimurium from aerated overnight cultures was opsonized with normal mouse serum and centrifuged onto adherent cells at an effector to target ratio of 1:10. The bacteria were allowed to internalize for 15 min, and washed with medium containing 6 μg/ml gentamicin to kill extracellular bacteria. At 0 h and 20 h, cells were lysed with PBS containing 0.5% deoxycholate (Sigma, St. Louis, Mo.), with plating of serial dilutions to enumerate colony-forming units.

EXAMPLE 4

Evaluation of Safety in the S. typhimurium Mouse Model of Salmonellosis

Virulence Tests With Strains Carrying Non-polar Mutations

DNA sequence analysis suggested that the sse genes might encode effector proteins of the secretion system, but apart from a possible polar effect from a transposon insertion in sscA no strains carrying mutations in these genes were recovered in the original STM screen for S. typhimurium virulence genes using mTn5 mutagenesis (Hensel et al., 1995), and their role in virulence was unclear. To address this question, strains carrying non-polar mutations in sseC, sseD and sseEsscB (FIG. 1) have been constructed and subjected to virulence tests. Table 4 shows that all mice inoculated with strains carrying mutations sseC and sseD survived a dose of 1×10$^4$ cfu, three orders of magnitude greater than the $LD_{50}$ of the wild-type strain, which is less than 10 cfu when the inoculum is administered by the i.p. route (Buchmeier et al., 1993; Shea et al, 1996). The same strains containing a plasmid carrying the corresponding wild-type allele were also inoculated into mice at a dose of 1×10$^4$ cfu. No mice survived these infections, which shows that each mutation can be complemented by the presence of a functional copy of each gene, and that each of these genes plays an important role in Salmonella virulence. Strains carrying non-polar mutations in sseEsscB caused lethal infections when approximately 1×10$^4$ cells of each strain were inoculated into mice by the i.p. route (Table 4) and were analyzed in more detail by a competition assay with the wild-type strain in mixed infections (five mice/test) to determine if they were attenuated in virulence. The competitive index, defined as the output ratio of mutant to wild-type bacteria, divided by the input ratio of mutant to wild-type bacteria, shows that the sseEsscB mutant was not significantly different to that of a fully virulent strain carrying an antibiotic resistance marker, which implies that this gene does not play a significant role in systemic Salmonella infection of the mouse.

TABLE 4

Virulence of S. typhimurium strains in mice.

| Strain | Genotype | Mouse survival after inoculation[a] with bacterial strain | Mouse survival after inoculation with mutant + complementing plasmid | Competitive index in vivo |
|---|---|---|---|---|
| NCTC12023 | wild-type | 0/5 | n.d. | 0.98[b] |
| MvP101 | ΔsseD::aphT | 5/5 | n.d. | >0.01 |
| MvP102 | ΔsseEsscB::aphT | 4/4 | n.d. | 0.79 |
| MvP103 | sseC::aphT | 5/5 | 0/5 | >0.01 (oral) |
| | | | | >0.01 (i.p.) |

[a]Mice were inoculated intraperitoneally with 1 × 10$^4$ cells of each strain
[b]Result of competition between wild-type strain NCTC12023 and a virulent mTn5 mutant identified in the STM screen.

EXAMPLE 5

Vaccination With the sseC::aphT, and ΔsseD::aphT Mutant S. typhimurium Strains MvP103 and MvP101

Strains Carrying Non-polar Mutations as Live Vaccine Carriers

To confirm the suitability of the MvP101 and MvP103 mutants as live vaccine carriers their level of attenuation was evaluated by determining the $LD_{50}$ after oral inoculation in mice. Groups of 10 mice were fed with serial dilutions of either MvP101, MvP103 or the wild-type parental strain NCTCNCTC12023 and dead animals were recorded within a period of 10 days postinfection. The obtained results demonstrated that both mutants are highly attenuated when given orally to BALB/c mice ($LD_{50}$ above 10$^9$) when compared with the parental strain ($LD_{50}$=6.9×10$^5$ CFU). After intraperitoneal inoculuation the $LD_{50}$ of S. typhimurium NCTC12023 wild-type in BALB/c is 6 bacteria, and the $LD_{50}$ of MvP103 in BALB/c is 2.77×10$^6$ after intraperitoneal inoculation. The mutation can be complemented by psseC, but no $LD_{50}$ determination for the complemented mutant strain was performed. $LD_{50}$ of MvP101 in BALB/c is 3.54×10$^6$ after intraperitoneal inoculation. A partial complementation by plasmid p5-K1 was possible. An intraperitoneal $LD_{50}$ for MvP101 [p5-K1] of 8.45×10$^2$ was determined. (Description of p5-K1: a 3.2 kb PstI fragment of p5-2 containing sseC'sseDsseEsscBsseF' was subcloned in low copy number cloning vector pWSK29).

Determination of the $LD_{50}$

Doses ranging from 10$^5$ to 10$^9$ CFU of either S. typhimurium NCTCNCTC12023 (wild-type) or the mutants MvP103 and MvP101 were orally inoculated into groups of 10 mice and survival was recorded over 10 days.

$LD_{50}$ of *S. typhimurium* wild-type and mutant strains MvP101 and MvP103 after intraperitoneal infection was determined by inoculation of doses ranging from $10^1$ to $10^7$ CFU into groups of 5 female BALB/c mice of 6–8 weeks of age. Survival was recorded over a period of three weeks. The $LD_{50}$ dose of the challenge strains was calculated by the method of Reed and Muench (Reed and Muench, 1938).

Immunization Protocols

For vaccination, bacteria were grown overnight until they reach medium log phase. Then, they were harvested by centrifugation (3,000×g) and resuspended in 5% sodium bicarbonate. Mice were immunized four times at 15 day intervals by gently feeding them with the bacterial suspension ($10^9$ CFU/mouse) in a volume of approximately 30 µl. Control mice were vaccinated with the carrier, lacking plasmid.

Cytotoxicity Assay

Spleen cells were obtained from mice 14 days after the last immunization and 2×$10^6$ effector cells were restimulated in vitro for 5 days in complete medium supplemented with 20 U/ml of rIL-2 and 20 µM of the βGP1 peptide (β-gal p876–884, TPHPARIGL), which encompasses the immunodominant $H-2L^d$-restricted β-gal epitope. After restimulation, the assay was performed using the [$^3$H]-thymidine incorporation method. In brief, 2×$10^6$ of P815 cells per ml were labelled with [$^3$H]-thymidine for 4 h in either complete medium or complete medium supplemented with 20 µM of βGP1 peptide and used as target cells. Following washing, 2×$10^5$ labelled targets were incubated with serial dilutions of effector cells in 200 µl of complete medium for 4 h at 37° C. Cells were harvested and specific lysis was determined as follows: [(retained c.p.m. in the absence of effectors)–(experimentally retained c.p.m. in the presence of effectors)/retained c.p.m. in the absence of effectors]×100.

EXAMPLE 6

Evaluation of the Induced Immune Response

Induction of Mucosal Immune Responses After Oral Vaccination

To achieve protection against mucosal pathogens using live Salmonella carriers, elicitation of an efficient mucosal response is highly desirable. Therefore, the presence of β-gal-specific antibodies in intestinal washes from mice immunized with either MvP101, MvP103 or SL7207 carrying pAH97 was investigated 52 days after immunization. As shown in FIG. 5., immunization with all three carriers stimulate the production of significant amounts of β-gal-specific IgA and, to a lesser extent, favor the transudation of antigen-specific IgG in the intestinal lumen. No statistically significant differences were observed among the mucosal responses to the different recombinant clones.

Cellular Immune Responses Triggered After Oral Immunization With sseC and sseD Mutants Expressing β-gal To evaluate the efficacy of the antigen-specific T cell responses generated in immunized mice, spleen cells were enriched in CD4+ T cells and restimulated in vitro during four days with β-gal. As shown in FIG. 6, although antigen-specific CD4+-enriched spleen cells were generated after vaccination with the three carriers, MvP103 and MvP101 were significantly more efficient than SL7207 ($P$ 0.05) at triggering specific cellular immune response. In contrast, cells isolated from mice immunized with the carrier alone failed to proliferate in the presence of β-gal.

To investigate the Th-type of immune response triggered by immunization, the content of IFN-γ, IL-2, IL-4, IL-5, IL-6 and IL-10 was measured in the supernatant fluids of restimulated cells. The results demonstrated that a predominant Th1 response pattern was induced in mice immunized with all the carriers. IFN-γ was the only cytokine with significantly increased levels in comparison to those observed in supernatants from spleen cells isolated from mice immunized with plasmidless carriers (FIG. 7). Interestingly, in agreement with the IgG isotype patterns, the levels of IFN-γ detected in supernatants from cells of mice immunized with MvP103 [pAH97] were significantly higher ($P$ 0.05) than those from animals receiving either MvP101 [pAH97] or SL7207 [pAH97] (FIG. 7).

Antigen-specific antibody responses generated in mice orally immunized with the attenuated *S. typhimurium* vaccine carriers expressing the model antigen β-gal.

Groups of mice were immunized with the recombinant strains MvP101 [pAH97] and MvP103 [pAH97]. To estimate the efficacy of the prototypes another group was vaccinated with the well-established carrier strain SL7207 [pAH97]. The abilities of the different carriers to induce a systemic humoral response was determined by measuring the titer of β-gal-specific antibodies in the serum of vaccinated mice. As shown in FIG. 8, significant titers of β-gal-specific IgG and IgM antibodies were detected at day 30 in all vaccinated animals. In contrast to the IgM titers which reach a plateau at day 30, the titers of IgG steadily increased until day 52 from immunization when the experiment was concluded. Although all tested carriers exhibit an excellent performance, the MvP103 mutant was the most efficient at inducing anti-β-gal IgG antibodies ($P$ 0.05). No significant levels of β-gal-specific IgA were detected in mice immunized with any of the three recombinant clones (data not shown).

To determine the subclass distribution of the anti-β-gal IgG, serum samples were analyzed for specific levels of IgG1, IgG2a, IgG2b and IgG3. The results shown in FIG. 9 demonstrate that the main β-gal-specific IgG isotype present in sera of all immunized mice was IgG2, suggesting of a predominant Th1 response. Interestingly, a lower concentration of IgG1 ($P$ 0.05) was observed in mice immunized with MvP103 than in those receiving MvP101 and SL7202, indicating a similar response pattern in animals immunized with the last two carriers.

Sample Collection

Serum samples were collected at different time points and monitored for the presence of β-gal-specific antibodies. At day 52 after immunization, intestinal ravages were obtained by flushing the small intestine with 2 ml of PBS supplemented with 50 mM EDTA, 0.1% bovine serum albumin and 0.1 mg/ml of soybean trypsin inhibitor (Sigma). Then, the lavages were centrifuged (10 min at 600×g) to remove debris, supernatants were removed and supplemented with phenylmethylsulfonyl fluoride (10 mM) and $NaN_3$, and stored at −20° C.

Antibody Assays

Antibody titres were determined by an enzyme-linked immunosorbent assay (ELISA). Briefly, 96 well Nunc-Immuno MaxiSorp™ assay plates (Nunc, Roskilde, Denmark) were coated with 50 µl/well β-gal (5 µg/ml) in coating buffer (0.1 M $Na_2HPO_4$, pH 9.0). After overnight incubation at 4° C., plates were blocked with 10% FCS in PBS for 1 h at 37° C. Serial two-fold dilutions of serum in FCS-PBS were added (100 µl/well) and plates were incubated for 2 h at 37° C. After four washes with PBS-0.05% Tween 20, secondary antibodies were added: biotinylated γ-chain specific goat anti-mouse IgG, µ-chain specific goat anti-mouse IgM, α-chain specific goat anti-mouse IgA antibodies (Sigma, St. Louis, Mo.) or, to determine IgG subclass, biotin-conjugated rat anti-mouse IgG1, IgG2a, IgG2b and IgG3 (Pharmingen) and plates were further incubated for 2 h at 37° C. After four washes, 100 μl of peroxidase-conjugated streptavidin (Pharmingen, St. Diego, Calif.) were added to each well and plates were incubated at room temperature for 1 h. After four washes, reactions were developed using ABTS[2,2'-azino-bis-(3-ethybenzthiazoline-6-sulfonic acid)] in 0.1 M citrate-phosphate buffer (pH 4.35) containing 0.01% $H_2O_2$. End-point titers were expressed as the reciprocal $\log_2$ of the last dilution which gave an optical density at 405 nm 0.1 unit above the values of the negative controls after a 30 min incubation.

To determine the concentration of total Ig present in the intestinal ravages, serial dilutions of the corresponding samples were incubated in microtiter plates that had been coated with goat anti-mouse IgG, IgM and IgA as capture antibodies (100 μg/well, Sigma) and serial dilutions of purified mouse IgG, IgM and IgA (Sigma) were used to generate standard curves. Detection of antigen-specific Ig was performed as described above.

Induction of Antigen-specific CTL Responses in Mice Orally Immunized With the Carrier Strains Expressing β-gal The elicitation of MHC class I restricted responses are particularly important for protection against many intracellular pathogens and tumors. It has been shown that antigen-specific CD8+ CTL can be generated both in vitro and in vivo after immunization with recombinant Salmonella spp. expressing heterologous antigens. Therefore, we considered it important to determine whether the tested carriers were also able to trigger a β-gal-specific CTL response. Spleen cells were collected from mice vaccinated with either MvP101 [pAH97], MvP103 [pAH97] or SL7207 [pAH97] at day 52 from immunization and restimulated in vitro with βGP1-pulsed syngenic spleen cells for 5 days. As shown in FIG. 10, the spleen cells from mice immunized with either of the three constructs induced significant lysis of βGP1-loaded target cells compared with unloaded controls. The more efficient responses were observed using the carrier strain MvP103. The lysis was mediated by CD8+ T cells since the cytotoxic activity was completely abrogated when CD8+ T effector cells were depleted (data not shown).

Cytokine Determination

Culture supernatants were collected from proliferating cells on days 2 and 4, and stored at −70° C. The determination of IL-2, IL-4, IL-5, IL-6, IL-10 and IFN-γ was performed by specific ELISA. In brief, 96-well microtiter plates were coated overnight at 4° C. with purified rat anti-mouse IL-2 mAb (clone JESG-1A12), anti-IL-4 mAb (clone 11B11), anti-IL-5 mAb (clone TRFK5), anti-IL-6 mAb (clone MP5-20F3), anti-IL-10 mAb (clone JES5-2A5), and anti-IFN-γ mAb (clone R4-6A2) (Pharmingen). After three washes, plates were blocked and two-fold dilutions of supernatant fluids were added. A standard curve was generated for each cytokine using recombinant murine IL-2 (rIL-2), rIL-4, rIL-5, rIL-6, rIFN-γ, and rIL-10 (Pharmingen). Plates were further incubated at 4° C. overnight. After washing, 100 μl/well of biotinylated rat anti-mouse IL-2 (clone JES6-5H4), IL-4 (clone BVD6-24G2), IL-5 (clone TRFK4), IL-6 (clone MP5-32C11), IL-10 (clone SXC-1) and INF-γ (clone XMG1.2) monoclonal antibodies were added and incubated for 45 min at RT. After six washes, streptavidin-peroxidase conjugated was added and incubated for 30 min at RT. Finally, the plates were developed using ABTS.

Depletion of CD8+ Spleen Cells.

The CD8+ cell subset was depleted using MiniMACS Magnetic Ly-2 Microbeads according to the manufacturer's instructions (Miltenyi Biotec). Depleted cell preparations contained 1% CD8+ cells.

FACScan Analysis

Approximately $5 \times 10^5$ cells were incubated in staining buffer (PBS supplemented with 2% FCS and 0.1% sodium azide) with the desired antibody or combination of antibodies for 30 min at 4° C. After washes, cells were analysed on a FACScan (Becton Dickinson). The monoclonal antibodies used were FITC-conjugated anti-CD4 and anti-CD8 (clones H129.19 and 53-6.7; Pharmingen).

EXAMPLE 7

Cell Proliferation

Cell Proliferation Assay

Spleen cell suspensions were enriched for CD4+ T cells using MiniMACS Magnetic Ly-2 and indirect goat-anti-mouse-IgG Microbeads according to the instructions of the manufacturer (Mitenyi Biotec GmbH, Germany). Cell preparations contained >65% of CD4+ cells. Cells were adjusted to $2 \times 10^6$ cells/ml in complete medium supplemented with 20 U/ml of mouse rIL-2 (Pharmigen), seeded at 100 μl/well in a flat-bottomed 96-well microtiter plate (Nunc, Roskilde, Denmark) and incubated for four days in the presence of different concentrations of soluble β-gal. During the final 18 hours of culture 1 μCi of [$^3$H]-thymidine (Amersham International, Amersham, U.K.) was added per well. The cells were harvested on paper filters using a cell harvester and the [$^3$H]-thymidine incorporated into the DNA of proliferating cells was determined in a β-scintillation counter.

EXAMPLE 8

Characterization of ssr Genes and Construction and Characterization of the ssr Mutant S. typhimurium Strains MvP284 MvP320 and MvP333

Homology of the Two Component Regulator Genes ssrA and ssrB of SPI2 With Other Bacterial Proteins The SPI2 gene ssrA encodes a protein similar to sensor components of bacterial two component regulatory systems as has been described before (Ochman et al., 1996). For consistency with the nomenclature of SPI2 virulence genes (Hensel et al., 1997b; Valdivia and Falkow, 1997), this gene is designated ssrA. Downstream of ssrA, an ORF with coding capacity for a 24.3 kDa protein was identified. This gene shares significant similarity with a family of genes encoding transcriptional activators like DegU of Bacillus subtilis, UvrY of E. coli and BvgA of Bordetella pertussis. Therefore, it is likely that the protein acts as the regulatory component of the ssr system and the gene was designated ssrB.

Inverse Regulation of SPI1 and SPI2

The expression of the type III secretions systems of SPI1 and SPI2 is tightly regulated by environmental conditions. While SPI1 is induced during late log/early stationary phase after growth in rich media of high osmolarity and limiting $O_2$ (oxygen) concentration, no induction of SPI2 gene expression was observed. In contrast, after growth in minimal medium with limiting amounts of $Mg^{2+}$ (8 μM) the ssaB::luc fusion was highly expressed while the sipC::lacZ fusion was not expressed. The expression of the ssaB::luc fusion is dependent on the function of SsrA/B, since there is no expression in the ssrB-negative background strain P8G12 (Hensel et al., 1998). The expression of the sipC::lacZ fusion is dependent on HilA, the transcriptional regulator of SPI1.

We also observed that a mutation in ssrB affects expression of the sipC::lacZ fusion. This indicates that SPI2 has a regulatory effect on the expression of SPI1 genes.

Bacterial strains harbouring a luc fusion to ssaB in SPI2 (strain MvP131) and a lacZ fusion to sipC in SPI1 (strain MvP239) were grown under conditions previously shown to induce SPI gene expression. Bacteria were grown over night in minimal medium containing 8 μM $Mg^{2+}$ or over night in LB broth containing 1% NaCl (LB 1% NaCl). The Luc activity of strain MvP131 and β-galactosidase activity of strain MvP239 were determined. As a control, both reporter fusions were assayed in the ssrB negative strain background of P8G12.

Expression levels of lacZ reporter-gene fusions to SPI genes were assayed as described by Miller, 1992.

Construction and Analysis of sseA Reporter Gene Fusion

A 1.1 kb SmaI/HincII fragment of p5-4 was subcloned into pGPLO1, a suicide vector for the generation of luc fusions (Gunn and Miller, 1996). The resulting construct, in which 1.0 kb upstream and 112 bp of sseA is transcriptionally fused to luc was used to transform E. coli S17-1 λpir, and conjugational transfer to S. typhimurium performed as described previously (Gunn and Miller, 1996). Strains that had integrated the reporter gene fusion into the chromosome by homologous recombination were confirmed by PCR and Southern hybridization analysis. Subsequently, the fusion was moved by P22 transduction into the wild-type and various mutant strain backgrounds with mTn5 insertions in SPI1 or SPI2 genes (Maloy et al., 1996). As a control, a strain was constructed harbouring a chromosomal integration of pLBO2, a suicide plasmid without a promoter fusion to the luc gene (Gunn and Miller, 1996). For the analysis of gene expression, strains were grown for 16 h in minimal medium with aeration. Aliquots of the bacterial cultures were lysed and luciferase activity was determined using a luciferase assay kit according to the manufacturer's protocol (Boehringer Mannheim). Photon detection was performed on a Microplate scintillation/luminescence counter (Wallac, Turku). All assay were done in triplicate, and replicated on independent occasions.

Expression of sseA is Dependent on SsrAB

To establish if the sse genes are part of the SPI2 secretion system, the expression of an sseA::luc reporter gene fusion, integrated by homologous recombination into the chromosome of different SPI2 mutant strains, has been investigated (FIG. 11). Transcriptional activity of sseA in a wild-type background during growth in minimal medium was dramatically reduced by inactivation of the SPI2 two-component system. Transposon insertions in ssrA (mutant strain P3F4) and ssrB (mutant strain P8G12), encoding the sensor component and the transcriptional activator, respectively, resulted in 250 to 300-fold reduced expression of sseA. Inactivation of hilA, the transcriptional activator of SPI1 (Bajaj et al., 1996), had no effect on sseA gene expression. Transposon insertions in two genes encoding components of the SPI2 type III secretion apparatus (ssaJ::mTn5 and ssaT-::mTn5; mutant strains P11D10 and P9B7; Shea et al., 1996) also had no significant effect on the expression of sseA. These data show that SsrA/B is required for the expression of sseA, but that hilA is not.

Expression of SPI2 Genes Within Macrophages is Dependent on SsrA/B

The presence of S. typhimurium within eukaryotic cells (macrophages) induces the expression of SPI2 genes as indicated by analysis of fusions to ssaB and ssaH. This expression is dependent on the two component regulatory system SsrA/B encoded by SPI2.

The murine macrophage-line cell line J744 was used for this experiment. Macrophages were infected at a multiplicity of infection of 10 bacteria per macrophage with MvP131 (luc fusion to ssaB), MvP266 (luc fusion of ssaH) and MvP244 (luc fusion to ssaB in a ssrB negative background). Extracellular bacteria were killed by the addition of gentamicin (20 μg/ml). At various time points, macrophages were lysed by the addition of 0.1% Triton X-100, and intracellular bacteria were enumerated by plating serial dilutions onto LB agar plates. A further aliquot of the bacteria was recovered and the luciferase activity was determined. Luciferase activities were expressed a relative light emission per bacteria.

Effects of a Mutation in ssrB on the Secreted Effector Protein of SPI1 SipC

Analysis of proteins secreted into the growth medium by the S. typhimurium SPI2 mutant strain MvP320 (non-polar mutation in a, FIG. 12) revealed the absence or strong reduction in the amounts of the secreted SPI effector protein (Hensel et al., 1997b). These SPI2 mutants are also reduced in their ability to invade cultured epithelial cells or cultured macrophages (Hensel et al., 1997b). To examine this phenomenon in greater detail, we expressed recombinant SipC (rSipC) and raised antibodies against rSipC in rabbits. In Western blots, antiserum against rSipC reacted with a 42 kDa protein from precipitates of culture supernatants of S. typhimurium wild-type strain NCTC12023. No reaction was observed with supernatants from cultures of EE638, a strain deficient in SipC (Hueck et al., 1995). Furthermore, in Western blots SipC could not be detected in culture supernatants of the SPI2 mutants MvP320. However, SipC was detected in culture supernatants of other SPI2 mutants like P2D6 (ssaV::mTn5), P9B6 (ssaV::mTn5) and NPssaV (ssaV::aphT) (Deiwick et al., 1998). The detection by antiserum of SipC in culture supernatants of various strains was in accord with the presence or absence of SipC as detected by SDS-PAGE. Further it was analyzed whether the absence of SipC in culture supernatants of SPI2 mutant strains was due to defective secretion of SipC via the type III secretion system or reduced synthesis of SipC in these strains. Antiserum against rSipC was used to detect SipC in pellets of cultures grown under inducing conditions for the expression of SPI1 genes (i.e. stationary phase, high osmolarity, low oxygen) (Bajaj et al., 1996). Analysis of wild-type and strains carrying various mutations in SPI1 and SPI2 genes indicated highly reduced amounts of SipC in the mutants with a non-polar mutation in ssrB. However, SipC was detected at levels comparable to those observed in pellets of wild-type cultures and SPI2 mutant strains P2D6, P9B6 and NPssaV. The effect on SipC synthesis is not due to reduced growth rates or reduced protein levels in SPI2 mutants, since both parameters were comparable for the wild-type and SPI2 mutants.

Effects of a Mutation in the SPI2 Gene ssrB on the Expression of SPI1 Genes

In order to assay the effect of SPI2 mutations on the expression of SPI1 genes, previously characterized fusions of lacZ to various SPI1 genes (Bajaj et al., 1995; Bajaj et al., 1996) were transduced into the SPI2 mutant MvP320 and various SPI1 mutants to generate a set of reporter fusion strains. The expression of the reporter β-galactosidase in cultures grown under conditions inducing for SPI1 expression (see above) was assayed. A Tn insertion in hilA (P4H2) reduced the expression of prgK as well as sipC, while an insertion in spaRS (P6E11) only affected the expression of sipC. Some mutant strains with a mutation in the SPI2 gene ssrB encoding a components of the two component regulatory system showed reduced expression of reporter fusions to prgK and sipC (FIG. 11). The effects on the expression of both genes was similar. Other mutant strains with Tn insertions in ssaV (P2D6, P9B6), as well as mutant NPssaV harbouring a non-polar insertions in ssaV, had levels of expression of prgK and sipC comparable to that of corresponding reporter fusions in a wild-type genetic background. Analysis of lacZ fusions to prgH and invF revealed a similar effect on expression as shown for prgK and sipC.

A Mutation in the SPI2 Gene ssrB Affects Expression of the SPI1 Regulator hilA

Analysis of reporter fusions to sipC and prgK indicated that expression of genes in two different operons of SPI1 can be affected by SPI2 mutations, suggesting that these mutations affect other SPI1 genes involved in regulation of sipC and prgK. It has been demonstrated previously that the expression of SPI1 genes is under the control of the transcriptional activator HilA. (Bajaj et al., 1995; Bajaj et al., 1996). The expression of hilA was therefore analyzed in the presence of a SPI2 mutation in ssrB. The SPI2 mutant strain MvP320 had largely diminished levels of hilA expression. Again, very low levels of hilA expression were observed in mutants that had reduced levels of prgk and sipC expression. To analyze whether the effect of the SPI2 mutation on sipC expression resulted from the reduced expression of hilA, we next performed complementation experiments in various mutant strains harbouring pVV135 (constitutive expression of hilA) (Bajai et al., 1996) or pVV214 (expression of hilA from the native promoter) (Bajaj et al., 1995). In accordance with a previous study (Bajaj et al., 1995), the hilA mutation of strain P4H2 was complemented by pVV214. However, the sipC expression was not restored in the mutant strain MvP320 harbouring either pVV135 or pVV214.

Construction of the ssrA and ssrB mutant S. typhimurium strains MvP284 and MvP320

Mutant MvP284, ssrA. The ssrA gene (FIG. 12) was subcloned from the phage clone λ2 derived plasmid p2-2 on a 5.7 kb BamHI fragment in pUC18 as indicated in Table 1. A 1.6 kb fragment was recovered after HindIII and EcoRV digestion of p2-2 and subcloned in HindIII/HincII-digested pBluescript II KS+. The resulting construct termed p2-20 was digested with HincII and dephosphorylated with alkaline phosphatase. The aphT cassette was isolated as described above and ligated to the linearized plasmid p2-20 in the same orientation into the unique HincII site. After transformation of E. coli XL-1 Blue and selection against kanamycin and carbenicillin (50 µg/ml each) one clone has been chosen and the harbouring plasmid isolated. This plasmid was termed p2-21 and its identity proved via restriction analysis. p2-21 was further digested with KpnI and XbaI, a 2.5 kb fragment isolated and ligated to KpnI/XbaI-digested pKAS32. This plasmid was electroporated into E. coli CC118 λpir and transformants selected to kanamycin and carbenicillin (50 µg/ml each). As done before, one clone was chosen, its plasmid with the according DNA fragment in pKAS32, termed p2-22, isolated and confirmed by restriction analysis. Plasmid p2-22 was electroporated into E. coli S17-1 λpir and transferred into S. typhimurium NCTC12023 (streptomycin resistant) by conjugation as has been described previously (de Lorenzo and Timmis, 1994). Exconjugants in which the ssrA gene had been replaced by the cloned gene disrupted by insertion of the aphT cassette were selected by its growth on M9+glucose minimal medium agar plates (Maloy et al., 1996) and its resistance to kanamycin and carbenicillin (100 µg/ml). The resulting exconjugants were finally shown to have a lactose negative phenotype and to be sensitive to kanamycin and streptomycin. Selected clones were further examined by Southernblot analysis. In order to exclude possible mutations which might have been developed during the cloning procedure the mutated ssrA allele was transfered into a fresh Salmonella background by P22 transduction (described by Maloy et al., 1996). The resulting Salmonella strain MvP284 was examined for the presence of the resistance cassette within the ssrA gene by the use of primers ssrA-For (5'-AAG GAA TTC AAC AGG CAA CTG GAG G-3') (SEQ ID NO:64) and ssrA-Rev (5-CTG CCC TCG CGA AAA TTA AGA TAA TA-3') (SEQ ID NO:65). Amplification of DNA from clones containing the wild-type ssrA allele resulted in a PCR product of 2800 bp, use of DNA from clones harbouring a ssrA allele disrupted by the aphT cassette resulted in a PCR product of 3750 bp. The resulting Salmonella strain MvP320 was examined for the presence of the resistance cassette within the ssrB gene by the use of Southern hybridization analysis of total DNA of exconjugants.

Mutant MvP320, ssrB. The ssrB gene (FIG. 12) was subcloned from the phage clone e1 derived plasmid p1-6 on a 4.8 kb PstI/BamHI-fragment in pT7-Blue as indicated in Table 1. A 1.7 kb fragment was recovered after BamHI and HincII digestion of p1-6 and subcloned in BamHI/HincII-digested pBluescript II KS+. The resulting construct-termed p1-20 was digested with EcoRV and dephosphorylated with alkaline phosphatase. The aphT cassette was isolated as described above and ligated to the linearized plasmid p1-20 in the same orientation into the unique EcoRV site. After transformation of E. coli XL-1 Blue and selection against kanamycin and carbenicillin (50 µg/ml each) one clone has been chosen and the harbouring plasmid isolated. This plasmid was termed p1-21 and its identity confirmed by restriction analysis. p1-21 was further digested with KpnI and XbaI, a 2.5 kb fragment isolated and ligated to KpnI/XbaI-digested pKAS32. This plasmid was electroporated into E. coli CC118 λpir and transformed bacteria selected to kanamycin and carbenicillin (50 µg/ml each) was performed. As done before, one clone was chosen, its plasmid with the according DNA fragment in pKAS32, termed p1-22, isolated and confirmed by restriction analysis. Plasmid p1-22 was electroporated into E. coli S17-1 λpir and transferred into S. typhimurium NCTC12023 (streptomycin resistant) by conjugation as has been described previously (de Lorenzo and Timmis, 1994). Exconjugants in which the ssrB gene had been replaced by the cloned gene disrupted by insertion of the aphT cassette were selected by its growth on M9+glucose minimal medium agar plates (Maloy et al., 1996) and its resistance to kanamycin and carbenicillin (100 µg/ml). The resulting exconjugants were finally shown to have a lactose negative phenotype and to be sensitive to kanamycin and streptomycin. Selected clones were further examined by Southernblot analysis. In order to exclude possible mutations which might have been acquired during the cloning procedure the mutated ssrB allele has been transferred into a fresh Salmonella background by P22 transduction (described by Maloy et al., 1996). Screening of mutants with a insertion of the aphT cassette within the ssrB locus was performed by PCR using primers ssrB-For (5'-CTT AAT TTT CGC GAG GG-3') (SEQ ID NO:66) and ssrB-Rev (5'-GGA CGC CCC TGG TTA ATA-3') (SEQ ID NO:67). Amplification of DNA from clones containing the wild-type ssrB allele resulted in a PCR product of 660 bp, use of DNA from clones harbouring a ssrB allele disrupted by insertion of the aphT cassette resulted in a PCR product of 1600 bp. The resulting Salmonella strain MvP320 was examined for the presence of the resistance cassette within the ssrB gene by the use of Southern hybridization analysis of total DNA of exconjugants.

Construction of the Mutant Strain MvP340 Carrying an In-frame Deletion in ssrA

A deletion of 407 codons between codon 44 and 451 of ssrB was generated. Plasmid p2-2 was digested by BamHI and KpnI, a fragment of 3.7 kb was recovered and subcloned in pBluescript KS+ to generate p2-50. Plasmid p2-50 was linearized by digestion with PstI, which cuts once within the subcloned fragment of the ssrA gene. Primers ssrA-del-1 (5'-GGT CTG CAG GAT TTT TCA CGC ATC GCG TC-3') (SEQ ID NO:68) and ssrB-del-2 (5'- GGT CTG CAG AAC CAT TGA TAT ATA AGC TGC-3') (SEQ ID NO:69) were designed to introduce PstI sites. PCR was performed using linearized p2-50 as template DNA. The TaqPlus polymerase (Stratagene) was used according to the instructions of the manufacturer. Reactions of 100 µl volume were set up using 10 µl of 10×TaqPlus Precision buffer containing magnesium chloride, 0.8 µl of 100 mM dNTPs, 250 ng DNA template (linearized p2-50), 250 ng of each primer and 5 U of TaqPlus DNA polymerase. PCR was carried out for 35 cycles of: 95EC for 1 minute, 60EC for 1 minute, 72EC for 6 minutes. Then a final step of 72EC for 10 minutes was added. 10 µl of the PCR reaction were analyzed. A product of the expected size was recovered, digested by PstI, self-ligated, and the ligation mixture was used to transform E. coli DH5α to resistance to carbenicillin. Plasmids were isolated from transformants and the integrity of the insert and the deletion was analyzed by restriction analysis and DNA sequencing. The insert of a confirmed construct was isolated after digestion with XbaI and KpnI and ligated to XbaI/KpnI-digested vector pKAS32. The resulting construct was used to transform E. coli S17-1 λpir to resistance to carbenicillin, and conjugational transfer of the plasmid to S. typhimurium (Nal$^R$, Strep$^R$) was performed according to standard procedures (de Lorenzo and Timmis, 1994). Exconjugants that had integrated the suicide plasmid by homologous recombination were selected by resistance to nalidixic acid and carbenicillin, and screened for sensitivity to streptomycin. Such clones were grown in LB to OD600 of about 0.5 and aliquots were plated on LB containing 250 µg/ml streptomycin to select for colonies which had lost the integrated plasmid and undergone allelic exchange. Clones resistant to streptomycin but sensitive to carbenicillin were used for further analysis. Screening of mutants with a deletion within the ssrA locus was performed by PCR using primers ssrA-For (5'-AAG GAA TTC AAC AGG CAA CTG GAG G-3') (SEQ ID NO:64) and ssrA-Rev (5-CTG CCC TCG CGA AAA TTA AGA TAA TA-3') (SEQ ID NO:65). Amplification of DNA from clones containing the wild-type ssrA allele resulted in a PCR product of 2800 bp, use of DNA from clones harbouring a ssrA allele with an internal deletion resulted in a PCR product of 1580 bp. The integrity of clones harbouring the ssrA deletion was further confirmed by Southern analysis of the ssrA locus. Finally, the ssrA locus containing the internal in-frame deletion was moved into a fresh strain background of S. typhimurium by P22 transduction (Maloy et al., 1996) and the resulting strain was designated MvP340.

Southern Hybridization

Genomic DNA of Salmonella was prepared as previously described (Hensel et al., 1997). For Southern hybridization analysis, genomic DNA was digested with EcoRI or EcoRV, fractionated on 0.6% agarose gels and transferred to Hybond N$^+$ membranes (Amersham, Braunschweig). Various probes corresponding to the ssrA and ssrB region were obtained as restriction fragments of the subcloned insert of λ1 and λ2.

EXAMPLE 9

Evaluation of Safety of S. typhimurium Strain MvP320

For competition assays between S. typhimurium wild-type and the mutant strain MvP320, bacteria were grown in LB to an optical density at 600 nm of 0.4–0.6. Cultures were diluted and aliquots of the two cultures were mixed to form an inoculum containing equal amounts of both strains. The ratio of both strains was determined by plating dilutions on LB plates containing antibiotics selective for individual strains. An inoculum of about $10^4$ colony forming units (cfu) was used to infect 6 to 8 weeks old female BALB/c mice (Charles River Breeders, Wiga) by injection into the peritoneal cavity. At several time points after infection mice were sacrificed by cervical dislocation and the bacterial load of liver and spleen was determined by plating tissue homogenates using the 'WASP' (Meintrup, Lähden) spiral plating device. Plating was performed using LB plates containing 50 µg/ml kanamycin or 100 µg/ml nalidixic acid to select for the mutant strains or the wild-type, respectively.

Strain MvP320 harbouring the aphT gene cassette in ssrB was recovered in at least 1000-fold lower numbers than the S. typhimurium wild-type strain. These data indicate that ssrB contributes significantly to systemic infections of S. typhimurium in the mouse model of salmonellosis.

Statistical Analysis of all Experiments.

Statistical significance between paired samples was determined by Student's t test. The significance of the obtained results was determined using the statgraphic plus for windows 2.0 software (Statistical Graphic Corp.).

EXAMPLE 10

Characterization of the in vivo Inducible $P_{saaE}$ Promoter (Promoter B, FIG. 24B)

The promoter which is located upstream of ssaE ($P_{ssaE}$, formerly called Promoter B) was shown to be regulated by the ssrAB locus. A DNA fragment comprising nucleotide 800 to 120 (800–1205) in the included sequence (FIG. 21A) was shown to confer ssrB-dependent regulation upon the expression of a reporter gene (gfp) fused to the promoter. The DNA fragment was cloned on a low-copy plasmid in front of the gfp gene. As has been shown previously for other reporter gene constructs, induction of expression from $P_{ssaE}$ (800–1205) was observed in magnesium minimal medium (Deiwick et al., 1999) and was dependent on the presence of a chromosomal wild type allele of ssrB. A shorter DNA fragment, comprising nucleotide 923 to 1205 (923–1205) in the included sequence, did not confer regulation upon expression of gfp. However, expression was reduced compared to the $P_{ssaE}$ (800–1205) fragment and was not induced in magnesium minimal medium nor was it dependent on ssrB. Thus, the $P_{ssaE}$ (800–1205) fragment comprises promoter active and regulatory sequences, probably including an SsrB-binding site.

DESCRIPTION OF THE DRAWINGS

FIG. 2a. Alignment of the deduced SseB amino acid sequence to EspA of EPEC (Elliot et al., 1998) (SEQ ID NO:40). The ClustalW algorithm of the MacVector 6.0 program was used to construct the alignments. Similar amino acid residues are boxed, identical residues are boxed and shaded.

FIG. 2b. Alignment of the deduced SseC amino acid sequence to EspD of EPEC (Elliot et al., 1998) (SEQ ID NO:41), YopB of *Yersinia enterocolitica* (Hakansson et al., 1993) (SEQ ID NO:42), and PepB of *Pseudomonas aeruinosa* (Hauser et al., 1998) (SEQ ID NO:43). The ClustalW algorithm of the MacVector 6.0 program was used to construct the alignments. Positions where at least three amino acid residues are similar are boxed, where at least three residues are identical are boxed and shaded.

FIG. 12. Map of Salmonella Pathogenicity Island 2 (A) indicating the positions of the mutations in strains MvP284 and MvP320 (B). A partial restriction map of the genomic region is shown, and the position of inserts of plasmids relevant for this work is indicated (C). B, BamHI; C, ClaI; H, HindIII; P, PstI; V; S, SmaI; EcoRV; II, HincII.

FIG. 16 illustrates the selective marker cassette.

FIG. 17 illustrates the gene expression cassette and the induction thereof in a two-phase system. The gene expression cassette comprises a promoter, optionally a gene cassette comprising one or more expression units and optionally one or more transcriptional terminators for the expression units and/or a transcribed sequence 5' to the gene expression cassette.

FIG. 18 shows the structural requirements of the gene expression unit for the delivery of heterologous antigens into various compartments, i.e. accessory sequences that direct the targeting of the expression product.

Figures 1A, 1B, 1C:
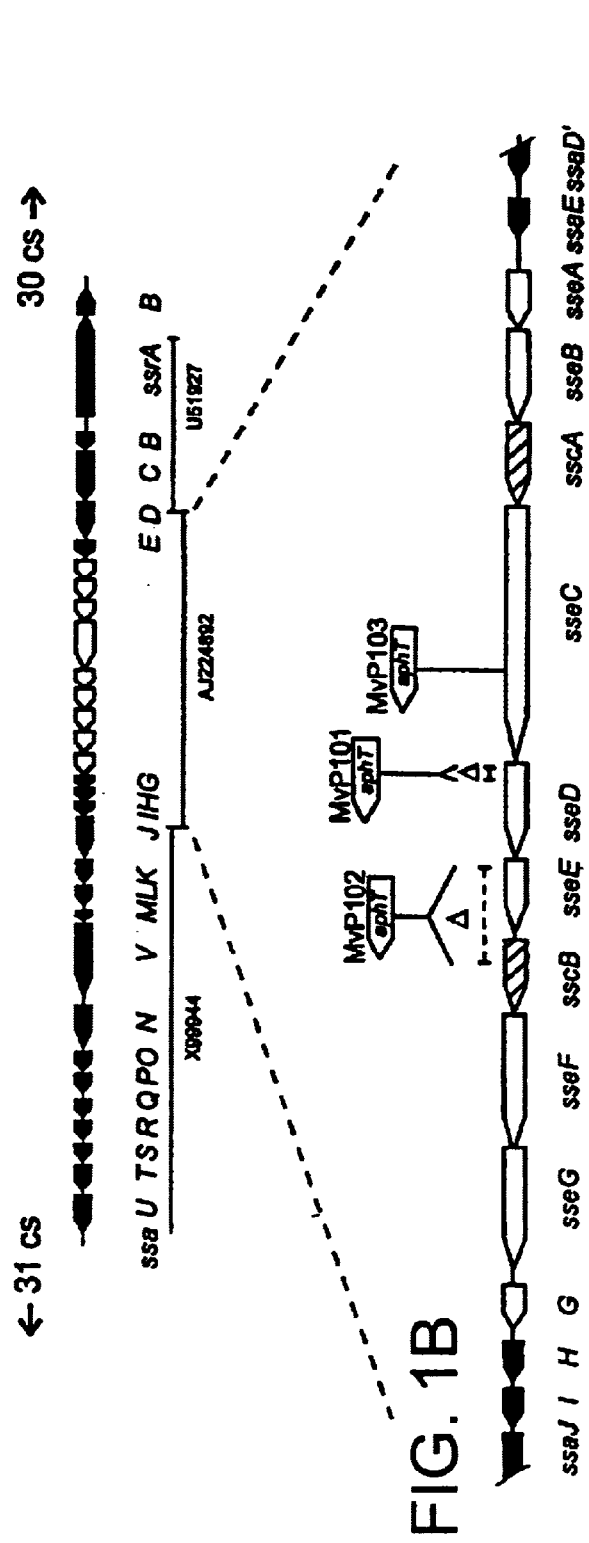
FIG. 1. Map of Salmonella Pathogenicity Island 2 (A) indicating the positions of the mutations in strains MvP101, MvP102, and MvP103 (B). A partial restriction map of the genomic region is shown, and the positions of plasmid inserts relevant for this work are indicated (C). B, BamHI; C, ClaI; E, EcoRI; P, PstI; V, EcoRV; S, SmaI; EMBL database accession numbers are indicated for the sequences in (A).
Figure 3:
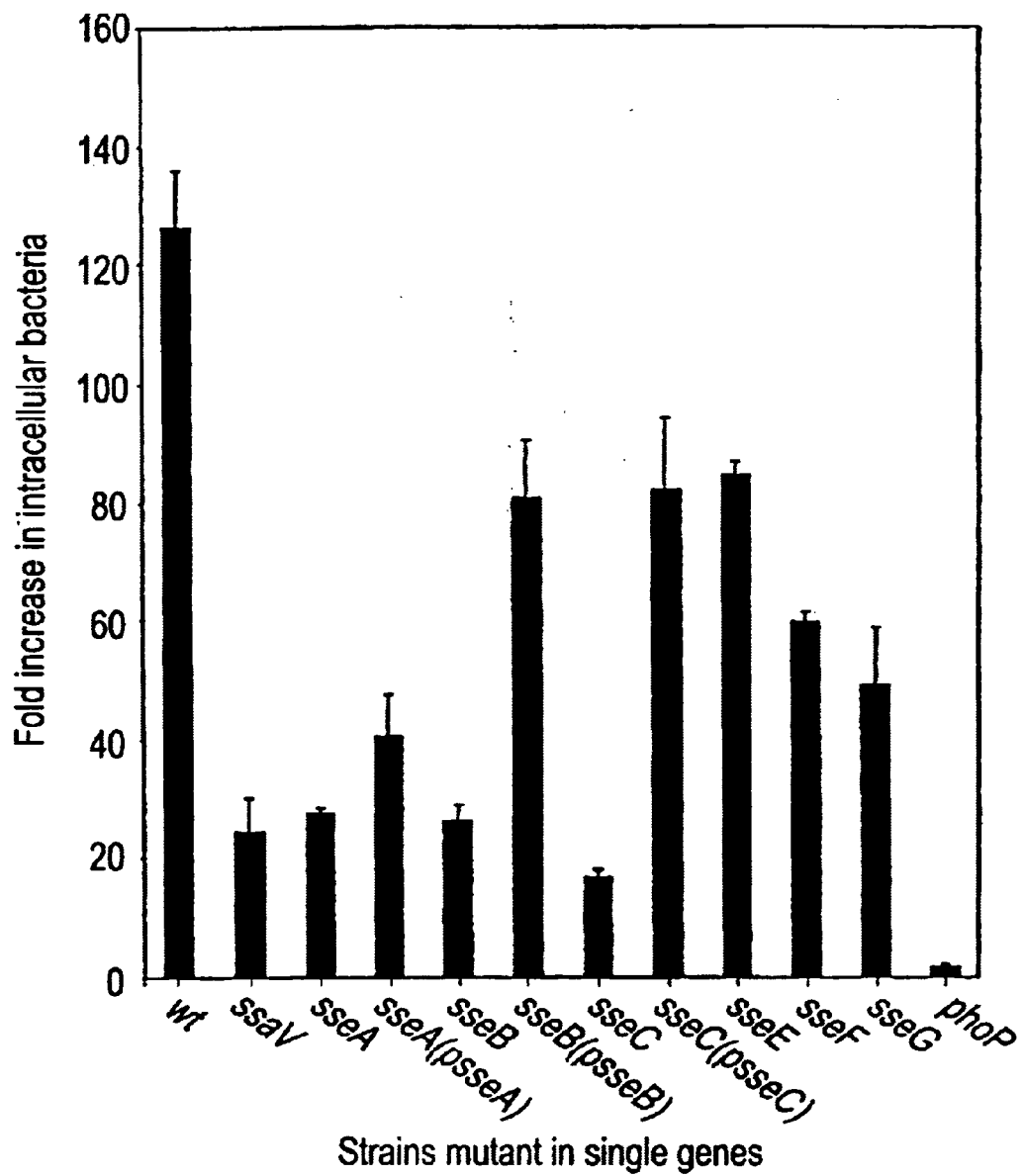
FIG. 3. Intracellular accumulation of *S. typhimurium*. SPI2 mutants in RAW 264.7 macrophages. Following opsonization and infection, macrophages were lysed and cultured for enumeration of intracellular bacteria (gentamicin protected) at 2 h and 16 h post-infection. The values shown represent the fold increase calculated as a ratio of the intracellular bacteria between 2 h and 16 h post-infection. Infection was performed in in triplicates for each strain and the standard error from the mean is shown.
Figure 4A:
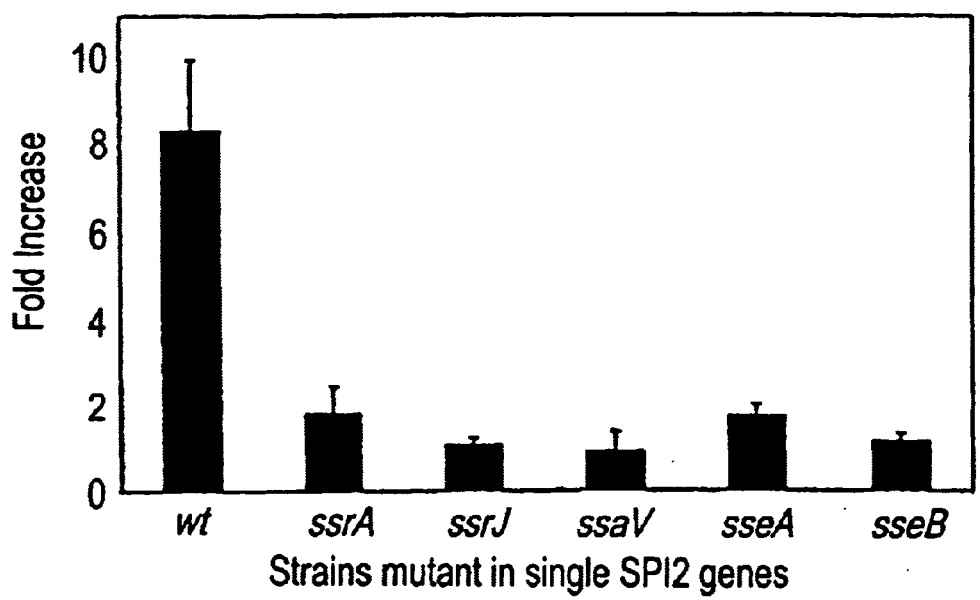
FIG. 4. Intracellular survival and replication of SPI2 mutant *S. typhimurium* in (A) J774.1 cells and (B) periodate-elicited peritoneal macrophages from C3H/HeN mice. After opsonization and internalization, phagocytes were lysed and cultured for enumeration of viable intracellular bacteria at time 0 h. The values shown represent the proportion of this intracellular inoculum viable at 20 h±the standard error of the mean. Samples were processed in triplicate, and each experiment was performed at least twice.
Figure 4B:
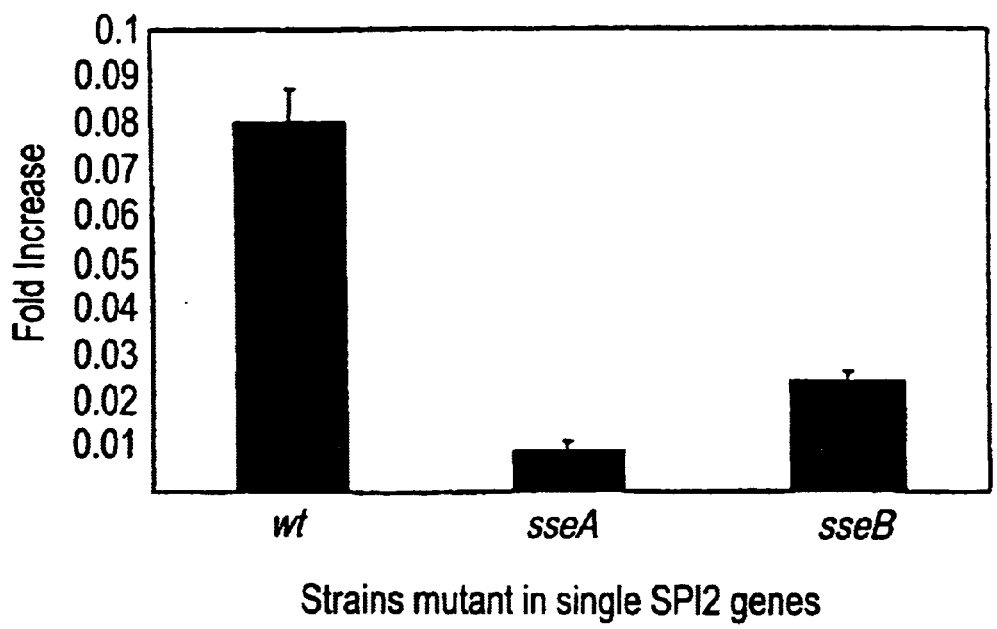
Figure 5:
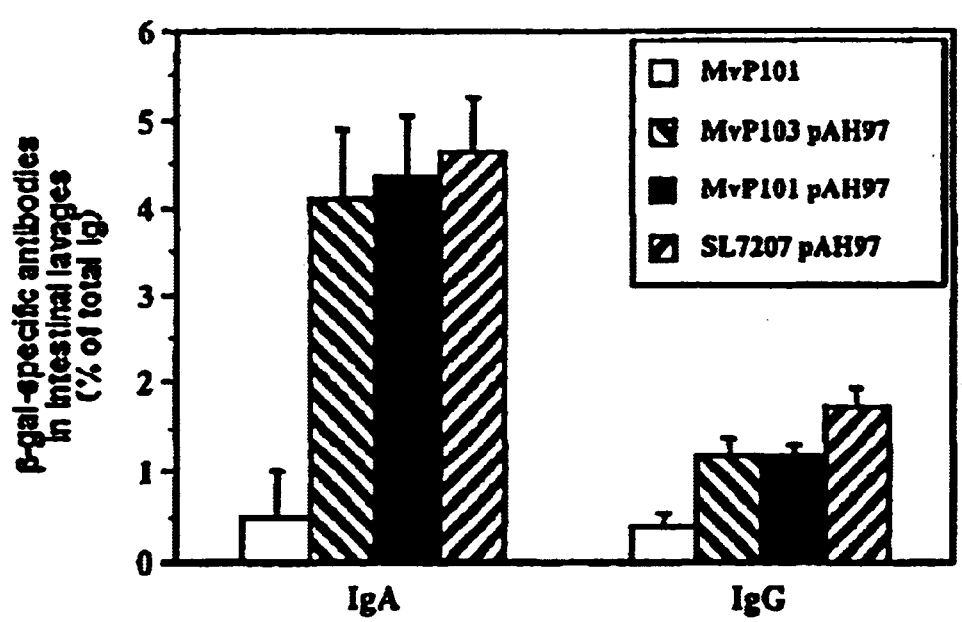
FIG. 5. β-gal-specific antibodies in intestinal lavages of mice orally immunized with either MvP101[pAH97], MvP103 [pAH97], SL7207 [pAH97] or MvP101 at day 52 after immunization. Results are expressed as percentage of the corresponding total Ig subclass present in the intestinal lavage, the SEM is indicated by vertical lines. Significant levels of antigen-specific IgM could not be detected in any of the groups. The results obtained with MvP103 and SL7207 (not shown) were similar to those for MvP101.
Figure 6:
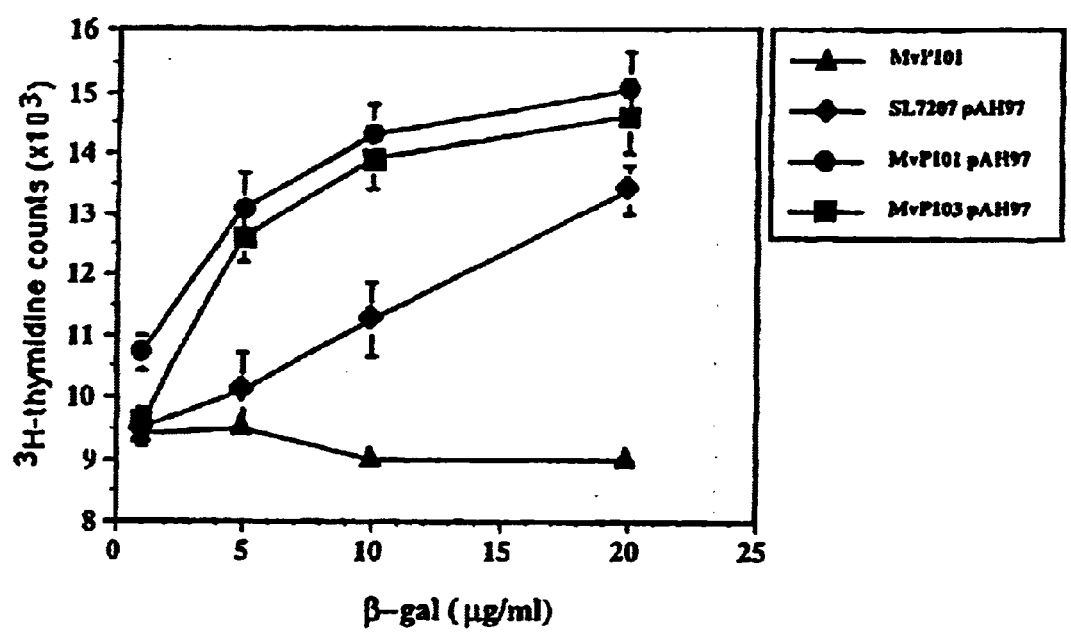
FIG. 6. β-gal-specific proliferative response of CD4+ enriched spleen cells from mice orally immunized with either MvP101 [pAH97], MvP103 [pAH97], SL7207 [pAH97] or MvP101. Cells were restimulated in vitro during a 4 day incubation with different concentrations of soluble β-gal. The values are expressed as mean cpm of triplicates; the SEM was in all cases lower than 10%. Background values obtained from wells without the stimulating antigen were subtracted. Results obtained with MvP103 and SL7207 (not shown) were similar to those obtained with MvP101.
Figure 7:
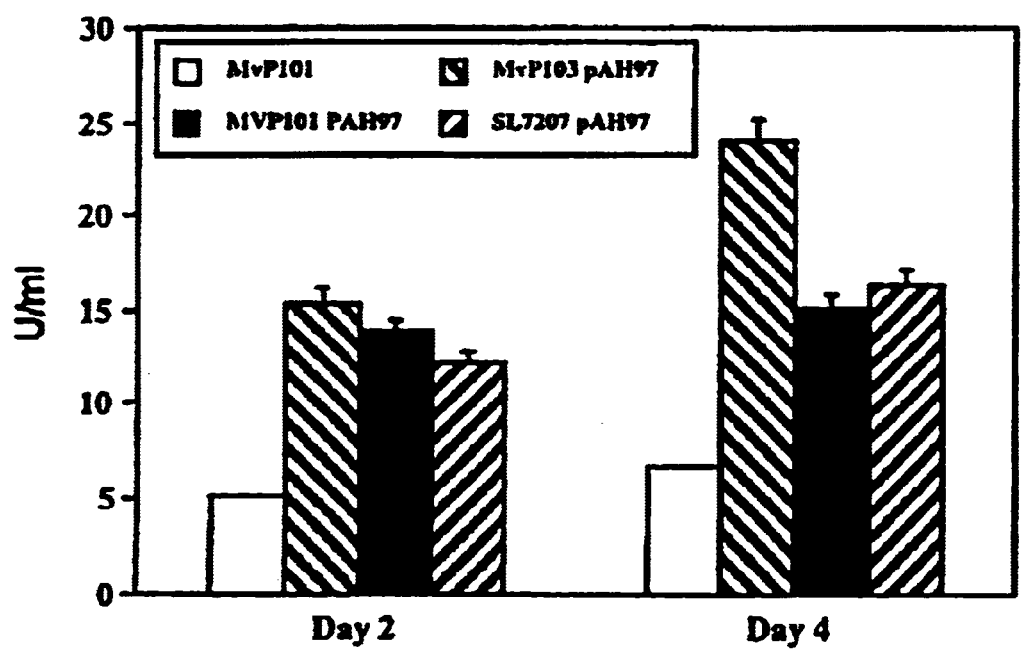
FIG. 7. IFN-γ present in supernatants from cultured CD4+ enriched spleen cells of mice orally immunized with either MvP101 [pAH97], MvP103 [pAH97], SL7207 [pAH97] or plasmidless MvP101 at day 2 and 4 of culture. Spleen cells were isolated from mice at day 52 after immunization, and CD4+ enriched populations were restimulated in vitro for four days in the presence of soluble β-gal (20 µg/ml). IFN-γ production was determined by ELISA, results represent the means of three determinations. The SEM is indicated by vertical lines, similar results were obtained using any of the plasmidless carriers (not shown). No significant differences with the control groups were observed when IL-2, IL-4, IL-5, IL-6 and IL-10 were tested (not shown).
Figure 8:
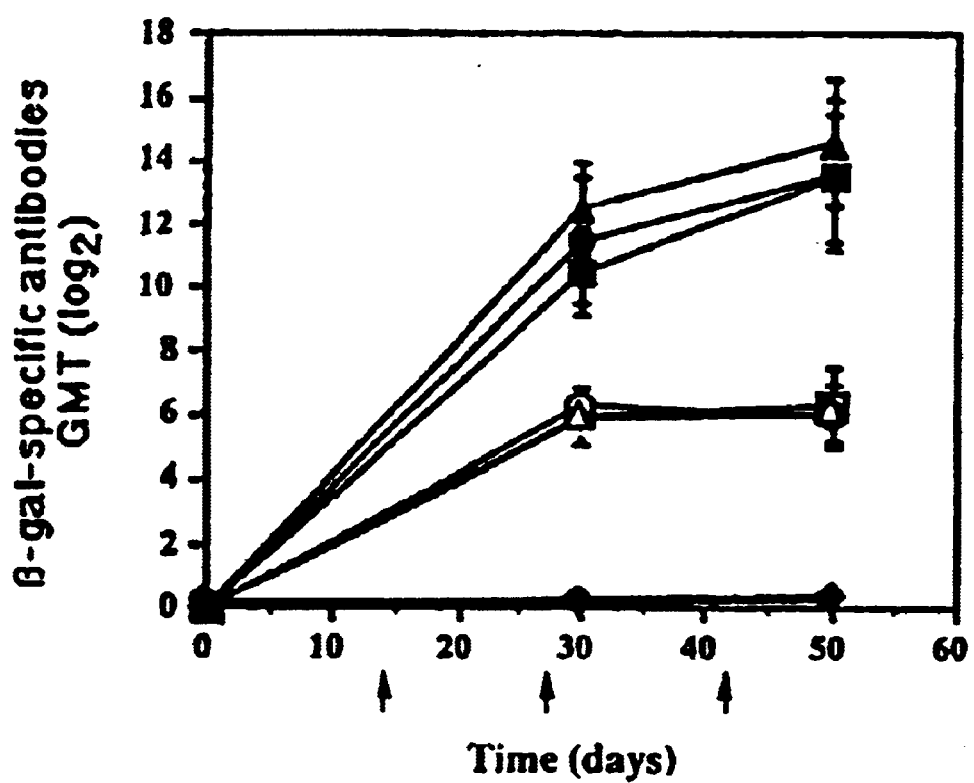
FIG. 8. Kinetics of the β-gal-specific serum IgG (closed symbols) and IgM (open symbols) antibody responses in mice (n=5) after oral immunization with either MvP101 [pAH97] (triangle), MvP103 [pAH97] (circle), SL7207 [pAH97] (square) or plasmidless MvP101 (diamond). Results are expressed as the reciprocal $\log_2$ of the geometric mean end point titer (GMT), the SEM was in all cases lower than 10%. Similar results were obtained using any of the plasmidless carriers (not shown), immunizations are indicated by arrows.
Figure 9:
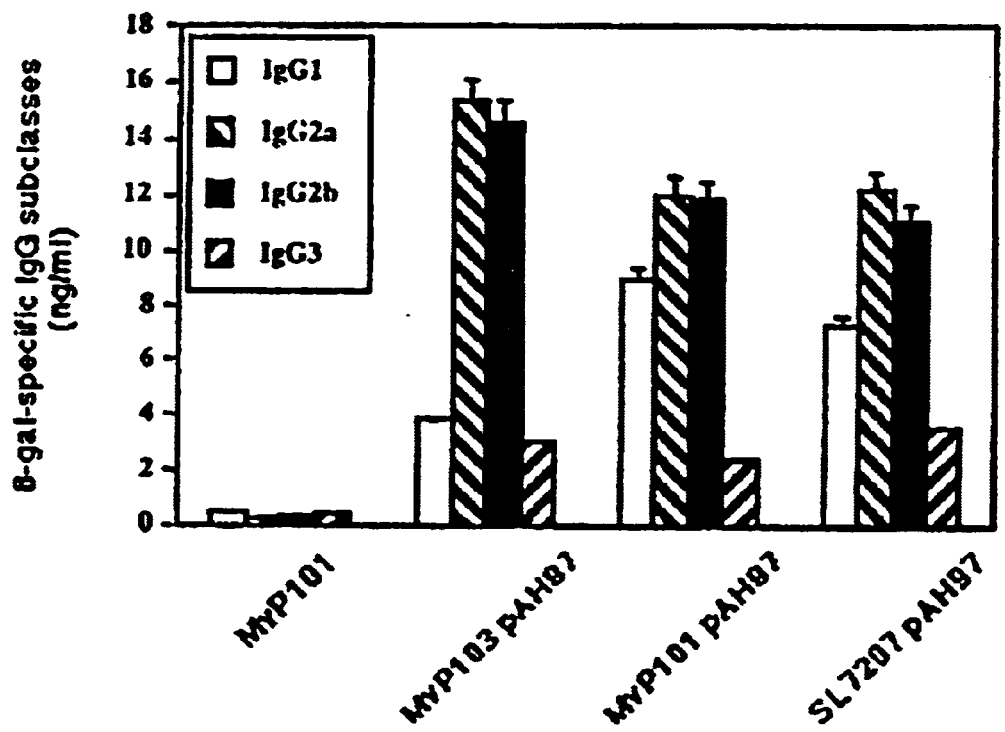
FIG. 9. Subclass profiles of the β-gal-specific IgG antibodies present in the serum of mice (n=5) orally immunized with either MvP101 [pAH97], MvP103 [pAH97], SL7207 [pAH97] or plasmidless MvP101 at day 52 post-immunization. Results are expressed as ng/ml, the SEM is indicated by vertical lines. Similar results were obtained using any of the plasmidless carriers (not shown).
Figure 10:
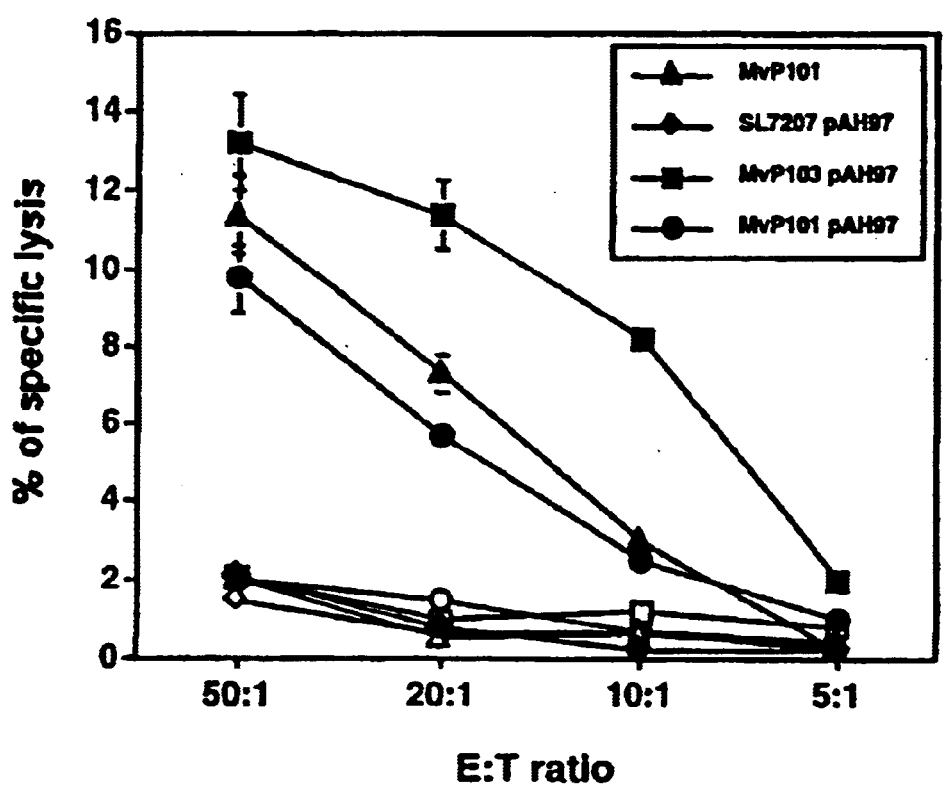
FIG. 10. Recognition of the MHC class I-restricted βGP1 epitope by lymphocytes primed in vivo in mice by oral vaccination with either MvP101 [pAH97], MvP103 [pAH97], SL7207 [pAH97] or plasmidless MvP101. Spleen cells from immunized mice were restimulated in vitro five days in the presence of 20 µM βGP1. At the end of the culture, lymphocytes were tested in a [$^3$H]-thymidine-release assay using P815 (open symbols) and βGP1-loaded P815 (closed symbols) as targets. Results are mean values of triplicate wells (one out of three independent experiments is shown) and are expressed as: [(retained cpm in the absence of effectors)−(experimentally retained cpm in the presence of effectors)/retained cpm in the absence of effectors]×100; SEM were lower than 5% of the values. Similar results were obtained using any of the plasmidless carriers (not shown).
Figure 11:
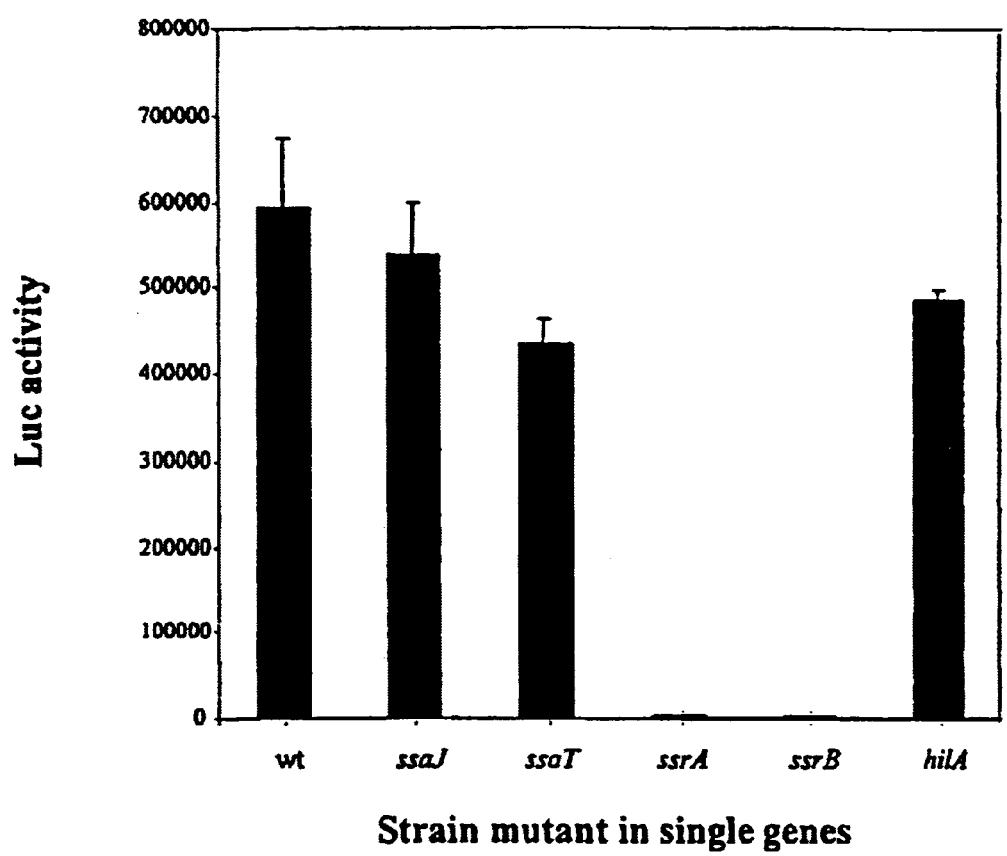
FIG. 11. Expression of an sseA::luc fusion in wild-type and mTn5 mutant strains of *S. typhimurium*.
Figure 13:
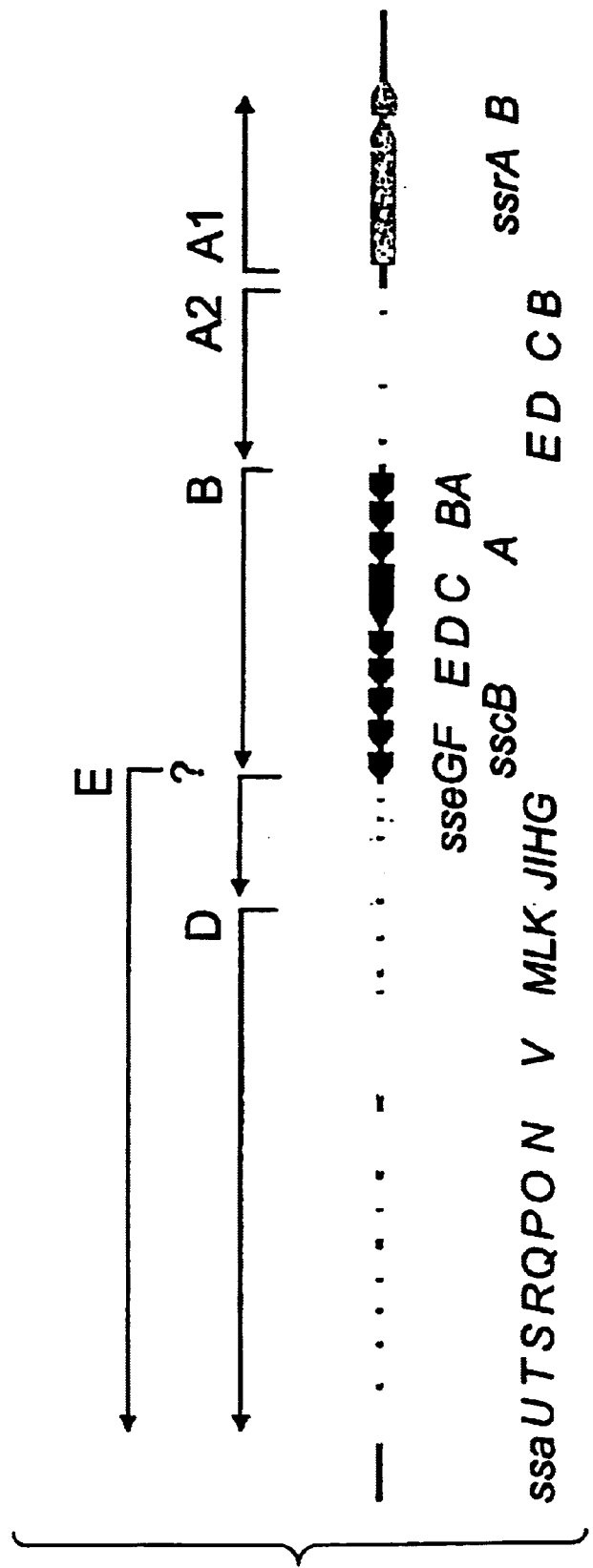
FIG. 13. Model for the transcriptional organization of SPI2 virulence genes. This model is based on the observation of the transcriptional direction of SPI2 genes, characterization of promoter activities
Figures 14, 14A:
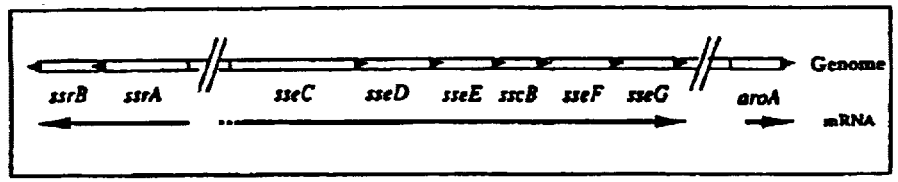
FIG. 14 shows the principle of how mutations having a different grade of attenuation can be generated. As shown in A, the inactivation of one effector gene such as sse results in a low grade of attenuation. As shown in B, the additional inactivation of a gene located outside the SPI2 locus such as aroA results in a medium grade of attenuation. By insertional mutation with a polar effect all genes in a polycistronic cluster are affected which results in a high grade of attenuation, as shown in C. As shown in D, the inactivation of a regulatory gene such as ssrB results in a supreme attenuation.
Figure 15:
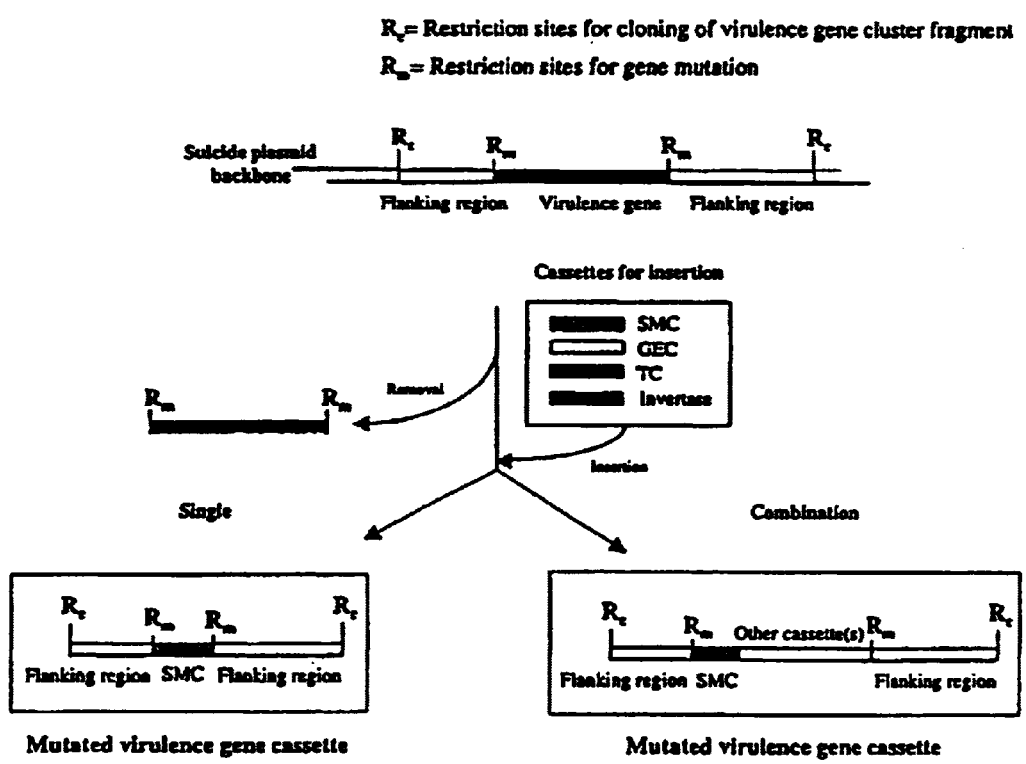
FIG. 15 shows the principle of insertional mutation by example of insertional mutation into a virulence gene. Different cassettes such as SMC, GEC, TC and/or invertase cassette may be inserted into a cloned virulence gene, thus yielding an inactivated virulence gene which may be introduced into a cell by homologous recombination using a virulence gene cassette.
Figure 20:
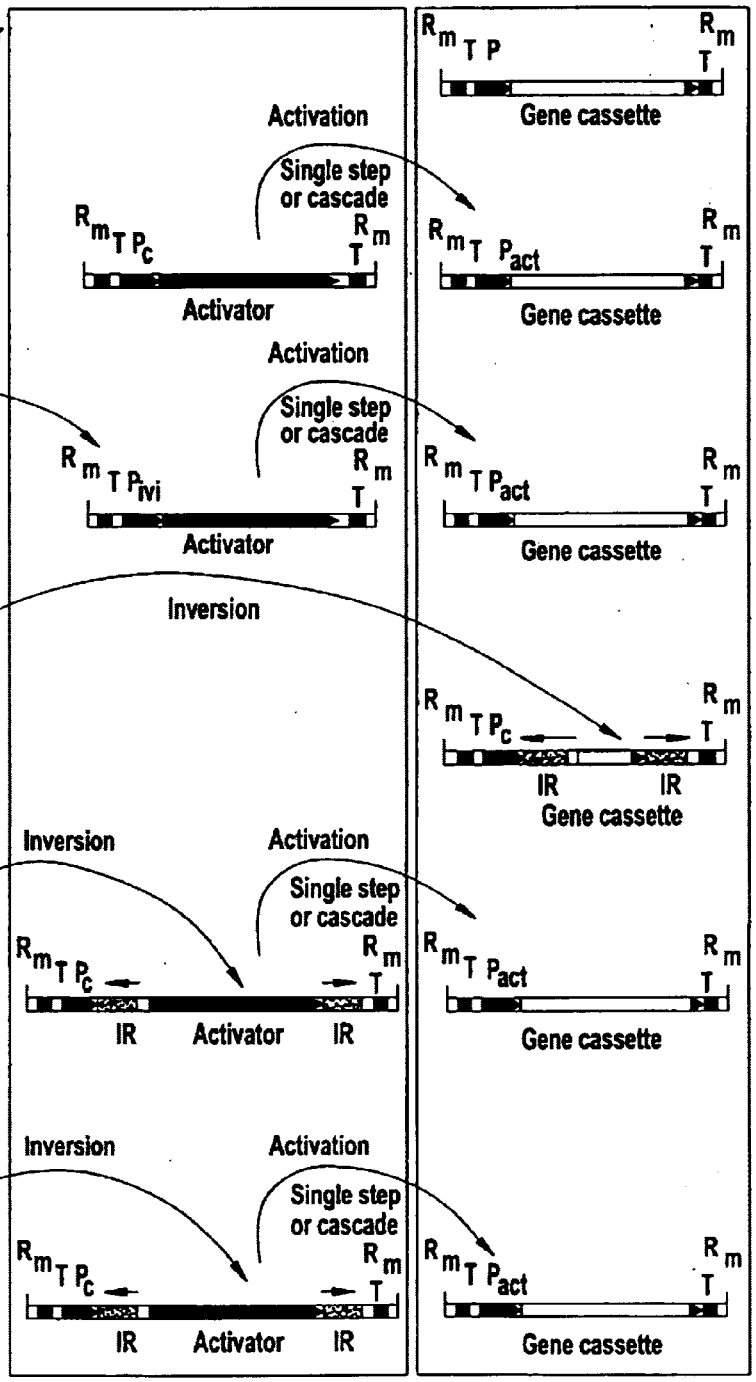

FIG. 19 shows a transactivator cassette in a one-phase system and a two-phase system.

FIG. 20 shows different modes of gene expression as realized by the combination of different accessory sequences and/or cassettes in a one-phase system and a two-phase system.

FIG. 21A shows the genomic sequence of a region of the SPI2 locus from Salmonella (SEQ ID NO.1) comprising the complete sequences of the genes ssaE to ssaI and partial sequences of ssaD and ssaJ (cf. FIG. 12).

FIG. 21B shows the nucleotide sequence of a region of the SPI2 locus from Salmonella (SEQ ID NO.2) comprising the coding sequences for ssrA and ssrB.

FIGS. 22A–Q each show the nucleotide sequence of the respective gene indicated. A: (SEQ ID NO.3); B: (SEQ ID NO.5); C: (SEQ ID NO.7); D: (SEQ ID NO.9); E: (SEQ ID NO.12); F: (SEQ ID NO.14); G: (SEQ ID NO.16); H: (SEQ ID NO.18); I: (SEQ ID NO.20); J: (SEQ ID NO.22); K: (SEQ ID NO.24); L: (SEQ ID NO.26); M: (SEQ ID NO.28); N: (SEQ ID NO.30); O: (SEQ ID NO.32); P: (SEQ ID NO.34); Q: (SEQ ID NO.36).

FIGS. 23A–Q each show the amino acid sequence of the respective polypeptide indicated A: (SEQ ID NO.4); B: (SEQ ID NO.6); C: (SEQ ID NO.8); D: (SEQ ID NO.11); E: (SEQ ID NO.13); F: (SEQ ID NO.15); G: (SEQ ID NO.17); H: (SEQ ID NO.19); I: (SEQ ID NO.21); J: (SEQ ID NO.23): K: (SEQ ID NO.25); L: (SEQ ID NO.27); M: (SEQ ID NO.29); N: (SEQ ID NO.31); O: (SEQ ID NO.33); P: (SEQ ID NO.35); Q: (SEQ ID NO.37).

FIGS. 24A, B each show a nucleotide sequence comprising an in vivo inducible promoter. A: (SEQ ID NO:38); B: (SEQ ID NO:39).

SEQUENCE LISTING

| | | | |
|---|---|---|---|
| SEQ ID NO: 1 | genomic region | nucleic acid | FIG. 21A |
| SEQ ID NO: 2 | genomic region | nucleic acid | FIG. 21B |
| SEQ ID NO: 3 | sseA | nucleic acid | FIG. 22A |
| SEQ ID NO: 4 | sseA | translation product | FIG. 23A |
| SEQ ID NO: 5 | sseB | nucleic acid | FIG. 22B |
| SEQ ID NO: 6 | sseB | translation product | FIG. 23B |
| SEQ ID NO: 7 | sseC | nueleic acid | FIG. 22C |
| SEQ ID NO: 8 | sseC | translation product | FIG. 23C |
| SEQ ID NO: 9 | sseD | nucleic acid | FIG. 22D |
| SEQ ID NO: 10 | sseD | translation product | |
| SEQ ID NO: 11 | sseD | protein | FIG. 23D |
| SEQ ID NO: 12 | sseE | nucleic acid | FIG. 22E |
| SEQ ID NO: 13 | sseE | translation product | FIG. 23E |
| SEQ ID NO: 14 | sseF | nucleic acid | FIG. 22F |
| SEQ ID NO: 15 | sseF | translation product | FIG. 23F |
| SEQ ID NO: 16 | sseG | nucleic acid | FIG. 22G |
| SEQ ID NO: 17 | sseG | translation product | FIG. 23G |
| SEQ ID NO: 18 | sscA | nucleic acid | FIG. 22H |
| SEQ ID NO: 19 | sscA | translation product | FIG. 23H |
| SEQ ID NO: 20 | sscB | nucleic acid | FIG. 22I |
| SEQ ID NO: 21 | sscB | translation product | FIG. 23I |
| SEQ ID NO: 22 | ssaD | nucleic acid | FIG. 22J |
| SEQ ID NO: 23 | ssaD | translation product | FIG. 23J |
| SEQ ID NO: 24 | ssaE | nucleic acid | FIG. 22K |
| SEQ ID NO: 25 | ssaE | translation product | FIG. 23K |
| SEQ ID NO: 26 | ssaG | nucleic acid | FIG. 22L |
| SEQ ID NO: 27 | ssaG | translation product | FIG. 23L |
| SEQ ID NO: 28 | ssaH | nucleic acid | FIG. 22M |
| SEQ ID NO: 29 | ssaH | translation product | FIG. 23M |
| SEQ ID NO: 30 | ssaI | nucleic acid | FIG. 22N |

-continued

SEQUENCE LISTING

| | | | |
|---|---|---|---|
| SEQ ID NO: 31 | ssaI | translation product | FIG. 23N |
| SEQ ID NO: 32 | ssaJ | nucleic acid | FIG. 22O |
| SEQ ID NO: 33 | ssaJ | translation product | FIG. 23O |
| SEQ ID NO: 34 | ssrA | nucleic acid | FIG. 22P |
| SEQ ID NO: 35 | ssrA | translation product | FIG. 23P |
| SEQ ID NO: 36 | ssrB | nucleic acid | FIG. 22Q |
| SEQ ID NO: 37 | ssrB | translation product | FIG. 23Q |
| SEQ ID NO: 38 | Promoter A2 | nucleic acid | FIG. 24A |
| SEQ ID NO: 39 | Promoter B | nucleic acid | FIG. 24B |
| SEQ ID NO: 40 | Esp A | protein | FIG. 2A |
| SEQ ID NO: 41 | Esp D | protein | FIG. 2B |
| SEQ ID NO: 42 | Yop B | protein | FIG. 2B |
| SEQ ID NO: 43 | Pep B | protein | FIG. 2B |
| SEQ ID NO: 44 | D89 | nucleic acid | page 33 |
| SEQ ID NO: 45 | D90 | nucleic acid | page 33 |
| SEQ ID NO: 46 | D91 | nucleic acid | page 33 |
| SEQ ID NO: 47 | D92 | nucleic acid | page 33 |
| SEQ ID NO: 48 | E25 | nucleic acid | page 41 |
| SEQ ID NO: 49 | E28 | nucleic acid | page 41 |
| SEQ ID NO: 50 | E6 | nucleic acid | page 42 |
| SEQ ID NO: 51 | E4 | nucleic acid | page 43 |
| SEQ ID NO: 52 | sseC-del1 | nucleic acid | page 44 |
| SEQ ID NO: 53 | sseE-del1 | nucleic acid | page 44 |
| SEQ ID NO: 54 | sseC-For | nucleic acid | page 45 |
| SEQ ID NO: 55 | sseC-Rev | nucleic acid | page 45 |
| SEQ ID NO: 56 | sseD-del1 | nucleic acid | page 45 |
| SEQ ID NO: 57 | sseD-del2 | nucleic acid | page 45 |
| SEQ ID NO: 58 | sseD-For | nucleic acid | page 46 |
| SEQ ID NO: 59 | sseD-Rev | nucleic acid | page 46 |
| SEQ ID NO: 60 | sscB-del1 | nucleic acid | page 47 |
| SEQ ID NO: 61 | sscB-del2 | nucleic acid | page 47 |
| SEQ ID NO: 62 | sscB-For | nucleic acid | page 47 |
| SEQ ID NO: 63 | sscB-Rev | nucleic acid | page 47/48 |
| SEQ ID NO: 64 | ssrA-For | nucleic acid | page 66 |
| SEQ ID NO: 65 | ssrA-Rev | nucleic acid | page 66 |
| SEQ ID NO: 66 | ssrB-For | nucleic acid | page 67 |
| SEQ ID NO: 67 | ssrB-Rev | nucleic acid | page 67 |
| SEQ ID NO: 68 | ssrA-del1 | nucleic acid | page 67 |
| SEQ ID NO: 69 | ssrB-del2 | nucleic acid | page 68 |

Literature

Bajaj, V., Lucas, R. L., Hwang, C., Lee, C. A. (1996). Co-ordinate regulation of *Salmonella typhimurium* invasion genes by environmental and regulatory factors is mediated by control of expression. *Mol. Microbiol.* 22: 703–714.

Bajaj, V., Hwang, C., Lee, C. A. (1995). hilA is a novel ompR/toxR family member that activates the expression of *Salmonella typhimurium* invasion genes. *Mol. Microbiol*. 18: 715–727.

Baudry, B., Kaczorek, M. and Sansonetti, P. J. (1988) Nucleotide sequence of the invasion plasmid antigen B and C genes (ipaB and ipaC) of *Shigella flexneri. Microb Pathog* 4: 345–357.

Bogdanove, A. J., Beer, S. V., Bonas, U., Boucher, C. A., Colimer, A., Coplin, D. L., Cornelis, G. R., Huang, H.-C., Hutcheson, S. W., Panopoulos, N. J., and van Gijsegem, F. (1996) Unified nomenclature for broadly conserved hrp genes of phytopathogenic bacteria. *Mol Microbiol* 20: 681–683.

Buchmeier, N. A., Lipps, C. J., So, M. Y. H., Heffron, F. (1993) Recombination-deficient mutants of *Salmonella typhimurium* are avirulent and sensitive to the oxidative burst of macrophages. *Mol. Microbiol*. 7: 933–936

Chang, A. C. and Cohen, S. N. (1978). Construction and characterization of amplifiable multicopy DNA cloning vehicles derived from the P15A cryptic miniplasmid. *J Bacteriol* 134: 1141–1156.

Cirillo, D. M., Valdivia, R. H., Monack, D. M., Falkow, S. (1998) Macrophage-dependent induction of the Salmonella pathogenicity island 2 type III secretion system and its role in intracellular survival. *Mol. Microbiol.* 30: 175–88

Cirillo, J. D., Stover, C. K., Bloom, B. R., Jacobs, W. R. Jr., Barletta, R. G. (1995). Bacterial vaccine vectors and bacillus Calmette-Guerin. *Clin. Infect. Dis.* 20: 1001–1009.

DeGroote, M. A., Ochsner, U. A., Shiloh, M. U., Nathan, C., McCord, J. M., Dinauer, M. C., Libby, S. J., Vazquez-Torres, A., Xu, Y., and Fang, F. C. (1997) Periplasmic superoxide dismutase protects Salmonella from products of phagocyte NADPH-oxidase and nitric oxide synthase. *Proc Natl Acad Sci USA* 94: 13997–14001.

de Lorenzo, V. and Timmis, K. N. (1994). Analysis and construction of stable phenotypes in Gram-negative bacteria with Tn5- and Tn10-derived minitransposons. *Methods Enzymol.* 235, 386–405.

Devereux, J., Haeberli, P., and Smithies, O. (1 984) A comprehensive set of sequence analysis programs for the VAX. *Nucleic Acids Res.* 12: 387–395.

Deiwick, J., Nikolaus, T., Erdogan, S., Hensel, M. (1999) Environmental regulation of Salmonella pathogenicity island 2 gene expression. *Mol. Microbiol.* 31: 1759–1773.

Deiwick, J., Nikolaus, T., Shea, J. E., Gleeson, C., Holden, D. W., Hensel, M. (1998). Mutations in SPI2 genes affecting transcription of SPI1 genes and resistance to anti-microbial agents. *J. Bacteriol.* 180: 4775–4780.

Donnenberg, M. S., and Kaper, J. B. (1991) Construction of an eae deletion mutant of enteropathogenic *Escherichia coli* using a positive-selection suizide vector. *Infect Immun* 59: 4310–4317

Elliot, S. J., Wainwright, L. A., McDaniel, T. K., Jarvis, K. G., Deng, Y. K., Lai., L. C., McNamara, B. P., Donnenberg, M. S., and Kaper, J. B. (1998) The complete sequence of the locus of enterocyte affacement (LEE) from enteropathogenic *Escherichia coli* E2348/69. *Mol Microbiol* 28: 1–4.

Fields, P. I., Swanson, R. V., Haidaris., C. G., and Heffron, F. (1986) Mutants of *Salmonella typhimurium* that cannot survive within the macrophage are avirulent. *Proc Natl Acad Sci USA* 83: 5189–5193.

Forsberg, A., Pavitt, G. D. and Higgins, C. F. (1994). Use of transcriptional fusions to monitor gene expression: a cautionary tale. *J. Bacteriol.* 176: 2128–2132.

Galán, J. E., Ginocchio, C. and Costeas, P. (1992). Molecular and functional characterization of the Salmonella invasion gene invA: homology of InvA to members of a new protein family. *J. Bacteriol.* 174: 4338–4349.

Gentschev, I., Glaser, I., Goebel, W., McKeever, D. J., Musoke, A., and Heussler, V. T. (1998) Delivery of the p67 sporozoite antigen of *Theileria parva* by using recombinant *Salmonella dublin*: secretion of the product enhances specific antibody responses in cattle. *Infect Immun* 66: 2060–2064.

Gunn, J. S., Miller, S. I. (1996). PhoP-PhoQ activatestranscription of pmrAB, encoding a two-component regulatory system involved in *Salmonella typhimurium* antimicrobial peptide resistance. *J. Bacteriol.* 178: 6857–6864.

Hakansson, S., Schesser, K., Persson, C., Galyov, E. E., Rosqvist, R., Homble, F., and Wolf Watz, H. (1 996) The YopB protein of *Yersinia pseudotuberculosis* is essential for the translocation of Yop effector proteins across the target cell plasma membrane and displays a contact-dependent membrane disrupting activity. *EMBO J* 15: 5812–5823.

Harlow, E., Lane, D. (1988). Antibodies: A laboratory manual. Cold Spring Harbour Laboratory Press, Cold Spring Harbour, N.Y.

Hauser, A. R., Fleiszig, S., Kang, P. J., Mostov, K., and Engel, J. N. (1998) Defects in type III secretion correlate with internalization of *Pseudomonas aeruginosa* by epithelial cells. *Infect Immun* 66: 1413–1420.

Heithoff, D. M., Sinsheimer, R. L., Low, D. A., and Mahan, M. J. (1999) An essential role for DNA adenine methylation in bacterial virulence. *Science* 284: 967–970.

Hensel, M., Nikolaus, T., Egelseer, C. (1999). Molecular and functional analysis indicates a mosaic structure of Salmonella Pathogenicity Island 2. *Mol. Microbiol.* 31: 489–98.

Hensel, M., Shea, J. E., Bäumler, A. J., Gleeson, C., and Holden, D. W. (1997a) Analysis of the boundaries of Salmonella pathogenicity island 2 and the corresponding chromosomal region of *Escherichia coli* K-12. *J Bacteriol* 179: 1105–1111.

Hensel, M., Shea, J. E., Raupach, B., Monack, D., Falkow, S., Gleeson, C., and Holden, D. W. (1997b) Functional analysis of ssaJ and the ssaK/U operon, 13 genes encoding components of the type III secretion apparatus of Salmonella pathogenicity island 2. *Mol Microbiol* 24: 155–167.

Hensel, M., Shea, J. E., Gleeson, C., Jones, M. D., Dalton, E., Holden, D. W. (1995). Simultaneous identification of bacterial virulence genes by negative selection. *Science* 269: 400–403.

Herrero, M., de Lorenzo, V., and Timmis, K. N. (1990) Transposon vectors containing non-antibiotic resistance selection markers for cloning and stable chromosomal insertion of foreign genes in gram-negative bacteria. *J Bacteriol* 172: 6557–6567.

Hess, J., Dietrich, G., Gentschev, I., Miko, D., Goebel, W., and Kaufmann, S. H. (1997a) Protection against murine listeriosis by an attenuated recombinant *Salmonella typhimurium* vaccine strain that secretes the naturally somatic antigen superoxide dismutase. *Infect Immun* 65: 1286–1292.

Hess, J., Gentschev, I., Miko, D., Weizel, M., Ladel, C., Goebel, W., and Kaufmann, S. H. (1996) Superior efficacy of secreted over somatic antigen display in recombinant Salmonella vaccine induced protection against listeriosis. *Proc Natl Acad Sci USA* 93: 1458–1463.

Hess, J., Miko, D., Gentschev, I., Dietrich, G., Goebel, W., Mollenkopf, H. J., Ladel, C., and Kaufmann, S. H. (1997b) Modulation of antigen display by attenuated *Salmonella typhimurium* strains and its impact on protective immunity against listeriosis. *Behring Inst Mitt* 160–171.

Hofmann, K. and Stoffel, W. (1993). TMbase—a database of membrane spanning proteins segments. *Biol Chem Hoppe-Seyler* 347: 166.

Holtel, A., Timmis, K. N., Ramos, J. L. (1992). Upstream binding sequences of the XylR activator protein and integration host factor in the xy/S-gene promoter region of the Pseudomonas TOL plasmid. *Nucleic. Acids. Res.* 20: 1755–1762.

Hueck, C. J. (1998). Type III protein secretion systems in bacterial pathogens of animals and plants. *Microbiol. Mol. Biol. Rev.* 62: 379–433.

Hueck, C. J., Hantman, M. J., Bajaj, V., Johnston, C., Lee, C. A., Miller, S. I. (1995). *Salmonella typhimurium* secreted invasion determinants are homologous to Shigella Ipa proteins. *Mol. Microbiol.* 18: 479–490.

Kaniga, K., Tucker, S., Trollinger, D., Galán, J. E. (1995). Homologs of the Shigella IpaB and IpaC invasins are required for *Salmonella typhimurium* entry into cultured epithelial cells. *J. Bacteriol.* 177: 3965–3971.

Kuwajima, G., Kawagishi, I., Homma, M., Asaka, J., Kondo, E., and Macnab, R. M. (1989) Export of an N-terminal fragment of *Escherichia coli* flagellin by a flagellum-specific pathway. *Proc Natl Acad Sci USA* 86: 4953–4957.

Laemmli, U. K. (1970). Cleavage of structural proteins during the assembly of the head of bacteriophage T4. *Nature* 227: 680–685.

Macnab, R. M. (1996) Flagella and motility. In *Escherichia coli* and Salmonella: cellular and molecular biology. F. C. Neidhardt, et al. (eds.). Washington, D.C.: ASM Press, pp. 123–145

Maloy, S. R., Steward, V. L. and Taylor, R. K. (1996). Genetic analysis of pathogenic bacteria, Cold Spring Harbor, N.Y.: Cold Spring Harbor Laboratory Press.

Miller, J. H. (1992). A short course in bacteria genetics. Cold Spring Harbor Laboratory Press, Cold Spring Harbor, N.Y.

Miller, S. I., Kukral, A. M., and Mekalanos, J. J. (1989) A two component regulatory system (phoP and phoQ) controls *Salmonella typhimurium* virulence. *Proc Natl Acad Sci USA* 86: 5054–5058.

Miller, V. L., Mekalanos, J. J. (1988). A novel suicide vector and its use in construction of invertion mutations: osmoregulation of outer membrane proteins and virulence determinants in *Vibrio cholerae* requires toxR. *J. Bacteriol.* 170, 2575–2583.

Minamino, T., and Macnab, R. M. (1999) Components of the Salmonella flagellar export apparatus and classification of export substrates. *J Bacteriol* 181: 1388–1394.

Monack, D. M., Raupach, B., Hromockyj, A. E., and Falkow, S. (1996) *Salmonella typhimurium* invasion induces apoptosis in infected macrophages. *Proc Natl Acad Sci USA* 93: 9833–9838.

O'Callaghan, D., Charbit, A. (1990). High efficiency transformation of *Salmonella typhimurium* and *Salmonella typhi* by electroporation. *Mol. Gen. Genet.* 223: 156–158.

Ochman, H., Soncini, F. C., Solomon, F., Groisman, E. A. (1996). Identification of a pathogenicity island required for Salmonella survival in host cells. *Proc. Natl. Acad. Sci. USA* 93: 7800–7804.

Orr, N., Galen, J. E., and Levine, M. M. (1999) Expression and immunogenicity of a mutant diphtheria toxin molecule, $CRM_{197}$, and its fragments in *Salmonella typhi* vaccine strain CVD 908-htrA. *Infect Immun* 67: 4290–4294.

Pallen, M. J., Dougan, G., and Frankel, G. (1997) Coiled-coil domains in proteins secreted by type III secretion systems. *Mol Microbiol* 25: 423–425.

Ralph, P., Prichard, J., and Cohn, M. (1975). Reticulum cell sarcoma: and effector cell in antibody-dependent cell-mediated immunity. *J. Immunol.* 114: 898–905.

Reed, L. J., Muench, H. (1938). A simple method of estimating fifty per cent end points. *Am. J. Hyg.* 27:493–497.

Sambrook, J., Fritsch, E. F., Maniatis, T. (1989). Molecular cloning: a laboratory manual. Cold Spring Harbor Laboratory Press, Cold Spring Harbor, N.Y.

Sanger, F., Nicklen, S., and Coulson, A. R. (1977) DNA sequencing with chain terminating inhibitors. *Proc Natl Acad Sci USA* 74: 5463–5467.

Schmitt, C. K., Darnell, S. C., and O'Brien, A. D. (1996) The attenuated phenotype of a *Salmonella typhimurium* flgM mutant is related to expression of FliC flagellin. *J Bacteriol* 178: 2911–2915

Shea, J. E., Hensel, M., Gleeson, C., Holden, D. W. (1996). Identification of a virulence locus encoding a second type III secretion system in *Salmonella typhimurium*. *Proc. Natl. Acad. Sci. USA* 93: 2593–2597.

Skorupski, K. and Taylor, R. K. (1996). Positive selection vectors for allelic exchange. *Gene* 169: 47–52.

Valdivia, R. H., and Falkow, S. (1997) Fluorescence-based isolation of bacterial genes expressed within host cells. *Science* 277: 2007–2011.

Valentine, P. J., Devore, B. P., and Heffron, F. (1998) Identification of three highly attenuated. *Salmonella typhimurium* mutants that are more immunogenic and protective in mice than a prototypical aroA mutant. *Infect Immun* 66: 3378–3383

Wattiau, P., Bernier, B., Deslée, P., Michiels, T., and Cornelis, G. R. (1994) Individual chaperones required for Yop secretion by Yersinia. *Proc Natl Acad Sci USA* 91: 10493–10497.

Yanisch-Perron, C., Vieira, J. and Messing, J. (1985). Gene 33, 103–119.

Young, G. M., Schmiel, D. H., and Miller, V. L. (1999) A new pathway for the secretion of virulence factors by bacteria: the flagellar export apparatus functions as a protein-secretion system. *Proc Natl Acad Sci USA* 96: 6456–6461.

Zhu, N., Liggitt, D., Liu, Y., Debs, R. (1993). Systemic gene expression after intravenous DNA delivery into adult mice. *Science* 261: 209–211.

What is claimed is:

1. A carrier for the presentation of an antigen to a host which is an attenuated gram-negative cell comprising the SP12 gene locus, wherein at least one of the effector genes selected from the group consisting of sseA, sseC, sseD, sseE, sseF and sseG is inactivated; and/or wherein the chaperon gene sscB is inactivated; and/or wherein at least one of the secretion apparatus genes selected from the group consisting of ssaE, ssaG and ssaH is inactivated; and wherein said inactivation results in an attenuation/reduction of virulence compared to the wild type of said cells, and wherein said cell comprises at least one heterologous nucleic acid molecule comprising a nucleic acid sequence coding for said antigen, wherein said cell is capable of expressing said nucleic acid molecule or capable of causing the expression of said nucleic acid molecule in a target cell.

2. The carrier according to claim 1, wherein said nucleic acid molecule comprises a nucleic acid sequence coding for an antigen selected from the group consisting of a bacterial antigen, viral antigen, and a tumor antigen.

3. The carrier according to claim 1, wherein said nucleic acid sequence codes for an antigen selected from the group consisting of *Helicobacter pylori, Chlamydia pneumoniae, Borrelia burgdorferi*, Nanobacteria, Hepatitis virus, human papilloma virus and Herpes virus.

4. The carrier according to claim 1, wherein said nucleic acid molecule is inserted into the SP12 locus.

5. The carrier according to claim 4, wherein said nucleic acid molecule is inserted into an sse gene.

6. The carrier according to claim 5, wherein said sse gene is selected from sseC, sseD and sseE.

7. The carrier according to claim 4, wherein said insertion is a non-polar insertion.

8. The carrier according to claim 1, wherein the expression of said heterologous nucleic acid molecule is tissue specific.

9. The carrier according to claim 1, wherein the expression of said heterologous nucleic acid molecule is inducible.

10. The carrier according to claim 1, wherein the expression of said heterologous nucleic acid is activated in the target cell.

11. The carrier according to claim 10, wherein said target cell is a macrophage.

12. The carrier according to claim 1, wherein said nucleic acid molecule comprises a nucleic acid sequence that codes for a domain selected from the group consisting of a polypeptide-targeting domain, a peptide-targeting domain, and an immunostimulating domain.

13. The carrier according to claim 1, wherein said nucleic acid molecule codes for a fusion protein.

14. The cell according to claim 1, wherein the expression product of said nucleic acid molecule remains in the cytosol of said carrier.

15. The carrier according to claim 1, wherein the expression product of said nucleic acid molecule is directed to the periplasmic space of said carrier.

16. The carrier according to claim 1, wherein the expression product of said nucleic acid molecule is directed to the outer membrane of said carrier.

17. The carrier according to claim 1, wherein the expression product of said nucleic acid molecule is secreted.

18. The carrier according to claim 17, wherein the expression product of said nucleic acid molecule is secreted by the type III secretion system.

19. The carrier according to claim 18, wherein the expression product of said nucleic acid molecule is secreted by the SP12 type III secretion system.

20. A carrier for the presentation of an antigen to host, which carrier is an attenuated gram-negative cell comprising the SP12 locus, characterized by a lack of at least one SP12 polypeptide, wherein said lack results in an attenuation/reduction of virulence compared to the wild type of said cell, further characterized by the presence of at least one heterologous peptide or polypeptide having immunogenic properties.

* * * * *

SEQUENCE LISTING

<160> NUMBER OF SEQ ID NOS: 73

<210> SEQ ID NO 1
<211> LENGTH: 8457
<212> TYPE: DNA
<213> ORGANISM: Salmonella

<400> SEQUENCE: 1

```
ctgcagttgt ccggttattg ctcgtcaagc gaacagatgc aaaaggtgag agcgactctc      60
gaatcatggg gggtcatgta tcgggatggt gtaatctgtg atgacttatt ggtacgagaa     120
gtgcaggatg ttttgataaa aatgggttac ccgcatgctg aagtatccag cgaagggccg     180
gggagcgtgt taattcatga tgatatacaa atggatcagc aatggcgcaa ggttcaacca     240
```

```
ttacttgcag atattcccgg gttattgcac tggcagatta gtcactctca tcagtctcag    300
ggggatgata ttatttctgc gataatagag aacggtttag tggggcttgt caatgttagc    360
ccaatgcggc gctctttttgt tatcagtggt gtactggatg aatctcatca acgcattttg   420
caagaaacgt tagcagcatt aaagaaaaag gatcccgctc tttctttaat ttatcaggat    480
attgcgcctt cccatgatga agcaagtat ctgcctgcgc cagtggctgg ctttgtacag     540
agtcgccatg gtaattactt attactgacg aataaagagc gtttacgtgt aggggcattg    600
ttacccaatg ggggagaaat tgtccatctg agtgccgatg tggtaacgat taaacattat   660
gatactttga ttaactatcc attagatttt aagtgagtgg aaaatgacaa ctttgacccg    720
gttagaagat tgctgcttc attcgcgtga agaggccaaa gcataatttt acaattaag     780
ggctgcccgg aaacagttag aagagaacaa cggcaagtta caggatccgc agcaatatca    840
gcaaaacacc ttattgcttg aagcgatcga gcaggccgaa aatatcatca acattattta    900
ttatcgttac cataacagcg cacttgtagt gagtgagcaa gagtaaagta aaatatctt    960
agagcctatc ccaccaggcg ttaattggcg cagccagttt ggacacggat agcgcgcaaa    1020
aaccgcagcg tacacgtagt acgtgaggtt tgactcgcta cgctcgccct tcgggccgcc   1080
gctagcggcg ttcaaaacgc taacgcgttt tggcgagcac tgcccaggtt caaaatggca    1140
agtaaaatag cctaatggga taggctctta gttagcacgt taattatcta tcgtgtatat    1200
ggagggaat gatgataaag aaaaaggctg cgtttagtga atatcgtgat ttagagcaaa    1260
gttacatgca gctaaatcac tgtcttaaaa aatttcacca aatccgggct aaggtgagtc    1320
aacagcttgc tgaaagggca gagagcccca aaaatagcag agagacagag agtattcttc    1380
ataacctatt tccacaaggc gttgccgggg ttaaccagga ggccgagaag gatttaaaga    1440
aaatagtaag tttgttttaaa caacttgaag tacgactgaa acaacttaat gctcaagccc    1500
cggtggagat accgtcagga aaaacaaaaa ggtaaagcat aatgtcttca ggaaacatct    1560
tatggggaag tcaaaaccct attgtgttta aaaatagctt cggcgtcagc aacgctgata    1620
ccggagccca ggatgactta tcccagcaaa atccgtttgc cgaagggtat ggtgttttgc    1680
ttattctcct tatggttatt caggctatcg caaataataa atttattgaa gtccagaaga    1740
acgctgaacg tgccagaaat acccaggaaa agtcaaatga gatggatgag gtgattgcta    1800
aagcagccaa aggggatgct aaaaccaaag aggaggtgcc tgaggatgta attaaataca    1860
tgcgtgataa tggtattctc atcgatggta tgaccattga tgattatatg gctaaatatg    1920
gcgatcatgg gaagctggat aaaggtggcc tacaggcgat caaagcggct ttggataatg    1980
acgccaaccg gaataccgat cttatgagtc aggggcagat aacaattcaa aaaatgtctc    2040
aggagcttaa cgctgtcctt acccaactga cagggcttat cagtaagtgg ggggaaattt    2100
ccagtatgat agcgcagaaa acgtactcat gaaaaaagac ccgaccctac aacaggcaca    2160
tgacacgatg cggttttttcc ggcgtggcgg ctcgctgcgt atgttgttgg atgacgatgt    2220
tacacagccg cttaatactc tgtatcgcta tgccacgcag cttatggagg taaaagaatt    2280
cgccggcgca gcgcgacttt ttcaattgct gacgatatat gatgcctggt catttgacta    2340
ctggtttcgg ttaggggaat gctgccaggc tcaaaaacat tgggggaag cgatatacgc    2400
ttatggacgc gcggcacaaa ttaagattga tgcgccgcag gcgccatggg ccgcagcgga    2460
atgctatctc gcgtgtgata acgtctgtta tgcaatcaaa gcgttaaagg ccgtggtgcg    2520
tatttgcggc gaggtcagtg aacatcaaat tctccgacag cgtgcagaaa agatgttaca    2580
gcaactttct gacaggagct aaaaatgaat cgaattcaca gtaatagcga cagcgccgca    2640
```

```
ggagtaaccg ccttaacaca tcatcactta agcaatgtca gttgcgtttc ctcgggttcg   2700
ctgggaaagc gccagcatcg tgtgaattct acttttggcg atggcaacgc cgcgtgtctg   2760
ctatccggga aaattagtct tcaggaggca agcaatgcgt tgaagcaact gcttgatgcc   2820
gtacccggaa atcataagcg tccatcattg cctgactttt tgcagaccaa tcccgcggtt   2880
ttatcaatga tgatgacgtc attaatactc aacgtctttg gtaataacgc tcaatcgtta   2940
tgccaacagc ttgagcgggc aactgaggtg caaaatgcat tacgtaataa gcaggtaaag   3000
gagtatcagg agcagatcca gaaagcgata gagcaggagg ataaagcgcg taaagcgggt   3060 attttttggcg ctatttttga ctggattacc ggcatatttg aaaccgtgat tggcgcctta   3120
aaagttgtgg aaggttttct gtccggaaat cccgcagaaa tggctagcgg cgtagcttat   3180
atggccgcag gttgtgcagg aatggttaaa gccggagccg aaacggcaat gatgtgcggt   3240
gctgaccacg atacctgtca ggcaattatt gacgtgacaa gtaagattca atttggttgt   3300
gaagccgtcg cgctggcact ggatgttttc cagattggcc gtgcttttat ggcgacgaga   3360
ggtttatctg gcgcagctgc aaaagtgctt gactccggtt ttggcgagga agtggttgag   3420
cgtatggtag gtgcagggga agcagaaata gaggagttgg ctgaaaagtt tggcgaagaa   3480
gtgagcgaaa gttttccaa acaatttgag ccgcttgaac gtgaaatggc tatggcgaat   3540
gagatggcag aggaggctgc cgagttttct cgtaacgtag aaaataatat gacgcgaagc   3600
gcggaaaaaa gctttacgaa agaggggggtg aaagccatgg caaaagaagc ggcaaaagaa   3660
gccctggaaa aatgtgtgca agaaggtgga agttcctgt taaaaaaatt ccgtaataaa   3720
gttctcttca atatgttcaa aaaaatcctg tatgccttac tgagggattg ttcatttaaa   3780
ggcttacagg ctatcagatg tgcaaccgag ggcgccagtc agatgaatac tggcatggtt   3840
aacacagaaa aagcgaagat cgaaagaaa atagagcaat taataactca gcaacggttt   3900
ctggatttca taatgcaaca aacagaaaac cagaaaaaga tagaacaaaa acgcttagag   3960
gagctttata aggggacggg tgccgcgctt agagatgtat tagataccat tgatcactat   4020
agtagcgttc aggcgagaat agctggctat cgcgcttaat ctgaggataa aaatatggaa   4080
gcgagtaacg tagcactggt attaccagcg ccttccttgt taacaccttc ttccactcca   4140
tctccctccg gggagggaat gggtactgaa tcaatgcttc tgttatttga tgatatctgg   4200
atgaagctaa tggagcttgc caaaaagctg cgcgatatca tgcgcagcta acgtagaa    4260 aaacaacggc tggcctggga actgcaagtc aatgttttac agacgcaaat gaaaacaatt   4320
gatgaagcgt ttagagcatc aatgattact gcgggtggcg caatgttgtc gggtgtactg   4380
acgataggat taggggccgt aggcgggggaa accggtctta tagcgggtca agccgtaggc   4440
cacacagctg ggggcgtcat gggcctgggg gctggtgtag cgcaacgtca aagtgatcaa   4500
gataaagcga ttgccgacct gcaacaaaat ggggcccaat cttataataa atccctgacg   4560
gaaattatgg agaaagcaac tgaaattatg cagcaaatca tcggcgtggg gtcgtcactg   4620
gtcacggttc ttgctgaaat actccgggca ttaacgaggt aaacatggtg caagaaatag   4680
agcaatggtt acgtcggcat caggtgttta ctgagcctgc atatttaggg gagaccgcca   4740
tattacttgg gcagcagttt atattatcgc cttacctggt gatctatcgt attgaggcaa   4800
aagaaatgat tatttgtgag ttcaggcgcc tgacgcccgg gcaacctcga ccacagcaat   4860
tgtttcactt actgggactt ttacgcggga tatttgtgca tcaccgcag ttaacatgtt   4920 taaagatgtt gataatcacc gacgttctgg atgaaaaaaa agccatgcta cgcaggaaat   4980
```

```
tattgcgcat cctgacagta atgggagcga cctttacaca gcttgatggc gataactgga   5040
cagttttatc cgccgagcat cttatccagc gacgttttta aatgaccttc ctgacgtaaa   5100
tcattatcac gtgaaaataa caatcaatag gtatgatgat gaaagaagat cagaaaaata   5160
aaatacccga agacattctg aaacagctat tatccgttga tccggaaacc gtttatgcca   5220
gtggttacgc ctcatggcag gaggggatt attcgcgcgc cgtaatcgat tttagttggc   5280
tggtgatggc ccagccatgg agttggcgtg cccatattgc attggctggc acctggatga   5340
tgcttaaaga atacacgacg gccattaatt tctatggaca tgccttgatg ctggatgcca   5400
gccatccaga accggtttac caaacgggcg tctgtctcaa aatgatgggg gaacccgggt   5460
tggcgagaga ggcttttcaa accgcaatca agatgagtta tgcggatgcc tcatggagtg   5520
agattcgcca gaatgcgcaa ataatggttg atactcttat tgcttaaata acagaacgaa   5580
atatgaaaat tcatattccg tcagcggcaa gtaatatagt cgatggtaat agtcctcctt   5640
ccgatataca agcgaaggag gtatcgtttc ctcccctga aattccagcg cctggcaccc   5700
ccgcagcccc tgtgctgctt acgcctgaac aaataaggca gcagagggat tatgcgatac   5760
attttatgca atacactatt cgtgcgctgg gtgcgacagt cgtgtttggg ttatcggttg   5820
ctgcagcggt aatttctggc ggggcaggat tacccattgc tattcttgcg ggggcggcgc   5880
tcgtgattgc tattggggat gcttgctgtg cgtatcataa ttatcaatcg atatgtcagc   5940
aaaaggagcc attacaaacc gccagtgata gcgttgctct tgtggtcagt gcgctggcct   6000
taaaatgtgg ggcaagtctt aactgcgcta acacccttgc taattgtctt tctttattaa   6060
tacgttcagg aatcgctatt tctatgttgg ttttaccct acagtttcca ctgcccgcgg   6120
ctgaaaatat tgcggcctct ttggacatgg ggagtgtaat tacctccgtt agcctgacgg   6180
cgataggtgc ggtactggat tattgccttg cccgcccctc tggcgacgat caggaaaatt   6240
ctgttgatga acttcatgcc gatcccagtg tgttattggc ggaacaaatg gcagcgctct   6300
gtcaatctgc tactacacct gcacctgcat taatggacag ttctgatcat acatctcggg   6360
gagaaccatg aaacctgtta gcccaaatgc tcaggtagga gggcaacgtc ctgttaacgc   6420
gcctgaggaa tcacctccat gtccttcatt gccacatccg gaaaccaata tggagagtgg   6480
tagaatagga cctcaacaag gaaaagagcg ggtattggcc ggacttgcga aacgagtgat   6540
agagtgtttt ccaaaagaaa tttttagttg gcaaacggtt attttgggcg gacagatttt   6600
atgctgttcc gctggaatag cattaacagt gctaagtggt ggaggcgcgc cgctcgtagc   6660
cctggcaggg attggccttg ctattgccat cgcggatgtc gcctgtctta tctaccatca   6720
taaacatcat ttgcctatgg ctcacgacag tataggcaat gccgtttttt atattgctaa   6780
ttgtttcgcc aatcaacgca aaagtatggc gattgctaaa gccgtctccc tgggcggtag   6840
attagcctta accgcgacgg taatgactca ttcatactgg agtggtagtt tgggactaca   6900
gcctcattta ttagagcgtc ttaatgatat tacctatgga ctaatgagtt ttactcgctt   6960
cggtatggat gggatggcaa tgaccggtat gcaggtcagc agcccattat atcgtttgct   7020
ggctcaggta acgccagaac aacgtgcgcc ggagtaatcg ttttcaggta tataccggat   7080
gttcattgct ttctaaattt tgctatgttg ccagtatcct tacgatgtat ttattttaag   7140
gaaaagcatt atggatattg cacaattagt ggatatgctc tcccacatgg cgcaccaggc   7200
aggccaggcc attaatgaca aaatgaatgg taatgatttg ctcaacccag aatcgatgat   7260
taaagcgcaa tttgccttac agcagtattc tacatttatt aattacgaaa gttcactgat   7320
caaaatgatc aaggatatgc ttagtggaat cattgctaaa atctgaagtt attagcgacg   7380
```

-continued

```
atgttcgacg gttgctgctg gaaatcatgt ttgcgggcgt taaccatagc ctgatttccc    7440
aggtacatgc gatgttacca gcgctaacgg ttattgttcc ggataaaaaa ttacagttgg    7500
tatgtctggc attattgttg gcgggtttaa atgagccgct aaaagccgcg aaaattttat    7560
cggatataga tttgccagag gctatggcgc tgcgtctgtt atttcctgca ccaaatgagg    7620
ggtttgaaaa ttgaatattt ctgatatgag cgtagtgcct gtaagcactc aatcttatgt    7680
aaagtcctct gcagaaccga gccaggagca aattaatttt tttgaacaat tgctgaaaga    7740
tgaagcatcc accagtaacg ccagtgcttt taccgcag gttatgttga ccagacaaat     7800
ggattatatg cagttaacgg taggcgtcga ttatcttgcc agaatatcag gcgcagcatc    7860
gcaagcgctt aataagctgg ataacatggc atgaaggttc atcgtatagt atttcttact    7920
gtccttacgt tctttcttac ggcatgtgat gtggatcttt atcgctcatt gccagaagat    7980
gaagcgaatc aaatgctggc attacttatg cagcatcata ttgatgcgga aaaaaaacag    8040
gaagaggatg gtgtaacctt acgtgtcgag cagtcgcagt ttattaatgc ggttgagcta    8100
cttagactta acggttatcc gcataggcag tttacaacgg cggataagat gtttccggct    8160
aatcagttag tggtatcacc ccaggaagaa cagcagaaga ttaatttttt aaaagaacaa    8220
agaattgaag gaatgctgag tcagatggag ggcgtgatta atgcaaaagt gaccattgcg    8280
ctaccgactt atgatgaggg aagtaacgct tctccgagct cagttgccgt atttataaaa    8340
tattcacctc aggtcaatat ggaggccttt cgggtaaaaa ttaaagattt aatagagatg    8400
tcaatccctg ggttgcaata cagtaagatt agtatcttga tgcagcctgc tgaattc      8457
```

<210> SEQ ID NO 2
<211> LENGTH: 3921
<212> TYPE: DNA
<213> ORGANISM: Salmonella

<400> SEQUENCE: 2

```
agcattgaca taaaaactta caatttgaaa aattatttat taaataaact gttacgatgt      60
ttttacatcg ccatcttatt aaaaagtaat tgtagtcatc gactgggtta tatatgaaga    120
aatttatctt cctaatgata acaccatcga ttaatcttct gatgaaacta tatgtactgc    180
gatagtgatc aagtgccaaa gattttgcaa caggcaactg gagggaagca ttatgaattt    240
gctcaatctc aagaatacgc tgcaaacatc tttagtaatc aggctaactt ttttattttt    300
attaacaaca ataattattt ggctgctatc tgtgcttacc gcagcttata tatcaatggt    360
tcagaaacgg cagcatataa tagaggattt atccgttcta ccgagatga atattgtact    420 aagcaatcaa cggtttgaag aagctgaacg tgacgctaaa aatttaatgt atcaatgctc    480
attagcgact gagattcatc ataacgatat tttccctgag gtgagccggc atctatctgt    540
cggtccttca aattgcacgc cgacgctaaa cggagagaag caccgtctct ttctgcagtc    600
ctctgatatc gatgaaaata gctttcgtcg cgatagtttt attcttaatc ataaaaatga    660
gatttcgtta ttatctactg ataacccttc agattattca actctacagc ctttaacgcg    720
aaaaagcttt cctttatacc caacccatgc cgggttttac tggagtgaac cagaatacat    780
aaacggcaaa ggatggcacg cttccgttgc ggttgccgat cagcaaggcg tatttttga    840 ggtgacggtt aaacttcccg atctcattac taagagccac ctgccattag atgatagtat    900
tcgagtatgg ctggatcaaa acaaccactt attgccgttt tcatacatcc cgcaaaaaat    960
acgtacacag ttagaaaatg taacgctgca tgatggatgg cagcaaattc ccggatttct   1020
```

-continued

```
gatattacgc acaaccttgc atggccccgg atggagtctg gttacgctgt acccatacgg    1080
taatctacat aatcgcatct taaaaattat ccttcaacaa atcccctttta cattaacagc    1140 attggtgttg atgacgtcgg cttttttgctg gttactacat cgctcactgg ccaaaccgtt    1200
atggcgtttt gtcgatgtca ttaataaaac cgcaactgca ccgctgagca cacgtttacc    1260
agcacaacga ctggatgaat tagatagtat tgccggtgct tttaaccaac tgcttgatac    1320
tctacaagtc caatacgaca atctggaaaa caaagtcgca gagcgcaccc aggcgctaaa    1380
tgaagcaaaa aaacgcgctg agcgagctaa caaacgtaaa agcattcatc ttacggtaat    1440
aagtcatgag ttacgtactc cgatgaatgg cgtactcggt gcaattgaat tattacaaac    1500 cacccctttta aacatagagc aacaaggatt agctgatacc gccagaaatt gtacactgtc    1560
tttgttagct attattaata atctgctgga ttttttcacgc atcgagtctg gtcatttcac    1620
attacatatg gaagaaacag cgttactgcc gttactggac caggcaatgc aaaccatcca    1680
ggggccagcg caaagcaaaa aactgtcatt acgtactttt gtcggtcaac atgtccctct    1740
ctattttcat accgacagta tccgtttacg gcaaattttg gttaatttac tcgggaacgc    1800
ggtaaaattt accgaaaccg gagggatacg tctgacggtc aagcgtcatg aggaacaatt    1860
aatatttctg gttagcgata gcggtaaagg gattgaaata cagcagcagt ctcaaatctt    1920
tactgctttt tatcaagcag acacaaattc gcaaggtaca ggaattggac tgactattgc    1980
gtcaagcctg gctaaaatga tgggcggtaa tctgacacta aaaagtgtcc ccggggttgg    2040
aacctgtgtc tcgctagtat taccccttaca agaataccag ccgcctcaac caattaaagg    2100
gacgctgtca gcgccgttct gcctgcatcg gcaactggct tgctggggaa tacgcggtga    2160 accacccccac cagcaaaatg cgcttctcaa cgcagagctt ttgtatttct ccggaaaact    2220
ctacgacctg gcgcaacagt taatattgtg tacaccaaat atgccagtaa taaataattt    2280
gttaccaccc tggcagttgc agattctttt ggttgatgat gccgatatta atcgggatat    2340
catcggcaaa atgcttgtca gcctgggcca acacgtcact attgccgcca gtagtaacga    2400
ggctctgact ttatcacaac agcagcgatt cgatttagta ctgattgaca ttagaatgcc    2460
agaaatagat ggtattgaat gtgtacgatt atggcatgat gagccgaata atttagatcc    2520
tgactgcatg tttgtggcac tatccgctag cgtagcgaca gaagatattc atcgttgtaa    2580
aaaaaatggg attcatcatt acattacaaa accagtgaca ttggctacct tagctcgcta    2640
catcagtatt gccgcagaat accaactttt acgaaatata gagctacagg agcaggatcc    2700
gagtcgctgc tcagcgctac tggcgacaga tgatatggtc attaatagca agattttcca    2760
atcactggac ctcttgctgg ctgatattga aaatgccgta tcggctggag aaaaaatcga    2820
tcagttaatt cacacattaa aaggctgttt aggtcaaata gggcagactg aattggtatg    2880
ctatgtcata gacattgaga atcgcgtaaa aatggggaaa atcatcgcgc tggaggaact    2940
aaccgactta cgccagaaaa tacgtatgat cttcaaaaac tacaccatta cttaatatta    3000
tcttaatttt cgcgagggca gcaaaatgaa agaatataag atcttattag tagacgatca    3060
tgaaatcatc attaacggca ttatgaatgc cttattaccc tggcctcatt ttaaaattgt    3120
agagcatgtt aaaaatggtc ttgaggttta taatgcctgt tgtgcatacg agcctgacat    3180
acttatcctt gatcttagtc tacctggcat caatggcctg gatatcattc tcaattaca    3240 tcagcgttgg ccagcaatga atattctggt ttacacagca taccaacaag agtatatgac    3300
cattaaaact ttagccgcag gtgctaatgg ctatgttttt aaaagcagta gtcagcaagt    3360
tctgttagcg gcattgcaaa cagtagcagt aaacaagcgt tacattgacc caacgttgaa    3420
```

```
tcgggaagct atcctggctg aattaaacgc tgacacgacc aatcatcaac tgcttacttt    3480
gcgcgagcgt caggttctta aacttattga cgaggggtat accaatcatg ggatcagcga    3540
aaagctacat atcagtataa aaaccgtcga acacaccgg atgaatatga tgagaaagct    3600
acaggttcat aaagtgacag agttacttaa ctgtgcccga agaatgaggt taatagagta    3660
ttaaccaggg gcgtccgatg gtattaagca ttggtcatat tttgatgagc cttacgccac    3720
gcagtattgc tcatcatcga caaaatccat acggatgccc tggtatgccg caccatttat    3780
cactacctta gtcttcattt gatcatgata tagtagaatc cccttattta acgggcttta    3840
ccatgtcgta ttctatcggc gaatttgcca gactatgcgg tatcaatgcc gccacgctaa    3900
gggcatggca gcgacgctat g                                              3921

<210> SEQ ID NO 3
<211> LENGTH: 327
<212> TYPE: DNA
<213> ORGANISM: Salmonella
<220> FEATURE:
<221> NAME/KEY: CDS
<222> LOCATION: (1)..(324)

<400> SEQUENCE: 3 atg atg ata aag aaa aag gct gcg ttt agt gaa tat cgt gat tta gag        48
Met Met Ile Lys Lys Lys Ala Ala Phe Ser Glu Tyr Arg Asp Leu Glu
  1               5                  10                  15 caa agt tac atg cag cta aat cac tgt ctt aaa aaa ttt cac caa atc        96
Gln Ser Tyr Met Gln Leu Asn His Cys Leu Lys Lys Phe His Gln Ile
             20                  25                  30 cgg gct aag gtg agt caa cag ctt gct gaa agg gca gag agc ccc aaa       144
Arg Ala Lys Val Ser Gln Gln Leu Ala Glu Arg Ala Glu Ser Pro Lys
         35                  40                  45 aat agc aga gag aca gag agt att ctt cat aac cta ttt cca caa ggc       192
Asn Ser Arg Glu Thr Glu Ser Ile Leu His Asn Leu Phe Pro Gln Gly
     50                  55                  60 gtt gcc ggg gtt aac cag gag gcc gag aag gat tta aag aaa ata gta       240
Val Ala Gly Val Asn Gln Glu Ala Glu Lys Asp Leu Lys Lys Ile Val
 65                  70                  75                  80 agt ttg ttt aaa caa ctt gaa gta cga ctg aaa caa ctt aat gct caa       288
Ser Leu Phe Lys Gln Leu Glu Val Arg Leu Lys Gln Leu Asn Ala Gln
                 85                  90                  95 gcc ccg gtg gag ata ccg tca gga aaa aca aaa agg taa                   327
Ala Pro Val Glu Ile Pro Ser Gly Lys Thr Lys Arg
                100                 105

<210> SEQ ID NO 4
<211> LENGTH: 108
<212> TYPE: PRT
<213> ORGANISM: Salmonella

<400> SEQUENCE: 4

Met Met Ile Lys Lys Lys Ala Ala Phe Ser Glu Tyr Arg Asp Leu Glu
  1               5                  10                  15

Gln Ser Tyr Met Gln Leu Asn His Cys Leu Lys Lys Phe His Gln Ile
             20                  25                  30

Arg Ala Lys Val Ser Gln Gln Leu Ala Glu Arg Ala Glu Ser Pro Lys
         35                  40                  45

Asn Ser Arg Glu Thr Glu Ser Ile Leu His Asn Leu Phe Pro Gln Gly
     50                  55                  60

Val Ala Gly Val Asn Gln Glu Ala Glu Lys Asp Leu Lys Lys Ile Val
```

```
                65                  70                  75                  80
Ser Leu Phe Lys Gln Leu Glu Val Arg Leu Lys Gln Leu Asn Ala Gln
                        85                  90                  95

Ala Pro Val Glu Ile Pro Ser Gly Lys Thr Lys Arg
            100                 105

<210> SEQ ID NO 5
<211> LENGTH: 591
<212> TYPE: DNA
<213> ORGANISM: Salmonella
<220> FEATURE:
<221> NAME/KEY: CDS
<222> LOCATION: (1)..(588)

<400> SEQUENCE: 5 atg tct tca gga aac atc tta tgg gga agt caa aac cct att gtg ttt      48
Met Ser Ser Gly Asn Ile Leu Trp Gly Ser Gln Asn Pro Ile Val Phe
 1               5                  10                  15 aaa aat agc ttc ggc gtc agc aac gct gat acc ggg agc cag gat gac      96
Lys Asn Ser Phe Gly Val Ser Asn Ala Asp Thr Gly Ser Gln Asp Asp
                20                  25                  30 tta tcc cag caa aat ccg ttt gcc gaa ggg tat ggt gtt ttg ctt att     144
Leu Ser Gln Gln Asn Pro Phe Ala Glu Gly Tyr Gly Val Leu Leu Ile
            35                  40                  45 ctc ctt atg gtt att cag gct atc gca aat aat aaa ttt att gaa gtc     192
Leu Leu Met Val Ile Gln Ala Ile Ala Asn Asn Lys Phe Ile Glu Val
     50                  55                  60 cag aag aac gct gaa cgt gcc aga aat acc cag gaa aag tca aat gag     240
Gln Lys Asn Ala Glu Arg Ala Arg Asn Thr Gln Glu Lys Ser Asn Glu
 65                  70                  75                  80 atg gat gag gtg att gct aaa gca gcc aaa ggg gat gct aaa acc aaa     288
Met Asp Glu Val Ile Ala Lys Ala Ala Lys Gly Asp Ala Lys Thr Lys
                 85                  90                  95 gag gag gtg cct gag gat gta att aaa tac atg cgt gat aat ggt att     336
Glu Glu Val Pro Glu Asp Val Ile Lys Tyr Met Arg Asp Asn Gly Ile
            100                 105                 110 ctc atc gat ggt atg acc att gat gat tat atg gct aaa tat ggc gat     384
Leu Ile Asp Gly Met Thr Ile Asp Asp Tyr Met Ala Lys Tyr Gly Asp
        115                 120                 125 cat ggg aag ctg gat aaa ggt ggc cta cag gcg atc aaa gcg gct ttg     432
His Gly Lys Leu Asp Lys Gly Gly Leu Gln Ala Ile Lys Ala Ala Leu
    130                 135                 140 gat aat gac gcc aac cgg aat acc gat ctt atg agt cag ggg cag ata     480
Asp Asn Asp Ala Asn Arg Asn Thr Asp Leu Met Ser Gln Gly Gln Ile
145                 150                 155                 160 aca att caa aaa atg tct cag gag ctt aac gct gtc ctt acc caa ctg     528
Thr Ile Gln Lys Met Ser Gln Glu Leu Asn Ala Val Leu Thr Gln Leu
                165                 170                 175 aca ggg ctt atc agt aag tgg ggg gaa att tcc agt atg ata gcg cag     576
Thr Gly Leu Ile Ser Lys Trp Gly Glu Ile Ser Ser Met Ile Ala Gln
            180                 185                 190 aaa acg tac tca tga                                                 591
Lys Thr Tyr Ser
        195

<210> SEQ ID NO 6
<211> LENGTH: 196
<212> TYPE: PRT
<213> ORGANISM: Salmonella

<400> SEQUENCE: 6
```

```
Met Ser Ser Gly Asn Ile Leu Trp Gly Ser Gln Asn Pro Ile Val Phe
  1               5                  10                  15

Lys Asn Ser Phe Gly Val Ser Asn Ala Asp Thr Gly Ser Gln Asp Asp
                 20                  25                  30

Leu Ser Gln Gln Asn Pro Phe Ala Glu Gly Tyr Gly Val Leu Leu Ile
             35                  40                  45

Leu Leu Met Val Ile Gln Ala Ile Ala Asn Asn Lys Phe Ile Glu Val
 50                      55                  60

Gln Lys Asn Ala Glu Arg Ala Arg Asn Thr Gln Glu Lys Ser Asn Glu
 65                  70                  75                  80

Met Asp Glu Val Ile Ala Lys Ala Ala Lys Gly Asp Ala Lys Thr Lys
                 85                  90                  95

Glu Glu Val Pro Glu Asp Val Ile Lys Tyr Met Arg Asp Asn Gly Ile
            100                 105                 110

Leu Ile Asp Gly Met Thr Ile Asp Asp Tyr Met Ala Lys Tyr Gly Asp
            115                 120                 125

His Gly Lys Leu Asp Lys Gly Gly Leu Gln Ala Ile Lys Ala Ala Leu
130                 135                 140

Asp Asn Asp Ala Asn Arg Asn Thr Asp Leu Met Ser Gln Gly Gln Ile
145                 150                 155                 160

Thr Ile Gln Lys Met Ser Gln Glu Leu Asn Ala Val Leu Thr Gln Leu
                165                 170                 175

Thr Gly Leu Ile Ser Lys Trp Gly Glu Ile Ser Ser Met Ile Ala Gln
            180                 185                 190

Lys Thr Tyr Ser
         195

<210> SEQ ID NO 7
<211> LENGTH: 1455
<212> TYPE: DNA
<213> ORGANISM: Salmonella
<220> FEATURE:
<221> NAME/KEY: CDS
<222> LOCATION: (1)..(1452)

<400> SEQUENCE: 7 atg aat cga att cac agt aat agc gac agc gcc gca gga gta acc gcc    48
Met Asn Arg Ile His Ser Asn Ser Asp Ser Ala Ala Gly Val Thr Ala
  1               5                  10                  15 tta aca cat cat cac tta agc aat gtc agt tgc gtt tcc tcg ggt tcg    96
Leu Thr His His His Leu Ser Asn Val Ser Cys Val Ser Ser Gly Ser
                 20                  25                  30 ctg gga aag cgc cag cat cgt gtg aat tct act ttt ggc gat ggc aac   144
Leu Gly Lys Arg Gln His Arg Val Asn Ser Thr Phe Gly Asp Gly Asn
             35                  40                  45 gcc gcg tgt ctg cta tcc ggg aaa att agt ctt cag gag gca agc aat   192
Ala Ala Cys Leu Leu Ser Gly Lys Ile Ser Leu Gln Glu Ala Ser Asn
 50                      55                  60 gcg ttg aag caa ctg ctt gat gcc gta ccc gga aat cat aag cgt cca   240
Ala Leu Lys Gln Leu Leu Asp Ala Val Pro Gly Asn His Lys Arg Pro
 65                  70                  75                  80 tca ttg cct gac ttt ttg cag acc aat ccc gcg gtt tta tca atg atg   288
Ser Leu Pro Asp Phe Leu Gln Thr Asn Pro Ala Val Leu Ser Met Met
                 85                  90                  95 atg acg tca tta ata ctc aac gtc ttt ggt aat aac gct caa tcg tta   336
Met Thr Ser Leu Ile Leu Asn Val Phe Gly Asn Asn Ala Gln Ser Leu
                100                 105                 110 tgc caa cag ctt gag cgg gca act gag gtg caa aat gca tta cgt aat   384
```

```
Cys Gln Gln Leu Glu Arg Ala Thr Glu Val Gln Asn Ala Leu Arg Asn
        115                 120                 125 aag cag gta aag gag tat cag gag cag atc cag aaa gcg ata gag cag       432
Lys Gln Val Lys Glu Tyr Gln Glu Gln Ile Gln Lys Ala Ile Glu Gln
        130                 135                 140 gag gat aaa gcg cgt aaa gcg ggt att ttt ggc gct att ttt gac tgg       480
Glu Asp Lys Ala Arg Lys Ala Gly Ile Phe Gly Ala Ile Phe Asp Trp
145                 150                 155                 160 att acc ggc ata ttt gaa acc gtg att ggc gcc tta aaa gtt gtg gaa       528
Ile Thr Gly Ile Phe Glu Thr Val Ile Gly Ala Leu Lys Val Val Glu
                165                 170                 175 ggt ttt ctg tcc gga aat ccc gca gaa atg gct agc ggc gta gct tat       576
Gly Phe Leu Ser Gly Asn Pro Ala Glu Met Ala Ser Gly Val Ala Tyr
            180                 185                 190 atg gcc gca ggt tgt gca gga atg gtt aaa gcc gga gcc gaa acg gca       624
Met Ala Ala Gly Cys Ala Gly Met Val Lys Ala Gly Ala Glu Thr Ala
        195                 200                 205 atg atg tgc ggt gct gac cac gat acc tgt cag gca att att gac gtg       672
Met Met Cys Gly Ala Asp His Asp Thr Cys Gln Ala Ile Ile Asp Val
    210                 215                 220 aca agt aag att caa ttt ggt tgt gaa gcc gtc gcg ctg gca ctg gat       720
Thr Ser Lys Ile Gln Phe Gly Cys Glu Ala Val Ala Leu Ala Leu Asp
225                 230                 235                 240 gtt ttc cag att ggc cgt gct ttt atg gcg acg aga ggt tta tct ggc       768
Val Phe Gln Ile Gly Arg Ala Phe Met Ala Thr Arg Gly Leu Ser Gly
                245                 250                 255 gca gct gca aaa gtg ctt gac tcc ggt ttt ggc gag gaa gtg gtt gag       816
Ala Ala Ala Lys Val Leu Asp Ser Gly Phe Gly Glu Glu Val Val Glu
            260                 265                 270 cgt atg gta ggt gca ggg gaa gca gaa ata gag gag ttg gct gaa aag       864
Arg Met Val Gly Ala Gly Glu Ala Glu Ile Glu Glu Leu Ala Glu Lys
        275                 280                 285 ttt ggc gaa gaa gtg agc gaa agt ttt tcc aaa caa ttt gag ccg ctt       912
Phe Gly Glu Glu Val Ser Glu Ser Phe Ser Lys Gln Phe Glu Pro Leu
    290                 295                 300 gaa cgt gaa atg gct atg gcg aat gag atg gca gag gag gct gcc gag       960
Glu Arg Glu Met Ala Met Ala Asn Glu Met Ala Glu Glu Ala Ala Glu
305                 310                 315                 320 ttt tct cgt aac gta gaa aat aat atg acg cga agc gcg gga aaa agc      1008
Phe Ser Arg Asn Val Glu Asn Asn Met Thr Arg Ser Ala Gly Lys Ser
                325                 330                 335 ttt acg aaa gag ggg gtg aaa gcc atg gca aaa gaa gcg gca aaa gaa      1056
Phe Thr Lys Glu Gly Val Lys Ala Met Ala Lys Glu Ala Ala Lys Glu
            340                 345                 350 gcc ctg gaa aaa tgt gtg caa gaa ggt gga aag ttc ctg tta aaa aaa      1104
Ala Leu Glu Lys Cys Val Gln Glu Gly Gly Lys Phe Leu Leu Lys Lys
        355                 360                 365 ttc cgt aat aaa gtt ctc ttc aat atg ttc aaa aaa atc ctg tat gcc      1152
Phe Arg Asn Lys Val Leu Phe Asn Met Phe Lys Lys Ile Leu Tyr Ala
    370                 375                 380 tta ctg agg gat tgt tca ttt aaa ggc tta cag gct atc aga tgt gca      1200
Leu Leu Arg Asp Cys Ser Phe Lys Gly Leu Gln Ala Ile Arg Cys Ala
385                 390                 395                 400 acc gag ggc gcc agt cag atg aat act ggc atg gtt aac aca gaa aaa      1248
Thr Glu Gly Ala Ser Gln Met Asn Thr Gly Met Val Asn Thr Glu Lys
                405                 410                 415 gcg aag atc gaa aag aaa ata gag caa tta ata act cag caa cgg ttt      1296
Ala Lys Ile Glu Lys Lys Ile Glu Gln Leu Ile Thr Gln Gln Arg Phe
            420                 425                 430
```

-continued

```
ctg gat ttc ata atg caa caa aca gaa aac cag aaa aag ata gaa caa    1344
Leu Asp Phe Ile Met Gln Gln Thr Glu Asn Gln Lys Lys Ile Glu Gln
        435                 440                 445 aaa cgc tta gag gag ctt tat aag ggg acg ggt gcc gcg ctt aga gat    1392
Lys Arg Leu Glu Glu Leu Tyr Lys Gly Thr Gly Ala Ala Leu Arg Asp
450                 455                 460 gta tta gat acc att gat cac tat agt agc gtt cag gcg aga ata gct    1440
Val Leu Asp Thr Ile Asp His Tyr Ser Ser Val Gln Ala Arg Ile Ala
465                 470                 475                 480 ggc tat cgc gct taa                                                 1455
Gly Tyr Arg Ala <210> SEQ ID NO 8
<211> LENGTH: 484
<212> TYPE: PRT
<213> ORGANISM: Salmonella

<400> SEQUENCE: 8

Met Asn Arg Ile His Ser Asn Ser Asp Ser Ala Ala Gly Val Thr Ala
  1               5                  10                  15

Leu Thr His His His Leu Ser Asn Val Ser Cys Val Ser Ser Gly Ser
                 20                  25                  30

Leu Gly Lys Arg Gln His Arg Val Asn Ser Thr Phe Gly Asp Gly Asn
             35                  40                  45

Ala Ala Cys Leu Leu Ser Gly Lys Ile Ser Leu Gln Glu Ala Ser Asn
         50                  55                  60

Ala Leu Lys Gln Leu Leu Asp Ala Val Pro Gly Asn His Lys Arg Pro
 65                  70                  75                  80

Ser Leu Pro Asp Phe Leu Gln Thr Asn Pro Ala Val Leu Ser Met Met
                 85                  90                  95

Met Thr Ser Leu Ile Leu Asn Val Phe Gly Asn Asn Ala Gln Ser Leu
                100                 105                 110

Cys Gln Gln Leu Glu Arg Ala Thr Glu Val Gln Asn Ala Leu Arg Asn
            115                 120                 125

Lys Gln Val Lys Glu Tyr Gln Glu Gln Ile Gln Lys Ala Ile Glu Gln
        130                 135                 140

Glu Asp Lys Ala Arg Lys Ala Gly Ile Phe Gly Ala Ile Phe Asp Trp
145                 150                 155                 160

Ile Thr Gly Ile Phe Glu Thr Val Ile Gly Ala Leu Lys Val Val Glu
                165                 170                 175

Gly Phe Leu Ser Gly Asn Pro Ala Glu Met Ala Ser Gly Val Ala Tyr
            180                 185                 190

Met Ala Ala Gly Cys Ala Gly Met Val Lys Ala Gly Ala Glu Thr Ala
        195                 200                 205

Met Met Cys Gly Ala Asp His Asp Thr Cys Gln Ala Ile Ile Asp Val
210                 215                 220

Thr Ser Lys Ile Gln Phe Gly Cys Glu Ala Val Ala Leu Ala Leu Asp
225                 230                 235                 240

Val Phe Gln Ile Gly Arg Ala Phe Met Ala Thr Arg Gly Leu Ser Gly
                245                 250                 255

Ala Ala Ala Lys Val Leu Asp Ser Gly Phe Gly Glu Glu Val Val Glu
            260                 265                 270

Arg Met Val Gly Ala Gly Glu Ala Glu Ile Glu Glu Leu Ala Glu Lys
        275                 280                 285

Phe Gly Glu Glu Val Ser Glu Ser Phe Ser Lys Gln Phe Glu Pro Leu
    290                 295                 300
```

-continued

```
Glu Arg Glu Met Ala Met Ala Asn Gly Met Ala Glu Ala Ala Glu
305                 310                 315                 320

Phe Ser Arg Asn Val Glu Asn Asn Met Thr Arg Ser Ala Gly Lys Ser
                325                 330                 335

Phe Thr Lys Glu Gly Val Lys Ala Met Ala Lys Glu Ala Ala Lys Glu
            340                 345                 350

Ala Leu Glu Lys Cys Val Gln Glu Gly Gly Lys Phe Leu Leu Lys Lys
            355                 360                 365

Phe Arg Asn Lys Val Leu Phe Asn Met Phe Lys Lys Ile Leu Tyr Ala
        370                 375                 380

Leu Leu Arg Asp Cys Ser Phe Lys Gly Leu Gln Ala Ile Arg Cys Ala
385                 390                 395                 400

Thr Glu Gly Ala Ser Gln Met Asn Thr Gly Met Val Asn Thr Glu Lys
                405                 410                 415

Ala Lys Ile Glu Lys Lys Ile Glu Gln Leu Ile Thr Gln Gln Arg Phe
            420                 425                 430

Leu Asp Phe Ile Met Gln Gln Thr Glu Asn Gln Lys Lys Ile Glu Gln
            435                 440                 445

Lys Arg Leu Glu Glu Leu Tyr Lys Gly Thr Gly Ala Ala Leu Arg Asp
        450                 455                 460

Val Leu Asp Thr Ile Asp His Tyr Ser Ser Val Gln Ala Arg Ile Ala
465                 470                 475                 480

Gly Tyr Arg Ala

<210> SEQ ID NO 9
<211> LENGTH: 504
<212> TYPE: DNA
<213> ORGANISM: Salmonella
<220> FEATURE:
<221> NAME/KEY: CDS
<222> LOCATION: (1)..(501)

<400> SEQUENCE: 9 atg ggt act gaa tca atg ctt ctg tta ttt gat gat atc tgg atg aag    48
Met Gly Thr Glu Ser Met Leu Leu Leu Phe Asp Asp Ile Trp Met Lys
 1               5                   10                  15 cta atg gag ctt gcc aaa aag ctg cgc gat atc atg cgc agc tat aac    96
Leu Met Glu Leu Ala Lys Lys Leu Arg Asp Ile Met Arg Ser Tyr Asn
            20                  25                  30 gta gaa aaa caa cgg ctg gcc tgg gaa ctg caa gtc aat gtt tta cag   144
Val Glu Lys Gln Arg Leu Ala Trp Glu Leu Gln Val Asn Val Leu Gln
        35                  40                  45 acg caa atg aaa aca att gat gaa gcg ttt aga gca tca atg att act   192
Thr Gln Met Lys Thr Ile Asp Glu Ala Phe Arg Ala Ser Met Ile Thr
    50                  55                  60 gcg ggt ggc gca atg ttg tcg ggt gta ctg acg ata gga tta ggg gcc   240
Ala Gly Gly Ala Met Leu Ser Gly Val Leu Thr Ile Gly Leu Gly Ala
65                  70                  75                  80 gta ggc ggg gaa acc ggt ctt ata gcg ggt caa gcc gta ggc cac aca   288
Val Gly Gly Glu Thr Gly Leu Ile Ala Gly Gln Ala Val Gly His Thr
                85                  90                  95 gct ggg ggc gtc atg ggc ctg ggg gct ggt gta gcg caa cgt caa agt   336
Ala Gly Gly Val Met Gly Leu Gly Ala Gly Val Ala Gln Arg Gln Ser
            100                 105                 110 gat caa gat aaa gcg att gcc gac ctg caa caa aat ggg gcc caa tct   384
Asp Gln Asp Lys Ala Ile Ala Asp Leu Gln Gln Asn Gly Ala Gln Ser
        115                 120                 125
```

```
tat aat aaa tcc ctg acg gaa att atg gag aaa gca act gaa att atg          432
Tyr Asn Lys Ser Leu Thr Glu Ile Met Glu Lys Ala Thr Glu Ile Met
    130                 135                 140 cag caa atc atc ggc gtg ggg tcg tca ctg gtc acg gtt ctt gct gaa          480
Gln Gln Ile Ile Gly Val Gly Ser Ser Leu Val Thr Val Leu Ala Glu
145                 150                 155                 160 ata ctc cgg gca tta acg agg taa                                          504
Ile Leu Arg Ala Leu Thr Arg
                165
```

<210> SEQ ID NO 10
<211> LENGTH: 167
<212> TYPE: PRT
<213> ORGANISM: Salmonella

<400> SEQUENCE: 10

```
Met Gly Thr Glu Ser Met Leu Leu Phe Asp Asp Ile Trp Met Lys
 1               5                  10                  15

Leu Met Glu Leu Ala Lys Lys Leu Arg Asp Ile Met Arg Ser Tyr Asn
                20                  25                  30

Val Glu Lys Gln Arg Leu Ala Trp Glu Leu Gln Val Asn Val Leu Gln
            35                  40                  45

Thr Gln Met Lys Thr Ile Asp Glu Ala Phe Arg Ala Ser Met Ile Thr
    50                  55                  60

Ala Gly Gly Ala Met Leu Ser Gly Val Leu Thr Ile Gly Leu Gly Ala
65                  70                  75                  80

Val Gly Gly Glu Thr Gly Leu Ile Ala Gly Gln Ala Val Gly His Thr
                85                  90                  95

Ala Gly Gly Val Met Gly Leu Gly Ala Gly Val Ala Gln Arg Gln Ser
            100                 105                 110

Asp Gln Asp Lys Ala Ile Ala Asp Leu Gln Gln Asn Gly Ala Gln Ser
        115                 120                 125

Tyr Asn Lys Ser Leu Thr Glu Ile Met Glu Lys Ala Thr Glu Ile Met
    130                 135                 140

Gln Gln Ile Ile Gly Val Gly Ser Ser Leu Val Thr Val Leu Ala Glu
145                 150                 155                 160

Ile Leu Arg Ala Leu Thr Arg
                165
```

<210> SEQ ID NO 11
<211> LENGTH: 195
<212> TYPE: PRT
<213> ORGANISM: Salmonella

<400> SEQUENCE: 11

```
Met Glu Ala Ser Asn Val Ala Leu Val Leu Pro Ala Pro Ser Leu Leu
 1               5                  10                  15

Thr Pro Ser Ser Thr Pro Ser Pro Ser Gly Glu Gly Met Gly Thr Glu
                20                  25                  30

Ser Met Leu Leu Leu Phe Asp Asp Ile Trp Met Lys Leu Met Glu Leu
            35                  40                  45

Ala Lys Lys Leu Arg Asp Ile Met Arg Ser Tyr Asn Val Glu Lys Gln
        50                  55                  60

Arg Leu Ala Trp Glu Leu Gln Val Asn Val Leu Gln Thr Gln Met Lys
65                  70                  75                  80

Thr Ile Asp Glu Ala Phe Arg Ala Ser Met Ile Thr Ala Gly Gly Ala
                85                  90                  95
```

```
Met Leu Ser Gly Val Leu Thr Ile Gly Leu Gly Ala Val Gly Gly Glu
            100                 105                 110

Thr Gly Leu Ile Ala Gly Gln Ala Val Gly His Thr Ala Gly Gly Val
        115                 120                 125

Met Gly Leu Gly Ala Gly Val Ala Gln Arg Gln Ser Asp Gln Asp Lys
    130                 135                 140

Ala Ile Ala Asp Leu Gln Gln Asn Gly Ala Gln Ser Tyr Asn Lys Ser
145                 150                 155                 160

Leu Thr Glu Ile Met Glu Lys Ala Thr Glu Ile Met Gln Gln Ile Ile
                165                 170                 175

Gly Val Gly Ser Ser Leu Val Thr Val Leu Ala Glu Ile Leu Arg Ala
            180                 185                 190

Leu Thr Arg
        195

<210> SEQ ID NO 12
<211> LENGTH: 417
<212> TYPE: DNA
<213> ORGANISM: Salmonella
<220> FEATURE:
<221> NAME/KEY: CDS
<222> LOCATION: (1)..(414)

<400> SEQUENCE: 12 atg gtg caa gaa ata gag caa tgg tta cgt cgg cat cag gtg ttt act      48
Met Val Gln Glu Ile Glu Gln Trp Leu Arg Arg His Gln Val Phe Thr
  1               5                  10                  15 gag cct gca tat tta ggg gag acc gcc ata tta ctt ggg cag cag ttt      96
Glu Pro Ala Tyr Leu Gly Glu Thr Ala Ile Leu Leu Gly Gln Gln Phe
                 20                  25                  30 ata tta tcg cct tac ctg gtg atc tat cgt att gag gca aaa gaa atg     144
Ile Leu Ser Pro Tyr Leu Val Ile Tyr Arg Ile Glu Ala Lys Glu Met
             35                  40                  45 att att tgt gag ttc agg cgc ctg acg ccc ggg caa cct cga cca cag     192
Ile Ile Cys Glu Phe Arg Arg Leu Thr Pro Gly Gln Pro Arg Pro Gln
         50                  55                  60 caa ttg ttt cac tta ctg gga ctt tta cgc ggg ata ttt gtg cat cac     240
Gln Leu Phe His Leu Leu Gly Leu Leu Arg Gly Ile Phe Val His His
 65                  70                  75                  80 ccg cag tta aca tgt tta aag atg ttg ata atc acc gac gtt ctg gat     288
Pro Gln Leu Thr Cys Leu Lys Met Leu Ile Ile Thr Asp Val Leu Asp
                 85                  90                  95 gaa aaa aaa gcc atg cta cgc agg aaa tta ttg cgc atc ctg aca gta     336
Glu Lys Lys Ala Met Leu Arg Arg Lys Leu Leu Arg Ile Leu Thr Val
            100                 105                 110 atg gga gcg acc ttt aca cag ctt gat ggc gat aac tgg aca gtt tta     384
Met Gly Ala Thr Phe Thr Gln Leu Asp Gly Asp Asn Trp Thr Val Leu
        115                 120                 125 tcc gcc gag cat ctt atc cag cga cgt ttt taa                         417
Ser Ala Glu His Leu Ile Gln Arg Arg Phe
    130                 135

<210> SEQ ID NO 13
<211> LENGTH: 138
<212> TYPE: PRT
<213> ORGANISM: Salmonella

<400> SEQUENCE: 13

Met Val Gln Glu Ile Glu Gln Trp Leu Arg Arg His Gln Val Phe Thr
  1               5                  10                  15
```

```
Glu Pro Ala Tyr Leu Gly Glu Thr Ala Ile Leu Leu Gly Gln Gln Phe
             20                  25                  30

Ile Leu Ser Pro Tyr Leu Val Ile Tyr Arg Ile Glu Ala Lys Glu Met
         35                  40                  45

Ile Ile Cys Glu Phe Arg Arg Leu Thr Pro Gly Gln Pro Arg Pro Gln
     50                  55                  60

Gln Leu Phe His Leu Leu Gly Leu Leu Arg Gly Ile Phe Val His His
 65                  70                  75                  80

Pro Gln Leu Thr Cys Leu Lys Met Leu Ile Ile Thr Asp Val Leu Asp
                 85                  90                  95

Glu Lys Lys Ala Met Leu Arg Arg Lys Leu Leu Arg Ile Leu Thr Val
                100                 105                 110

Met Gly Ala Thr Phe Thr Gln Leu Asp Gly Asp Asn Trp Thr Val Leu
            115                 120                 125

Ser Ala Glu His Leu Ile Gln Arg Arg Phe
        130                 135
```

<210> SEQ ID NO 14
<211> LENGTH: 789
<212> TYPE: DNA
<213> ORGANISM: Salmonella
<220> FEATURE:
<221> NAME/KEY: CDS
<222> LOCATION: (1)..(786)

<400> SEQUENCE: 14

```
atg aaa att cat att ccg tca gcg gca agt aat ata gtc gat ggt aat      48
Met Lys Ile His Ile Pro Ser Ala Ala Ser Asn Ile Val Asp Gly Asn
  1               5                  10                  15 agt cct cct tcc gat ata caa gcg aag gag gta tcg ttt cct ccc cct      96
Ser Pro Pro Ser Asp Ile Gln Ala Lys Glu Val Ser Phe Pro Pro Pro
             20                  25                  30 gaa att cca gcg cct ggc acc ccc gca gcc cct gtg ctg ctt acg cct     144
Glu Ile Pro Ala Pro Gly Thr Pro Ala Ala Pro Val Leu Leu Thr Pro
         35                  40                  45 gaa caa ata agg cag cag agg gat tat gcg ata cat ttt atg caa tac     192
Glu Gln Ile Arg Gln Gln Arg Asp Tyr Ala Ile His Phe Met Gln Tyr
     50                  55                  60 act att cgt gcg ctg ggt gcg aca gtc gtg ttt ggg tta tcg gtt gct     240
Thr Ile Arg Ala Leu Gly Ala Thr Val Val Phe Gly Leu Ser Val Ala
 65                  70                  75                  80 gca gcg gta att tct ggc ggg gca gga tta ccc att gct att ctt gcg     288
Ala Ala Val Ile Ser Gly Gly Ala Gly Leu Pro Ile Ala Ile Leu Ala
                 85                  90                  95 ggg gcg gcg ctc gtg att gct att ggg gat gct tgc tgt gcg tat cat     336
Gly Ala Ala Leu Val Ile Ala Ile Gly Asp Ala Cys Cys Ala Tyr His
                100                 105                 110 aat tat caa tcg ata tgt cag caa aag gag cca tta caa acc gcc agt     384
Asn Tyr Gln Ser Ile Cys Gln Gln Lys Glu Pro Leu Gln Thr Ala Ser
            115                 120                 125 gat agc gtt gct ctt gtg gtc agt gcg ctg gcc tta aaa tgt ggg gca     432
Asp Ser Val Ala Leu Val Val Ser Ala Leu Ala Leu Lys Cys Gly Ala
        130                 135                 140 agt ctt aac tgc gct aac acc ctt gct aat tgt ctt tct tta tta ata     480
Ser Leu Asn Cys Ala Asn Thr Leu Ala Asn Cys Leu Ser Leu Leu Ile
145                 150                 155                 160 cgt tca gga atc gct att tct atg ttg gtt tta ccc cta cag ttt cca     528
Arg Ser Gly Ile Ala Ile Ser Met Leu Val Leu Pro Leu Gln Phe Pro
                165                 170                 175
```

```
ctg ccc gcg gct gaa aat att gcg gcc tct ttg gac atg ggg agt gta    576
Leu Pro Ala Ala Glu Asn Ile Ala Ala Ser Leu Asp Met Gly Ser Val
        180                 185                 190 att acc tcc gtt agc ctg acg gcg ata ggt gcg gta ctg gat tat tgc    624
Ile Thr Ser Val Ser Leu Thr Ala Ile Gly Ala Val Leu Asp Tyr Cys
        195                 200                 205 ctt gcc cgc ccc tct ggc gac gat cag gaa aat tct gtt gat gaa ctt    672
Leu Ala Arg Pro Ser Gly Asp Asp Gln Glu Asn Ser Val Asp Glu Leu
    210                 215                 220 cat gcc gat ccc agt gtg tta ttg gcg gaa caa atg gca gcg ctc tgt    720
His Ala Asp Pro Ser Val Leu Leu Ala Glu Gln Met Ala Ala Leu Cys
225                 230                 235                 240 caa tct gct act aca cct gca cct gca tta atg gac agt tct gat cat    768
Gln Ser Ala Thr Thr Pro Ala Pro Ala Leu Met Asp Ser Ser Asp His
                245                 250                 255 aca tct cgg gga gaa cca tga                                        789
Thr Ser Arg Gly Glu Pro
            260
```

<210> SEQ ID NO 15
<211> LENGTH: 262
<212> TYPE: PRT
<213> ORGANISM: Salmonella

<400> SEQUENCE: 15

```
Met Lys Ile His Ile Pro Ser Ala Ala Ser Asn Ile Val Asp Gly Asn
1               5                   10                  15

Ser Pro Pro Ser Asp Ile Gln Ala Lys Glu Val Ser Phe Pro Pro
            20                  25                  30

Glu Ile Pro Ala Pro Gly Thr Pro Ala Ala Pro Val Leu Leu Thr Pro
        35                  40                  45

Glu Gln Ile Arg Gln Arg Asp Tyr Ala Ile His Phe Met Gln Tyr
    50                  55                  60

Thr Ile Arg Ala Leu Gly Ala Thr Val Val Phe Gly Leu Ser Val Ala
65                  70                  75                  80

Ala Ala Val Ile Ser Gly Gly Ala Gly Leu Pro Ile Ala Ile Leu Ala
                85                  90                  95

Gly Ala Ala Leu Val Ile Ala Ile Gly Asp Ala Cys Cys Ala Tyr His
            100                 105                 110

Asn Tyr Gln Ser Ile Cys Gln Gln Lys Glu Pro Leu Gln Thr Ala Ser
        115                 120                 125

Asp Ser Val Ala Leu Val Val Ser Ala Leu Ala Leu Lys Cys Gly Ala
    130                 135                 140

Ser Leu Asn Cys Ala Asn Thr Leu Ala Asn Cys Leu Ser Leu Leu Ile
145                 150                 155                 160

Arg Ser Gly Ile Ala Ile Ser Met Leu Val Leu Pro Leu Gln Phe Pro
                165                 170                 175

Leu Pro Ala Ala Glu Asn Ile Ala Ala Ser Leu Asp Met Gly Ser Val
            180                 185                 190

Ile Thr Ser Val Ser Leu Thr Ala Ile Gly Ala Val Leu Asp Tyr Cys
        195                 200                 205

Leu Ala Arg Pro Ser Gly Asp Asp Gln Glu Asn Ser Val Asp Glu Leu
    210                 215                 220

His Ala Asp Pro Ser Val Leu Leu Ala Glu Gln Met Ala Ala Leu Cys
225                 230                 235                 240

Gln Ser Ala Thr Thr Pro Ala Pro Ala Leu Met Asp Ser Ser Asp His
                245                 250                 255
```

Thr Ser Arg Gly Glu Pro
           260

<210> SEQ ID NO 16
<211> LENGTH: 690
<212> TYPE: DNA
<213> ORGANISM: Salmonella
<220> FEATURE:
<221> NAME/KEY: CDS
<222> LOCATION: (1)..(687)

<400> SEQUENCE: 16

| atg aaa cct gtt agc cca aat gct cag gta gga ggg caa cgt cct gtt | 48 |
| Met Lys Pro Val Ser Pro Asn Ala Gln Val Gly Gly Gln Arg Pro Val | |
| 1               5                   10                  15     | |

| aac gcg cct gag gaa tca cct cca tgt cct tca ttg cca cat ccg gaa | 96 |
| Asn Ala Pro Glu Glu Ser Pro Pro Cys Pro Ser Leu Pro His Pro Glu | |
|                 20                  25                  30     | |

| acc aat atg gag agt ggt aga ata gga cct caa caa gga aaa gag cgg | 144 |
| Thr Asn Met Glu Ser Gly Arg Ile Gly Pro Gln Gln Gly Lys Glu Arg | |
|             35                  40                  45         | |

| gta ttg gcc gga ctt gcg aaa cga gtg ata gag tgt ttt cca aaa gaa | 192 |
| Val Leu Ala Gly Leu Ala Lys Arg Val Ile Glu Cys Phe Pro Lys Glu | |
|     50                  55                  60                 | |

| att ttt agt tgg caa acg gtt att ttg ggc gga cag att tta tgc tgt | 240 |
| Ile Phe Ser Trp Gln Thr Val Ile Leu Gly Gly Gln Ile Leu Cys Cys | |
| 65                  70                  75                  80 | |

| tcc gct gga ata gca tta aca gtg cta agt ggt gga ggc gcg ccg ctc | 288 |
| Ser Ala Gly Ile Ala Leu Thr Val Leu Ser Gly Gly Gly Ala Pro Leu | |
|                 85                  90                  95     | |

| gta gcc ctg gca ggg att ggc ctt gct att gcc atc gcg gat gtc gcc | 336 |
| Val Ala Leu Ala Gly Ile Gly Leu Ala Ile Ala Ile Ala Asp Val Ala | |
|             100                 105                 110        | |

| tgt ctt atc tac cat cat aaa cat cat ttg cct atg gct cac gac agt | 384 |
| Cys Leu Ile Tyr His His Lys His His Leu Pro Met Ala His Asp Ser | |
|         115                 120                 125            | |

| ata ggc aat gcc gtt ttt tat att gct aat tgt ttc gcc aat caa cgc | 432 |
| Ile Gly Asn Ala Val Phe Tyr Ile Ala Asn Cys Phe Ala Asn Gln Arg | |
|     130                 135                 140                | |

| aaa agt atg gcg att gct aaa gcc gtc tcc ctg ggc ggt aga tta gcc | 480 |
| Lys Ser Met Ala Ile Ala Lys Ala Val Ser Leu Gly Gly Arg Leu Ala | |
| 145                 150                 155                 160| |

| tta acc gcg acg gta atg act cat tca tac tgg agt ggt agt ttg gga | 528 |
| Leu Thr Ala Thr Val Met Thr His Ser Tyr Trp Ser Gly Ser Leu Gly | |
|                 165                 170                 175    | |

| cta cag cct cat tta tta gag cgt ctt aat gat att acc tat gga cta | 576 |
| Leu Gln Pro His Leu Leu Glu Arg Leu Asn Asp Ile Thr Tyr Gly Leu | |
|             180                 185                 190        | |

| atg agt ttt act cgc ttc ggt atg gat ggg atg gca atg acc ggt atg | 624 |
| Met Ser Phe Thr Arg Phe Gly Met Asp Gly Met Ala Met Thr Gly Met | |
|         195                 200                 205            | |

| cag gtc agc agc cca tta tat cgt ttg ctg gct cag gta acg cca gaa | 672 |
| Gln Val Ser Ser Pro Leu Tyr Arg Leu Leu Ala Gln Val Thr Pro Glu | |
|     210                 215                 220                | |

| caa cgt gcg ccg gag taa | 690 |
| Gln Arg Ala Pro Glu     | |
| 225                     | |

<210> SEQ ID NO 17
<211> LENGTH: 229
<212> TYPE: PRT

-continued

<213> ORGANISM: Salmonella

<400> SEQUENCE: 17

Met Lys Pro Val Ser Pro Asn Ala Gln Val Gly Gly Gln Arg Pro Val
 1               5                  10                  15

Asn Ala Pro Glu Glu Ser Pro Pro Cys Pro Ser Leu Pro His Pro Glu
                20                  25                  30

Thr Asn Met Glu Ser Gly Arg Ile Gly Pro Gln Gln Gly Lys Glu Arg
            35                  40                  45

Val Leu Ala Gly Leu Ala Lys Arg Val Ile Glu Cys Phe Pro Lys Glu
    50                  55                  60

Ile Phe Ser Trp Gln Thr Val Ile Leu Gly Gly Gln Ile Leu Cys Cys
 65                  70                  75                  80

Ser Ala Gly Ile Ala Leu Thr Val Leu Ser Gly Gly Ala Pro Leu
                85                  90                  95

Val Ala Leu Ala Gly Ile Gly Leu Ala Ile Ala Ile Ala Asp Val Ala
                100                 105                 110

Cys Leu Ile Tyr His His Lys His His Leu Pro Met Ala His Asp Ser
            115                 120                 125

Ile Gly Asn Ala Val Phe Tyr Ile Ala Asn Cys Phe Ala Asn Gln Arg
        130                 135                 140

Lys Ser Met Ala Ile Ala Lys Ala Val Ser Leu Gly Gly Arg Leu Ala
145                 150                 155                 160

Leu Thr Ala Thr Val Met Thr His Ser Tyr Trp Ser Gly Ser Leu Gly
                165                 170                 175

Leu Gln Pro His Leu Leu Glu Arg Leu Asn Asp Ile Thr Tyr Gly Leu
            180                 185                 190

Met Ser Phe Thr Arg Phe Gly Met Asp Gly Met Ala Met Thr Gly Met
        195                 200                 205

Gln Val Ser Ser Pro Leu Tyr Arg Leu Leu Ala Gln Val Thr Pro Glu
    210                 215                 220

Gln Arg Ala Pro Glu
225

<210> SEQ ID NO 18
<211> LENGTH: 474
<212> TYPE: DNA
<213> ORGANISM: Salmonella
<220> FEATURE:
<221> NAME/KEY: CDS
<222> LOCATION: (1)..(471)

<400> SEQUENCE: 18 atg aaa aaa gac ccg acc cta caa cag gca cat gac acg atg cgg ttt     48
Met Lys Lys Asp Pro Thr Leu Gln Gln Ala His Asp Thr Met Arg Phe
 1               5                  10                  15 ttc cgg cgt ggc ggc tcg ctg cgt atg ttg ttg gat gac gat gtt aca     96
Phe Arg Arg Gly Gly Ser Leu Arg Met Leu Leu Asp Asp Asp Val Thr
                20                  25                  30 cag ccg ctt aat act ctg tat cgc tat gcc acg cag ctt atg gag gta    144
Gln Pro Leu Asn Thr Leu Tyr Arg Tyr Ala Thr Gln Leu Met Glu Val
            35                  40                  45 aaa gaa ttc gcc ggc gca gcg cga ctt ttt caa ttg ctg acg ata tat    192
Lys Glu Phe Ala Gly Ala Ala Arg Leu Phe Gln Leu Leu Thr Ile Tyr
        50                  55                  60 gat gcc tgg tca ttt gac tac tgg ttt cgg tta ggg gaa tgc tgc cag    240
Asp Ala Trp Ser Phe Asp Tyr Trp Phe Arg Leu Gly Glu Cys Cys Gln
 65                  70                  75                  80

```
gct caa aaa cat tgg ggg gaa gcg ata tac gct tat gga cgc gcg gca    288
Ala Gln Lys His Trp Gly Glu Ala Ile Tyr Ala Tyr Gly Arg Ala Ala
             85                  90                  95 caa att aag att gat gcg ccg cag gcg cca tgg gcc gca gcg gaa tgc    336
Gln Ile Lys Ile Asp Ala Pro Gln Ala Pro Trp Ala Ala Ala Glu Cys
            100                 105                 110 tat ctc gcg tgt gat aac gtc tgt tat gca atc aaa gcg tta aag gcc    384
Tyr Leu Ala Cys Asp Asn Val Cys Tyr Ala Ile Lys Ala Leu Lys Ala
        115                 120                 125 gtg gtg cgt att tgc ggc gag gtc agt gaa cat caa att ctc cga cag    432
Val Val Arg Ile Cys Gly Glu Val Ser Glu His Gln Ile Leu Arg Gln
    130                 135                 140 cgt gca gaa aag atg tta cag caa ctt tct gac agg agc taa            474
Arg Ala Glu Lys Met Leu Gln Gln Leu Ser Asp Arg Ser
145                 150                 155
```

<210> SEQ ID NO 19
<211> LENGTH: 157
<212> TYPE: PRT
<213> ORGANISM: Salmonella

<400> SEQUENCE: 19

```
Met Lys Lys Asp Pro Thr Leu Gln Gln Ala His Asp Thr Met Arg Phe
  1               5                  10                  15

Phe Arg Arg Gly Gly Ser Leu Arg Met Leu Leu Asp Asp Val Thr
                 20                  25                  30

Gln Pro Leu Asn Thr Leu Tyr Arg Tyr Ala Thr Gln Leu Met Glu Val
             35                  40                  45

Lys Glu Phe Ala Gly Ala Ala Arg Leu Phe Gln Leu Leu Thr Ile Tyr
         50                  55                  60

Asp Ala Trp Ser Phe Asp Tyr Trp Phe Arg Leu Gly Glu Cys Cys Gln
 65                  70                  75                  80

Ala Gln Lys His Trp Gly Glu Ala Ile Tyr Ala Tyr Gly Arg Ala Ala
                 85                  90                  95

Gln Ile Lys Ile Asp Ala Pro Gln Ala Pro Trp Ala Ala Ala Glu Cys
            100                 105                 110

Tyr Leu Ala Cys Asp Asn Val Cys Tyr Ala Ile Lys Ala Leu Lys Ala
        115                 120                 125

Val Val Arg Ile Cys Gly Glu Val Ser Glu His Gln Ile Leu Arg Gln
    130                 135                 140

Arg Ala Glu Lys Met Leu Gln Gln Leu Ser Asp Arg Ser
145                 150                 155
```

<210> SEQ ID NO 20
<211> LENGTH: 435
<212> TYPE: DNA
<213> ORGANISM: Salmonella
<220> FEATURE:
<221> NAME/KEY: CDS
<222> LOCATION: (1)..(432)

<400> SEQUENCE: 20

```
atg atg atg aaa gaa gat cag aaa aat aaa ata ccc gaa gac att ctg    48
Met Met Met Lys Glu Asp Gln Lys Asn Lys Ile Pro Glu Asp Ile Leu
  1               5                  10                  15 aaa cag cta tta tcc gtt gat ccg gaa acc gtt tat gcc agt ggt tac    96
Lys Gln Leu Leu Ser Val Asp Pro Glu Thr Val Tyr Ala Ser Gly Tyr
                 20                  25                  30 gcc tca tgg cag gag ggg gat tat tcg cgc gcc gta atc gat ttt agt   144
Ala Ser Trp Gln Glu Gly Asp Tyr Ser Arg Ala Val Ile Asp Phe Ser
```

```
Ala Ser Trp Gln Glu Gly Asp Tyr Ser Arg Ala Val Ile Asp Phe Ser
         35                  40                  45 tgg ctg gtg atg gcc cag cca tgg agt tgg cgt gcc cat att gca ttg     192
Trp Leu Val Met Ala Gln Pro Trp Ser Trp Arg Ala His Ile Ala Leu
 50                  55                  60 gct ggc acc tgg atg atg ctt aaa gaa tac acg acg gcc att aat ttc     240
Ala Gly Thr Trp Met Met Leu Lys Glu Tyr Thr Thr Ala Ile Asn Phe
 65                  70                  75                  80 tat gga cat gcc ttg atg ctg gat gcc agc cat cca gaa ccg gtt tac     288
Tyr Gly His Ala Leu Met Leu Asp Ala Ser His Pro Glu Pro Val Tyr
                 85                  90                  95 caa acg ggc gtc tgt ctc aaa atg atg ggg gaa ccc ggg ttg gcg aga     336
Gln Thr Gly Val Cys Leu Lys Met Met Gly Glu Pro Gly Leu Ala Arg
            100                 105                 110 gag gct ttt caa acc gca atc aag atg agt tat gcg gat gcc tca tgg     384
Glu Ala Phe Gln Thr Ala Ile Lys Met Ser Tyr Ala Asp Ala Ser Trp
            115                 120                 125 agt gag att cgc cag aat gcg caa ata atg gtt gat act ctt att gct     432
Ser Glu Ile Arg Gln Asn Ala Gln Ile Met Val Asp Thr Leu Ile Ala
130                 135                 140 taa                                                                 435
```

<210> SEQ ID NO 21
<211> LENGTH: 144
<212> TYPE: PRT
<213> ORGANISM: Salmonella

<400> SEQUENCE: 21

```
Met Met Met Lys Glu Asp Gln Lys Asn Lys Ile Pro Glu Asp Ile Leu
  1               5                  10                  15

Lys Gln Leu Leu Ser Val Asp Pro Glu Thr Val Tyr Ala Ser Gly Tyr
                 20                  25                  30

Ala Ser Trp Gln Glu Gly Asp Tyr Ser Arg Ala Val Ile Asp Phe Ser
         35                  40                  45

Trp Leu Val Met Ala Gln Pro Trp Ser Trp Arg Ala His Ile Ala Leu
 50                  55                  60

Ala Gly Thr Trp Met Met Leu Lys Glu Tyr Thr Thr Ala Ile Asn Phe
 65                  70                  75                  80

Tyr Gly His Ala Leu Met Leu Asp Ala Ser His Pro Glu Pro Val Tyr
                 85                  90                  95

Gln Thr Gly Val Cys Leu Lys Met Met Gly Glu Pro Gly Leu Ala Arg
            100                 105                 110

Glu Ala Phe Gln Thr Ala Ile Lys Met Ser Tyr Ala Asp Ala Ser Trp
            115                 120                 125

Ser Glu Ile Arg Gln Asn Ala Gln Ile Met Val Asp Thr Leu Ile Ala
130                 135                 140
```

<210> SEQ ID NO 22
<211> LENGTH: 1212
<212> TYPE: DNA
<213> ORGANISM: Salmonella
<220> FEATURE:
<221> NAME/KEY: CDS
<222> LOCATION: (1)..(1209)

<400> SEQUENCE: 22

```
atg gca tat ctc atg gtt aat cca aag agt tcc tgg aaa ata cgt ttt      48
Met Ala Tyr Leu Met Val Asn Pro Lys Ser Ser Trp Lys Ile Arg Phe
  1               5                  10                  15
```

-continued

| | | |
|---|---|---|
| tta ggt cac gtt tta caa ggc cgg gaa gta tgg ctg aat gaa ggt aac<br>Leu Gly His Val Leu Gln Gly Arg Glu Val Trp Leu Asn Glu Gly Asn<br>             20                        25                 30 | 96 |
| ctg tca ctg ggg gag aag gga tgc gat att tgt att ccg ctg gct ata<br>Leu Ser Leu Gly Glu Lys Gly Cys Asp Ile Cys Ile Pro Leu Ala Ile<br>        35                    40                     45 | 144 |
| aat gaa aaa att att ctg aga gaa cag gca gat agt tta ttt gtt gat<br>Asn Glu Lys Ile Ile Leu Arg Glu Gln Ala Asp Ser Leu Phe Val Asp<br>50                    55                    60 | 192 |
| gcc ggg aaa gcc aga gtt aga gtt aat ggc cgc aga ttt aat cca aat<br>Ala Gly Lys Ala Arg Val Arg Val Asn Gly Arg Arg Phe Asn Pro Asn<br>65                  70                    75                 80 | 240 |
| aag ccg cta cca tcc agt ggg gtt ttg cag gtt gcg gga gtg gct atc<br>Lys Pro Leu Pro Ser Ser Gly Val Leu Gln Val Ala Gly Val Ala Ile<br>                      85                    90                 95 | 288 |
| gcg ttt ggt aaa cag gat tgt gaa ctt gct gat tat caa ata ccc gtt<br>Ala Phe Gly Lys Gln Asp Cys Glu Leu Ala Asp Tyr Gln Ile Pro Val<br>                 100                 105               110 | 336 |
| tcc aga tca ggg tac tgg tgg ttg gct ggc gta ttc ttg att ttc atc<br>Ser Arg Ser Gly Tyr Trp Trp Leu Ala Gly Val Phe Leu Ile Phe Ile<br>               115                 120               125 | 384 |
| ggt gga atg ggt gtc ctg tta agt att agt ggt cag cct gaa acg gta<br>Gly Gly Met Gly Val Leu Leu Ser Ile Ser Gly Gln Pro Glu Thr Val<br>130                    135                140 | 432 |
| aat gac tta cct ttg cgg gtt aag ttt tta tta gac aaa agc aat att<br>Asn Asp Leu Pro Leu Arg Val Lys Phe Leu Leu Asp Lys Ser Asn Ile<br>145                  150                 155               160 | 480 |
| cat tat gtg cgg gcg caa tgg aaa gaa gat ggc agc ctg cag ttg tcc<br>His Tyr Val Arg Ala Gln Trp Lys Glu Asp Gly Ser Leu Gln Leu Ser<br>               165                 170               175 | 528 |
| ggt tat tgc tcg tca agc gaa cag atg caa aag gtg aga gcg act ctc<br>Gly Tyr Cys Ser Ser Ser Glu Gln Met Gln Lys Val Arg Ala Thr Leu<br>                 180                 185               190 | 576 |
| gaa tca tgg ggg gtc atg tat cgg gat ggt gta atc tgt gat gac tta<br>Glu Ser Trp Gly Val Met Tyr Arg Asp Gly Val Ile Cys Asp Asp Leu<br>             195                 200               205 | 624 |
| ttg gta cga gaa gtg cag gat gtt ttg ata aaa atg ggt tac ccg cat<br>Leu Val Arg Glu Val Gln Asp Val Leu Ile Lys Met Gly Tyr Pro His<br>         210                 215               220 | 672 |
| gct gaa gta tcc agc gaa ggg ccg ggg agc gtg tta att cat gat gat<br>Ala Glu Val Ser Ser Glu Gly Pro Gly Ser Val Leu Ile His Asp Asp<br>225                  230                 235               240 | 720 |
| ata caa atg gat cag caa tgg cgc aag gtt caa cca tta ctt gca gat<br>Ile Gln Met Asp Gln Gln Trp Arg Lys Val Gln Pro Leu Leu Ala Asp<br>               245                 250               255 | 768 |
| att ccc ggg tta ttg cac tgg cag att agt cac tct cat cag tct cag<br>Ile Pro Gly Leu Leu His Trp Gln Ile Ser His Ser His Gln Ser Gln<br>             260                 265               270 | 816 |
| ggg gat gat att att tct gcg ata ata gag aac ggt tta gtg ggg ctt<br>Gly Asp Asp Ile Ile Ser Ala Ile Ile Glu Asn Gly Leu Val Gly Leu<br>         275                 280               285 | 864 |
| gtc aat gtt agc cca atg cgg cgc tct ttt gtt atc agt ggt gta ctg<br>Val Asn Val Ser Pro Met Arg Arg Ser Phe Val Ile Ser Gly Val Leu<br>         290                 295               300 | 912 |
| gat gaa tct cat caa cgc att ttg caa gaa acg tta gca gca tta aag<br>Asp Glu Ser His Gln Arg Ile Leu Gln Glu Thr Leu Ala Ala Leu Lys<br>305                  310                 315               320 | 960 |
| aaa aag gat ccc gct ctt tct tta att tat cag gat att gcg cct tcc<br>Lys Lys Asp Pro Ala Leu Ser Leu Ile Tyr Gln Asp Ile Ala Pro Ser<br>               325                 330               335 | 1008 |

```
cat gat gaa agc aag tat ctg cct gcg cca gtg gct ggc ttt gta cag      1056
His Asp Glu Ser Lys Tyr Leu Pro Ala Pro Val Ala Gly Phe Val Gln
            340                 345                 350 agt cgc cat ggt aat tac tta tta ctg acg aat aaa gag cgt tta cgt      1104
Ser Arg His Gly Asn Tyr Leu Leu Leu Thr Asn Lys Glu Arg Leu Arg
        355                 360                 365 gta ggg gca ttg tta ccc aat ggg gga gaa att gtc cat ctg agt gcc      1152
Val Gly Ala Leu Leu Pro Asn Gly Gly Glu Ile Val His Leu Ser Ala
    370                 375                 380 gat gtg gta acg att aaa cat tat gat act ttg att aac tat cca tta      1200
Asp Val Val Thr Ile Lys His Tyr Asp Thr Leu Ile Asn Tyr Pro Leu
385                 390                 395                 400 gat ttt aag tga                                                      1212
Asp Phe Lys <210> SEQ ID NO 23
<211> LENGTH: 403
<212> TYPE: PRT
<213> ORGANISM: Salmonella

<400> SEQUENCE: 23

Met Ala Tyr Leu Met Val Asn Pro Lys Ser Ser Trp Lys Ile Arg Phe
  1               5                  10                  15

Leu Gly His Val Leu Gln Gly Arg Glu Val Trp Leu Asn Glu Gly Asn
             20                  25                  30

Leu Ser Leu Gly Glu Lys Gly Cys Asp Ile Cys Ile Pro Leu Ala Ile
         35                  40                  45

Asn Glu Lys Ile Ile Leu Arg Glu Gln Ala Asp Ser Leu Phe Val Asp
     50                  55                  60

Ala Gly Lys Ala Arg Val Arg Val Asn Gly Arg Arg Phe Asn Pro Asn
 65                  70                  75                  80

Lys Pro Leu Pro Ser Ser Gly Val Leu Gln Val Ala Gly Val Ala Ile
                 85                  90                  95

Ala Phe Gly Lys Gln Asp Cys Glu Leu Ala Asp Tyr Gln Ile Pro Val
            100                 105                 110

Ser Arg Ser Gly Tyr Trp Trp Leu Ala Gly Val Phe Leu Ile Phe Ile
        115                 120                 125

Gly Gly Met Gly Val Leu Leu Ser Ile Ser Gly Gln Pro Glu Thr Val
    130                 135                 140

Asn Asp Leu Pro Leu Arg Val Lys Phe Leu Leu Asp Lys Ser Asn Ile
145                 150                 155                 160

His Tyr Val Arg Ala Gln Trp Lys Glu Asp Gly Ser Leu Gln Leu Ser
                165                 170                 175

Gly Tyr Cys Ser Ser Glu Gln Met Gln Lys Val Arg Ala Thr Leu
            180                 185                 190

Glu Ser Trp Gly Val Met Tyr Arg Asp Gly Val Ile Cys Asp Asp Leu
        195                 200                 205

Leu Val Arg Glu Val Gln Asp Val Leu Ile Lys Met Gly Tyr Pro His
    210                 215                 220

Ala Glu Val Ser Ser Glu Gly Pro Gly Ser Val Leu Ile His Asp Asp
225                 230                 235                 240

Ile Gln Met Asp Gln Gln Trp Arg Lys Val Gln Pro Leu Leu Ala Asp
                245                 250                 255

Ile Pro Gly Leu Leu His Trp Gln Ile Ser His Ser His Gln Ser Gln
            260                 265                 270
```

```
Gly Asp Asp Ile Ile Ser Ala Ile Ile Glu Asn Gly Leu Val Gly Leu
            275                 280                 285

Val Asn Val Ser Pro Met Arg Arg Ser Phe Val Ile Ser Gly Val Leu
290                     295                 300

Asp Glu Ser His Gln Arg Ile Leu Gln Glu Thr Leu Ala Ala Leu Lys
305                 310                 315                 320

Lys Lys Asp Pro Ala Leu Ser Leu Ile Tyr Gln Asp Ile Ala Pro Ser
                325                 330                 335

His Asp Glu Ser Lys Tyr Leu Pro Ala Pro Val Ala Gly Phe Val Gln
            340                 345                 350

Ser Arg His Gly Asn Tyr Leu Leu Thr Asn Lys Glu Arg Leu Arg
            355                 360                 365

Val Gly Ala Leu Leu Pro Asn Gly Gly Glu Ile Val His Leu Ser Ala
370                     375                 380

Asp Val Val Thr Ile Lys His Tyr Asp Thr Leu Ile Asn Tyr Pro Leu
385                     390                 395                 400

Asp Phe Lys

<210> SEQ ID NO 24
<211> LENGTH: 243
<212> TYPE: DNA
<213> ORGANISM: Salmonella
<220> FEATURE:
<221> NAME/KEY: CDS
<222> LOCATION: (1)..(240)

<400> SEQUENCE: 24 atg aca act ttg acc cgg tta gaa gat ttg ctg ctt cat tcg cgt gaa      48
Met Thr Thr Leu Thr Arg Leu Glu Asp Leu Leu Leu His Ser Arg Glu
1               5                   10                  15 gag gcc aaa ggc ata att tta caa tta agg gct gcc cgg aaa cag tta      96
Glu Ala Lys Gly Ile Ile Leu Gln Leu Arg Ala Ala Arg Lys Gln Leu
                20                  25                  30 gaa gag aac aac ggc aag tta cag gat ccg cag caa tat cag caa aac     144
Glu Glu Asn Asn Gly Lys Leu Gln Asp Pro Gln Gln Tyr Gln Gln Asn
            35                  40                  45 acc tta ttg ctt gaa gcg atc gag cag gcc gaa aat atc atc aac att     192
Thr Leu Leu Leu Glu Ala Ile Glu Gln Ala Glu Asn Ile Ile Asn Ile
        50                  55                  60 att tat tat cgt tac cat aac agc gca ctt gta gtg agt gag caa gag     240
Ile Tyr Tyr Arg Tyr His Asn Ser Ala Leu Val Val Ser Glu Gln Glu
65                  70                  75                  80 taa                                                                  243

<210> SEQ ID NO 25
<211> LENGTH: 80
<212> TYPE: PRT
<213> ORGANISM: Salmonella

<400> SEQUENCE: 25

Met Thr Thr Leu Thr Arg Leu Glu Asp Leu Leu Leu His Ser Arg Glu
1               5                   10                  15

Glu Ala Lys Gly Ile Ile Leu Gln Leu Arg Ala Ala Arg Lys Gln Leu
                20                  25                  30

Glu Glu Asn Asn Gly Lys Leu Gln Asp Pro Gln Gln Tyr Gln Gln Asn
            35                  40                  45

Thr Leu Leu Leu Glu Ala Ile Glu Gln Ala Glu Asn Ile Ile Asn Ile
        50                  55                  60
```

```
Ile Tyr Tyr Arg Tyr His Asn Ser Ala Leu Val Val Ser Glu Gln Glu
 65                  70                  75                  80
```

<210> SEQ ID NO 26
<211> LENGTH: 216
<212> TYPE: DNA
<213> ORGANISM: Salmonella
<220> FEATURE:
<221> NAME/KEY: CDS
<222> LOCATION: (1)..(213)

<400> SEQUENCE: 26

```
atg gat att gca caa tta gtg gat atg ctc tcc cac atg gcg cac cag      48
Met Asp Ile Ala Gln Leu Val Asp Met Leu Ser His Met Ala His Gln
 1               5                  10                  15 gca ggc cag gcc att aat gac aaa atg aat ggt aat gat ttg ctc aac      96
Ala Gly Gln Ala Ile Asn Asp Lys Met Asn Gly Asn Asp Leu Leu Asn
                 20                  25                  30 cca gaa tcg atg att aaa gcg caa ttt gcc tta cag cag tat tct aca     144
Pro Glu Ser Met Ile Lys Ala Gln Phe Ala Leu Gln Gln Tyr Ser Thr
             35                  40                  45 ttt att aat tac gaa agt tca ctg atc aaa atg atc aag gat atg ctt     192
Phe Ile Asn Tyr Glu Ser Ser Leu Ile Lys Met Ile Lys Asp Met Leu
         50                  55                  60 agt gga atc att gct aaa atc tga                                     216
Ser Gly Ile Ile Ala Lys Ile
 65                  70
```

<210> SEQ ID NO 27
<211> LENGTH: 71
<212> TYPE: PRT
<213> ORGANISM: Salmonella

<400> SEQUENCE: 27

```
Met Asp Ile Ala Gln Leu Val Asp Met Leu Ser His Met Ala His Gln
 1               5                  10                  15

Ala Gly Gln Ala Ile Asn Asp Lys Met Asn Gly Asn Asp Leu Leu Asn
                 20                  25                  30

Pro Glu Ser Met Ile Lys Ala Gln Phe Ala Leu Gln Gln Tyr Ser Thr
             35                  40                  45

Phe Ile Asn Tyr Glu Ser Ser Leu Ile Lys Met Ile Lys Asp Met Leu
         50                  55                  60

Ser Gly Ile Ile Ala Lys Ile
 65                  70
```

<210> SEQ ID NO 28
<211> LENGTH: 228
<212> TYPE: DNA
<213> ORGANISM: Salmonella
<220> FEATURE:
<221> NAME/KEY: CDS
<222> LOCATION: (1)..(225)

<400> SEQUENCE: 28

```
atg ttt gcg ggc gtt aac cat agc ctg att tcc cag gta cat gcg atg      48
Met Phe Ala Gly Val Asn His Ser Leu Ile Ser Gln Val His Ala Met
 1               5                  10                  15 tta cca gcg cta acg gtt att gtt ccg gat aaa aaa tta cag ttg gta      96
Leu Pro Ala Leu Thr Val Ile Val Pro Asp Lys Lys Leu Gln Leu Val
                 20                  25                  30 tgt ctg gca tta ttg ttg gcg ggt tta aat gag ccg cta aaa gcc gcg     144
Cys Leu Ala Leu Leu Leu Ala Gly Leu Asn Glu Pro Leu Lys Ala Ala
             35                  40                  45
```

```
aaa att tta tcg gat ata gat ttg cca gag gct atg gcg ctg cgt ctg     192
Lys Ile Leu Ser Asp Ile Asp Leu Pro Glu Ala Met Ala Leu Arg Leu
 50                  55                  60 tta ttt cct gca cca aat gag ggg ttt gaa aat tga                     228
Leu Phe Pro Ala Pro Asn Glu Gly Phe Glu Asn
 65                  70                  75

<210> SEQ ID NO 29
<211> LENGTH: 75
<212> TYPE: PRT
<213> ORGANISM: Salmonella

<400> SEQUENCE: 29

Met Phe Ala Gly Val Asn His Ser Leu Ile Ser Gln Val His Ala Met
 1               5                  10                  15

Leu Pro Ala Leu Thr Val Ile Val Pro Asp Lys Lys Leu Gln Leu Val
                 20                  25                  30

Cys Leu Ala Leu Leu Ala Gly Leu Asn Glu Pro Leu Lys Ala Ala
             35                  40                  45

Lys Ile Leu Ser Asp Ile Asp Leu Pro Glu Ala Met Ala Leu Arg Leu
 50                  55                  60

Leu Phe Pro Ala Pro Asn Glu Gly Phe Glu Asn
 65                  70                  75

<210> SEQ ID NO 30
<211> LENGTH: 249
<212> TYPE: DNA
<213> ORGANISM: Salmonella
<220> FEATURE:
<221> NAME/KEY: CDS
<222> LOCATION: (1)..(246)

<400> SEQUENCE: 30 atg agc gta gtg cct gta agc act caa tct tat gta aag tcc tct gca    48
Met Ser Val Val Pro Val Ser Thr Gln Ser Tyr Val Lys Ser Ser Ala
 1               5                  10                  15 gaa ccg agc cag gag caa att aat ttt ttt gaa caa ttg ctg aaa gat    96
Glu Pro Ser Gln Glu Gln Ile Asn Phe Phe Glu Gln Leu Leu Lys Asp
                 20                  25                  30 gaa gca tcc acc agt aac gcc agt gct tta tta ccg cag gtt atg ttg    144
Glu Ala Ser Thr Ser Asn Ala Ser Ala Leu Leu Pro Gln Val Met Leu
             35                  40                  45 acc aga caa atg gat tat atg cag tta acg gta ggc gtc gat tat ctt    192
Thr Arg Gln Met Asp Tyr Met Gln Leu Thr Val Gly Val Asp Tyr Leu
 50                  55                  60 gcc aga ata tca ggc gca gca tcg caa gcg ctt aat aag ctg gat aac    240
Ala Arg Ile Ser Gly Ala Ala Ser Gln Ala Leu Asn Lys Leu Asp Asn
 65                  70                  75                  80 atg gca tga                                                        249
Met Ala

<210> SEQ ID NO 31
<211> LENGTH: 82
<212> TYPE: PRT
<213> ORGANISM: Salmonella

<400> SEQUENCE: 31

Met Ser Val Val Pro Val Ser Thr Gln Ser Tyr Val Lys Ser Ser Ala
 1               5                  10                  15

Glu Pro Ser Gln Glu Gln Ile Asn Phe Phe Glu Gln Leu Leu Lys Asp
                 20                  25                  30
```

```
Glu Ala Ser Thr Ser Asn Ala Ser Ala Leu Leu Pro Gln Val Met Leu
         35                  40                  45

Thr Arg Gln Met Asp Tyr Met Gln Leu Thr Val Gly Val Asp Tyr Leu
     50                  55                  60

Ala Arg Ile Ser Gly Ala Ala Ser Gln Ala Leu Asn Lys Leu Asp Asn
 65                  70                  75                  80

Met Ala

<210> SEQ ID NO 32
<211> LENGTH: 750
<212> TYPE: DNA
<213> ORGANISM: Salmonella
<220> FEATURE:
<221> NAME/KEY: CDS
<222> LOCATION: (1)..(747)

<400> SEQUENCE: 32 atg aag gtt cat cgt ata gta ttt ctt act gtc ctt acg ttc ttt ctt       48
Met Lys Val His Arg Ile Val Phe Leu Thr Val Leu Thr Phe Phe Leu
 1               5                  10                  15 acg gca tgt gat gtg gat ctt tat cgc tca ttg cca gaa gat gaa gcg       96
Thr Ala Cys Asp Val Asp Leu Tyr Arg Ser Leu Pro Glu Asp Glu Ala
             20                  25                  30 aat caa atg ctg gca tta ctt atg cag cat cat att gat gcg gaa aaa      144
Asn Gln Met Leu Ala Leu Leu Met Gln His His Ile Asp Ala Glu Lys
         35                  40                  45 aaa cag gaa gag gat ggt gta acc tta cgt gtc gag cag tcg cag ttt      192
Lys Gln Glu Glu Asp Gly Val Thr Leu Arg Val Glu Gln Ser Gln Phe
     50                  55                  60 att aat gcg gtt gag cta ctt aga ctt aac ggt tat ccg cat agg cag      240
Ile Asn Ala Val Glu Leu Leu Arg Leu Asn Gly Tyr Pro His Arg Gln
 65                  70                  75                  80 ttt aca acg gcg gat aag atg ttt ccg gct aat cag tta gtg gta tca      288
Phe Thr Thr Ala Asp Lys Met Phe Pro Ala Asn Gln Leu Val Val Ser
                 85                  90                  95 ccc cag gaa gaa cag cag aag att aat ttt tta aaa gaa caa aga att      336
Pro Gln Glu Glu Gln Gln Lys Ile Asn Phe Leu Lys Glu Gln Arg Ile
            100                 105                 110 gaa gga atg ctg agt cag atg gag ggc gtg att aat gca aaa gtg acc      384
Glu Gly Met Leu Ser Gln Met Glu Gly Val Ile Asn Ala Lys Val Thr
        115                 120                 125 att gcg cta ccg act tat gat gag gga agt aac gct tct ccg agc tca      432
Ile Ala Leu Pro Thr Tyr Asp Glu Gly Ser Asn Ala Ser Pro Ser Ser
    130                 135                 140 gtt gcc gta ttt ata aaa tat tca cct cag gtc aat atg gag gcc ttt      480
Val Ala Val Phe Ile Lys Tyr Ser Pro Gln Val Asn Met Glu Ala Phe
145                 150                 155                 160 cgg gta aaa att aaa gat tta ata gag atg tca atc cct ggg ttg caa      528
Arg Val Lys Ile Lys Asp Leu Ile Glu Met Ser Ile Pro Gly Leu Gln
                165                 170                 175 tac agt aag att agt atc ttg atg cag cct gct gaa ttc aga atg gta      576
Tyr Ser Lys Ile Ser Ile Leu Met Gln Pro Ala Glu Phe Arg Met Val
            180                 185                 190 gct gac gta ccc gcg aga caa aca ttc tgg att atg gac gtt atc aac      624
Ala Asp Val Pro Ala Arg Gln Thr Phe Trp Ile Met Asp Val Ile Asn
        195                 200                 205 gcc aat aaa ggg aag gtg gtg aag tgg ttg atg aaa tac cct tat ccg      672
Ala Asn Lys Gly Lys Val Val Lys Trp Leu Met Lys Tyr Pro Tyr Pro
    210                 215                 220
```

```
ttg atg tta tcg ttg aca gga ctg tta tta gga gtg ggc atc ctg atc    720
Leu Met Leu Ser Leu Thr Gly Leu Leu Leu Gly Val Gly Ile Leu Ile
225             230                 235                 240 ggc tat ttt tgc ctg aga cgc cgt ttt tga                            750
Gly Tyr Phe Cys Leu Arg Arg Arg Phe
                245
```

<210> SEQ ID NO 33
<211> LENGTH: 249
<212> TYPE: PRT
<213> ORGANISM: Salmonella

<400> SEQUENCE: 33

```
Met Lys Val His Arg Ile Val Phe Leu Thr Val Leu Thr Phe Phe Leu
1               5                   10                  15

Thr Ala Cys Asp Val Asp Leu Tyr Arg Ser Leu Pro Glu Asp Glu Ala
                20                  25                  30

Asn Gln Met Leu Ala Leu Leu Met Gln His His Ile Asp Ala Glu Lys
            35                  40                  45

Lys Gln Glu Glu Asp Gly Val Thr Leu Arg Val Glu Gln Ser Gln Phe
        50                  55                  60

Ile Asn Ala Val Glu Leu Leu Arg Leu Asn Gly Tyr Pro His Arg Gln
65                  70                  75                  80

Phe Thr Thr Ala Asp Lys Met Phe Pro Ala Asn Gln Leu Val Val Ser
                85                  90                  95

Pro Gln Glu Glu Gln Gln Lys Ile Asn Phe Leu Lys Glu Gln Arg Ile
            100                 105                 110

Glu Gly Met Leu Ser Gln Met Glu Gly Val Ile Asn Ala Lys Val Thr
        115                 120                 125

Ile Ala Leu Pro Thr Tyr Asp Glu Gly Ser Asn Ala Ser Pro Ser Ser
130                 135                 140

Val Ala Val Phe Ile Lys Tyr Ser Pro Gln Val Asn Met Glu Ala Phe
145                 150                 155                 160

Arg Val Lys Ile Lys Asp Leu Ile Glu Met Ser Ile Pro Gly Leu Gln
                165                 170                 175

Tyr Ser Lys Ile Ser Ile Leu Met Gln Pro Ala Glu Phe Arg Met Val
            180                 185                 190

Ala Asp Val Pro Ala Arg Gln Thr Phe Trp Ile Met Asp Val Ile Asn
        195                 200                 205

Ala Asn Lys Gly Lys Val Val Lys Trp Leu Met Lys Tyr Pro Tyr Pro
210                 215                 220

Leu Met Leu Ser Leu Thr Gly Leu Leu Leu Gly Val Gly Ile Leu Ile
225                 230                 235                 240

Gly Tyr Phe Cys Leu Arg Arg Arg Phe
                245
```

<210> SEQ ID NO 34
<211> LENGTH: 2763
<212> TYPE: DNA
<213> ORGANISM: Salmonella
<220> FEATURE:
<221> NAME/KEY: CDS
<222> LOCATION: (1)..(2760)

<400> SEQUENCE: 34

```
atg aat ttg ctc aat ctc aag aat acg ctg caa aca tct tta gta atc    48
Met Asn Leu Leu Asn Leu Lys Asn Thr Leu Gln Thr Ser Leu Val Ile
1               5                   10                  15
```

-continued

| | |
|---|---|
| agg cta act ttt tta ttt tta tta aca aca ata att att tgg ctg cta<br>Arg Leu Thr Phe Leu Phe Leu Leu Thr Thr Ile Ile Ile Trp Leu Leu<br>                 20                      25                   30 | 96 |
| tct gtg ctt acc gca gct tat ata tca atg gtt cag aaa cgg cag cat<br>Ser Val Leu Thr Ala Ala Tyr Ile Ser Met Val Gln Lys Arg Gln His<br>        35                      40                   45 | 144 |
| ata ata gag gat tta tcc gtt cta tcc gag atg aat att gta cta agc<br>Ile Ile Glu Asp Leu Ser Val Leu Ser Glu Met Asn Ile Val Leu Ser<br>50                      55                   60 | 192 |
| aat caa cgg ttt gaa gaa gct gaa cgt gac gct aaa aat tta atg tat<br>Asn Gln Arg Phe Glu Glu Ala Glu Arg Asp Ala Lys Asn Leu Met Tyr<br>65                      70                   75                   80 | 240 |
| caa tgc tca tta gcg act gag att cat cat aac gat att ttc cct gag<br>Gln Cys Ser Leu Ala Thr Glu Ile His His Asn Asp Ile Phe Pro Glu<br>                 85                      90                   95 | 288 |
| gtg agc cgg cat cta tct gtc ggt cct tca aat tgc acg ccg acg cta<br>Val Ser Arg His Leu Ser Val Gly Pro Ser Asn Cys Thr Pro Thr Leu<br>               100                    105                   110 | 336 |
| aac gga gag aag cac cgt ctc ttt ctg cag tcc tct gat atc gat gaa<br>Asn Gly Glu Lys His Arg Leu Phe Leu Gln Ser Ser Asp Ile Asp Glu<br>               115                    120                   125 | 384 |
| aat agc ttt cgt cgc gat agt ttt att ctt aat cat aaa aat gag att<br>Asn Ser Phe Arg Arg Asp Ser Phe Ile Leu Asn His Lys Asn Glu Ile<br>130                   135                    140 | 432 |
| tcg tta tta tct act gat aac cct tca gat tat tca act cta cag cct<br>Ser Leu Leu Ser Thr Asp Asn Pro Ser Asp Tyr Ser Thr Leu Gln Pro<br>145                   150                    155                   160 | 480 |
| tta acg cga aaa agc ttt cct tta tac cca acc cat gcc ggg ttt tac<br>Leu Thr Arg Lys Ser Phe Pro Leu Tyr Pro Thr His Ala Gly Phe Tyr<br>                   165                    170                   175 | 528 |
| tgg agt gaa cca gaa tac ata aac ggc aaa gga tgg cac gct tcc gtt<br>Trp Ser Glu Pro Glu Tyr Ile Asn Gly Lys Gly Trp His Ala Ser Val<br>               180                    185                   190 | 576 |
| gcg gtt gcc gat cag caa ggc gta ttt ttt gag gtg acg gtt aaa ctt<br>Ala Val Ala Asp Gln Gln Gly Val Phe Phe Glu Val Thr Val Lys Leu<br>               195                    200                   205 | 624 |
| ccc gat ctc att act aag agc cac ctg cca tta gat gat agt att cga<br>Pro Asp Leu Ile Thr Lys Ser His Leu Pro Leu Asp Asp Ser Ile Arg<br>210                   215                    220 | 672 |
| gta tgg ctg gat caa aac aac cac tta ttg ccg ttt tca tac atc ccg<br>Val Trp Leu Asp Gln Asn Asn His Leu Leu Pro Phe Ser Tyr Ile Pro<br>225                   230                    235                   240 | 720 |
| caa aaa ata cgt aca cag tta gaa aat gta acg ctg cat gat gga tgg<br>Gln Lys Ile Arg Thr Gln Leu Glu Asn Val Thr Leu His Asp Gly Trp<br>               245                    250                   255 | 768 |
| cag caa att ccc gga ttt ctg ata tta cgc aca acc ttg cat ggc ccc<br>Gln Gln Ile Pro Gly Phe Leu Ile Leu Arg Thr Thr Leu His Gly Pro<br>               260                    265                   270 | 816 |
| gga tgg agt ctg gtt acg ctg tac cca tac ggt aat cta cat aat cgc<br>Gly Trp Ser Leu Val Thr Leu Tyr Pro Tyr Gly Asn Leu His Asn Arg<br>               275                    280                   285 | 864 |
| atc tta aaa att atc ctt caa caa atc ccc ttt aca tta aca gca ttg<br>Ile Leu Lys Ile Ile Leu Gln Gln Ile Pro Phe Thr Leu Thr Ala Leu<br>290                   295                    300 | 912 |
| gtg ttg atg acg tcg gct ttt tgc tgg tta cta cat cgc tca ctg gcc<br>Val Leu Met Thr Ser Ala Phe Cys Trp Leu Leu His Arg Ser Leu Ala<br>305                   310                    315                   320 | 960 |
| aaa ccg tta tgg cgt ttt gtc gat gtc att aat aaa acc gca act gca<br>Lys Pro Leu Trp Arg Phe Val Asp Val Ile Asn Lys Thr Ala Thr Ala<br>               325                    330                   335 | 1008 |

```
ccg ctg agc aca cgt tta cca gca caa cga ctg gat gaa tta gat agt      1056
Pro Leu Ser Thr Arg Leu Pro Ala Gln Arg Leu Asp Glu Leu Asp Ser
            340                 345                 350 att gcc ggt gct ttt aac caa ctg ctt gat act cta caa gtc caa tac      1104
Ile Ala Gly Ala Phe Asn Gln Leu Leu Asp Thr Leu Gln Val Gln Tyr
        355                 360                 365 gac aat ctg gaa aac aaa gtc gca gag cgc acc cag gcg cta aat gaa      1152
Asp Asn Leu Glu Asn Lys Val Ala Glu Arg Thr Gln Ala Leu Asn Glu
    370                 375                 380 gca aaa aaa cgc gct gag cga gct aac aaa cgt aaa agc att cat ctt      1200
Ala Lys Lys Arg Ala Glu Arg Ala Asn Lys Arg Lys Ser Ile His Leu
385                 390                 395                 400 acg gta ata agt cat gag tta cgt act ccg atg aat ggc gta ctc ggt      1248
Thr Val Ile Ser His Glu Leu Arg Thr Pro Met Asn Gly Val Leu Gly
                405                 410                 415 gca att gaa tta tta caa acc acc cct tta aac ata gag caa caa gga      1296
Ala Ile Glu Leu Leu Gln Thr Thr Pro Leu Asn Ile Glu Gln Gln Gly
            420                 425                 430 tta gct gat acc gcc aga aat tgt aca ctg tct ttg tta gct att att      1344
Leu Ala Asp Thr Ala Arg Asn Cys Thr Leu Ser Leu Leu Ala Ile Ile
        435                 440                 445 aat aat ctg ctg gat ttt tca cgc atc gag tct ggt cat ttc aca tta      1392
Asn Asn Leu Leu Asp Phe Ser Arg Ile Glu Ser Gly His Phe Thr Leu
    450                 455                 460 cat atg gaa gaa aca gcg tta ctg ccg tta ctg gac cag gca atg caa      1440
His Met Glu Glu Thr Ala Leu Leu Pro Leu Leu Asp Gln Ala Met Gln
465                 470                 475                 480 acc atc cag ggg cca gcg caa agc aaa aaa ctg tca tta cgt act ttt      1488
Thr Ile Gln Gly Pro Ala Gln Ser Lys Lys Leu Ser Leu Arg Thr Phe
                485                 490                 495 gtc ggt caa cat gtc cct ctc tat ttt cat acc gac agt atc cgt tta      1536
Val Gly Gln His Val Pro Leu Tyr Phe His Thr Asp Ser Ile Arg Leu
            500                 505                 510 cgg caa att ttg gtt aat tta ctc ggg aac gcg gta aaa ttt acc gaa      1584
Arg Gln Ile Leu Val Asn Leu Leu Gly Asn Ala Val Lys Phe Thr Glu
        515                 520                 525 acc gga ggg ata cgt ctg acg gtc aag cgt cat gag gaa caa tta ata      1632
Thr Gly Gly Ile Arg Leu Thr Val Lys Arg His Glu Glu Gln Leu Ile
    530                 535                 540 ttt ctg gtt agc gat agc ggt aaa ggg att gaa ata cag cag cag tct      1680
Phe Leu Val Ser Asp Ser Gly Lys Gly Ile Glu Ile Gln Gln Gln Ser
545                 550                 555                 560 caa atc ttt act gct ttt tat caa gca gac aca aat tcg caa ggt aca      1728
Gln Ile Phe Thr Ala Phe Tyr Gln Ala Asp Thr Asn Ser Gln Gly Thr
                565                 570                 575 gga att gga ctg act att gcg tca agc ctg gct aaa atg atg ggc ggt      1776
Gly Ile Gly Leu Thr Ile Ala Ser Ser Leu Ala Lys Met Met Gly Gly
            580                 585                 590 aat ctg aca cta aaa agt gtc ccc ggg gtt gga acc tgt gtc tcg cta      1824
Asn Leu Thr Leu Lys Ser Val Pro Gly Val Gly Thr Cys Val Ser Leu
        595                 600                 605 gta tta ccc tta caa gaa tac cag ccg cct caa cca att aaa ggg acg      1872
Val Leu Pro Leu Gln Glu Tyr Gln Pro Pro Gln Pro Ile Lys Gly Thr
    610                 615                 620 ctg tca gcg ccg ttc tgc ctg cat cgg caa ctg gct tgc tgg gga ata      1920
Leu Ser Ala Pro Phe Cys Leu His Arg Gln Leu Ala Cys Trp Gly Ile
625                 630                 635                 640 cgc ggt gaa cca ccc cac cag caa aat gcg ctt ctc aac gca gag ctt      1968
Arg Gly Glu Pro Pro His Gln Gln Asn Ala Leu Leu Asn Ala Glu Leu
```

-continued

```
                      645                 650                 655
ttg tat ttc tcc gga aaa ctc tac gac ctg gcg caa cag tta ata ttg    2016
Leu Tyr Phe Ser Gly Lys Leu Tyr Asp Leu Ala Gln Gln Leu Ile Leu
            660                 665                 670 tgt aca cca aat atg cca gta ata aat aat ttg tta cca ccc tgg cag    2064
Cys Thr Pro Asn Met Pro Val Ile Asn Asn Leu Leu Pro Pro Trp Gln
            675                 680                 685 ttg cag att ctt ttg gtt gat gat gcc gat att aat cgg gat atc atc    2112
Leu Gln Ile Leu Leu Val Asp Asp Ala Asp Ile Asn Arg Asp Ile Ile
    690                 695                 700 ggc aaa atg ctt gtc agc ctg ggc caa cac gtc act att gcc gcc agt    2160
Gly Lys Met Leu Val Ser Leu Gly Gln His Val Thr Ile Ala Ala Ser
705                 710                 715                 720 agt aac gag gct ctg act tta tca caa cag cag cga ttc gat tta gta    2208
Ser Asn Glu Ala Leu Thr Leu Ser Gln Gln Gln Arg Phe Asp Leu Val
                725                 730                 735 ctg att gac att aga atg cca gaa ata gat ggt att gaa tgt gta cga    2256
Leu Ile Asp Ile Arg Met Pro Glu Ile Asp Gly Ile Glu Cys Val Arg
            740                 745                 750 tta tgg cat gat gag ccg aat aat tta gat cct gac tgc atg ttt gtg    2304
Leu Trp His Asp Glu Pro Asn Asn Leu Asp Pro Asp Cys Met Phe Val
        755                 760                 765 gca cta tcc gct agc gta gcg aca gaa gat att cat cgt tgt aaa aaa    2352
Ala Leu Ser Ala Ser Val Ala Thr Glu Asp Ile His Arg Cys Lys Lys
    770                 775                 780 aat ggg att cat cat tac att aca aaa cca gtg aca ttg gct acc tta    2400
Asn Gly Ile His His Tyr Ile Thr Lys Pro Val Thr Leu Ala Thr Leu
785                 790                 795                 800 gct cgc tac atc agt att gcc gca gaa tac caa ctt tta cga aat ata    2448
Ala Arg Tyr Ile Ser Ile Ala Ala Glu Tyr Gln Leu Leu Arg Asn Ile
                805                 810                 815 gag cta cag gag cag gat ccg agt cgc tgc tca gcg cta ctg gcg aca    2496
Glu Leu Gln Glu Gln Asp Pro Ser Arg Cys Ser Ala Leu Leu Ala Thr
            820                 825                 830 gat gat atg gtc att aat agc aag att ttc caa tca ctg gac ctc ttg    2544
Asp Asp Met Val Ile Asn Ser Lys Ile Phe Gln Ser Leu Asp Leu Leu
        835                 840                 845 ctg gct gat att gaa aat gcc gta tcg gct gga gaa aaa atc gat cag    2592
Leu Ala Asp Ile Glu Asn Ala Val Ser Ala Gly Glu Lys Ile Asp Gln
    850                 855                 860 tta att cac aca tta aaa ggc tgt tta ggt caa ata ggg cag act gaa    2640
Leu Ile His Thr Leu Lys Gly Cys Leu Gly Gln Ile Gly Gln Thr Glu
865                 870                 875                 880 ttg gta tgc tat gtc ata gac att gag aat cgc gta aaa atg ggg aaa    2688
Leu Val Cys Tyr Val Ile Asp Ile Glu Asn Arg Val Lys Met Gly Lys
                885                 890                 895 atc atc gcg ctg gag gaa cta acc gac tta cgc cag aaa ata cgt atg    2736
Ile Ile Ala Leu Glu Glu Leu Thr Asp Leu Arg Gln Lys Ile Arg Met
            900                 905                 910 atc ttc aaa aac tac acc att act taa                                2763
Ile Phe Lys Asn Tyr Thr Ile Thr
        915                 920

<210> SEQ ID NO 35
<211> LENGTH: 920
<212> TYPE: PRT
<213> ORGANISM: Salmonella

<400> SEQUENCE: 35

Met Asn Leu Leu Asn Leu Lys Asn Thr Leu Gln Thr Ser Leu Val Ile
```

-continued

```
  1               5                  10                 15
Arg Leu Thr Phe Leu Phe Leu Thr Thr Ile Ile Ile Trp Leu Leu
             20                 25                 30

Ser Val Leu Thr Ala Ala Tyr Ile Ser Met Val Gln Lys Arg Gln His
             35                 40                 45

Ile Ile Glu Asp Leu Ser Val Leu Ser Glu Met Asn Ile Val Leu Ser
             50                 55                 60

Asn Gln Arg Phe Glu Glu Ala Glu Arg Asp Ala Lys Asn Leu Met Tyr
 65                 70                 75                 80

Gln Cys Ser Leu Ala Thr Glu Ile His His Asn Asp Ile Phe Pro Glu
             85                 90                 95

Val Ser Arg His Leu Ser Val Gly Pro Ser Asn Cys Thr Pro Thr Leu
            100                105                110

Asn Gly Glu Lys His Arg Leu Phe Leu Gln Ser Ser Asp Ile Asp Glu
            115                120                125

Asn Ser Phe Arg Arg Asp Ser Phe Ile Leu Asn His Lys Asn Glu Ile
    130                135                140

Ser Leu Leu Ser Thr Asp Asn Pro Ser Asp Tyr Ser Thr Leu Gln Pro
145                150                155                160

Leu Thr Arg Lys Ser Phe Pro Leu Tyr Pro Thr His Ala Gly Phe Tyr
                165                170                175

Trp Ser Glu Pro Glu Tyr Ile Asn Gly Lys Gly Trp His Ala Ser Val
            180                185                190

Ala Val Ala Asp Gln Gln Gly Val Phe Phe Glu Val Thr Val Lys Leu
            195                200                205

Pro Asp Leu Ile Thr Lys Ser His Leu Pro Leu Asp Asp Ser Ile Arg
210                215                220

Val Trp Leu Asp Gln Asn Asn His Leu Leu Pro Phe Ser Tyr Ile Pro
225                230                235                240

Gln Lys Ile Arg Thr Gln Leu Glu Asn Val Thr Leu His Asp Gly Trp
                245                250                255

Gln Gln Ile Pro Gly Phe Leu Ile Leu Arg Thr Thr Leu His Gly Pro
            260                265                270

Gly Trp Ser Leu Val Thr Leu Tyr Pro Tyr Gly Asn Leu His Asn Arg
            275                280                285

Ile Leu Lys Ile Ile Leu Gln Gln Ile Pro Phe Thr Leu Thr Ala Leu
    290                295                300

Val Leu Met Thr Ser Ala Phe Cys Trp Leu Leu His Arg Ser Leu Ala
305                310                315                320

Lys Pro Leu Trp Arg Phe Val Asp Val Ile Asn Lys Thr Ala Thr Ala
                325                330                335

Pro Leu Ser Thr Arg Leu Pro Ala Gln Arg Leu Asp Glu Leu Asp Ser
            340                345                350

Ile Ala Gly Ala Phe Asn Gln Leu Leu Asp Thr Leu Gln Val Gln Tyr
            355                360                365

Asp Asn Leu Glu Asn Lys Val Ala Glu Arg Thr Gln Ala Leu Asn Glu
    370                375                380

Ala Lys Lys Arg Ala Glu Arg Ala Asn Lys Arg Lys Ser Ile His Leu
385                390                395                400

Thr Val Ile Ser His Glu Leu Arg Thr Pro Met Asn Gly Val Leu Gly
                405                410                415

Ala Ile Glu Leu Leu Gln Thr Thr Pro Leu Asn Ile Glu Gln Gln Gly
            420                425                430
```

-continued

```
Leu Ala Asp Thr Ala Arg Asn Cys Thr Leu Ser Leu Leu Ala Ile Ile
        435                 440                 445

Asn Asn Leu Leu Asp Phe Ser Arg Ile Glu Ser Gly His Phe Thr Leu
    450                 455                 460

His Met Glu Glu Thr Ala Leu Leu Pro Leu Leu Asp Gln Ala Met Gln
465                 470                 475                 480

Thr Ile Gln Gly Pro Ala Gln Ser Lys Lys Leu Ser Leu Arg Thr Phe
                485                 490                 495

Val Gly Gln His Val Pro Leu Tyr Phe His Thr Asp Ser Ile Arg Leu
            500                 505                 510

Arg Gln Ile Leu Val Asn Leu Gly Asn Ala Val Lys Phe Thr Glu
        515                 520                 525

Thr Gly Gly Ile Arg Leu Thr Val Lys Arg His Glu Glu Gln Leu Ile
    530                 535                 540

Phe Leu Val Ser Asp Ser Gly Lys Gly Ile Glu Ile Gln Gln Gln Ser
545                 550                 555                 560

Gln Ile Phe Thr Ala Phe Tyr Gln Ala Asp Thr Asn Ser Gln Gly Thr
                565                 570                 575

Gly Ile Gly Leu Thr Ile Ala Ser Ser Leu Ala Lys Met Met Gly Gly
            580                 585                 590

Asn Leu Thr Leu Lys Ser Val Pro Gly Val Gly Thr Cys Val Ser Leu
        595                 600                 605

Val Leu Pro Leu Gln Glu Tyr Gln Pro Pro Gln Pro Ile Lys Gly Thr
    610                 615                 620

Leu Ser Ala Pro Phe Cys Leu His Arg Gln Leu Ala Cys Trp Gly Ile
625                 630                 635                 640

Arg Gly Glu Pro Pro His Gln Gln Asn Ala Leu Leu Asn Ala Glu Leu
                645                 650                 655

Leu Tyr Phe Ser Gly Lys Leu Tyr Asp Leu Ala Gln Gln Leu Ile Leu
            660                 665                 670

Cys Thr Pro Asn Met Pro Val Ile Asn Asn Leu Leu Pro Pro Trp Gln
        675                 680                 685

Leu Gln Ile Leu Leu Val Asp Asp Ala Asp Ile Asn Arg Asp Ile Ile
    690                 695                 700

Gly Lys Met Leu Val Ser Leu Gly Gln His Val Thr Ile Ala Ala Ser
705                 710                 715                 720

Ser Asn Glu Ala Leu Thr Leu Ser Gln Gln Arg Phe Asp Leu Val
                725                 730                 735

Leu Ile Asp Ile Arg Met Pro Glu Ile Asp Gly Ile Glu Cys Val Arg
            740                 745                 750

Leu Trp His Asp Glu Pro Asn Asn Leu Asp Pro Asp Cys Met Phe Val
        755                 760                 765

Ala Leu Ser Ala Ser Val Ala Thr Glu Asp Ile His Arg Cys Lys Lys
    770                 775                 780

Asn Gly Ile His His Tyr Ile Thr Lys Pro Val Thr Leu Ala Thr Leu
785                 790                 795                 800

Ala Arg Tyr Ile Ser Ile Ala Ala Glu Tyr Gln Leu Leu Arg Asn Ile
                805                 810                 815

Glu Leu Gln Glu Gln Asp Pro Ser Arg Cys Ser Ala Leu Leu Ala Thr
            820                 825                 830

Asp Asp Met Val Ile Asn Ser Lys Ile Phe Gln Ser Leu Asp Leu Leu
        835                 840                 845
```

-continued

```
Leu Ala Asp Ile Glu Asn Ala Val Ser Ala Gly Glu Lys Ile Asp Gln
        850                 855                 860
Leu Ile His Thr Leu Lys Gly Cys Leu Gly Gln Ile Gly Gln Thr Glu
865                 870                 875                 880
Leu Val Cys Tyr Val Ile Asp Ile Glu Asn Arg Val Lys Met Gly Lys
                885                 890                 895
Ile Ile Ala Leu Glu Glu Leu Thr Asp Leu Arg Gln Lys Ile Arg Met
        900                 905                 910
Ile Phe Lys Asn Tyr Thr Ile Thr
        915                 920

<210> SEQ ID NO 36
<211> LENGTH: 639
<212> TYPE: DNA
<213> ORGANISM: Salmonella
<220> FEATURE:
<221> NAME/KEY: CDS
<222> LOCATION: (1)..(636)

<400> SEQUENCE: 36 atg aaa gaa tat aag atc tta tta gta gac gat cat gaa atc atc att      48
Met Lys Glu Tyr Lys Ile Leu Leu Val Asp Asp His Glu Ile Ile Ile
  1               5                  10                  15 aac ggc att atg aat gcc tta tta ccc tgg cct cat ttt aaa att gta      96
Asn Gly Ile Met Asn Ala Leu Leu Pro Trp Pro His Phe Lys Ile Val
                 20                  25                  30 gag cat gtt aaa aat ggt ctt gag gtt tat aat gcc tgt tgt gca tac     144
Glu His Val Lys Asn Gly Leu Glu Val Tyr Asn Ala Cys Cys Ala Tyr
             35                  40                  45 gag cct gac ata ctt atc ctt gat ctt agt cta cct ggc atc aat ggc     192
Glu Pro Asp Ile Leu Ile Leu Asp Leu Ser Leu Pro Gly Ile Asn Gly
         50                  55                  60 ctg gat atc att cct caa tta cat cag cgt tgg cca gca atg aat att     240
Leu Asp Ile Ile Pro Gln Leu His Gln Arg Trp Pro Ala Met Asn Ile
 65                  70                  75                  80 ctg gtt tac aca gca tac caa caa gag tat atg acc att aaa act tta     288
Leu Val Tyr Thr Ala Tyr Gln Gln Glu Tyr Met Thr Ile Lys Thr Leu
                 85                  90                  95 gcc gca ggt gct aat ggc tat gtt tta aaa agc agt agt cag caa gtt     336
Ala Ala Gly Ala Asn Gly Tyr Val Leu Lys Ser Ser Ser Gln Gln Val
            100                 105                 110 ctg tta gcg gca ttg caa aca gta gca gta aac aag cgt tac att gac     384
Leu Leu Ala Ala Leu Gln Thr Val Ala Val Asn Lys Arg Tyr Ile Asp
        115                 120                 125 cca acg ttg aat cgg gaa gct atc ctg gct gaa tta aac gct gac acg     432
Pro Thr Leu Asn Arg Glu Ala Ile Leu Ala Glu Leu Asn Ala Asp Thr
    130                 135                 140 acc aat cat caa ctg ctt act ttg cgc gag cgt cag gtt ctt aaa ctt     480
Thr Asn His Gln Leu Leu Thr Leu Arg Glu Arg Gln Val Leu Lys Leu
145                 150                 155                 160 att gac gag ggg tat acc aat cat ggg atc agc gaa aag cta cat atc     528
Ile Asp Glu Gly Tyr Thr Asn His Gly Ile Ser Glu Lys Leu His Ile
                165                 170                 175 agt ata aaa acc gtc gaa aca cac cgg atg aat atg atg aga aag cta     576
Ser Ile Lys Thr Val Glu Thr His Arg Met Asn Met Met Arg Lys Leu
            180                 185                 190 cag gtt cat aaa gtg aca gag tta ctt aac tgt gcc cga aga atg agg     624
Gln Val His Lys Val Thr Glu Leu Leu Asn Cys Ala Arg Arg Met Arg
        195                 200                 205
```

```
tta ata gag tat taa                                              639
Leu Ile Glu Tyr
    210

<210> SEQ ID NO 37
<211> LENGTH: 212
<212> TYPE: PRT
<213> ORGANISM: Salmonella

<400> SEQUENCE: 37

Met Lys Glu Tyr Lys Ile Leu Leu Val Asp Asp His Glu Ile Ile Ile
  1               5                  10                  15

Asn Gly Ile Met Asn Ala Leu Leu Pro Trp Pro His Phe Lys Ile Val
             20                  25                  30

Glu His Val Lys Asn Gly Leu Glu Val Tyr Asn Ala Cys Cys Ala Tyr
         35                  40                  45

Glu Pro Asp Ile Leu Ile Leu Asp Leu Ser Leu Pro Gly Ile Asn Gly
     50                  55                  60

Leu Asp Ile Ile Pro Gln Leu His Gln Arg Trp Pro Ala Met Asn Ile
 65                  70                  75                  80

Leu Val Tyr Thr Ala Tyr Gln Gln Glu Tyr Met Thr Ile Lys Thr Leu
                 85                  90                  95

Ala Ala Gly Ala Asn Gly Tyr Val Leu Lys Ser Ser Gln Gln Val
            100                 105                 110

Leu Leu Ala Ala Leu Gln Thr Val Ala Val Asn Lys Arg Tyr Ile Asp
        115                 120                 125

Pro Thr Leu Asn Arg Glu Ala Ile Leu Ala Glu Leu Asn Ala Asp Thr
    130                 135                 140

Thr Asn His Gln Leu Leu Thr Leu Arg Glu Arg Gln Val Leu Lys Leu
145                 150                 155                 160

Ile Asp Glu Gly Tyr Thr Asn His Gly Ile Ser Glu Lys Leu His Ile
                165                 170                 175

Ser Ile Lys Thr Val Glu Thr His Arg Met Asn Met Met Arg Lys Leu
            180                 185                 190

Gln Val His Lys Val Thr Glu Leu Leu Asn Cys Ala Arg Arg Met Arg
        195                 200                 205

Leu Ile Glu Tyr
    210

<210> SEQ ID NO 38
<211> LENGTH: 388
<212> TYPE: DNA
<213> ORGANISM: Salmonella

<400> SEQUENCE: 38
gcttccctcc agttgcctgt tgcaaaatct ttggcacttg atcactatcg cagtacatat      60
agtttcatca gaagattaat cgatggtgtt atcattagga agataaattt cttcatatat     120
aacccagtcg atgactacaa ttactttta ataagatggc gatgtaaaaa catcgtaaca     180
gtttatttaa taataatttt ttcaaattgt aagttttat gtcaatgctg aaaatgtaat     240
tgtgaattta tcggaaaatc cgaatgatag aatcgcctgt gacaaggtat atgtagacag     300
catcctgata ttgtacaaga agagatagtc gaaataaatg tgaatcaggc ttttacgga     360 tgtggttgtg agcgaatttg atagaaac                                         388

<210> SEQ ID NO 39
<211> LENGTH: 262
```

```
<212> TYPE: DNA
<213> ORGANISM: Salmonella

<400> SEQUENCE: 39
taaaaatatc ttagagccta tcccaccagg cgttaattgg cgcagccagt ttggacacgg      60
atagcgcgca aaaccgcag cgtacacgta gtacgtgagg tttgactcgc tacgctcgcc     120
cttcgggccg ccgctagcgg cgttcaaaac gctaacgcgt tttggcgagc actgcccagg    180
ttcaaaatgg caagtaaaat agcctaatgg gataggctct tagttagcac gttaattatc    240
tatcgtgtat atggagggga at                                              262

<210> SEQ ID NO 40
<211> LENGTH: 192
<212> TYPE: PRT
<213> ORGANISM: EPEC
<300> PUBLICATION INFORMATION:
<303> JOURNAL: Mol. Microbiol.
<304> VOLUME: 28
<306> PAGES: 1-4
<307> DATE: 1998

<400> SEQUENCE: 40
```

Met Asp Thr Ser Thr Thr Ala Ser Val Ala Ser Ala Asn Ala Ser Thr
1               5                   10                  15

Ser Thr Ser Met Ala Tyr Asp Leu Gly Ser Met Ser Lys Asp Asp Val
            20                  25                  30

Ile Asp Leu Phe Asn Lys Leu Gly Val Phe Gln Ala Ala Ile Leu Met
        35                  40                  45

Phe Ala Tyr Met Tyr Gln Ala Gln Ser Asp Leu Ser Ile Ala Lys Phe
    50                  55                  60

Ala Asp Met Asn Glu Ala Ser Lys Glu Ser Thr Thr Ala Gln Lys Met
65                  70                  75                  80

Ala Asn Leu Val Asp Ala Lys Ile Ala Asp Val Gln Ser Ser Ser Asp
                85                  90                  95

Lys Asn Ala Lys Ala Gln Leu Pro Asp Glu Val Ile Ser Tyr Ile Asn
            100                 105                 110

Asp Pro Arg Asn Asp Ile Thr Ile Ser Gly Ile Asp Asn Ile Asn Ala
        115                 120                 125

Gln Leu Gly Ala Gly Asp Leu Gln Thr Val Lys Ala Ala Ile Ser Ala
    130                 135                 140

Lys Ala Asn Asn Leu Thr Thr Thr Val Asn Asn Ser Gln Leu Glu Ile
145                 150                 155                 160

Gln Gln Met Ser Asn Thr Leu Asn Leu Leu Thr Ser Ala Arg Ser Asp
                165                 170                 175

Met Gln Ser Leu Gln Tyr Arg Thr Ile Ser Gly Ile Ser Leu Gly Lys
            180                 185                 190

```
<210> SEQ ID NO 41
<211> LENGTH: 380
<212> TYPE: PRT
<213> ORGANISM: EPEC
<300> PUBLICATION INFORMATION:
<303> JOURNAL: Mol. Microbiol.
<304> VOLUME: 28
<306> PAGES: 1-4
<307> DATE: 1998

<400> SEQUENCE: 41
```

Met Leu Asn Val Asn Asn Asp Ile Gln Ser Val Arg Ser Gly Ala Ser
1               5                   10                  15

```
Ala Ala Thr Ala Thr Ser Gly Ile Asn Gln Ser Glu Val Thr Ser Ala
             20                  25                  30

Leu Asp Leu Gln Leu Val Lys Ser Thr Ala Pro Ser Ala Ser Trp Thr
         35                  40                  45

Glu Ser Thr Ala Leu Ala Thr Pro Pro Ala Gly His Ser Leu Val Thr
     50                  55                  60

Pro Ser Ala Ala Glu Asp Val Leu Ser Lys Leu Phe Gly Gly Ile Ser
 65                  70                  75                  80

Gly Glu Val Thr Ser Arg Thr Glu Gly Thr Glu Pro Gln Arg Ser Thr
                 85                  90                  95

Gln Asn Ala Ser Ser Gly Tyr Pro Tyr Leu Ser Gln Val Asn Asn Val
            100                 105                 110

Asp Pro Gln Ala Met Met Met Met Ala Thr Leu Leu Ser Leu Asp Ala
        115                 120                 125

Ser Ala Gln Arg Val Ala Ser Met Lys Asn Ser Asn Glu Ile Tyr Ala
    130                 135                 140

Asp Gly Gln Asn Lys Ala Leu Asp Asn Lys Thr Leu Glu Phe Lys Lys
145                 150                 155                 160

Gln Leu Glu Glu Gln Gln Lys Ala Glu Glu Lys Ala Gln Lys Ser Lys
                165                 170                 175

Ile Val Gly Gln Val Phe Gly Trp Leu Gly Val Ala Ala Thr Ala Ile
            180                 185                 190

Ala Ala Ile Phe Asn Pro Ala Leu Trp Ala Val Val Ala Ile Ser Ala
        195                 200                 205

Thr Ala Met Ala Leu Gln Thr Ala Val Asp Val Met Gly Asp Asp Ala
    210                 215                 220

Pro Gln Ala Leu Lys Thr Ala Ala Gln Ala Phe Gly Gly Leu Ser Leu
225                 230                 235                 240

Ala Ala Gly Ile Leu Thr Ala Gly Ile Gly Gly Val Ser Ser Leu Ile
                245                 250                 255

Ser Lys Val Gly Asp Val Ala Asn Lys Val Gly Ser Asn Ile Val Lys
            260                 265                 270

Val Val Thr Thr Leu Ala Asp Thr Phe Val Asp Asn Val Ala Ser Lys
        275                 280                 285

Ile Ser Ala Val Ala Asn Gly Leu Thr Thr Ser Arg Ser Ile Gly
    290                 295                 300                Gly

Thr Thr Val Leu Asn Asn Asp Ala Ala Tyr Tyr Asn Val Leu Ser Gln
305                 310                 315                 320

Val Ser Ala Phe Ala Val Glu Asn Leu Thr Arg Gln Ser Glu Tyr Leu
                325                 330                 335

Ser Gln Ser Ala Lys Ala Glu Leu Glu Lys Ala Thr Leu Glu Leu Gln
            340                 345                 350

Asn Gln Ala Asn Tyr Ile Gln Ser Ala Ser Gln Leu Met Ser Asp Ser
        355                 360                 365

Ala Arg Val Asn Ile Arg Ile Val Ser Gly Arg Val
    370                 375                 380

<210> SEQ ID NO 42
<211> LENGTH: 401
<212> TYPE: PRT
<213> ORGANISM: Yersinia enterocolitica
<300> PUBLICATION INFORMATION:
<301> AUTHORS: Hakansson, S.

-continued

```
    Galyov, E. E.
    Rosqvist, R.
    Homble, F.
    Wolf Watz, H.
<303> JOURNAL: EMBO J.
<304> VOLUME: 15
<306> PAGES: 5812-5823
<307> DATE: 1996

<400> SEQUENCE: 42

Met Ser Ala Leu Ile Thr His Asp Arg Ser Thr Pro Val Thr Gly Ser
  1               5                  10                  15

Leu Val Pro Tyr Ile Glu Thr Pro Ala Pro Ala Pro Leu Gln Thr Gln
                 20                  25                  30

Gln Val Ala Gly Glu Leu Lys Asp Lys Asn Gly Gly Val Ser Ser Gln
             35                  40                  45

Gly Val Gln Leu Pro Ala Pro Leu Ala Val Val Ala Ser Gln Val Thr
         50                  55                  60

Glu Gly Gln Gln Gln Glu Ile Thr Lys Leu Leu Glu Ser Val Thr Arg
 65                  70                  75                  80

Gly Thr Ala Gly Ser Gln Leu Ile Ser Asn Tyr Val Ser Val Leu Thr
                 85                  90                  95

Asn Phe Thr Leu Ala Ser Pro Asp Thr Phe Glu Ile Glu Leu Gly Lys
                100                 105                 110

Leu Val Ser Asn Leu Glu Glu Val Arg Lys Asp Ile Lys Ile Ala Asp
            115                 120                 125

Ile Gln Arg Leu His Glu Gln Asn Met Lys Lys Ile Glu Glu Asn Gln
        130                 135                 140

Glu Lys Ile Lys Glu Thr Glu Glu Asn Ala Lys Gln Val Lys Lys Ser
145                 150                 155                 160

Gly Met Ala Ser Lys Ile Phe Gly Trp Leu Ile Ala Ile Ala Ser Val
                165                 170                 175

Val Ile Gly Ala Ile Met Val Ala Ser Gly Val Gly Ala Val Ala Gly
                180                 185                 190

Ala Met Met Ile Ala Ser Gly Val Ile Gly Met Ala Asn Met Ala Val
            195                 200                 205

Lys Gln Ala Ala Glu Asp Gly Leu Ile Ser Gln Glu Ala Met Gln Val
        210                 215                 220

Leu Gly Pro Ile Leu Thr Ala Ile Glu Val Ala Leu Thr Val Val Ser
225                 230                 235                 240

Thr Val Met Thr Phe Gly Gly Ser Ala Leu Lys Cys Leu Ala Asp Ile
                245                 250                 255

Gly Ala Lys Leu Gly Ala Asn Thr Ala Ser Leu Ala Ala Lys Gly Ala
            260                 265                 270

Glu Phe Ser Ala Lys Val Ala Gln Ile Ser Thr Gly Ile Ser Asn Thr
        275                 280                 285

Val Gly Ser Ala Val Thr Lys Leu Gly Gly Ser Phe Gly Ser Leu Thr
    290                 295                 300

Met Ser His Val Ile Arg Thr Gly Ser Gln Ala Thr Gln Val Ala Val
305                 310                 315                 320

Gly Val Gly Ser Gly Ile Thr Gln Thr Ile Asn Asn Lys Lys Gln Ala
                325                 330                 335

Asp Leu Gln His Asn Asn Ala Asp Leu Ala Leu Asn Lys Ala Asp Met
            340                 345                 350

Ala Ala Leu Gln Ser Ile Ile Asp Arg Leu Lys Glu Glu Leu Ser His
        355                 360                 365
```

```
Leu Ser Glu Ser His Arg Gln Val Met Glu Leu Ile Phe Gln Met Ile
    370                 375                 380

Asn Ala Lys Gly Asp Met Leu His Asn Leu Ala Gly Arg Pro His Thr
385                 390                 395                 400

Val
```

<210> SEQ ID NO 43
<211> LENGTH: 390
<212> TYPE: PRT
<213> ORGANISM: Pseudomonas aeruginosa
<300> PUBLICATION INFORMATION:
<301> AUTHORS: Hauser, A. R.
       Fleiszig, S.
       Kang, P. J.
       Mostov, K.
       Engel, J. N.
<303> JOURNAL: Infect. Immun.
<304> VOLUME: 66
<306> PAGES: 1413-1420
<307> DATE: 1998

<400> SEQUENCE: 43

```
Met Asn Pro Ile Thr Leu Glu Arg Ala Gly Leu Pro Tyr Gly Val Ala
 1               5                  10                  15

Asp Ala Gly Asp Ile Pro Ala Leu Gly Arg Pro Val Ala Arg Asp Val
                20                  25                  30

Glu Ser Leu Arg Val Glu Arg Leu Ala Pro Ala Ala Ala Ser Ala
            35                  40                  45

Ser Gly Thr Gly Val Ala Leu Thr Pro Pro Ser Ala Ala Ser Gln Gln
        50                  55                  60

Arg Leu Glu Val Ala Asn Arg Ala Glu Ile Ala Ser Leu Val Gln Ala
 65                  70                  75                  80

Val Gly Glu Asp Ala Gly Leu Ala Arg Gln Val Val Leu Ala Gly Ala
                85                  90                  95

Ser Thr Leu Leu Ser Ala Gly Leu Met Ser Pro Gln Ala Phe Glu Ile
            100                 105                 110

Glu Leu Ala Lys Ile Thr Gly Glu Val Glu Asn Gln Gln Lys Lys Leu
        115                 120                 125

Lys Leu Thr Glu Ile Glu Gln Ala Arg Lys Gln Asn Leu Gln Lys Met
130                 135                 140

Glu Asp Asn Gln Gln Lys Ile Arg Glu Ser Glu Ala Ala Lys Glu
145                 150                 155                 160

Ala Gln Lys Ser Gly Leu Ala Ala Lys Ile Phe Gly Trp Ile Ser Ala
                165                 170                 175

Ile Ala Ser Ile Ile Val Gly Ala Ile Met Val Ala Thr Gly Val Gly
            180                 185                 190

Ala Ala Ala Gly Ala Leu Met Ile Ala Gly Gly Val Met Gly Val Val
        195                 200                 205

Ser Gln Ser Val Gln Gln Ala Ala Asp Gly Leu Ile Ser Lys Glu
210                 215                 220

Val Met Glu Lys Leu Gly Pro Ala Leu Met Gly Ile Glu Ile Ala Val
225                 230                 235                 240

Ala Leu Leu Ala Ala Val Val Ser Phe Gly Gly Ser Ala Val Gly Gly
                245                 250                 255

Leu Ala Lys Leu Gly Ala Lys Ile Gly Gly Lys Ala Ala Glu Met Thr
            260                 265                 270

Ala Ser Leu Ala Ser Lys Val Ala Asn Leu Gly Gly Lys Phe Gly Ser
```

```
            275                 280                 285
Leu Ala Gly Gln Ser Leu Ser His Ser Leu Lys Leu Gly Val Gln Val
    290                 295                 300

Ser Asp Leu Thr Leu Asp Val Ala Asn Gly Ala Ala Gln Ala Thr His
305                 310                 315                 320

Ser Gly Phe Gln Ala Lys Ala Ala Asn Arg Gln Ala Asp Val Gln Glu
                325                 330                 335

Ser Arg Ala Asp Leu Thr Thr Leu Gln Gly Val Ile Glu Arg Leu Lys
            340                 345                 350

Glu Glu Leu Ser Arg Met Leu Glu Ala Phe Gln Glu Ile Met Glu Arg
                355                 360                 365

Ile Phe Ala Met Leu Gln Ala Lys Gly Glu Thr Leu His Asn Leu Ser
    370                 375                 380

Ser Arg Pro Ala Ala Ile
385                 390
```

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 44
tttttacgtg aagcggggtg                                               20

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 45
ggcattagcg gatgtctgac tg                                            22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 46
caccaggaac cattttctct gg                                            22

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 47
cagcgatgac gatattcgac aag                                           23

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence: Primer

```
<400> SEQUENCE: 48
gaaatcccgc agaaatg                                              17

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 49
aaggcgataa tataaac                                              17

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 50
agagatgtat tagatac                                              17

<210> SEQ ID NO 51
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 51
gcaataagag tatcaac                                              17

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 52
gctaagcttc ggctcaaatt gtttggaaaa c                              31

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 53
gctaagctta gagatgtatt agatacc                                   27

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 54
attggatccg caagcgtcca gaa                                       23

<210> SEQ ID NO 55
<211> LENGTH: 23
```

```
<212> TYPE: DNA
<213> ORGANISM: Artificial Sequence
<220> FEATURE:
<223> OTHER INFORMATION: Description of Artificial Sequence: Primer

<400> SEQUENCE: 55
tatggatcct cagattaagc gcg                                         23

<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 56
atagaattcg gagggagatg gagtggaag                                   29

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 57
atagaattcg aagataaagc gattgccgac                                  30

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 58
gaaggatcca ctccatctcc ctc                                         23

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 59
gaaggatcca tttgctctat ttcttgc                                     27

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 60
atgggatccg agattcgcca gaatgcgcaa                                  30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 61
```

```
atgggatcca ctggcataaa cggtttccgg                                    30
```

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 62

```
attggatcct gacgtaaatc attatca                                       27
```

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 63

```
attggatcct taagcaataa gtgaatc                                       27
```

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 64

```
aaggaattca acaggcaact ggagg                                         25
```

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 65

```
ctgccctcgc gaaaattaag ataata                                        26
```

<210> SEQ ID NO 66
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 66

```
cttatttttc gcgaggg                                                  17
```

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 67

```
ggacgcccct ggttaata                                                 18
```

<210> SEQ ID NO 68
<211> LENGTH: 29
<212> TYPE: DNA
<213> ORGANISM: Artificial Sequence

```
<220> FEATURE:
<223> OTHER INFORMATION: Description of Artificial Sequence: Primer

<400> SEQUENCE: 68
ggtctgcagg atttttcacg catcgcgtc                                      29

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 69
ggtctgcaga accattgata tataagctgc                                     30

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 70
gctgtcgact tgtagtgagt gagcaag                                        27

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 71
ggatctagat tttagctcct gtcagaaag                                      29

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 72
ggatctagat ctgaggataa aaatatgg                                       28

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 73
gctgagctct gccgctgacg gaatatg                                        27
```